(12) United States Patent
Arista et al.

(10) Patent No.: US 11,541,056 B2
(45) Date of Patent: Jan. 3, 2023

(54) 3-HYDROXY-N-(3-(7H-PYRROLO[2,3-D]PYRIMIDIN-4-YL)PHENYL)PYRROLIDINE-1-CARBOXAMIDE DERIVATIVES

(71) Applicant: NOVARTIS AG, Basel (CH)

(72) Inventors: Luca Arista, Riehen (CH); Christina Hebach, Muenchenstein (CH); Gregory John Hollingworth, Kent (GB); Philipp Holzer, Sissach (CH); Patricia Imbach-Weese, Bielefeld (DE); Rainer Machauer, Freiburg (DE); Niko Schmiedeberg, Riehen (CH); Anna Vulpetti, Basel (CH); Thomas Zoller, Andolsheim (FR)

(73) Assignee: NOVARTIS AG, Basel (CH)

( * ) Notice: Subject to any disclaimer, the term of this patent is extended or adjusted under 35 U.S.C. 154(b) by 48 days.

(21) Appl. No.: 16/981,208

(22) PCT Filed: Mar. 25, 2019

(86) PCT No.: PCT/IB2019/052392
§ 371 (c)(1),
(2) Date: Sep. 15, 2020

(87) PCT Pub. No.: WO2019/186358
PCT Pub. Date: Oct. 3, 2019

(65) Prior Publication Data
US 2021/0251996 A1   Aug. 19, 2021

(30) Foreign Application Priority Data
Mar. 26, 2018 (EP) .................... 18164085

(51) Int. Cl.
*C07D 519/00* (2006.01)
*C07D 487/04* (2006.01)
*A61K 31/519* (2006.01)
*A61P 35/00* (2006.01)

(52) U.S. Cl.
CPC ............ *A61K 31/519* (2013.01); *A61P 35/00* (2018.01); *C07D 487/04* (2013.01); *C07D 519/00* (2013.01)

(58) Field of Classification Search
CPC ..... A61K 31/519; A61P 35/00; C07D 487/04; C07D 519/00
See application file for complete search history.

(56) References Cited

U.S. PATENT DOCUMENTS

2009/0118276 A1   5/2009   Gopalsamy et al.
2021/0002285 A1   1/2021   Arista et al.

FOREIGN PATENT DOCUMENTS

| WO | 2013008095 A1 | 1/2013 | |
| WO | 2013157021 A1 | 1/2013 | |
| WO | WO 2013/157021 | * 10/2013 | ........... C07D 473/00 |
| WO | 2015/197028 A1 | 12/2015 | |
| WO | 2016169989 A1 | 10/2016 | |
| WO | 2018033556 A1 | 2/2018 | |
| WO | 2019/186343 A1 | 10/2019 | |

OTHER PUBLICATIONS

Huang, et al.; A Chemoproteomic Approach to Query the Degradable Kinome Using a Multi-kinase Degrader; Cell Chemical Biology; Jan. 18, 2018; vol. 25; pp. 1-12.
Doig, Peter et al., "Rational design of inhibitors of the bacterial cell wall synthetic enzyme GlmU using virtual screening and lead-hopping," Bioorg. Med. Chem. 22 (2014) 6256-6269.
Donner, Pamela, et al., "High potency improvements to weak aryl uracil HCV polymerase inhibitor leads," Bioorganic & Medicinal Chemistry Letters 23 (2013) 4367-4369.
Randolph, John T., et al.," Synthesis and Biological Characterization of Aryl Uracil Inhibitors of Hepatitis C Virus NS5B Polymerase: Discovery of ABT-072, a trans-Stilbene Analog with Good Oral Bioavailability", Journal of Medicial Chemistry 2018, 61, 1153-1163.

* cited by examiner

*Primary Examiner* — Erich A Leeser

(57) ABSTRACT

The invention relates to compounds of the formula (I)

(I)

or a pharmaceutically acceptable salt thereof, wherein the substituents are as defined in the specification; to intermediates in the preparation of the compounds, to pharmaceutical compositions comprising the compounds and to use of the compounds in the treatment of disease.

13 Claims, No Drawings
Specification includes a Sequence Listing.

3-HYDROXY-N-(3-(7H-PYRROLO[2,3-D]PYRIMIDIN-4-YL)PHENYL)PYRROLIDINE-1-CARBOXAMIDE DERIVATIVES

This application is a national phase application, filed under 35 U.S.C. 371 of International Application No. PCT/IB2019/052392 filed Mar. 25, 2019, which claims the benefit to EP18164085.5 filed Mar. 26, 2018, the content of which is incorporated by reference herein in its entirety.

FIELD OF THE INVENTION

The present invention relates to 3-hydroxy-N-(3-(7H-pyrrolo[2,3-d]pyrimidin-4-yl)phenyl)pyrrolidine-1-carboxamide derivatives, to their preparation, to pharmaceutical compositions comprising them and to their use in the treatment of conditions, diseases and disorders mediated by Bruton's Tyrosine Kinase.

BACKGROUND OF THE INVENTION

Bruton's Tyrosine Kinase (BTK) is a critical node for B-cell receptor (BCR) signaling, and an important target in cancer. Many cancers and lymphomas express BTK and are dependent on BTK function, and BCR signaling in tumor infiltrating B-cells has also been implicated in the tumor-promoting microenvironment of solid cancers (J. A. Burger and A. Wiestner, *Nat Rev Cancer* 2018, 18, 148). Pharmacological blockade of BTK using inhibitors, particularly inhibitors which irreversibly bind BTK through cysteine-481 is an established strategy, BTK being a primary target of the molecule ibrutinib (J. A. Burger and J. J. Buggy, *Leukemia and Lymphoma* 2013, 54, 2385) which is indicated for the treatment of several cancers (C-S Lee et al., *J. Oncol. Pharm. Practice* 2016, 22, 92-104. V. Kaur & A. Swami, *Ann. Hematol.* 2017, 96, 1175), as well as for acalabrutinib which is indicated for the treatment of patients with mantle cell lymphoma who have received at least one prior treatment (Wang M et al, *Lancet* 2018, 391, Issue 10121, 659-667).

BTK also plays an essential role in autoimmune disease. BTK-deficient mice are protected in standard preclinical models for rheumatoid arthritis (L. Jansson and R. Holmdahl, *Clinical and experimental immunology* 1993, 94, 459; L. E. Nyhoff et al, *Arthritis Rheumatol.* 2016, 68, 1856), systemic lupus erythematosus (Steinberg, B. J. et al., *J. Clin. Invest.* 1982, 70, 587-597), as well as allergic disease and anaphylaxis (Hata, D. et al., *J. Exp. Med.* 1998, 187, 1235-1247), thus pharmacological blockade of BTK may be useful in the treatment of immune disorders.

In view of the above, modulators of BTK may be useful in the treatment of proliferative disorders such as cancer and of immune (e.g. autoimmune) disorders.

There remains a need for new medications to treat BTK-dependent diseases, particularly those resistant to or poorly responding to currently available medications.

A molecule designed to reduce or remove BTK protein by inducing its degradation (hereinafter referred to as a 'BTK degrader') may be efficacious in treating a range of BTK mediated diseases such as proliferative disorders (such as cancers) and immune disorders. Furthermore, BTK degraders may be effective in settings of resistance to irreversible BTK inhibitors (which bind covalently to BTK). Resistance may arise through, for example, mutation of cysteine-481 to serine (or other amino acid substitutions).

Potential indications for a BTK degrader include, but are not limited to, cancers of hematopoietic origin such as Hodgkin lymphoma, non-Hodgkin lymphoma, post-transplant lymphoproliferative disorder, hairy cell leukemia, histiocytic and dendritic neoplasms and B-cell neoplasms such as chronic lymphocytic leukemia (CLL), mantle cell lymphoma (MCL), small lymphocytic lymphoma (SLL), Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia.

Potential indications for a BTK degrader also include, but are not limited to, autoimmune disorders such as rheumatoid arthritis, systemic lupus erythematosus, allergic diseases, anaphylaxis and inflammatory conditions. Furthermore, potential indications for a BTK degrader include chronic graft-versus-host disease (cGvHD) and immunoglobulin Light Chain Amyloidosis (AL).

The principle of induced degradation of protein targets as a potential therapeutic approach has been described in, for example, C. M. Crews, 2018, *J. Med. Chem.,* 61(2), 403-404 and references cited therein. A BTK degrader molecule which incorporates an ibrutinib substructure as the BTK binding moiety is described in WO 2016/169989 at page 12 and incorporates an E3 ligase IAP binding moiety for recruitment of the target protein to the E3 ubiquitin ligase IAP for degradation. Two further BTK degrader molecules are described in Huang et. al., 2018, Cell Chemical Biology 25, 88-99 which incorporate two structurally different moieties as the BTK binding components. The molecules described in that publication incorporate an immunomodulatory imide drug (IMiD) moiety (pomalidomide) for recruitment of BTK to the E3 ligase complex comprising cereblon (CRBN) for ubiquitination and consequent degradation. Also described in Huang et al. is a molecule (TL12-186) based on a promiscuous kinase binder which degrades multiple targets including BTK, and is reported to also degrade certain non-kinase targets including the zinc finger DNA-binding protein IKZF1 (Ikaros). IKZF1 and the related protein IKZF3 (Aiolos) are known to be degraded by pomalidomide and lenalidomide (Krönke, J. et. al. 2014, *Science* 343, 301-305; Petzold et. al., *Nature* 2016, 532, 127-130; Bjorklund et. al., 2015, *Blood Cancer Journal,* 5, e354; Lu et. al., 2014, *Science,* 343, 305-309; Gandhi et. al., 2014, *Br. J. Haematol.* 164, 811-821).

SUMMARY OF THE INVENTION

The present invention provides compounds of formula (I), or a pharmaceutically acceptable salt thereof, as defined herein below. The compounds of formula (I) are BTK degraders and are therefore potentially useful in the treatment of conditions, diseases and disorders mediated by BTK.

In one aspect of the present invention, a compound of formula (I) is provided,

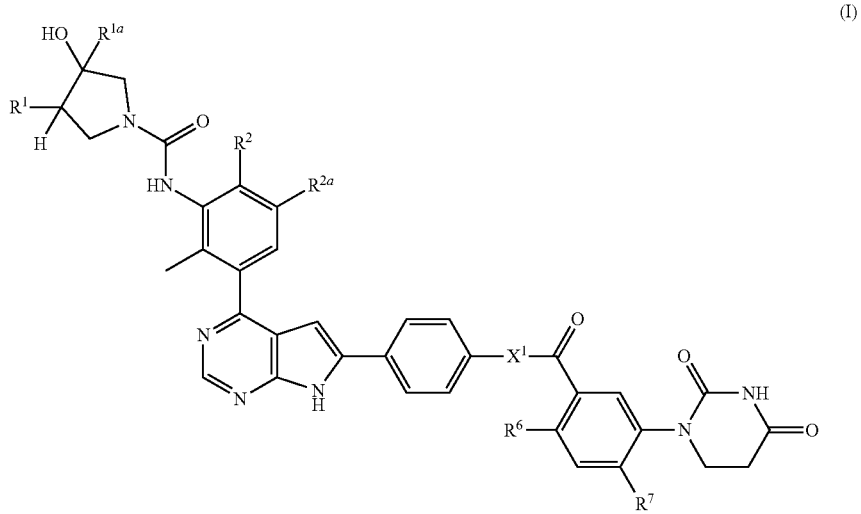

(I)

wherein:
$R^1$ is isobutyl;
$R^{1a}$ is H;
$R^2$ is H or F;
$R^{2a}$ is H or F;
$R^6$ is H or F;
$R^7$ is selected from H, F, Cl, —CH$_3$, —OCH$_3$, and —OCH$_2$CH$_3$;
$X^1$ is a group of formula (A) or (B):

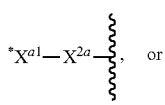   (A)

or

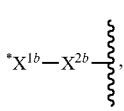   (B)

wherein,
*$X^{1a}$ is selected from *—(CH$_2$)$_{1-3}$—, and *—CH$_2$C(CH$_3$)$_2$—, wherein the * indicates the point of attachment of the $X^{1a}$ group to the phenyl ring in formula (I);
*$X^{1b}$ is selected from *—O—, *—OCH$_2$—, and *—CH$_2$O— wherein the * indicates the point of attachment of the $X^{1b}$ group to the phenyl ring in formula (I);
$X^{2a}$ is selected from formula (C), (D), (E), (F), and (G):

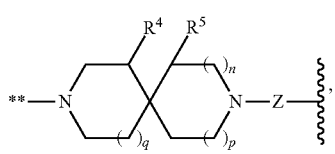   (C)

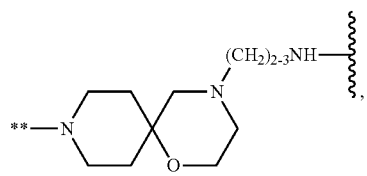   (D)

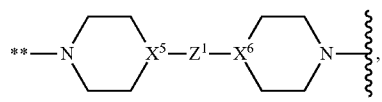   (E)

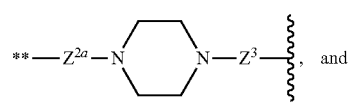   (F)

and

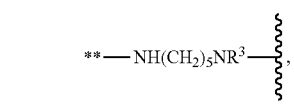   (G)

wherein ** indicates the point of attachment to $X^{1a}$;
$X^{2b}$ is selected from formula (E1) and (F1):

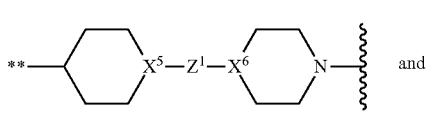   (E1)

and

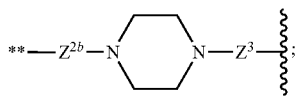

(F1)

wherein ** indicates the point of attachment to $X^{1b}$;
$X^5$ is CH or N;
$X^6$ is CH or N;
$R^3$ is H or —$CH_3$;
$R^4$ is H or —$CH_2OH$;
$R^5$ is H or —$CH_2OH$;
Z is absent or *—$(CH_2)_{2-3}NH$—, wherein * indicates the point of attachment of Z to the N atom in formula (C);
$Z^1$ is selected from *—O—, *—C(O)—, *—$(CH_2)_{1-3}$—, *—$(CH_2)_2O$—, and *—$CH_2CH(CH_2OH)O$—, wherein * indicates the point of attachment of $Z^1$ to $X^5$ in formula (E) and formula (E1);
$Z^{2a}$ is absent or —$NH(CH_2)_4$—**;
$Z^{2b}$ is —$(CH_2)_{3-4}NH(CH_2)_2$—**;
$Z^3$ is absent or —$(CH_2)_4NH$—, wherein $Z^{2a}$ and $Z^3$ are not both at the same time absent; and wherein  in each of $Z^{2a}$, $Z^{2b}$ and $Z^3$ indicates the point of attachment to the respective N atoms in formulae (F) and (F1);
q is 0 or 1; and
n and p are independently 0 or 1; and
wherein (i) when $Z^1$ in formula (E) or formula (E1) is *—O—, then $X^5$ and $X^6$ are not N, and (ii) when $Z^1$ in formula (E) or formula (E1) is *—$(CH_2)_2$—O— or *—$CH_2CH(CH_2OH)O$—, then $X^6$ is not N;
or a pharmaceutically acceptable salt thereof.

The present invention relates to novel 3-hydroxy-N-(3-(7H-pyrrolo[2,3-d]pyrimidin-4-yl)phenyl)pyrrolidine-1-carboxamide compounds of formula (I) which bring about degradation of Bruton's Tyrosine Kinase (BTK). These compounds are designed to induce degradation of BTK by recruiting BTK (including BTK mutants, especially those that confer resistance to BTK inhibitors, in particular irreversible BTK inhibitors such as ibrutinib), to an E3 ligase, thus prompting ubiquitination of BTK and its subsequent degradation by the proteasome. The compounds of the present invention comprise a novel BTK-binding domain moiety joined to a novel ligand which binds to the E3-ligase cereblon (CRBN).

Accordingly, compounds of the present invention may therefore be potentially useful in the treatment of a range of diseases and disorders, including proliferative and autoimmune diseases, particularly disorders and diseases mediated by BTK, including those in which resistance has arisen, e.g. through mutation of cysteine-481 to serine (or other amino acid substitutions). The compounds of the present invention further may show selectivity for BTK degradation over other proteins, in particular over other tyrosine kinase proteins and/or the (non-tyrosine kinase) IKZF family of proteins such as IKZF1 and/or IKZF3, which have been shown to be degraded by IMiDs e.g. thalidomide, lenalidomide and pomalidomide, and also by the protein degrading molecule TL12-186 mentioned supra. The compounds of the present invention further may exhibit kinase selectivity and/or selectivity over other off target proteins such as ion channels and G-protein coupled receptor (GPCRs).

The compounds of formula (I), including their pharmaceutically acceptable salts, are therefore considered suitable for use in the treatment of conditions, diseases, and disorders mediated by BTK, especially proliferative conditions, diseases and disorders such as cancer, in particular, hematopoietic cancers, including B-cell neoplasms such as chronic lymphocytic leukemia (CLL), mantle cell lymphoma (MCL), small lymphocytic lymphoma (SLL), Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia.

In another aspect, the invention provides compounds of formula (I), or pharmaceutically acceptable salts thereof, for use in methods of treating, preventing, or ameliorating a BTK-mediated condition, disease, or disorder.

In another aspect, the invention provides compositions which comprise (e.g. a therapeutically effective amount of) a compound of formula (I), or a pharmaceutically acceptable salt thereof, and one or more pharmaceutically acceptable carriers.

In another aspect, the invention provides a combination, comprising (e.g. a therapeutically effective amount of) a compound of formula (I), or a pharmaceutically acceptable salt thereof, and one or more therapeutically active agents.

DETAILED DESCRIPTION OF THE INVENTION

Various embodiments of the invention are described herein. It will be recognized that features specified in each embodiment may be combined with other specified features to provide further embodiments of the present invention. Various (enumerated) embodiments of the invention are also described herein.

The definition of the substituents applies to compounds of formulae (I), (I'), (I''), (I'''), (Ia), (Ib), and (Ic) as applicable.

The definition of the substituents applies to the end-products as well as to the corresponding intermediates.

The invention therefore provides a compound of formula (I)

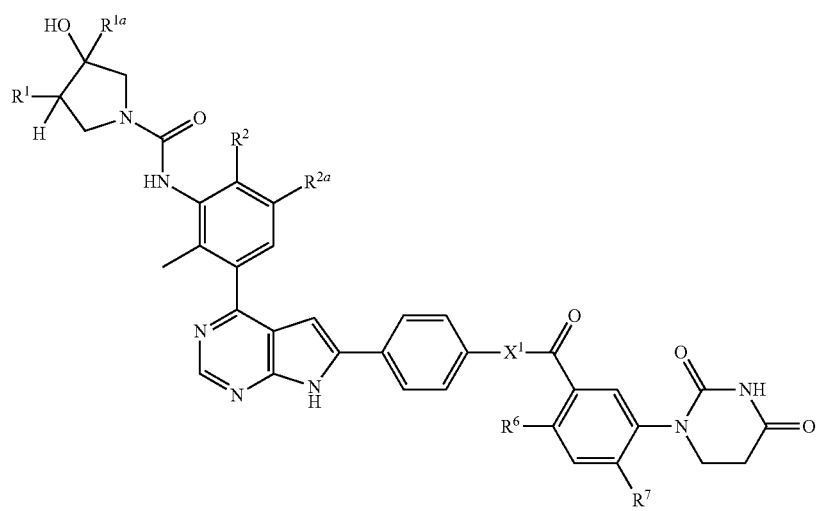

(I)

wherein:
R$^1$ is isobutyl;
R$^{1a}$ is H;
R$^2$ is H or F;
R$^{2a}$ is H or F;
R$^6$ is H or F;
R$^7$ is selected from H, F, Cl, —CH$_3$, —OCH$_3$, and —OCH$_2$CH$_3$;
X$^1$ is a group of formula (A) or (B):

*X$^{1a}$—X$^{2a}$—  (A)

or

*X$^{1b}$—X$^{2b}$—  (B)

wherein,
*X$^{1a}$ is selected from *—(CH$_2$)$_{1-3}$—, and *—CH$_2$C(CH$_3$)$_2$—, wherein the * indicates the point of attachment of the X$^{1a}$ group to the phenyl ring in formula (I);
*X$^{1b}$ is selected from *—O—, *—OCH$_2$—, and *—CH$_2$O— wherein the * indicates the point of attachment of the X$^{1b}$ group to the phenyl ring in formula (I);
X$^{2a}$ is selected from formula (C), (D), (E), (F), and (G):

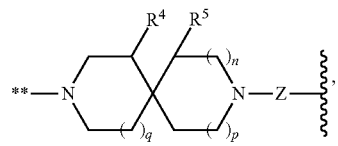

(C)

(D)

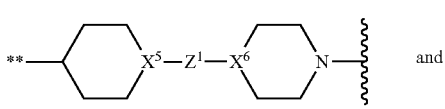

(E)

**—N⏜⏝X$^5$—Z$^1$—X$^6$⏜⏝N—, (F)

**—Z$^{2a}$—N⏜⏝N—Z$^3$—, and (G)

—NH(CH$_2$)$_5$NR$^3$—, wherein  indicates the point of attachment to X$^{1a}$;
X$^{2b}$ is selected from formula (E1) and (F1):

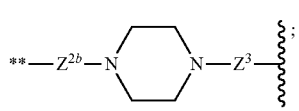

(E1)

and (F1)

**—Z$^{2b}$—N⏜⏝N—Z$^3$—;

wherein ** indicates the point of attachment to X$^{1b}$;
X$^5$ is CH or N;
X$^6$ is CH or N;
R$^3$ is H or —CH$_3$;

$R^4$ is H or —$CH_2OH$;
$R^5$ is H or —$CH_2OH$;
Z is absent or *—$(CH_2)_{2-3}NH$—, wherein * indicates the point of attachment of Z to the N atom in formula (C);
$Z^1$ is selected from *—O—, *—C(O)—, *—$(CH_2)_{1-3}$—, *—$(CH_2)_2O$—, and *—$CH_2CH(CH_2OH)O$—, wherein * indicates the point of attachment of $Z^1$ to $X^5$ in formula (E) and formula (E1);
$Z^{2a}$ is absent or —$NH(CH_2)_4$—**;
$Z^{2b}$ is —$(CH_2)_{3-4}NH(CH_2)_2$—**;
$Z^3$ is absent or —$(CH_2)_4NH$—, wherein $Z^{2a}$ and $Z^3$ are not both at the same time absent; and wherein  in each of $Z^{2a}$, $Z^{2b}$ and $Z^3$ indicates the point of attachment to the respective N atoms in formulae (F) and (F1);
q is 0 or 1; and
n and p are independently 0 or 1; and
wherein (i) when $Z^1$ in formula (E) or formula (E1) is *—O—, then $X^5$ and $X^6$ are not N, and (ii) when $Z^1$ in formula (E) or formula (E1) is *—$(CH_2)_2$—O— or *—$CH_2CH(CH_2OH)O$—, then $X^6$ is not N;
or a pharmaceutically acceptable salt thereof.

Compounds of formula (I) may be represented by formula (Ia):

well as all stereoisomers (including diastereoisomers and enantiomers), rotamers, tautomers (including formulae (I') and (I")) and isotopically labeled compounds (including deuterium substitutions e.g. compounds of formula (I''')), as well as inherently formed moieties.

Unless indicated otherwise, the expressions used in this invention have the following meanings:

As used herein, the term —$(CH_2)_{1-3}$— refers to a (in particular) straight or branched hydrocarbon chain bi-radical consisting solely of carbon and hydrogen atoms, containing no unsaturation, having from one to three carbon atoms, and which is attached to the rest of the molecule at each end by a single bond. The end which is attached to the rest of the molecule at a particular location for such groups may be specified by the indicator symbols * or **. Groups incorporating analogous terms such as —$(CH_2)_2O$—, —$(CH_2)_{2-3}NH$—, —$(CH_2)_{3-4}NH(CH_2)_2$—, and —$(CH_2)_4NH$— are to be construed accordingly.

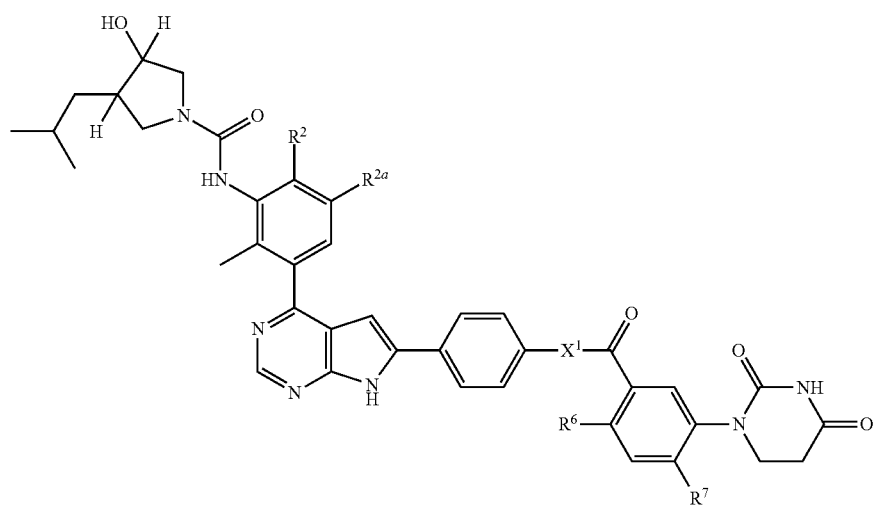

(Ia)

wherein, $R^2$, $R^{2a}$, $X^1$, $R^6$ and $R^7$ are defined as for compounds of formula (I).

Unless specified otherwise, the term "compounds of the present invention" or "compound of the present invention" refers to compounds of formula (I), subformulae (Ia), (Ib) and (Ic) and exemplified compounds, and salts thereof, as

ENUMERATED EMBODIMENTS

Embodiment 1. A compound of the formula (I) or (Ia), or a pharmaceutically acceptable salt thereof, as described above.

Embodiment 2. A compound according to embodiment 1, of formula (1b):

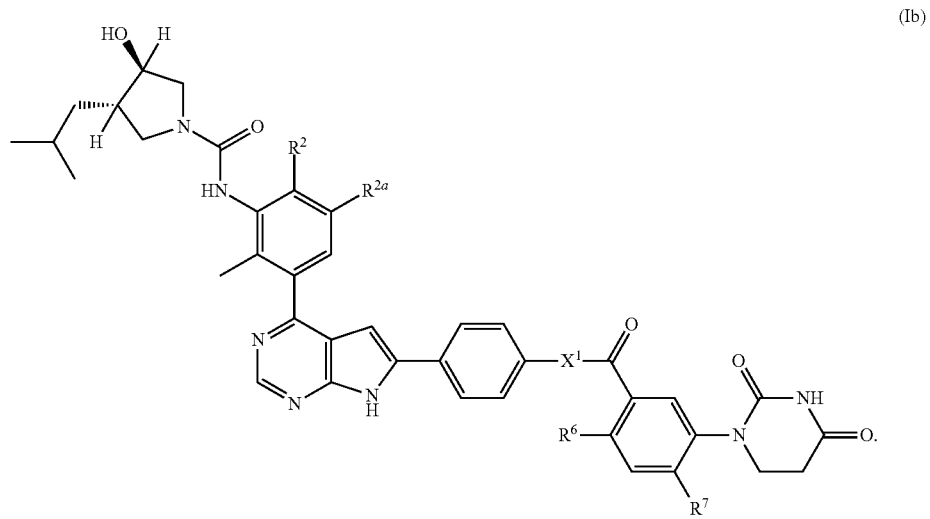

(Ib)

Embodiment 3. A compound according to embodiment 1, of formula (Ic):

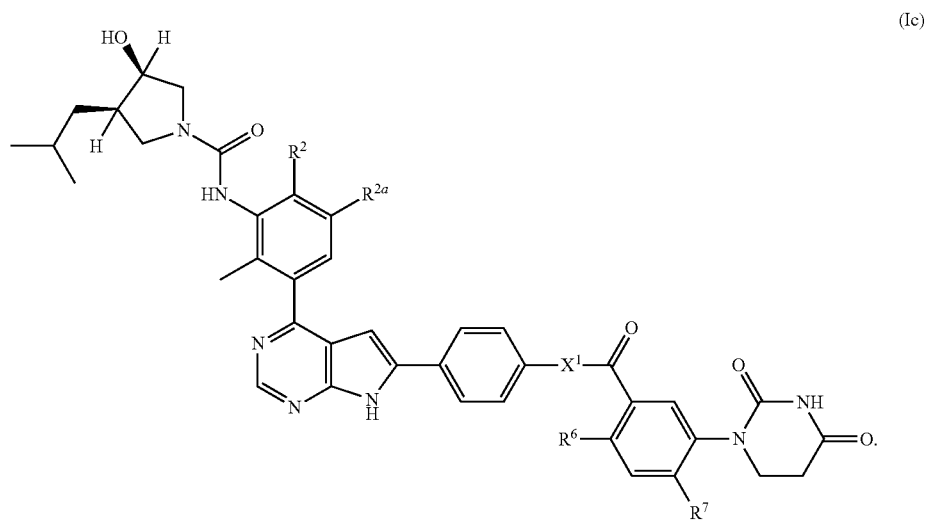

(Ic)

Embodiment 4. A compound, or a pharmaceutically acceptable salt thereof, according to any one of embodiments 1 to 3, wherein $R^2$ is H and $R^{2a}$ is F.

Embodiment 5. A compound, or a pharmaceutically acceptable salt thereof, according to any one of embodiments 1 to 3, wherein $R^2$ is F and $R^{2a}$ is H.

Embodiment 6. A compound, or a pharmaceutically acceptable salt thereof, according to any one of embodiments 1 to 5, wherein $R^6$ is H.

Embodiment 7. A compound, or a pharmaceutically acceptable salt thereof, according to any one of embodiments 1 to 6, wherein $R^7$ is selected from —$OCH_3$ and —$OCH_2CH_3$.

Embodiment 8. A compound, or a pharmaceutically acceptable salt thereof, according to embodiment 7, wherein $R^7$ is —$OCH_3$.

Embodiment 9. A compound, or a pharmaceutically acceptable salt thereof, according to any one of embodiments 1 to 8, wherein *$X^{1a}$ is *—$(CH_2)_{1-3}$—.

Embodiment 10. A compound, or a pharmaceutically acceptable salt thereof, according to embodiment 9, wherein *$X^{1a}$ is selected from *—$CH_2$— and *—$(CH_2)_2$—.

Embodiment 11. A compound, or a pharmaceutically acceptable salt thereof, according to any one of embodiments 1 to 10, wherein $X^{2a}$ is selected from formula (C) and (E):

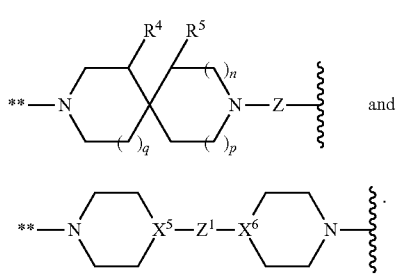

(C)

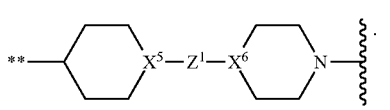

(E)

Embodiment 12. A compound, or a pharmaceutically acceptable salt thereof, according to any one of embodiments 1 to 8, wherein $*X^{1b}$ is selected from $*-O-$, $*-OCH_2-$, and $*-CH_2O-$.

Embodiment 13. A compound, or a pharmaceutically acceptable salt thereof, according to embodiment 12, wherein $*X^{1b}$ is $*-O-$.

Embodiment 14. A compound, or a pharmaceutically acceptable salt thereof, according to any one of embodiments 1 to 8 or embodiment 12 or embodiment 13, wherein $X^{2b}$ is formula (E1):

(E1)

Embodiment 15. A compound, or a pharmaceutically acceptable salt thereof, according to any one of embodiments 1 to 14, wherein $R^4$ is H.

Embodiment 16. A compound, or a pharmaceutically acceptable salt thereof, according to any one of embodiments 1 to 15, wherein $R^5$ is H.

Embodiment 17. A compound, or a pharmaceutically acceptable salt thereof, according to any one of embodiments 1 to 16, wherein q is 1.

Embodiment 18. A compound, or a pharmaceutically acceptable salt thereof, according to any one of embodiments 1 to 17, wherein n and p are both 1.

Embodiment 19. A compound, or a pharmaceutically acceptable salt thereof, according to any one of embodiments 1 to 18, wherein Z is absent.

Embodiment 20. A compound, or a pharmaceutically acceptable salt thereof, according to any one of embodiments 1 to 19, wherein $X^6$ is CH.

Embodiment 21. A compound of formula (I), or a pharmaceutically acceptable salt thereof, according to any one of embodiments 1 to 20, wherein $Z^1$ is selected from $*-O-$, $*-(CH_2)_{1-3}-$, and $*-(CH_2)_2O-$.

Embodiment 22. A compound, or a pharmaceutically acceptable salt thereof, according to embodiment 21, wherein $Z^1$ is selected from $*-O-$, $*-CH_2-$, $*-(CH_2)_2-$, and $*-(CH_2)_2O-$.

Embodiment 23. A compound, or a pharmaceutically acceptable salt thereof, according to embodiment 22, wherein $Z^1$ is selected from $*-O-$, $*-CH_2-$, and $*-(CH_2)_2O-$.

Embodiment 24. A compound, or a pharmaceutically acceptable salt thereof, according to any one of embodiments 1 to 8, wherein, $X^1$ is selected from:

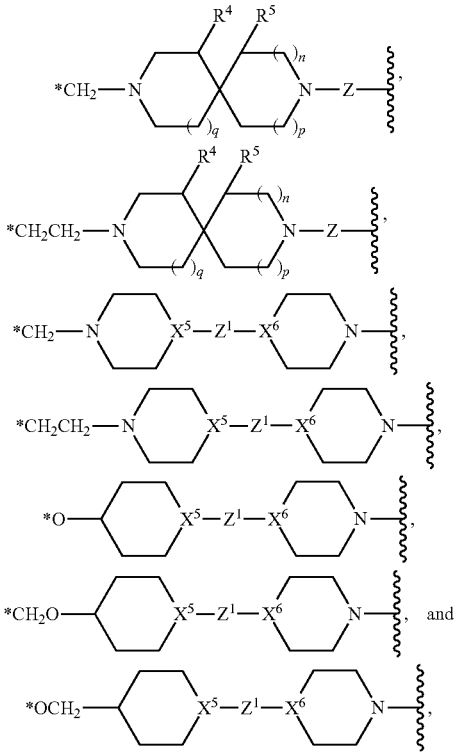

wherein * indicates the point of attachment to the phenyl ring in formula (I), formula (Ia), formula (Ib) or formula (Ic);

or a pharmaceutically acceptable salt thereof.

Embodiment 25. A compound, or a pharmaceutically acceptable salt thereof, according to embodiment 24, wherein, $X^1$ is selected from:

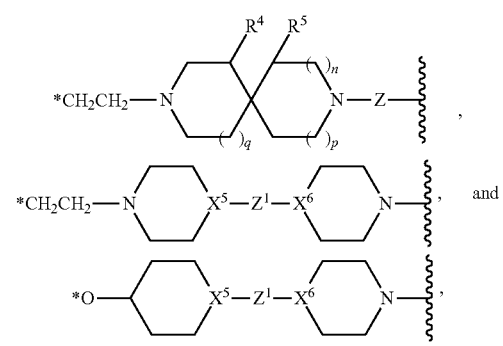

wherein * indicates the atom which is attached to the phenyl ring in formula (I), formula (Ia), formula (Ib) or formula (Ic).

Embodiment 26. A compound, or a pharmaceutically acceptable salt thereof, according to embodiment 24 or embodiment 25, wherein $R^4$ is H.

Embodiment 27. A compound, or a pharmaceutically acceptable salt thereof, according to any one of embodiments 24 to 26, wherein $R^5$ is H.

Embodiment 28. A compound, or a pharmaceutically acceptable salt thereof, according to any one of embodiments 24 to 27, wherein n, p and q are each 1.

Embodiment 29. A compound, or a pharmaceutically acceptable salt thereof, according to any one of embodiments 24 to 28, wherein Z is absent.

Embodiment 30. A compound, or a pharmaceutically acceptable salt thereof, according to any one of embodiments 24 to 29, wherein $X^6$ is CH.

Embodiment 31. A compound, or a pharmaceutically acceptable salt thereof, according to any one of embodiments 24 to 30, wherein $Z^1$ is selected from *—O—, *—$(CH_2)_{1-3}$—, and *—$(CH_2)_2O$—.

Embodiment 32. A compound, or a pharmaceutically acceptable salt thereof, according to embodiment 31, wherein $Z^1$ is selected from *—O—, *—$CH_2$—, *—$(CH_2)_2$—, and *—$(CH_2)_2O$—.

Embodiment 33. A compound, or a pharmaceutically acceptable salt thereof, according to embodiment 32, wherein $Z^1$ is selected from *—O—, *—$CH_2$—, and *—$(CH_2)_2O$—.

Embodiment 34. A compound, or a pharmaceutically acceptable salt thereof, according to any one of embodiments 1 to 8, wherein,
$X^1$ is selected from:

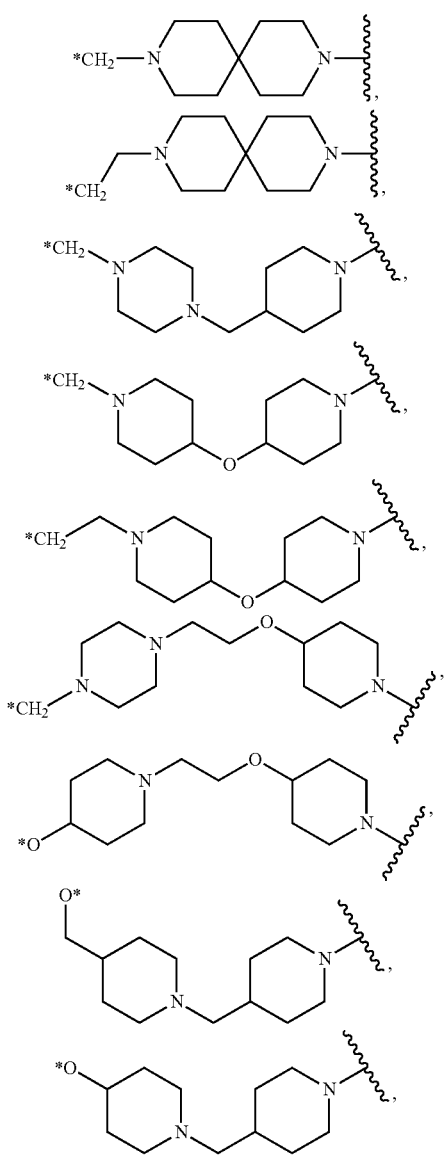

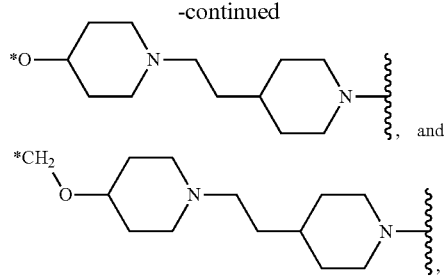

wherein * indicates the atom which is attached to the phenyl ring in formula (I), formula (Ia), formula (Ib) or formula (Ic).

Embodiment 35. A compound, or a pharmaceutically acceptable salt thereof, according to embodiment 34, wherein, $X^1$ is selected from:

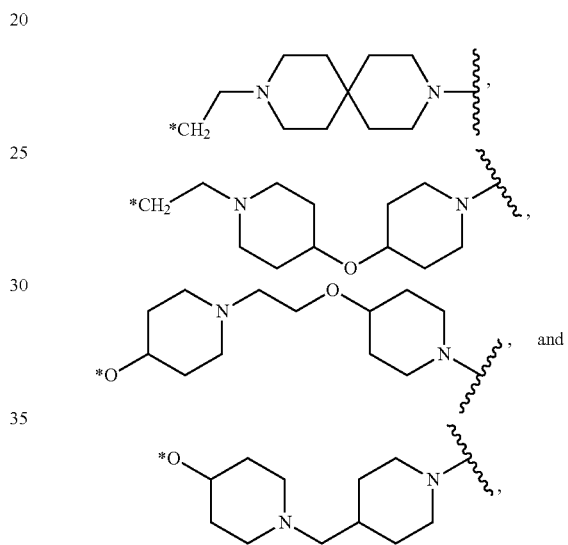

wherein * indicates the atom which is attached to the phenyl ring in Formula (I) or (Ia).

Embodiment 36. A compound of formula (I), wherein the compound is:
(3S,4R)—N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((4-(2-((1-(3-(2,4-dioxotetrahydropyrimidin-1(2H)-yl)-4-methoxybenzoyl)piperidin-4-yl)oxy)ethyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-(2-(1-(3-(2,4-dioxotetrahydropyrimidin-1 (2H)-yl)-4-methoxybenzoyl)piperidin-4-yl)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, (cis-rac)-N-(3-(6-(4-(((1-(2-(1-(3-(2,4-dioxotetrahydropyrimidin-1 (2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide, trans-rac-N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((9-(3-(2,4-dioxotetrahydropyrimidin-1 (2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (cis-rac-N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3S,4R)—N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(4-((1-(3-(2,4-dioxotetrahydropyrimidin-1 (2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)methoxy)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1 (2H)-yl)-4-ethoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3S,4R)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, (3S,4R)—N-(3-(6-(4-(((1-(2-(1-(3-(2,4-dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(((1-(2-(1-(3-(2,4-dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide, or (cis-rac)-N-(3-(6-(4-((9-(3-(2,4-dioxotetrahydropyrimidin-1 (2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide or a pharmaceutically acceptable salt thereof.

Embodiment 37. A compound of formula (I), wherein the compound is (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

Embodiment 38. The compound (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

Embodiment 39. The compound (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

Embodiment 40. The compound (3R,4S)—N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

Embodiment 41. The compound (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

Embodiment 42. The compound (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, or a pharmaceutically acceptable salt thereof.

Embodiment 43. The compound (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

Embodiment 44. The compound (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diastereomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of formulae (I), (Ia), (Ib), or (Ic) may occur in various tautomeric forms. All tautomeric forms of the compounds of formulae (I), (Ia), (Ib), or (Ic) are embraced by the invention. For example, compounds of formula (I), may exist in tautomeric form according to formulae (I') and (I''), thus:

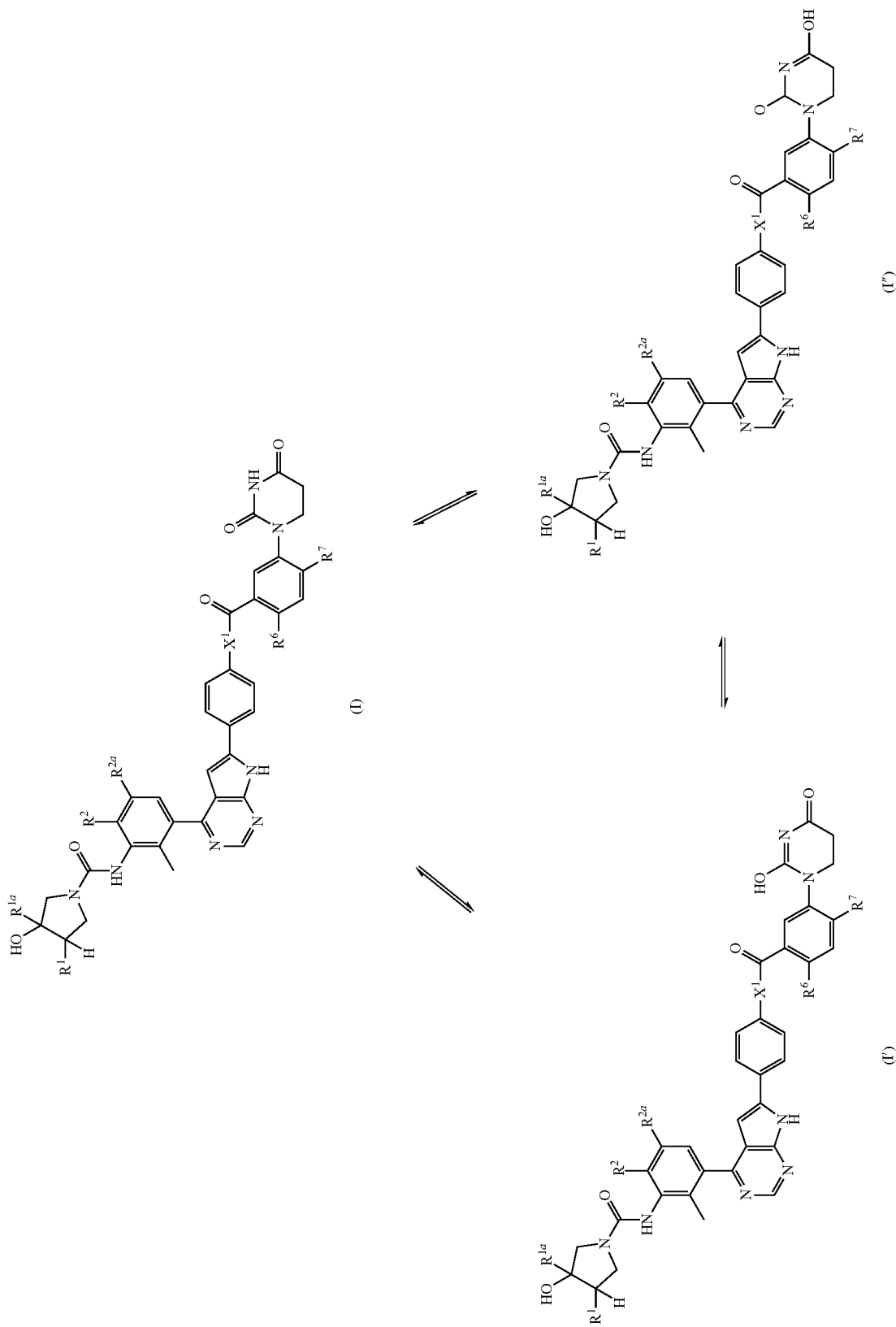

in which $R^1$, $R^{1a}$, $R^2$, $R^{2a}$, $X^1$, $R^6$, and $R^7$ are as defined according to formulae (I), (Ia), (Ib), or (Ic).

As used herein, the terms "salt" or "salts" refers to an acid addition or base addition salt of a compound of the invention. "Salts" include in particular "pharmaceutically acceptable salts".

The term "pharmaceutically acceptable salts" refers to salts that retain the biological effectiveness and properties of the compounds of this invention and, which typically are not biologically or otherwise undesirable. The compounds of the invention may be capable of forming acid and/or base salts by virtue of the presence of amino and/or carboxyl groups or groups similar thereto.

The pharmaceutically acceptable salts of the invention can be synthesized from a basic or acidic moiety, by conventional chemical methods. Generally, such salts can be prepared by reacting free acid forms of these compounds with a stoichiometric amount of the appropriate base or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, acetonitrile or tetrahydrofuran is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the invention may also form internal salts, e.g., zwitterionic molecules.

The compounds of the invention are particularly suited for forming acid addition salts by virtue that the compounds contain at least one basic group such as an amino group.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate orxinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

In another aspect of the invention a compound of formula (I''') is provided:

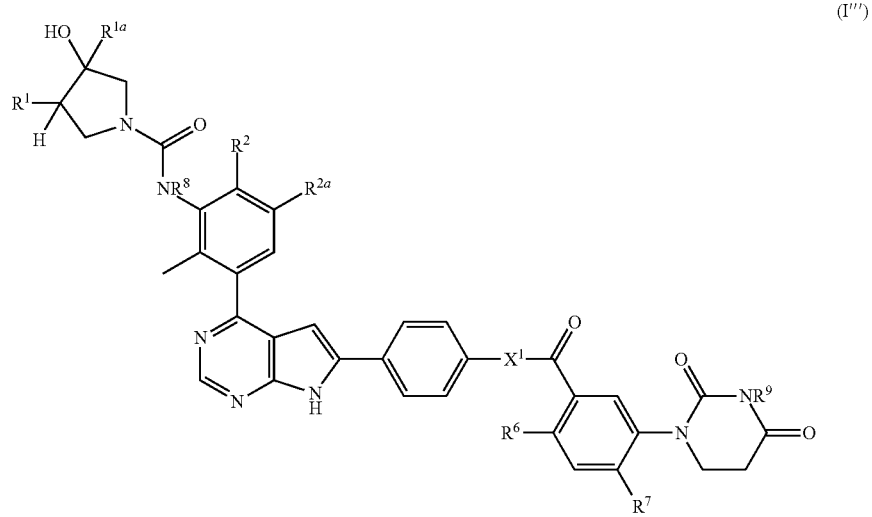

wherein $R^1$, $R^{1a}$, $R^2$, $R^{2a}$, $R^6$ are as defined as for formula (I) or (Ia), $R^7$ is —$C(R^{10})_3$, —$OC(R^{10})_3$ or —$OC(R^{10})_2C(R^{10})_3$, and $X^1$ is selected from:

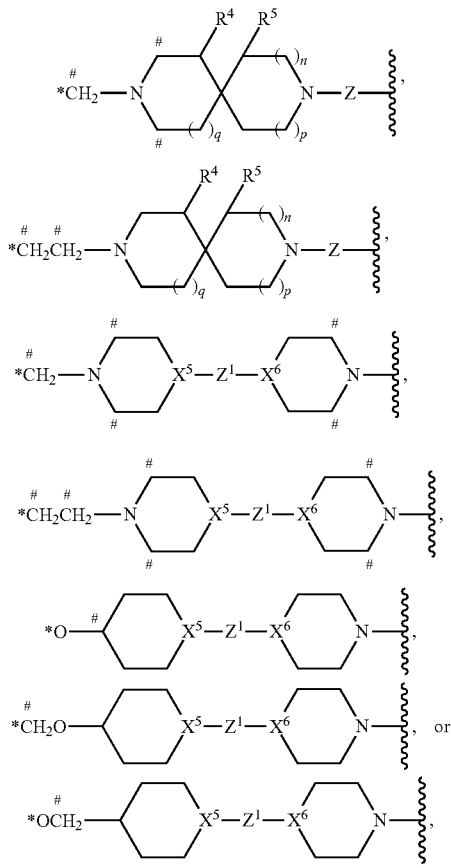

wherein each $R^8$, $R^9$ and $R^{10}$ is independently at each occurrence selected from H or deuterium and the symbol # indicates the positions shown to be substituted by H which may independently at each occurrence be substituted by H or deuterium.

Incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of formulae (I) and (Ia). The concentration of deuterium may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, and $^{125}$I respectively. Accordingly, it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagent in place of the non-labeled reagent previously employed.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington's Pharmaceutical Sciences, 18th Ed. Mack Printing Company, 1990, pp. 1289-1329).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound of the present invention that, when administered to a subject, is effective to (1) at least partially alleviate, prevent and/or ameliorate a condition, or a disorder or a disease (i) mediated by BTK, or (ii) associated with BTK activity, or (iii) characterized by activity (normal or abnormal) of BTK; or (2) reduce or inhibit the activity of BTK; or (3) reduce or inhibit the expression of BTK. These effects may be achieved for example by reducing the amount of BTK by degrading BTK. In another embodiment, the term "a therapeutically effective amount" refers to the amount of the compound of the present invention that, when administered to a cell, or a tissue, or a non-cellular biological material, or a medium, is effective to at least partially reduce or inhibit the activity of BTK; or at least partially reduce or inhibit the expression of BTK, for example by degrading BTK.

As used herein, the term "subject" refers to primates (e.g., humans, male or female), dogs, rabbits, guinea pigs, pigs, rats and mice. In certain embodiments, the subject is a primate. In an embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the terms "degrades", "degrading", or "degradation" refers to the partial or full breakdown of a target protein, e.g. BTK, by the cellular proteasome system to an extent which reduces or eliminates the biological activity (especially aberrant activity) of BTK. Degradation may be achieved through mediation of an E3 ligase, in particular, E3-ligase complexes comprising the protein Cereblon. As used herein, the term "modulation of BTK activity" or "modulating BTK activity" means the alteration of, especially reduction, suppression or elimination, of BTK activity. This may be achieved by degrading BTK. The Amount of BTK degraded can be measured by comparing the amount of BTK remaining after treatment with a compound of the invention as compared to the initial amount or level of BTK present as measured prior to treatement with a compound of the invention. In an embodiment, at least about 30% of BTK is degraded compared to initial levels. In an embodiment, at least about 40% of BTK is degraded compared to initial levels. In an embodiment, at least about 50% of BTK is degraded compared to initial levels. In an embodiment, at least about 60% of BTK is degraded compared to initial levels. In an embodiment, at least about 70% of BTK is degraded compared to initial levels. In an embodiment, at least about 80% of BTK is degraded compared to initial levels. In an embodiment, at least about 90% of BTK is degraded compared to initial levels. In an embodiment, at least about 95% of BTK is degraded compared to initial levels. In an embodiment, over 95% of BTK is degraded compared to initial levels. In an embodiment, at least about 99% of BTK is degraded compared to initial levels.

In an embodiment, the BTK is degraded in an amount of from about 30% to about 99% compared to initial levels. In an embodiment, the BTK is degraded in an amount of from about 40% to about 99% compared to initial levels. In an embodiment, the BTK is degraded in an amount of from about 50% to about 99% compared to initial levels. In an embodiment, the BTK is degraded in an amount of from about 60% to about 99% compared to initial levels. In an embodiment, the BTK is degraded in an amount of from about 70% to about 99% compared to initial levels. In an embodiment, the BTK is degraded in an amount of from about 80% to about 99% compared to initial levels. In an embodiment, the BTK is degraded in an amount of from about 90% to about 99% compared to initial levels. In an embodiment, the BTK is degraded in an amount of from about 95% to about 99% compared to initial levels. In an embodiment, the BTK is degraded in an amount of from about 90% to about 95% compared to initial levels.

As used herein, the term "selectivity for BTK" means, for example, a compound of the invention degrades BTK in preference to, or to a greater extent than, another protein or proteins.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder As used herein, a subject is "in need of" a treatment if such subject would benefit biologically, medically, or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as" or "for example") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)-, or (Re-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

The compounds of the present application can be prepared in a number of ways well known to those skilled in the art of organic synthesis using commercially available starting materials, compounds known in the literature, or from readily prepared intermediates, by employing standard synthetic methods and procedures either known to those skilled in the art, or which will be apparent to the skilled chemist in light of the teachings herein. For all examples, a potential alternative orthogonal protecting group strategy could be applied, following standard text book knowledge as described for example in *Protective Groups in Organic Synthesis*, 3rd edition, John Wiley & Sons: New York, 1999 or *Protecting Groups*, 3rd edition, Thieme, Stuttgart, 2004. Those skilled in the art will recognize if a stereocentre exists in the compounds disclosed herein.

Compounds of the invention can be synthesized according to the following schemes. The compounds may be assembled in various ways, building up the final molecules using related reaction procedures in a modular fashion which allows for different reaction orders.

Several reaction types are of particular utility for making these compounds. All compounds of the invention contain an amide functionality which is generally formed by an amide coupling reaction between an amine and a carboxylic acid, using a coupling reagent (e.g. HATU or HBTU) and a base (e.g. DIPEA or NMM) in a solvent such as DMF or DMA. Alternatively the carboxylic acid may be first converted to its pentafluorophenol ester. This allows subsequent facile reaction with an amine in the presence of a base such as TEA in a solvent such as DMF to form the amide. Compounds of the invention containing a carbon-nitrogen bond can often be made using a reductive amination reaction starting from an amine and an aldehyde or ketone. Reaction occurs using conditions such as $NaBH_3CN$, $ZnCl_2$, and TEA in a solvent mixture such as THF and MeOH. Carbon-nitrogen bonds can also be formed by nucleophilic substitution reactions of an amine with a suitable reacting partner containing a leaving group, such as an alkyl halide or an alkyl mesylate generally in the presence of a base (such as TEA) in a solvent such as THF. Compounds containing an ether can also be made by nucleophilic substitution reactions, in this case by reacting an alcohol with a suitable partner containing a leaving group, such as a benzyl halide in the presence of a base (such as TEA) in a solvent such as THF. Another generally useful method to make compounds of the invention containing ethers is the Mitsunobu reaction. In this reaction a phenol and another alcohol are reacted together in the presence of a phosphine (such as triphenylphosphine) and an azodicarboxylate ester (such as diethylazodicarboxylate or diisopropylazodicarboxylate) in a solvent such as THF. Another reaction of high utility for the synthesis of compounds of the invention is the palladium (Pd) catalysed cross coupling reaction to link together two aromatic groups. Of particular utility is the Suzuki coupling reaction between an aromatic halide and an aromatic boronic acid or ester using a catalyst (e.g. $PdCl_2(dppf)$) and a base (e.g. $Na_2CO_3$ or $Cs_2CO_3$) in a solvent mixture such as dioxane/water.

Specifically, compounds of formula (I) may be made as shown in Scheme 1 wherein $R^1$, $R^{1a}$, $R^2$, $R^{2a}$, $X^1$, $R^6$, $R^7$, $X^{1a}$, and $X^{2a}$ are as previously defined. M is defined as H or as a protecting group such as —$SO_2Ph$ or -SEM and LG is defined as a leaving group such as mesylate (OMs).

Thus a compound of formula (I) can be made from a compound of formula (II) and a compound of formula (III) by an amide coupling formation between an amine and a carboxylic acid, using a coupling reagent (e.g. HATU) and a base (e.g. DIPEA or NMM) in a solvent such as DMF or DMA. Alternatively, a compound of formula (I) can be made by an amide coupling between an amine of formula (II) and the pentafluorophenyl ester of the acid (IIIa) by treating with TEA in a solvent such as DMF. A compound of formula (II) can be made from a compound of formula (IV). For compounds of formula (IV) where M is a protecting group such as —$SO_2Ph$, deprotection may be accomplished using a base (e.g. NaOH) in a solvent mixture (e.g. DMSO, THF and water); where M is a -SEM protecting group, deprotection using an acid such as TFA in a solvent such as DCM may be utilized and possibly combined with the subsequent amine deprotection step. Further deprotection of the t-butoxycarbonyl (Boc) group using an acid, (e.g. TFA) in a solvent such as DCM provides a compound of formula (II).

Scheme 1

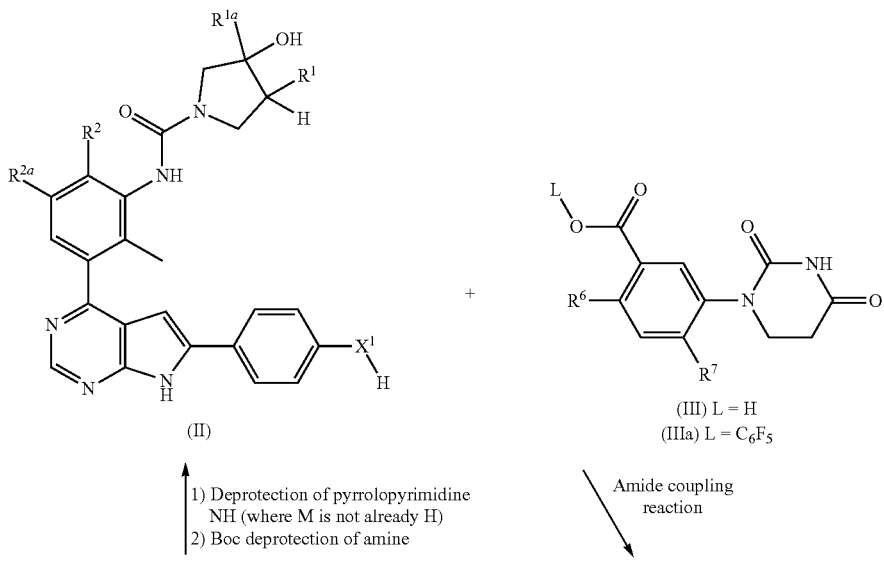

-continued

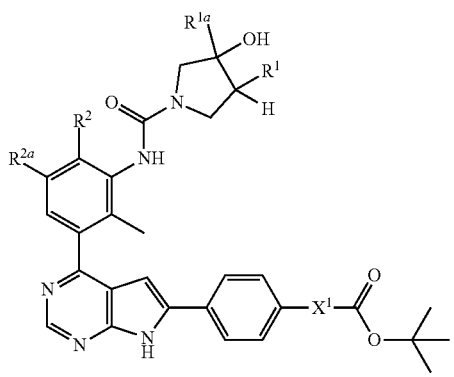

(IV)

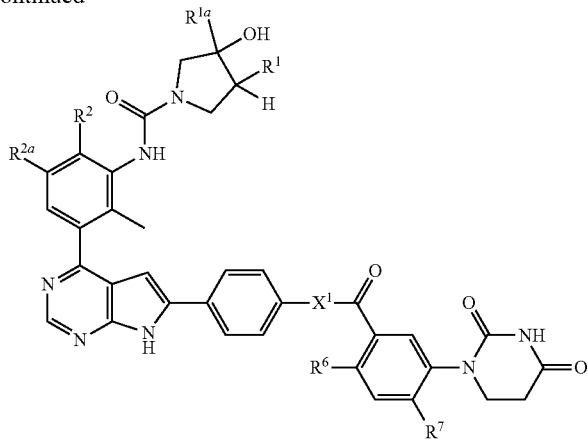

(I)

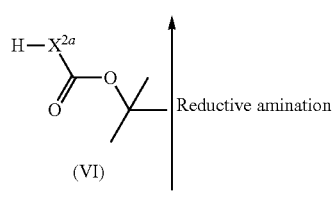

(VI) Reductive amination

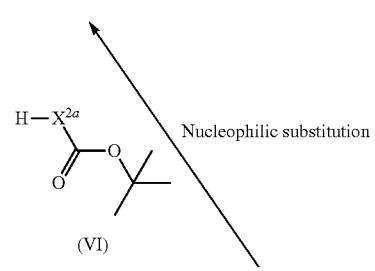

(VI) Nucleophilic substitution

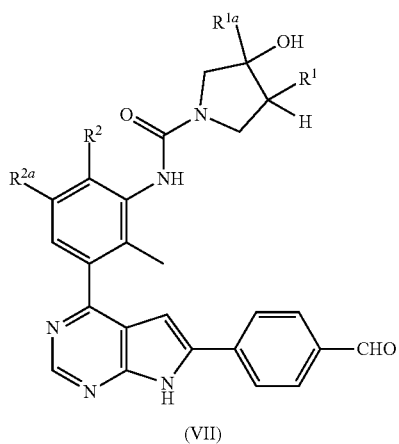

(VII)

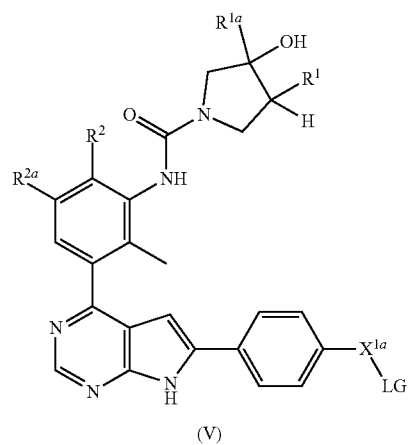

(V)

A compound of formula (IV) may be provided by reaction of a compound of formula (V) with a compound of formula (VI), for example in a nucleophilic substitution reaction, using a base (e.g. $K_2OO_3$) in a solvent mixture (e.g. DMF and AON). A compound of formula (IV) may alternatively be provided by reaction of a compound of formula (VII) with a compound of formula (VI), for example in a reductive amination reaction, under conditions using $NaBH_3CN$, $ZnCl_2$, and TEA in a solvent mixture such as THF and MeOH.

Compounds of formula (V) can be made according to Scheme 2 wherein $R^1$, $R^{1a}$, $R^2$, $R^{2a}$, $X^{1a}$, M and LG are as previously defined. The group —$B(OR^x)_2$ defines a boronic acid or boronic ester functionality (including cyclic boronates e.g. boron pinacol esters). Thus, Pd-catalysed coupling, such as a Suzuki reaction between a compound of formula (VIII) and a compound of formula (IX) using a catalyst (e.g. $PdCl_2(dppf)$) and a base (e.g. $Cs_2CO_3$) in a solvent mixture (e.g. dioxane/water) followed in a second step by conversion of the alcohol function connected to $X^{1a}$ into a leaving group LG, for example by mesylation using $Ms_2O$ and TEA in a solvent such as THF provides compounds of formula (V). Compounds of formula (VIII) can be made by Pd-catalysed coupling, such as a Suzuki reaction between a compound of formula (X) and a compound of formula (XI) using a catalyst (e.g. $PdCl_2(dppf)$) and a base (e.g. $Cs_2CO_3$) in a solvent mixture (e.g. dioxane/water).

Scheme 2

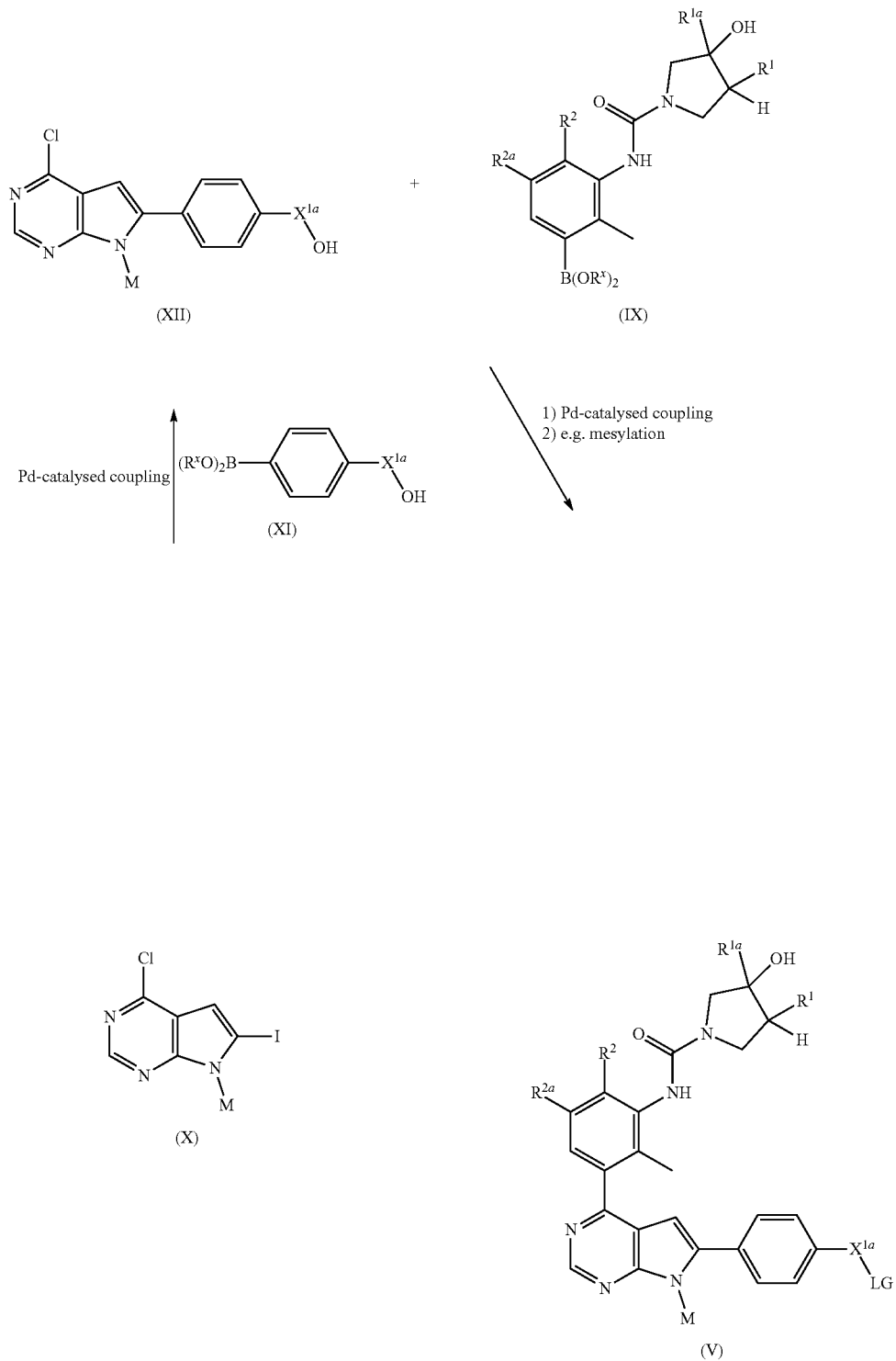

By analogy, compounds of formula (VII) can be made according to Scheme 3 wherein $R^1$, $R^{1a}$, $R^2$, $R^{2a}$, M, LG and —B(OR$^x$)$_2$ are as previously defined.

Thus, Pd-catalysed coupling, such as a Suzuki reaction between a compound of formula (XII) and a compound of formula (IX) using a catalyst (e.g. PdCl$_2$(dppf)) and a base (e.g. Cs$_2$CO$_3$) in a solvent mixture (e.g. dioxane/water) provides compounds of formula (VII). Compounds of formula (XII) can also be made by Pd-catalysed coupling, such as a Suzuki reaction between a compound of formula (X) and a compound of formula (XIII) using a catalyst (e.g. PdCl$_2$(dppf)) and a base (e.g. Cs$_2$CO$_3$) in a solvent mixture (e.g. dioxane/water).

Scheme 3

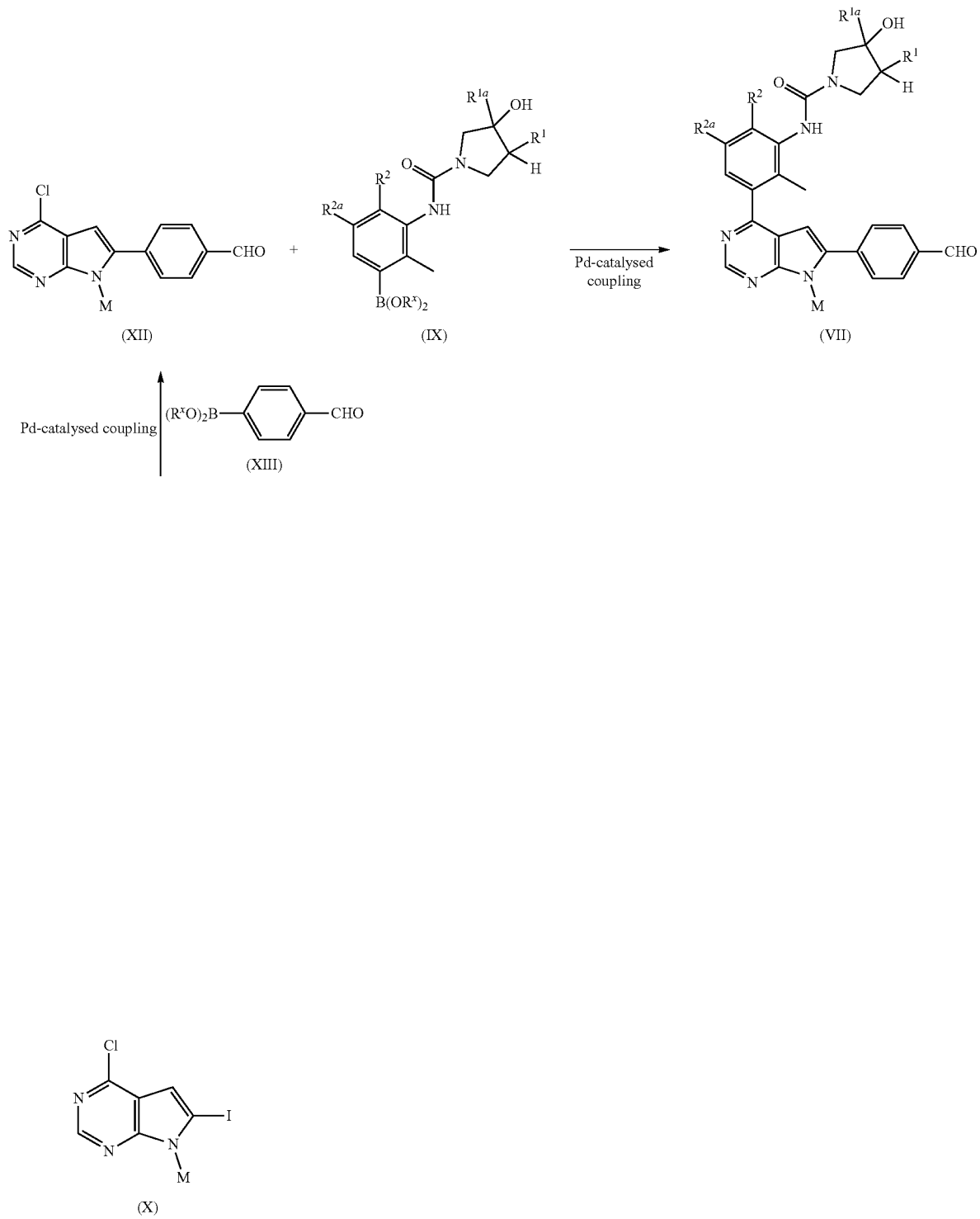

Compounds of formula (II) can also be made according to Scheme 4. Thus, reductive amination between compounds of formula (XIV) and (XV) for example when M is H, using conditions such as NaBH$_3$CN, ZnCl$_2$, and TEA in a solvent mixture such as THF and MeOH followed by deprotection of the amine with an acid (e.g. TFA) in a solvent such as DCM gives a compound of formula (II). Compounds of formula (XIV) are made by a similar sequence starting from compounds of formula (VII), which can undergo reductive amination with N-(t-butoxycarbonyl)piperazine using conditions such as NaBH$_3$CN, ZnCl$_2$, and TEA in a solvent mixture such as THF and MeOH followed by deprotection of the amine with an acid (e.g. TFA) in a solvent such as DCM to provide (XIV).

Scheme 4

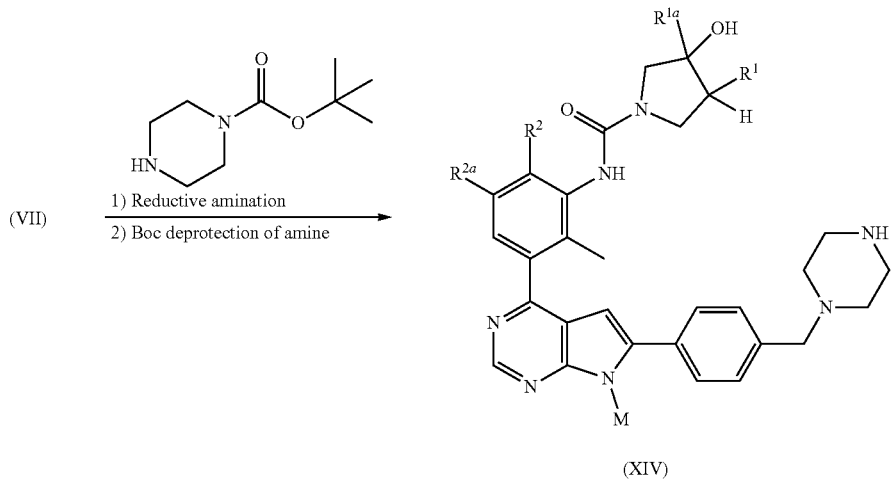

(VII)

1) Reductive amination
2) Boc deprotection of amine (XIV)

1) Reductive amination
2) Boc deprotection of amine (XV)

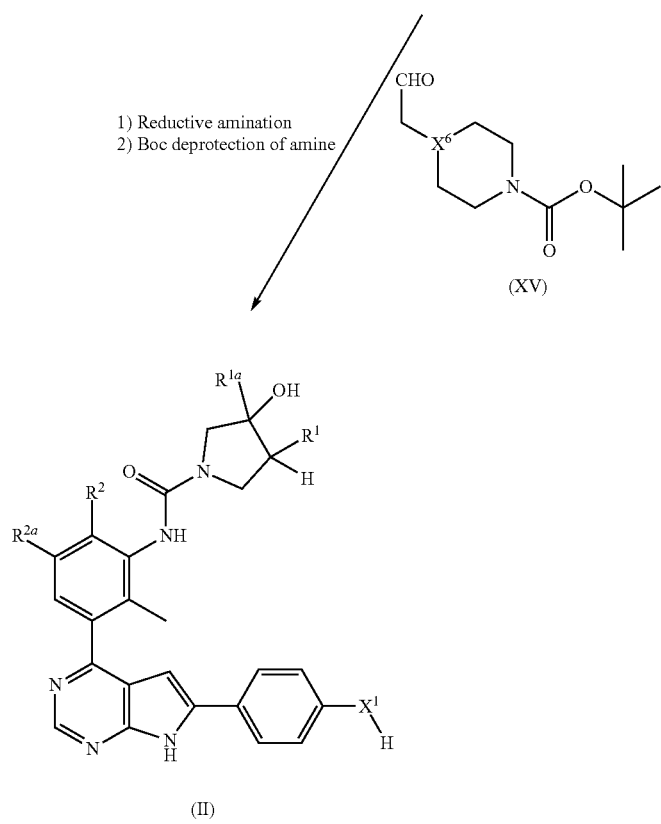

(II)

Compounds of formula (IV) can be made from a compound of formula (XVI), according to Scheme 5, by reacting with a compound of formula (IX) using a Pd-catalysed coupling, such as a Suzuki reaction using a catalyst (e.g. $PdCl_2(dppf)$) and a base (e.g. $Cs_2CO_3$) in a solvent mixture (e.g. dioxane/water). Compounds of formula (XVI) can in turn be made from compounds of formula (XVII), also by a Pd-catalysed coupling, such as a Suzuki reaction with a compound of formula (X) using a catalyst (e.g. $PdCl_2(dppf)$) and a base (e.g. $Cs_2CO_3$) in a solvent mixture (e.g. dioxane/water).

Scheme 5

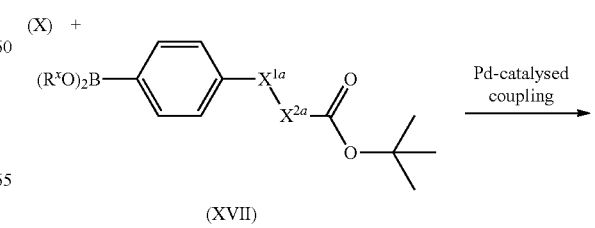

(XVII)

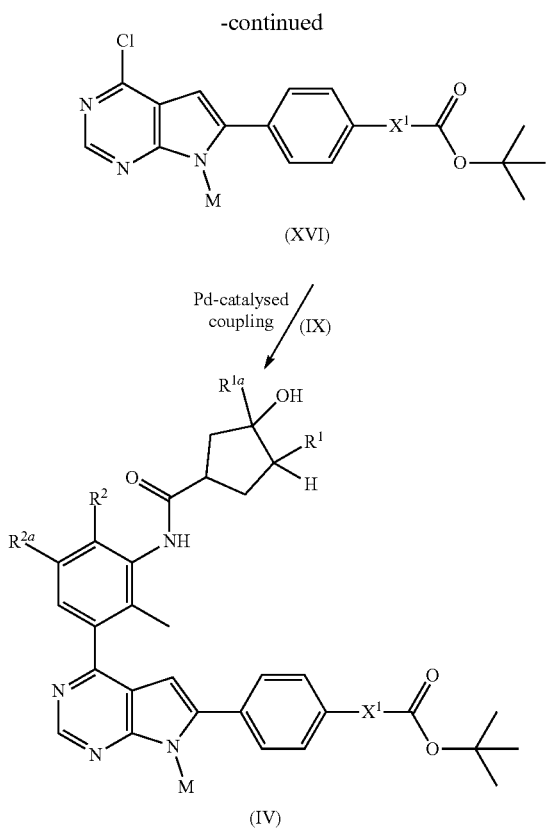

Compounds of formula (XVII) can be made as shown in Scheme 6 by halogen-boron exchange reaction starting from compounds (XVIII) using a boronic ester dimer (e.g. bis(pinacolato)diboron), a Pd catalyst such as PdCl$_2$(dppf) and a base such as KOAc in a solvent such as dioxane. Compounds (XVIII) where Hal denotes a halogen, can be accessed from compounds (XIX) and (VI) using a nucleophilic substitution reaction, for example when Hal and LG in formula (XIX) are both bromine using a base such as K$_2$CO$_3$ in a solvent such as acetonitrile A particular subset of compounds (XVIII), described by formula (XVIIIa) can be synthesized from a halophenyl acetic acid derivative (XX) and a compound of formula (VI) in a two-step procedure involving amide coupling reaction using a coupling reagent (e.g. HATU) and a base (e.g. DIPEA or NMM) in a solvent such as DMF or DMA, followed by addition of a Grignard reagent such as MeMgBr, in the presence of a catalyst (e.g. ZrCl$_4$) in a solvent such as THF. Compounds (XVIIIa) can be converted to compounds (XVII) by halogen-boron exchange in an analogous manner to the conversion described for compounds (XVIII).

Scheme 6

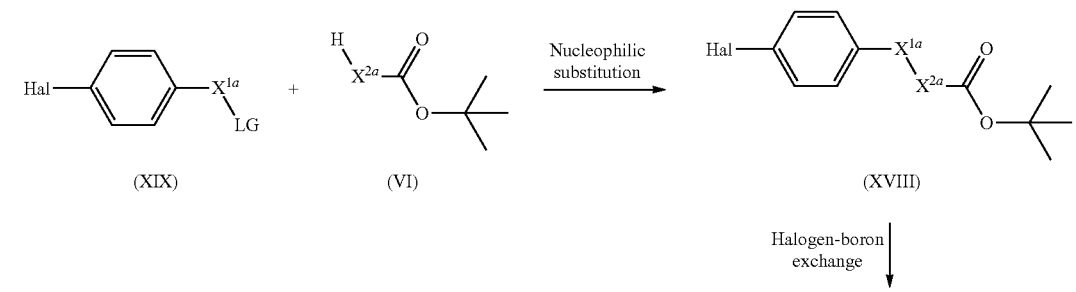

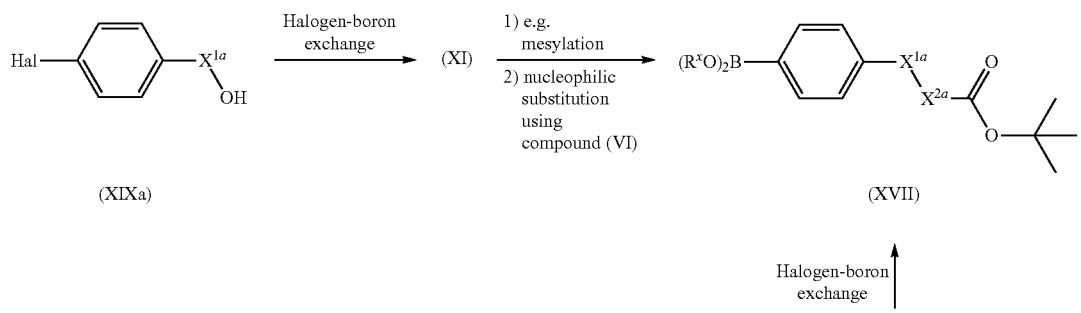

-continued

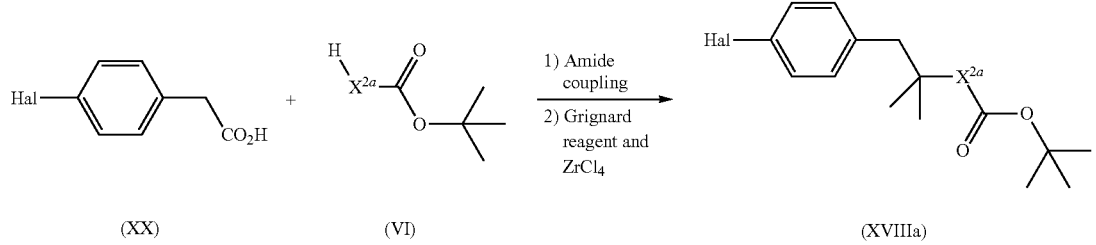

Compounds of formula (I) can be made according to Scheme 7 from compounds of formula (XXI) and compounds of formula (VIIa), a specific embodiment of compound type (VII) where M=H, using a reductive amination coupling using for example NaBH$_3$CN, ZnCl$_2$, and TEA in a solvent mixture such as THF and MeOH. Alternatively, compounds of formula (I) can be made by reaction of a compound of formula (Va), a specific embodiment of compound type (V) where M=H, with a compound of formula (XXI) in a nucleophilic substitution reaction using a base (e.g. K$_2$CO$_3$) in a solvent mixture (e.g. DMF and ACN).

Scheme 7

(VI) + (III)

1) Amide coupling reaction
2) deprotection of amine

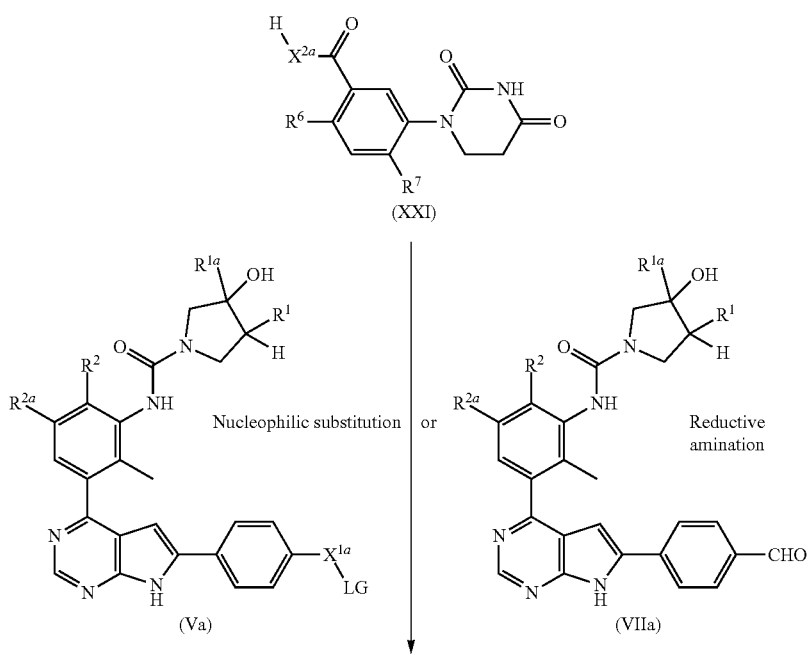

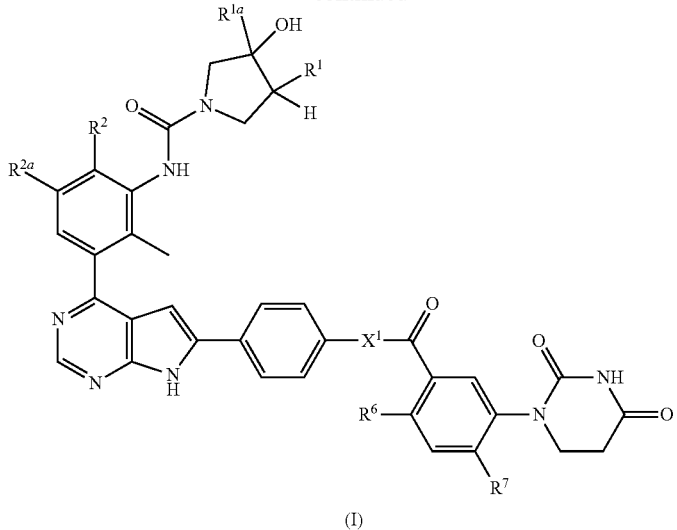

(I)

Compounds of formula (XXI) are synthesized from compounds of formula (VI) and compounds of formula (III) by an amide coupling reaction using a coupling reagent (e.g. HATU) and a base (e.g. DIPEA or NMM) in a solvent such as DMF or DMA, followed by deprotection of the t-butoxycarbonyl (Boc) group of the amine using an acid, (e.g. TFA) in a solvent such as DCM.

Compounds of formula (I) where Z is not absent can be made by reacting a compound of formula (XXII) with a compound of formula (XXIII), where Z, $R^1$, $R^{1a}$, $R^2$, $R^{2a}$, $X^{1a}$, $R^4$, $R^5$, $R^6$, $R^7$, n, p and q are as previously defined, in a reductive amination coupling using for example $NaBH_3CN$, $ZnCl_2$, and TEA in a solvent mixture such as THF and MeOH. By analogy, compounds (XXIV) and (XXIII) may react under similar conditions to provide compounds of formula (I), according to Scheme 8.

Scheme 8

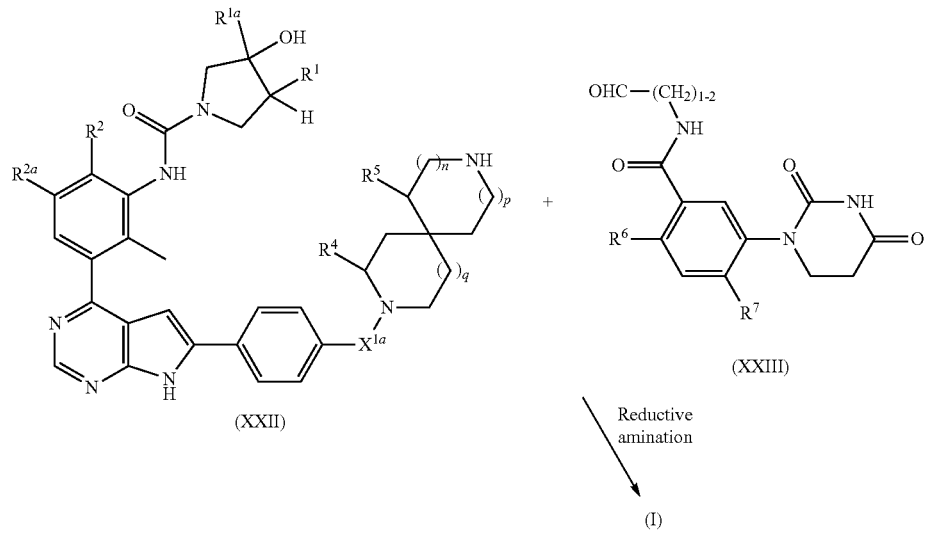

(XXIII) +

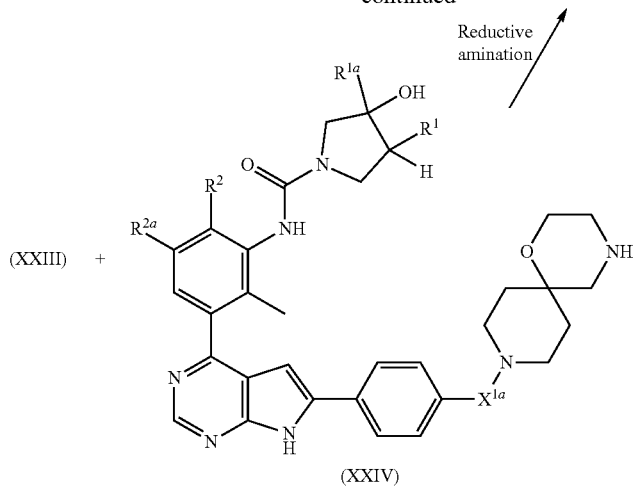

(XXIV)

Compounds of formula (XVI) can be synthesized according to Scheme 9 from a compound of formula (X) and compounds of formula (XXV) using a Pd-catalysed coupling, such as a Suzuki reaction, with a catalyst (e.g. PdCl$_2$(dppf)) and a base (e.g. Cs$_2$CO$_3$) in a solvent mixture (e.g. dioxane/water).

Scheme 9

(X) +

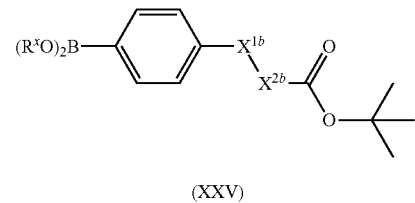

(XXV)

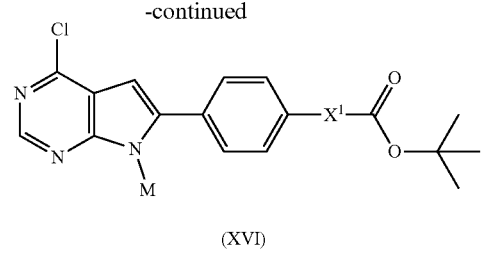

(XVI)

Compounds of formula (XXV) can be made using a variety of procedures under reaction conditions previously described. For example, in Scheme 10, starting from the common boronic acid/ester starting material (XXVIII), a Mitsunobu reaction using a compound of structure (XXIX) followed by deprotection provides an intermediate of formula (XXVI) which can then undergo a nucleophilic substitution reaction with compounds of formula (XXVII) to furnish compounds of formula (XXV). In some cases, the Mitsunobu reaction of (XXVIII) with a compound of formula (XXX) can directly provide (XXV).

Scheme 10

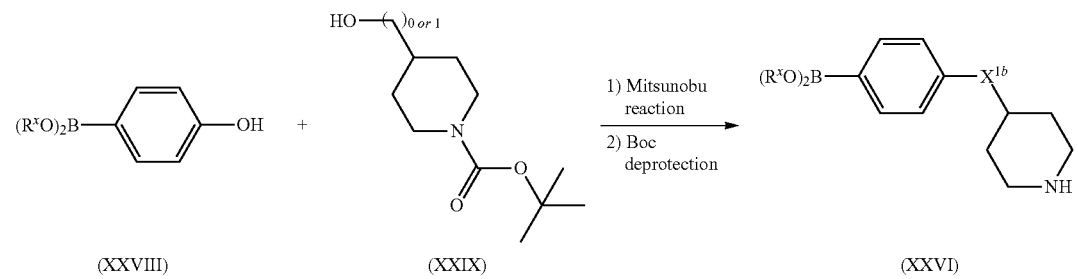

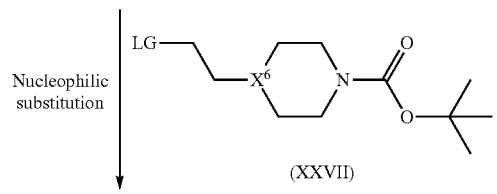

-continued

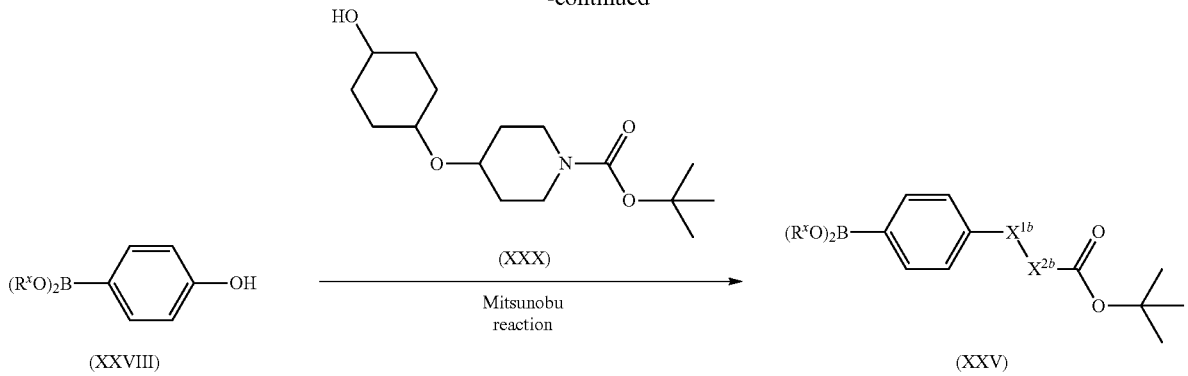

Compounds of formula (XXV) may also be synthesized from the common starting material 4-bromobenzyl bromide (XXXI). In these cases, as shown in Scheme 11, a nucleophilic substitution reaction with compound (XXX) using a base such as potassium t-butoxide in a solvent such as THF followed by halogen-boron exchange using conditions previously described can directly lead to (XXV). In other cases, a nucleophilic substitution reaction with compound (XXXII) followed by halogen-boron exchange and Boc-deprotection gives a new intermediate (XXXIII) which can be reacted in a further nucleophilic substitution reaction with compounds of type (XXVII) leading to (XXV) under similar reaction conditions to those previously described.

Scheme 11

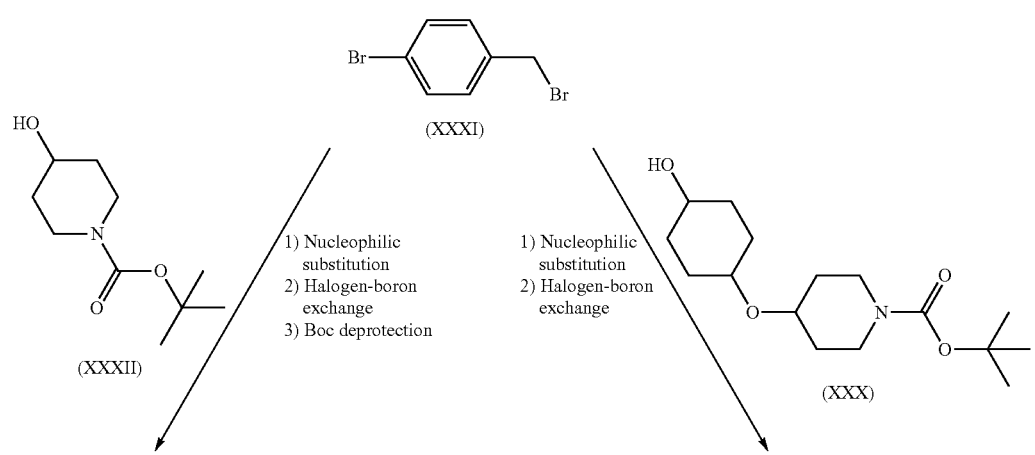

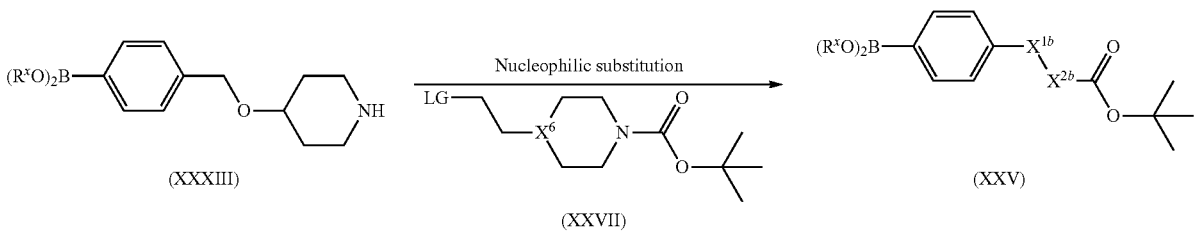

Well known to those skilled in the art, reaction sequence orders can often be changed while leading to similar compounds. Scheme 12 shows alternative methods for constructing compounds of formula (IV) using similar procedures to those already described. Thus, a Pd-catalysed coupling, such as a Suzuki reaction, using compounds (X) and (XXVIII) with a catalyst (e.g. PdCl$_2$(dppf)) and a base (e.g. Cs$_2$CO$_3$) in a solvent mixture (e.g. dioxane/water) gives intermediate (XXXIV) which can undergo a Mitsunobu reaction with compound of formula (XXXII) to provide intermediate (XXXV). Compound (XXXV) can then undergo a further Suzuki coupling, this time with a compound of formula (IX) and subsequent deprotection sequence to give a compound of formula (XXXVI). Compounds of formula (XXXVI) can undergo reductive amination with a compound of formula (XXXVII) to give a compound of formula (IV).

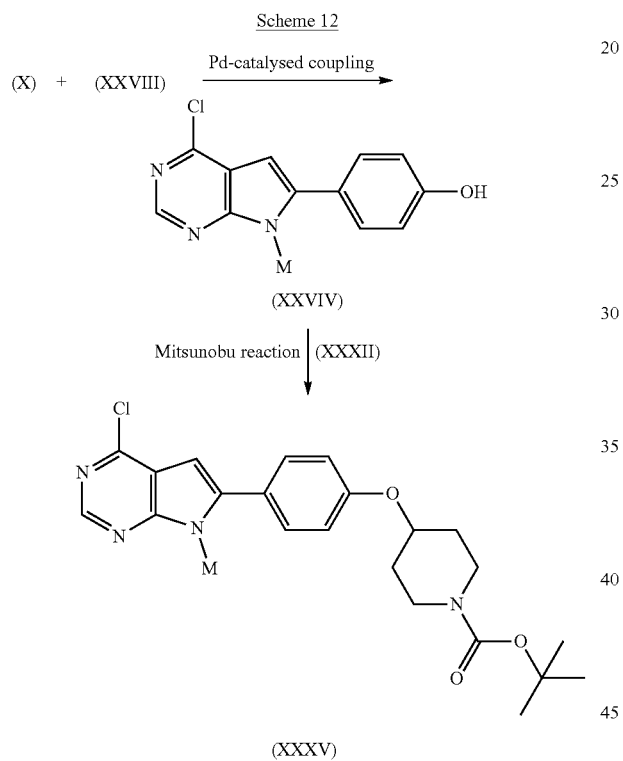

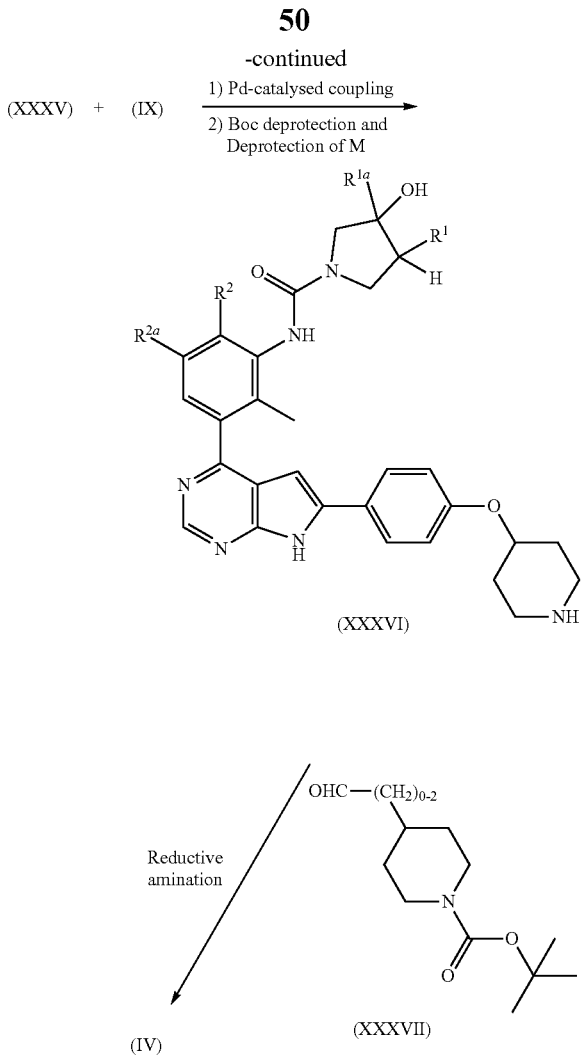

Compounds of formula (XXXVI) can also undergo reductive amination with a compound of formula (XXXVIII) to give compounds of formula (IV). In this case, shown in Scheme 13, two products may be produced (where Q is H or where Q is CH$_2$OH). The compound (IV) where Q is H may be alternatively prepared using the masked aldehyde (XXXIX) in place of (XXXVIII).

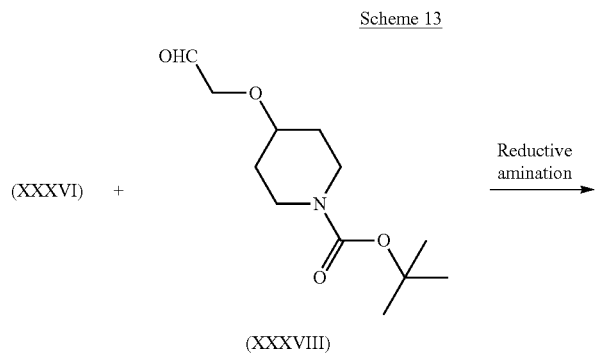

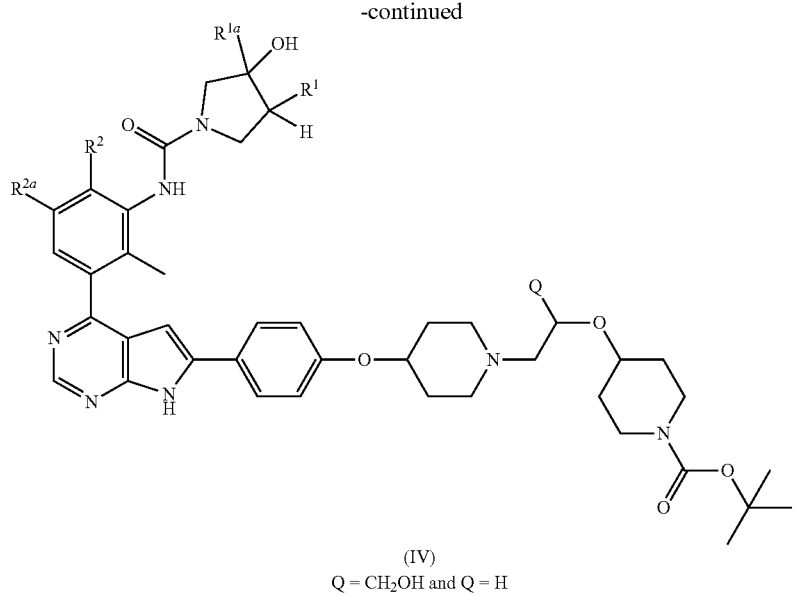

(IV)
Q = CH₂OH and Q = H

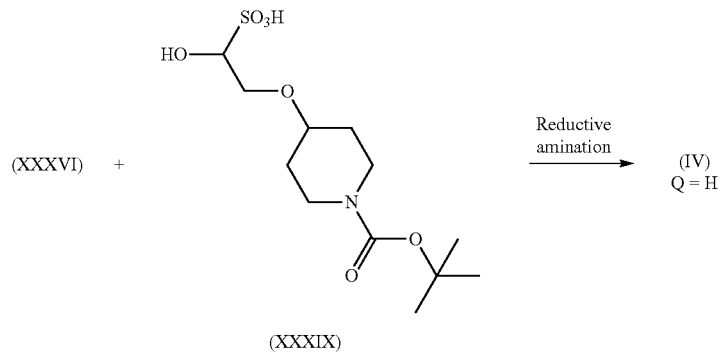

Scheme 14 shows yet more approaches to provide compounds of formula (IV). Thus, intermediates of formula (XL) can be generated by, for example, a Mitsunobu reaction between compounds (XXVIII) and (XXIX). Alternatively, (XL) may be produced in two steps from a nucleophilic substitution between compounds of formula (XXXI) and (XXXII), followed by a halogen-boron exchange reaction. Reaction of intermediate (XL) in a Pd-catalysed coupling reaction with a compound of formula (X) gives a compound of formula (XLI) which may undergo a further Pd-catalysed coupling reaction with a compound of formula (IX) followed by deprotection to give a compound of formula (XLII). Compound (XLII) may undergo a reductive amination reaction with compounds of formula (XXXVII) to provide (IV).

Scheme 14

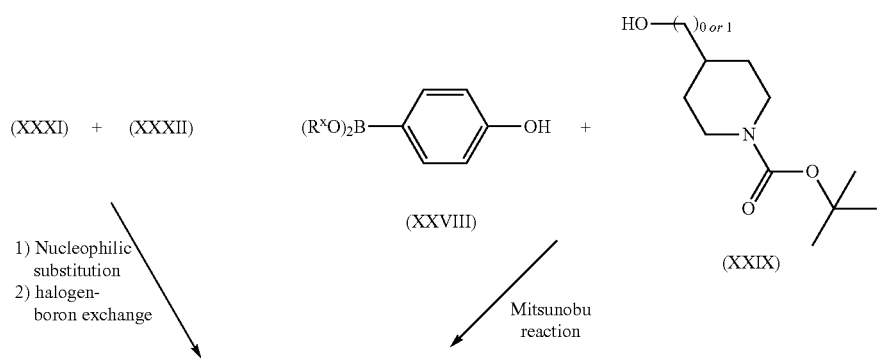

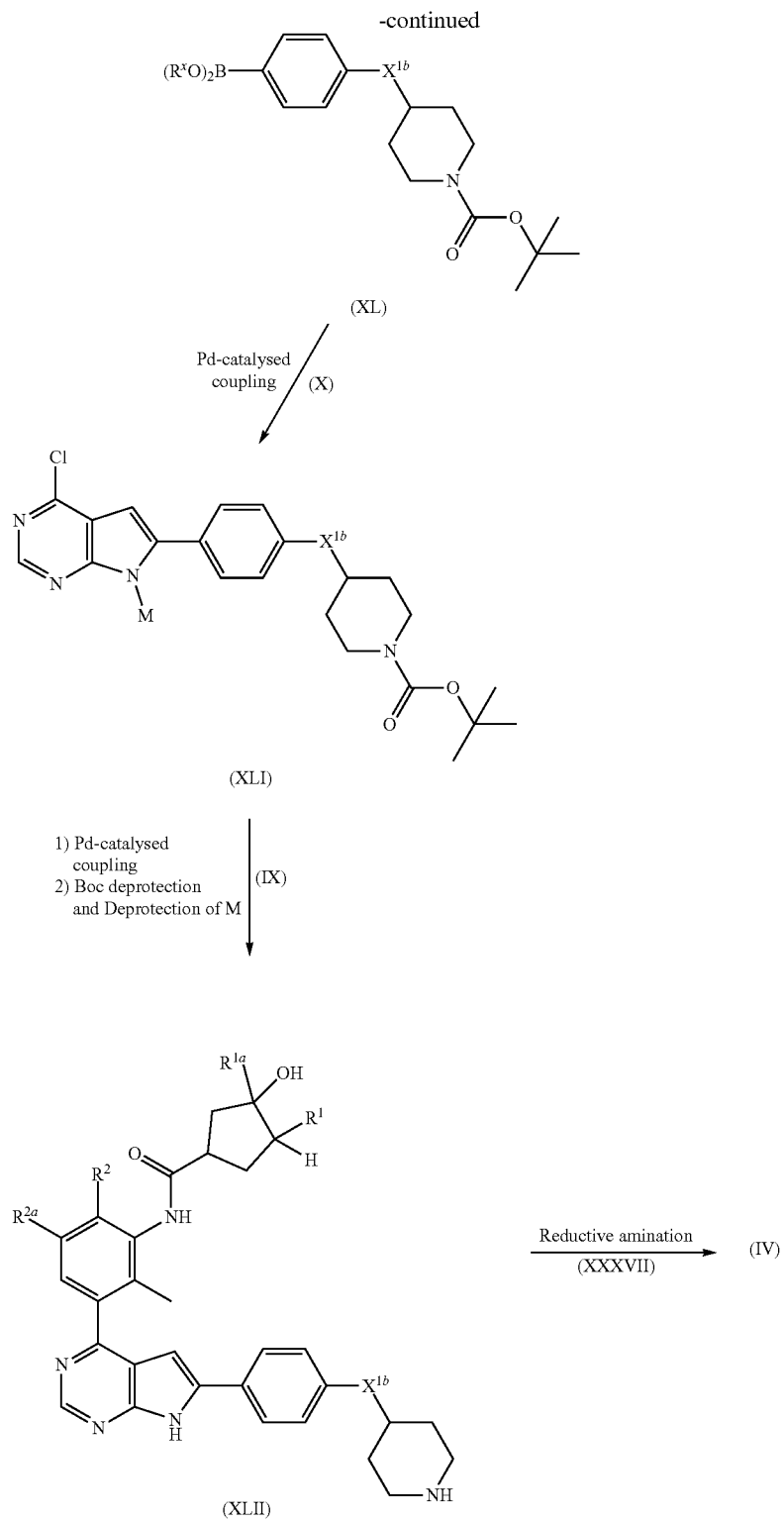

Compounds of formula (I) may be made as shown in Scheme 15 from an intermediate of formula (XLIV) which itself can be made by direct analogy to compound (XL) in Scheme 14. Thus intermediate (XLIV) is derived from either (XXVIII) or (XXXI) combined with (XLIII). Compound (XLIV) then undergoes two Pd-catalysed coupling reactions and a de-protection sequence to furnish (XLV). Compound (XLV) may be reacted with a compound of formula (XLVI) in a reductive amination reaction to furnish (I). Compound (XLVI) is made from compound of formula (III) using an amide coupling reaction with N-(2-hydroxyethyl)piperazine, followed by an oxidation reaction such as a Swern oxidation, using, for example, oxalyl chloride and DMSO, followed by addition of TEA in a solvent such as DCM.

Scheme 15
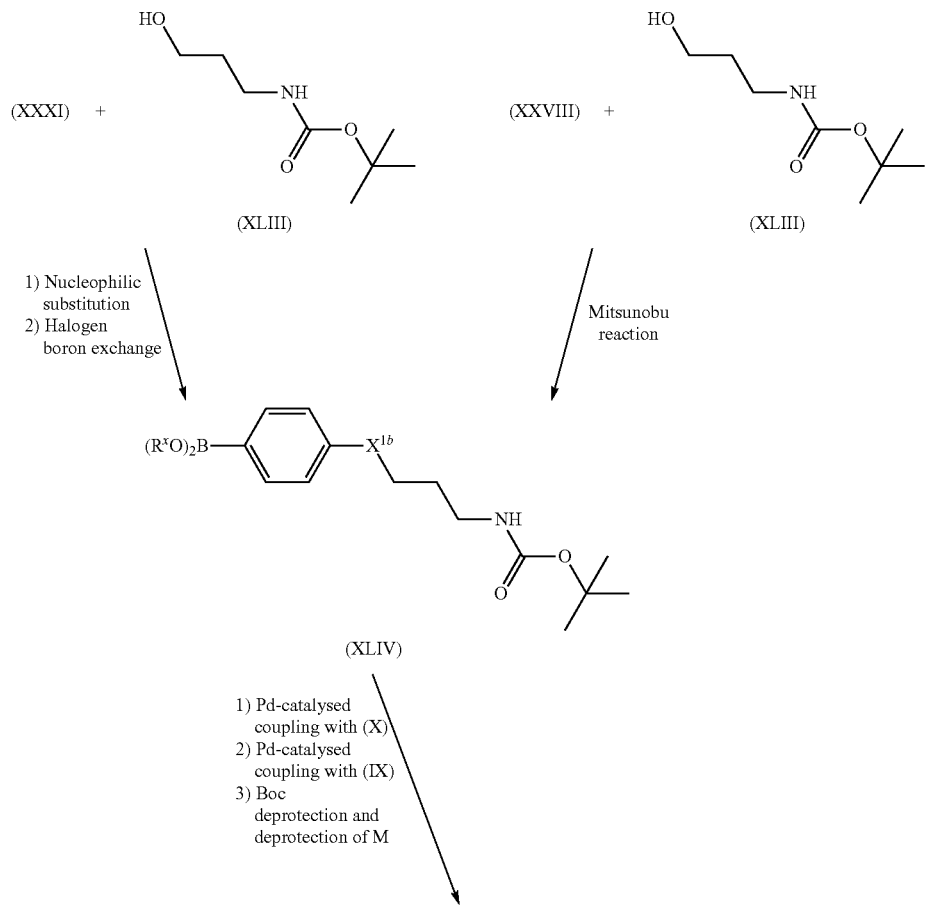
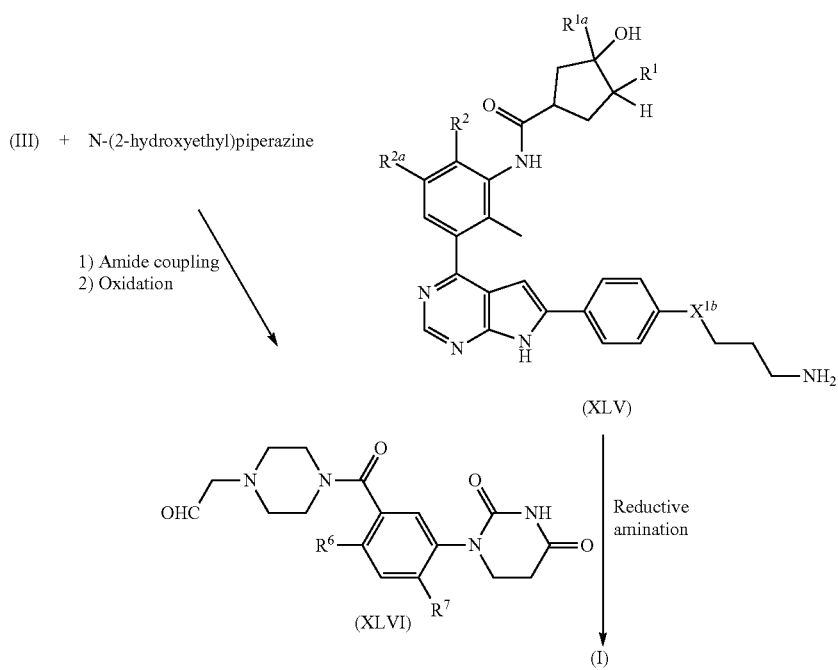

Dihydrouracil molecules of formula (III) may be made by cyclisation of molecules of formula (XLVII) using urea in acetic acid heated to around 120° C. Compounds (XLVII) are in turn synthesized from the corresponding aniline derivatives (XLVIII) by heating in acrylic acid (Scheme 16), typically at temperatures around 100° C.

Compounds of formula (IX) wherein $R^1$, $R^{1a}$, $R^2$, $R^{2a}$ and —$B(OR^x)_2$ are as previously defined are made according to Scheme 17 using a urea forming reaction between compounds of formula (XLIX) and (L), by treating compound (XLIX) with phosgene or an equivalent such as triphosgene at low temperature (e.g. −20° C.) followed by addition of an amine of formula (L) in a solvent such as THF or DCM.

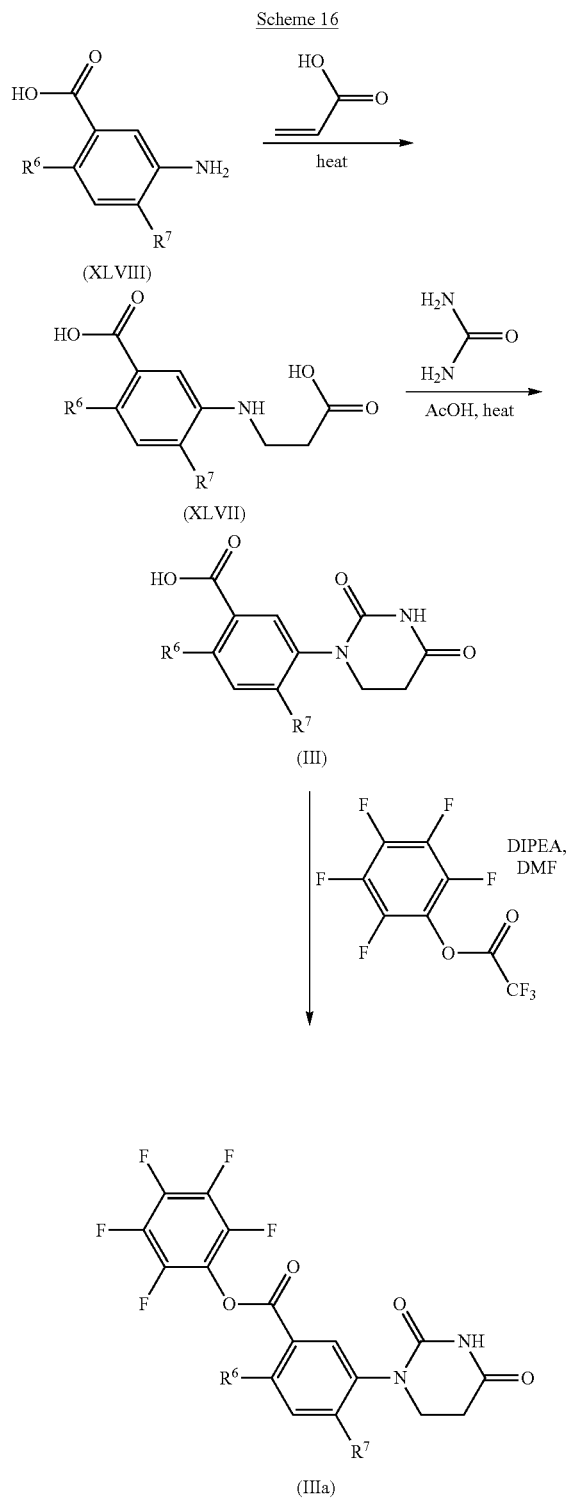

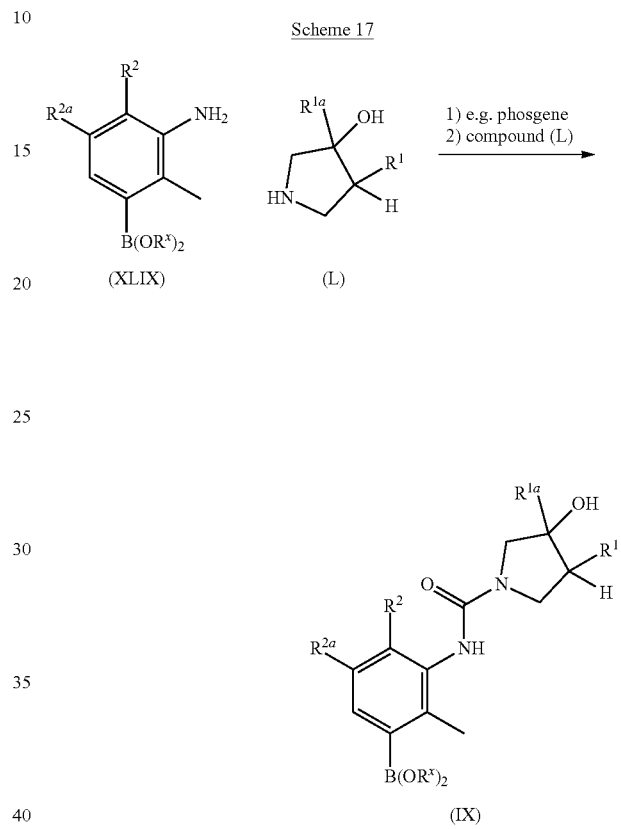

Finally, amines of formula (L) may be made according to Scheme 18, from the protected pyrrolidine (LIN) where PG is defined as a protecting group such as -Boc or —CBz (benzyloxycarbonyl). Grignard reagent addition in a solvent such as ether or THF using an additive such as Cu(I)bromide dimethyl sulfide complex opens the epoxide in a stereoselective manner to provide the racemic material (LII)—relative stereochemistry is depicted. This material can undergo deprotection to give the racemic mixture of trans-isomers of compound (L). Alternatively, chiral separation prior to de-protection leads to the individual trans enantiomers of compound (L). Compounds (LII) may also undergo a Mitsunobu inversion reaction using a reagent such as 4-nitrobenzoic acid to provide molecules of formula (LI)—relative stereochemistry is depicted. This material (LI) can undergo deprotection to give the racemic mixture of cis-isomers of compound (L). Alternatively, chiral separation prior to de-protection leads to the individual cis enantiomers of compound (L). Thus all enantiomers of (L) may be accessed by this route and it is also understood by one skilled in the art that specific enantiomers can also be produced starting from a non-racemic chirally pure compound (LIII), thus effecting the chiral resolution at an earlier stage of the synthesis.

Scheme 18

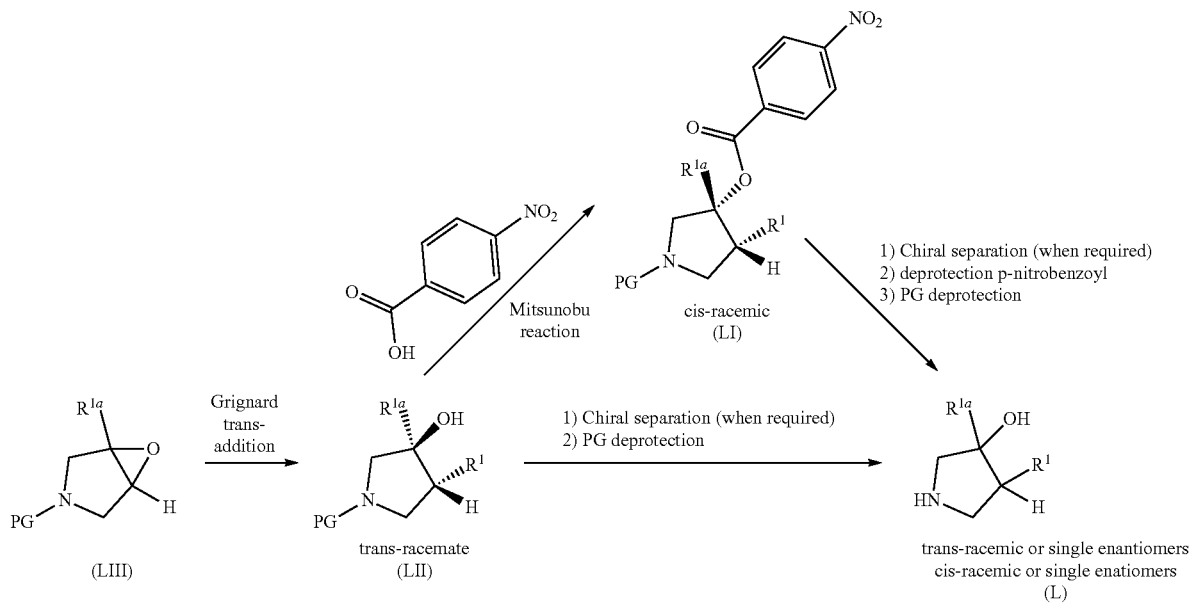

The specific preparation of intermediates and examples using the general methods described above is provided in detail in the experimental section.

In an additional embodiment, there is provided a compound according to Formula (III), or salt thereof,

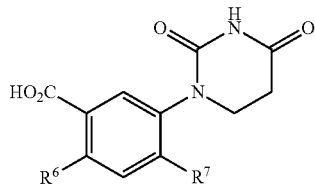

(III)

wherein $R^6$ is selected from H and F; and $R^7$ is selected from H, F, Cl, —$CH_3$, —$OCH_3$, and —$OCH_2CH_3$.

In another embodiment, there is provided a compound according to Formula (IIIa), or salt thereof,

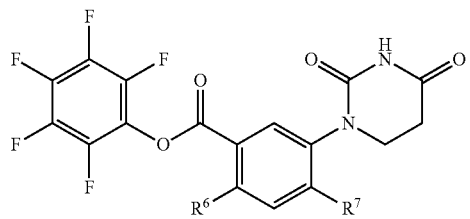

(IIIa)

wherein $R^6$ is selected from H and F; and $R^7$ is selected from H, F, Cl, —$CH_3$, —$OCH_3$, and —$OCH_2CH_3$.

In another embodiment, there is provided a compound according to Formula (XXIa), or salt thereof,

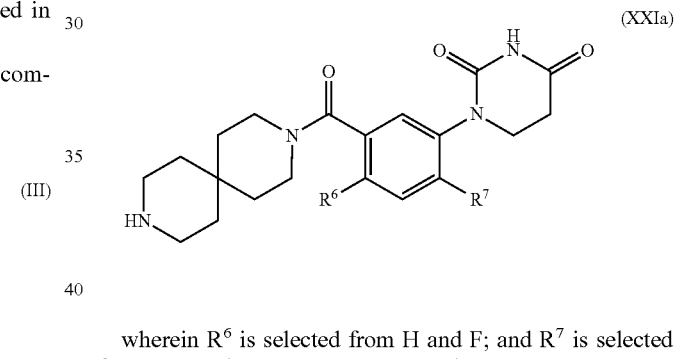

(XXIa)

wherein $R^6$ is selected from H and F; and $R^7$ is selected from H, F, Cl, —$CH_3$, —$OCH_3$, and —$OCH_2CH_3$.

In another embodiment, there is provided a compound according to Formula (IX), or salt thereof,

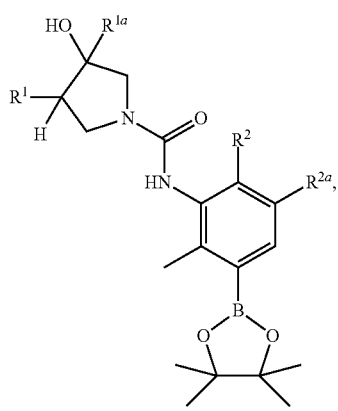

(IX)

Wherein $R^1$, $R^{1a}$, $R^2$ and $R^{2a}$ are as defined for formula (I).

In an additional embodiment, there is provided a compound or salt thereof selected from the group consisting of:

3-(2,4-Dioxotetrahydropyrimidin-1(2H)-yl)-4-methoxybenzoic acid

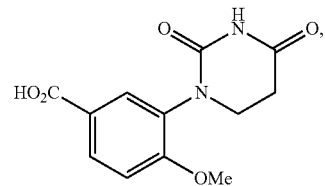 [SMILES: COc1ccc(C(=O)O)cc1N1CCC(=O)NC1=O]

pentafluorophenyl 3-(2,4-dioxotetrahydropyrimidin-1(2H)-yl)-4-methoxybenzoate

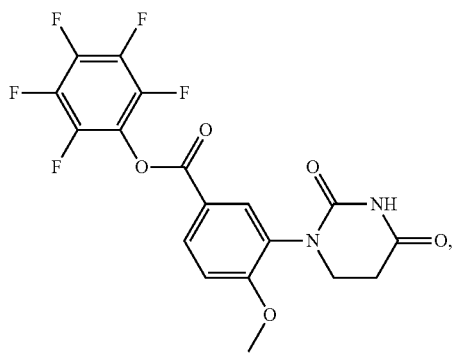 [SMILES: COc1ccc(C(=O)Oc2c(F)c(F)c(F)c(F)c2F)cc1N1CCC(=O)NC1=O]

1-(2-Methoxy-5-(3,9-diazaspiro[5.5]undecane-3-carbonyl)phenyl)dihydropyrimidine-2,4(1H,3H)-dione

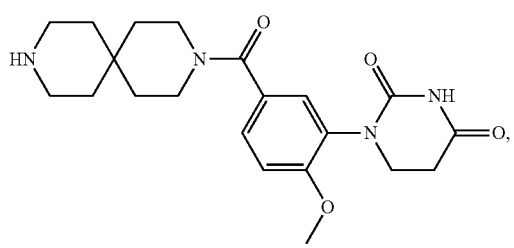 [SMILES: COc1ccc(C(=O)N2CCC3(CCNCC3)CC2)cc1N1CCC(=O)NC1=O]

N-(5-fluoro-2-methyl-3-(4,4,5,5-tetramethyl-1,3,2-dioxaborolan-2-yl)phenyl)-3-hydroxy-4-isobutylpyrrolidine-1-carboxamide, in particular (cis-rac)-N-(5-fluoro-2-methyl-3-(4,4,5,5-tetramethyl-1,3,2-dioxaborolan-2-yl)phenyl)-3-hydroxy-4-isobutylpyrrolidine-1-carboxamide or (trans-rac)-N-(5-fluoro-2-methyl-3-(4,4,5,5-tetramethyl-1,3,2-dioxaborolan-2-yl)phenyl)-3-hydroxy-4-isobutylpyrrolidine-1-carboxamide

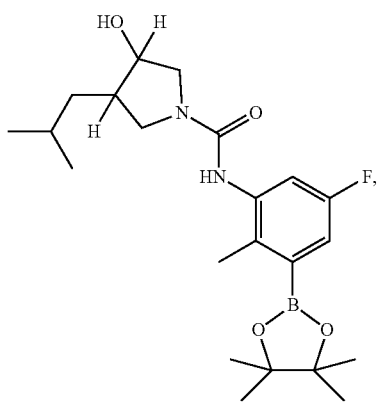 [SMILES: Cc1c(NC(=O)N2CC(O)C(CC(C)C)C2)cc(F)cc1B1OC(C)(C)C(C)(C)O1]

(3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide

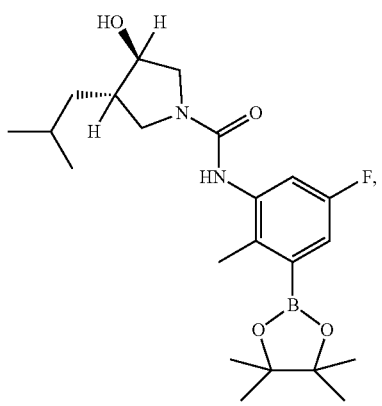 [SMILES: Cc1c(NC(=O)N2C[C@H](CC(C)C)[C@@H](O)C2)cc(F)cc1B1OC(C)(C)C(C)(C)O1]

(3S,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide

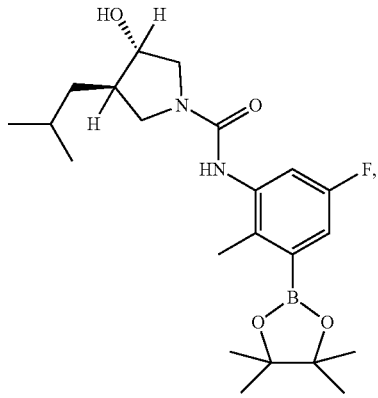 [SMILES: Cc1c(NC(=O)N2C[C@@H](CC(C)C)[C@H](O)C2)cc(F)cc1B1OC(C)(C)C(C)(C)O1]

and (3R,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide

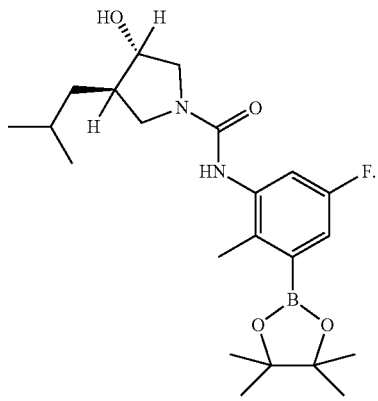 [SMILES: Cc1c(NC(=O)N2C[C@@H](CC(C)C)[C@H](O)C2)cc(F)cc1B1OC(C)(C)C(C)(C)O1]

Compounds of these embodiments are useful in the preparation of compounds of the present invention.

The invention further includes any variant of the present processes, in which an intermediate obtainable at any stage thereof is used as starting material and the remaining steps are carried out, or in which the starting materials are formed in situ under the reaction conditions, or in which the reaction components are used in the form of their salts or optically pure material. Compounds of the present invention and intermediates can also be converted into each other according to methods generally known to those skilled in the art e.g. by reduction, oxidation and/or other functionalization of resulting compounds and/or by cleavage of any protecting group(s) optionally present or linker moieties, and of recovering the so obtainable compound.

In another aspect, the present invention provides a pharmaceutical composition comprising a compound of the present invention, or a pharmaceutically acceptable salt thereof, and a pharmaceutically acceptable carrier.

In another aspect, the present invention provides a pharmaceutical composition comprising a therapeutically effective amount of a compound of the present invention, or a pharmaceutically acceptable salt thereof, and a pharmaceutically acceptable carrier.

In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

The compounds of formula (I) or (Ia), or pharmaceutical acceptable salts thereof, exhibit valuable pharmacological properties, for example, modulation of BTK activity, for example by acting as BTK degraders. This can be determined in vitro, for example, in cells by using engineered cell lines over-expressing BTK or BTK C481S mutant fusion proteins as described herein, for fluorescent readouts as well as in cell lines expressing endogenous BTK. The pharmacological usefulness of the compounds of the present invention can also be determined in vivo, for example, by administering compounds of the invention to animals, such as mice, bearing tumors such as TMD8 tumors and measuring the reduction of BTK in tumor tissue and reduction of tumor volume as a consequence of dosing the compound. The compounds of formula (I) or (Ia) may therefore be useful for the treatment of diseases mediated by BTK.

The compounds of formula (I) or (Ia) may be useful for research on diseases mediated by BTK, e.g. as tool compounds.

The compounds of the present invention, in free form or in pharmaceutically acceptable salt form, may be useful in the prevention or treatment of cancer, for example a cancer selected from solid tumor cancers and hematopoietic cancers.

Examples of solid tumor cancers include central nervous system cancer, brain cancer, breast cancer, head and neck cancer, lung cancer; esophageal and esophagogastric junction cancer, gastric cancer, colorectal cancer, rectal cancer, anal cancer, hepatobiliary cancer, pancreatic cancer, non-melanoma skin cancer, melanoma, renal cancer, prostate cancer, bladder cancer, uterine cancer, cervical cancer, ovarian cancer, bone cancer, neuroendocrine cancer, mesothelioma cancer, testicular cancer, thymoma and thymic carcinoma, and thyroid cancer.

Examples of hematopoietic cancers include B-cell neoplasms (including rare B-cell malignancies), Hodgkin lymphoma, non-Hodgkin lymphoma, post-transplant lymphoproliferative disorder, hairy cell leukemia, histiocytic and dendritic neoplasms.

Examples of B-cell neoplasms include chronic lymphocytic leukemia (CLL), mantle cell lymphoma (MCL), small lymphocytic lymphoma (SLL), Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia.

In a particular embodiment, the cancer is selected from chronic lymphocytic leukemia (CLL), diffuse large B-cell lymphoma (DLBCL), mantle cell lymphoma (MCL), small lymphocytic lymphoma (SLL), and Waldenström's macroglobulinemia.

In a further embodiment, the cancer is chronic lymphocytic leukemia (CLL).

In another embodiment, the cancer is diffuse large B-cell lymphoma (DLBCL).

The compounds of the present invention may have particular application in the treatment of subjects in which the cancer (e.g. CLL, DLBCL, MCL, SLL and Waldenström's macroglobulinemia) has acquired resistance to ibrutinib, for example in cancers in which resistance has arisen for example through mutation of cysteine-481 to serine (i.e. mutation C481S). Such subjects may have for example already been treated or are continuing to be treated with ibrutinib and where the subject has a reduced response or is no longer responding to treatment with ibrutinib. The compounds of the invention may therefore be beneficially used in the treatment of ibrutinib resistant cancer, especially ibrutinib resistant CLL, DLBCL, MCL, SLL and Waldenström's macroglobulinemia, in particular, ibrutinib resistant CLL.

In an another embodiment, the compounds of the present invention, in free form or in pharmaceutically acceptable salt form, may be useful in the prevention or treatment of autoimmune disorders, inflammatory disorders, allergic diseases, anaphylaxis, allergic asthma and airway diseases, and in transplantation. For example the compounds of the present invention, in free form or in pharmaceutically acceptable salt form, may be useful in the prevention or treatment of asthma; chronic obstructive pulmonary disease (COPD); transplant rejection; diseases in which antibody production, antigen presentation, cytokine production or lymphoid organogenesis are abnormal or are undesirable; rheumatoid arthritis; systemic onset juvenile idiopathic arthritis (SO-JIA); gout; pemphigus vulgaris; idiopathic thrombocytopenic purpura; systemic lupus erythematosus; multiple sclerosiss; myasthenia gravis; Sjögren's syndrome; autoimmune hemolytic anemia; anti-neutrophil cytoplasmic antibodies (ANCA)-associated vasculitides; cryoglobulinemia; thrombotic thrombocytopenic purpura; chronic autoimmune urticarial; allergy (atopic dermatitis, contact dermatitis, allergic rhinitis); atherosclerosis; type 1 diabetes; type 2 diabetes; inflammatory bowel disease; ulcerative colitis; morbus Crohn; pancreatitis; glomerolunephritis; Goodpasture's syndrome; Hashimoto's thyroiditis; Grave's disease; antibody-mediated transplant rejection (AMR); graft versus host disease (GvHD); chronic graft versus host disease (cGvHD); B cell-mediated hyperacute; acute and chronic transplant rejection; thromboembolic disorders; myocardial infarct; angina pectoris; stroke; ischemic disorders; pulmonary embolism; polycythemia vera; essential thrombocythemia; and myelofibrosis with myeloid metaplasia.

In another embodiment, the compounds of the present invention, in free form or in pharmaceutically acceptable salt form, may be useful in the prevention or treatment of immunoglobulin Light Chain Amyloidosis (AL).

In a further aspect, the present invention provides the use of a compound of the invention, or a pharmaceutically acceptable salt thereof, in therapy. In an embodiment, the present invention provides the use of a compound of the invention, or a pharmaceutically acceptable salt thereof, in the prevention or treatment of diseases mediated by BTK. In another embodiment, the present invention provides the use of a compound of the invention, or a pharmaceutically acceptable salt thereof, in the prevention or treatment of cancer. In a further embodiment, the cancer is a hematopoietic cancer. In a further embodiment the hematopoietic cancer is chronic lymphocytic leukemia (CLL), diffuse large B-cell lymphoma (DLBCL), mantle cell lymphoma (MCL), small lymphocytic lymphoma (SLL), and Waldenström's macroglobulinemia, especially CLL or DLBCL.

In an embodiment, the compound is (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, or a pharmaceutically acceptable salt thereof.

In an embodiment, the compound is (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In a further aspect, the present invention provides a compound of the invention, or a pharmaceutically acceptable salt thereof, for use in therapy. In an embodiment, the present invention provides a compound of the invention, or a pharmaceutically acceptable salt thereof, for use in the prevention or treatment of a disease mediated by BTK. In an embodiment, the present invention provides a compound of the invention, or a pharmaceutically acceptable salt thereof, for use in the prevention or treatment of cancer. In a further embodiment, the cancer is a hematopoietic cancer. In a further embodiment the hematopoietic cancer is chronic lymphocytic leukemia (CLL), diffuse large B-cell lymphoma (DLBCL), mantle cell lymphoma (MCL), small lymphocytic lymphoma (SLL), and Waldenström's macroglobulinemia, especially CLL or DLBCL.

In an embodiment, the compound is (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, or a pharmaceutically acceptable salt thereof.

In an embodiment, the compound is (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In a further aspect, the present invention provides a method of treating a disease mediated by BTK comprising administering to a patient in need thereof a therapeutically acceptable amount of a compound of the invention, or a pharmaceutically acceptable salt thereof. In an embodiment, the present invention provides a method of treating cancer comprising administering to a patient in need thereof a therapeutically acceptable amount of a compound of the invention, or a pharmaceutically acceptable salt thereof. In a further aspect, the cancer is a hematopoietic cancer. In a further embodiment the hematopoietic cancer is chronic lymphocytic leukemia (CLL), diffuse large B-cell lymphoma (DLBCL), mantle cell lymphoma (MCL), small lymphocytic lymphoma (SLL), and Waldenström's macroglobulinemia, especially CLL or DLBCL.

In an embodiment, the compound is (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, or a pharmaceutically acceptable salt thereof.

In an embodiment, the compound is (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In a further aspect, the present invention provides the use of a compound of the invention, or a pharmaceutically acceptable salt thereof, for the manufacture of a medicament. In an embodiment, the present invention provides the use of a compound of the invention, or a pharmaceutically acceptable salt thereof, for the manufacture of a medicament, for the prevention or treatment of a disease mediated by BTK. In an embodiment, the present invention provides the use of a compound of the invention, or a pharmaceutically acceptable salt thereof, for the manufacture of a medicament, for the prevention or treatment of cancer. In a further embodiment, the cancer is a hematopoietic cancer. In a further embodiment the hematopoietic cancer is chronic lymphocytic leukemia (CLL), diffuse large B-cell lymphoma (DLBCL), mantle cell lymphoma (MCL), small lymphocytic lymphoma (SLL), and Waldenström's macroglobulinemia, especially CLL or DLBCL.

In an embodiment, the compound is (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)

phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(4-((1-(3-(2,4-dioxotetrahydropyrimidin-1 (2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, or a pharmaceutically acceptable salt thereof.

In an embodiment, the compound is (cis-rac)-N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

In an embodiment, the compound is (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^6$ molar and $10^{10}$ molar concentrations. A therapeutically effective amount in vivo may range depending on the route of administration, between about 0.1-500 mg/kg, or between about 1-100 mg/kg.

A compound of the present invention may be administered either simultaneously with, or before or after, one or more other therapeutic agent. A compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present invention.

In one embodiment, the invention provides a product comprising a compound of the present invention and at least one other therapeutic agent as a combined preparation for simultaneous, separate or sequential use in therapy. In one embodiment, the therapy is the treatment of a disease or condition mediated by BTK. In another embodiment, the therapy is the treatment of a cancer described herein. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical composition comprising a compound of the present invention and another therapeutic agent(s). In another embodiment, the invention provides a pharmaceutical composition comprising a therapeutically effective amount of a compound of the present invention and another therapeutic agent(s).

Optionally, the pharmaceutical composition may comprise a pharmaceutically acceptable carrier, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

Accordingly, the invention also provides the use of another therapeutic agent for treating a disease or condition mediated by BTK, wherein the other therapeutic agent is administered with a compound of the present invention.

The invention also provides a compound of the present invention for use in a method of treating a disease or condition mediated by BTK, wherein the compound of the present invention is administered with another therapeutic agent.

The invention also provides another therapeutic agent for use in a method of treating a disease or condition mediated by BTK, wherein the other therapeutic agent is administered with a compound of the present invention.

The invention also provides the use of a compound of the present invention for treating a disease or condition mediated by BTK, wherein the patient has previously (e.g. within 24 hours) been treated with another therapeutic agent.

The invention also provides the use of another therapeutic agent for treating a disease or condition mediated by BTK, wherein the patient has previously (e.g. within 24 hours) been treated with a compound of the present invention.

The invention also provides the use of another therapeutic agent for treating cancer wherein the other therapeutic agent is administered with a compound of the present invention.

The invention also provides a compound of the present invention for use in a method of treating cancer, wherein the compound of the present invention is administered with another therapeutic agent.

The invention also provides another therapeutic agent for use in a method of treating cancer, wherein the other therapeutic agent is administered with a compound of the present invention.

The invention also provides the use of a compound of the present invention for treating cancer, wherein the patient has previously (e.g. within 24 hours) been treated with another therapeutic agent.

The invention also provides the use of another therapeutic agent for treating cancer, wherein the patient has previously (e.g. within 24 hours) been treated with a compound of the present invention.

In one embodiment, the other therapeutic agent is selected from:

Apoptosis modulators, Anti-CD20 antibodies, Anti-CD22 antibodies, PI3K inhibitors, Tyrosine kinase inhibitors, Immune checkpoint agents, CART therapeutic agents, Immunomodulators, bispecific antibodies targeting CD20 and CD3, antibody-drug conjugates (ADC), Proteasome inhibitors, epigenetic modifiers, Anti-CD38 mAb, Anti-SLAMF7 agent, XP01 inhibitors and other agents such as chemotherapeutic agents.

In an embodiment the apoptosis modulators are selected from Bcl2 inhibitors (such as Antimycin, obatoclax, venetoclax (Venclexta®), ethyl-2-amino-6-cyclopentyl-4-(1-cyano-2-ethoxy-2-oxoethyl)-4H-chromone-3-carboxylate (HA14-1), oblimersen (G3139, Genasense®), Bak BH3 peptide, (−)-Gossypol (AT-101, BL-193), Navitoclax (ABT-263)), Mcl1 inhibitors (such as AMG176, S63845, AZD5991, MIK665), and MDM2/p53 inhibitors (such as NVP-HDM201, NVP-CGM-097, ALRN-6924, idasanutlin, AMG232, and DS-3032B).

In an embodiment the Anti-CD20 antibodies are selected from Rituximab, obinutuzumab, ofatumumab, ocrelizumab, and ublituximab.

In an embodiment the Anti-CD22 antibodies are selected from Inotuzumab, epratuzumab, bectumomab, and moxetumomab.

In an embodiment the PI3K inhibitors are selected from duvelisib, umbralisib tosylate, INCB050465, apilimod mesylate (LAM-002), copanlisib hydrochloride (Aliqopa®), tenalisib, pictilisib (GDC 0941), sonolisib (PX866), pilaralisib (SAR 245408 or XL 147), alpelisib (BYL719), and leniolisib (CDZ173).

In an embodiment the Tyrosine kinase inhibitors are selected from BTK inhibitors (such as ibrutinib, acalabrutinib, zanubrutinib (BGB-3111), tirabrutinib (ONO-4059), ARQ531, CC-292 (AVL-292), CT-1530, DTRMWXHS-12, GDC-0853, M7583, and vecabrutinib (SNS-062), SYK inhibitors (such as entospletinib (GS9973), fostamatinib, and HMPL-523, the SYK/JAK inhibitor cerdulatinib (PRT062070), SYK/FLT inhibitors such as TAK-659, FLT3 inhibitors such as FF-10101, the FLT3/BTK inhibitor (CG806), JAK inhibitors (such as itacitanib, INCB052793, BMS911543, fedratinib, WP-1066, NS-018, and ruxolitinib (Jakavi®)), Erlotinib hydrochloride (Tarceva®), Linifanib (ABT869), Sunitinib malate (Sutent®), Bosutinib (Bosulif®), Dasatinib (Sprycel®), Pazopanib (Votrient®), Sorafenib (Nexavar®), Zactima (ZD6474), Imatinib or Imatinib mesylate (Gilvec® and Gleevec®), and tozasertib (VX680 or MK-0457).

In an embodiment the Immune checkpoint agent is an Anti-PD-1 agent, anti-PD-L1 agent selected from Pembrolizumab, nivolumab, tislelizumab, atezolizumab, ipilimumab, cemiplimab, TLR4 agonist, CCR4 mAb mogamulizumab and CD47 mAb fusion protein (TTI-621).

In an embodiment the CART therapy is selected from CD19, BCMA CART, CD20, CD79b, CD22, CD30.

In an embodiment the immunomodulators are selected from lenalidomide (Revlimid®), thalidomide (Thalomid®), avadomide (CC-122), and pomalidomide (Actimid®, Imnovid®, Pomalyst®).

In an embodiment the bispecific antibody targeting CD20 and CD3 is selected from REGN-1979, XmAb-13676, BTCT-4465-A, CD20-TCB, and 8RG-6026.

In an embodiment the ADC is selected from CD79 ADC polatuzumab vedotin, CD30 ADC brentuximab vedotin, CD25 ADC camidanlumab tesirine, and CD19 ADC loncastuximab tesirine.

In an embodiment the proteasome inhibitors are selected from Bortezomib (Velcade®), carfilzomib (Kyprolis®), marizomib (NPI-0052), ixazomib citrate (MLN-9708, Ninlaro®), delanzomib (CEP-18770), and oprozomib (ONX-0912).

In an embodiment the epigenetic modifiers such as HDAC and DNA methylation inhibitors are selected from Vorinostat (Zolinza®), Romidepsin (Istodax®), azacitidine (Mylosar®, Vidaza®), Pyroxamide, Spiruchostatin A, Mylproin (Valproic acid), Entinostat, and guadecitabine.

In an embodiment the Anti-CD38 mAb is selected from Daratumumab and Isatuximab.

In an embodiment the Anti-SLAMF7 agent is Elotuzumab.

In an embodiment the XP01 inhibitors are selected from Selinexorand Eltanexor.

In an embodiment other agents, such as general chemotherapeutic agents, which may be combined with a compound of the invention are selected from anastrozole (Arimidex®), bendamustine (Treanda®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), epirubicin (Ellence®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), ROR mAb cirmtuzumab, Dual PI3K/HDAC inhibitor (CUDC-907), Bet inhibitors (INCB357643), ALK inhibitors (crizotinib), EZH½ inhibitors (DS-3201b), MAPK inhibitors, Aplidin, Plitidepsin (eEF1A2 inhibitor), Wnt inhibitors, radiopharmaceuticals, idiotype vaccines, Pegfilgrastim (Neulasta®), citoplurikin (IRX-2).

In a further embodiment, the other therapeutic agent is selected from:
venetoclax, oblimersen, navitoclax, MIK665, NVP-HDM201, Rituximab, obinutuzumab, ofatumumab, ocrelizumab, ublituximab, Inotuzumab, epratuzumab, bectumomab, moxetumomab, duvelisib, umbralisib tosylate, INCB050465, leniolisib (CDZ173), apilimod mesylate (LAM-002), copanlisib hydrochloride, tenalisib, pictilisib, alpelisib, ibrutinib, acalabrutinib, zanubrutinib (BGB-3111), tirabrutinib (ONO-4059), ARQ531, CC-292 (AVL-292), CT-1530, DTRMWXHS-12, GDC-0853, M7583, vecabrutinib (SNS-062), entospletinib, (GS9973), fostamatinib, HMPL-523, cerdulatinib (PRT062070), (TAK-659), FF-10101, FLT3/BTK inhibitor (CG806), itacitanib, INCB052793, BMS911543, fedratinib, WP-1066, NS-018, ruxolitinib (Jakavi®), Pembrolizumab, nivolumab, tislelizumab, atezolizumab, ipilimumab, cemiplimab, TLR4 agonist, CCR4 mAb mogamulizumab, CD47 mAb fusion protein (TTI-621), CD19, BCMA CART, CD20, CD79b, CD22, CD30, lenalidomide, thalidomide, avadomide, pomalidomide, XmAb-13676, CD79 ADC polatuzumab vedotin, CD30 ADC brentuximab vedotin, CD25 ADC camidanlumab tesirine, CD19 ADC loncastuximab tesirine, Carfilzomib, Bortezomib, Ixazomib, marizomib, oprozomib, Azacitidine, Romidepsin, Vorinostat, guadecitabine, Daratumumab, Isatuximab, Elotuzumab, Selinexor, Eltanexor, Fludarabine, carmustine, cyclophosphamide, chlorambucil, bendamustine, melphalan, cladribine, dacarbazine, pentostatin, vincristine, etoposide, epirubicin, doxorubicin, anthracyclines and antifolate agents.

In a further embodiment, the other therapeutic agent is selected from a Bcl2 inhibitor and a BTK inhibitor.

In a further embodiment, the other therapeutic agent is selected from venetoclax, ibrutinib, and acalabrutinib.

Specific individual combinations which may provide particular treatment benefits include a compound selected from:
(3R,4R)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-(2-(4-((1-(3-(2,4-dioxotetrahydropyrimidin-1 (2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide,
(cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, and
(3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide,
or a pharmaceutically acceptable salt thereof, in combination with venetoclax.

Further specific individual combinations which may provide particular treatment benefits include a compound selected from:
(3R,4R)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-cl]pyrimidin-4-yl)-5-fluoro-2-methylphenyl)-3-hydroxy-4-isobutylpyrrolidine-1-carboxamide,
(3R,4S)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide,
(cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-cl]pyrimidin-4-yl)-5-fluoro-2-methylphenyl)-3-hydroxy-4-isobutylpyrrolidine-1-carboxamide, and
(3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide,
or a pharmaceutically acceptable salt thereof, in combination with ibrutinib.

Yet further specific individual combinations which may provide particular treatment benefits include a compound selected from:

(3R,4R)—N-(3-(6-(4-(2-(9-(3-(2,4-dioxotetrahydropyrimidin-1 (2H)-yl)-4-methoxybenzoyl)-3,9-diazaspiro[5.5] undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1 (2H)-yl)-4-methoxybenzoyl)-3,9-diazaspiro[5.5] undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1 (2H)-yl)-4-methoxybenzoyl)-3,9-diazaspiro[5.5] undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, and (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, or a pharmaceutically acceptable salt thereof, in combination with acalabrutinib.

These combinations may be provided as a pharmaceutical composition comprising an afore-mentioned compound of the present invention, or pharmaceutically acceptable salt thereof, and venetoclax, ibrutinib or acalabrutinib.

Alternatively these combinations may be provided as a combined preparation of an afore-mentioned compound of the present invention, or pharmaceutically acceptable salt thereof, for simultaneous, separate or sequential use with venetoclax, ibrutinib or acalabrutinib in therapy.

These combinations, especially with ibrutinib, may be particularly effective in the treatment of hematopoietic cancers, in particular CLL and DLBCL.

The activity of a compound of the invention can be assessed by the following in vitro methods described herein.

Compounds of the present invention can be prepared as described in the following Examples.

EXAMPLES

The following examples illustrate the invention and are not to be construed as being limitations thereon. Temperatures are given in degrees Celsius. Abbreviations used are those conventional in the art and listed below.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Abbreviations

ACN ACN
AcOH acetic acid
aq. aqueous
BISPIN bis(pinacolato)diboron
Boc tertiary butyl carboxy
br broad
CHX cyclohexane
d doublet
DCM dichloromethane
dd doublet of doublets
DEA diethylamine
DEAD diethyl azodicarboxylate
DIAD diisopropyl azodicarboxylate
DIPEA Diisopropylethylamine
DMA N,N-dimethylacetamide
DME 1,4-dimethoxyethane
DMEM Dulbecco's Modified Eagle's medium
DMF N,N-dimethylformamide
DMSO dimethylsulfoxide
$Et_2O$ diethyl ether
EtOAc ethyl acetate
EtOH ethanol
FCS fetal calf serum
h hour(s)
HATU 1-[Bis(dimethylamino)methylene]-1H-1,2,3-triazolo[4,5-b]pyridinium 3-oxid hexafluorophosphate
HBTU 2-(1H-benzotriazol-1-yl)-1,1,3,3-tetramethyluronium hexafluorophosphate
HPLC high pressure liquid chromatography
HV high vacuum
KOAc potassium acetate
LC-MS liquid chromatography and mass spectrometry
m multiplet
m/z mass to charge ratio
MeOH methanol
min minutes
MS mass spectrometry
MsCl methanesulfonyl chloride
$MS_2O$ methanesulfonic anhydride
NaOAc sodium acetate
NaPyr. Sodiumpyruvate
NEAA none essential amino acid
NMM N-methylmorpholine
NMR nuclear magnetic resonance
PBS phosphate buffered saline
$PdCl_2$(dppf) [1,1'-Bis(diphenylphosphino)ferrocene]palladium(II) dichloride
$PdCl_2$(dppf)-$CH_2Cl_2$ [1,1'-Bis(diphenylphosphino)ferrocene]palladium(II) dichloride-dichloromethane adduct
$PdCl_2(PPh_3)_2$ Bis(triphenylphosphine)palladium(II) dichloride
PG protecting group
$PPh_3$ triphenylphosphine
ppm parts per million
rac racemic
RM reaction mixture
Rt retention time
RT room temperature
s singlet
sat. saturated SFC Supercritical Fluid Chromatography t triplet TBME tert-butyl methyl ether TEA triethylamine TFA trifluoroacetic acid THF tetrahydrofuran Analytical Methods General Conditions:

NMR:

NMR spectra were recorded on Bruker AVANCE 400 MHz, 500 MHz or 600 MHz NMR spectrometers using ICON-NMR, under TopSpin program control. Spectra were measured at 298 K, unless indicated otherwise, and were referenced relative to known solvent resonances.

LC-MS:

Mass spectra were acquired on LC-MS, SFC-MS, or GC-MS systems using electrospray, chemical and electron impact ionization methods from a range of instruments of the following configurations: Waters Acquity UPLC/SQD system, using a photodiode array detector and a single quadrupole mass detector or Agilent 1200 systems with G 6110 series Mass Spectrometer [M+H]$^+$ refers to the protonated molecular ion of the chemical species.

Waters Acquity UPLC/SQD System:

Method A

| | |
|---|---|
| Column | Waters Acquity HSS T3 1.8 μm 2.1 × 50 mm or 2.1 × 100 mm |
| Column temperature | 60° C. |
| Eluents | A: water + 0.05% formic acid + 3.75 mM ammonium acetate, B: ACN + 0.04% formic acid |
| Flow rate | 1.0 ml/min |
| Gradient | 5% to 98% B in 1.4 min |

Method B

| | |
|---|---|
| Column | Waters Acquity HSS T3 1.8 μm 2.1 × 50 mm or 2.1 × 100 mm |
| Column temperature | 60° C. |
| Eluents | A: water + 0.05% formic acid + 3.75 mM ammonium acetate, B: ACN + 0.04% formic acid |
| Flow rate | 0.8 ml/min |
| Gradient | 5% to 98% B in 9.4 min |

Method C

| | |
|---|---|
| Column | Waters Acquity HSS T3 1.8 μm 2.1 × 50 mm or 2.1 × 100 mm |
| Column temperature | 50° C. |
| Eluents | A: water + 0.05% formic acid + 3.75 mM ammonium acetate, B: ACN + 0.04% formic acid |
| Flow rate | 1.2 ml/min |
| Gradient | 2% to 98% B in 1.4 min |

Method D

| | |
|---|---|
| Column | Waters Acquity HSS T3 1.8 μm 2.1 × 50 mm or 2.1 × 100 mm |
| Column temperature | 50° C. |
| Eluents | A: water + 0.05% formic acid + 3.75 mM ammonium acetate, B: ACN + 0.04% formic acid |
| Flow rate | 1.2 ml/min |
| Gradient | 1% to 98% B in 1.4 min |

Agilent 1200 Systems:

Method E

| | |
|---|---|
| Column | XBridge C18, 4.6 × 50 mm, 3.5 μm |
| Column temperature | 50° C. |
| Eluents | A: water (10 mM ammonium hydrogen carbonate), B: ACN |
| Flow rate | 1.8 ml/min |
| Gradient | 5% to 95% B in 1.5 min, 95% B for 1.5 min, back to 5% B within 0.01 min |

Method F

| | |
|---|---|
| Column | SunFire C18, 3 × 30 mm, 2.5 μm |
| Column temperature | 50° C. |
| Eluents | A: water, B: ACN, both containing 0.01% TFA |
| Flow rate | 1.5 ml/min |
| Gradient | 5% to 95% B in 1.5 min |

Method G

| | |
|---|---|
| Column | SunFire C18, 4.6 × 50 mm, 3.5 μm |
| Column temperature | 50° C. |
| Eluents | A: water, B: ACN, both containing 0.01% TFA |
| Flow rate | 2.0 ml/min |
| Gradient | 5% to 95% B in 1.4 min |

Method H

| | |
|---|---|
| Column | SunFire C18, 4.6 × 50 mm, 3.5 μm |
| Column temperature | 50° C. |
| Eluents | A: water, B: ACN, both containing 0.01% TFA |
| Flow rate | 2.0 ml/min |
| Gradient | 5% to 95% B in 1.2 min, 95% B for 1.3 min, back to 5% B within 0.01 min |

Method I

| | |
|---|---|
| Column | XBridge C18, 4.6 × 50 mm, 3.5 μm |
| Column temperature | 40° C. |
| Eluents | A: water (10 mM ammonium hydrogen carbonate) B: ACN |
| Flow rate | 1.8 ml/min |
| Gradient | 5% to 95% B in 1.4 min, 95% B for 1.6 min, back to 5% B within 0.01 min |

Method J

| Column | Phenomenex, 3.0 × 30 mm, 5 μm |
|---|---|
| Column temperature | 50° C. |
| Eluents | A: water (10mM ammonium hydrogen carbonate), B: ACN |
| Flow rate | 1.5 ml/min |
| Gradient | 5% to 95% B in 1.5 min, 95% B for 0.7 min |

Method K

| Column | XBridge C18, 4.6 × 50 mm, 3.5 μm |
|---|---|
| Column temperature | 40° C. |
| Eluents | A: water (10 mM ammonium hydrogen carbonate), B: ACN |
| Flow rate | 2.0 ml/min |
| Gradient | 5% to 95% B in 1.5 min |

Chiral Analytical HPLC:

Chiral analytical HPLC data were produced with a Shimadzu LC-20A analytical HPLC, using a photodiode array detector.

Method L

| Column | ChiralCel OJ, 5 μm, 250 × 4.6 mm |
|---|---|
| Column temperature | 25° C. |
| Eluents | hexane/EtOH (+0.05% DEA) 90:10 |
| Flow rate | 1.0 ml/min |
| UV detection | 220 nm (DAD detector) |

Chiral Analytical SFC:

Chiral analytical SFC data were produced with a Waters Acquity UPC2 system, using a photodiode array detector.

Method M

| Column | Daicel Chiralpak AD-H, 5 μm, 250 × 4.6 mm |
|---|---|
| Column temperature | 22° C. |
| Mobile Phase | CO$_2$/MeOH (80:20) |
| Flow rate | 3.0 ml/min |
| UV detection | 210 nm (DAD detector) |

Preparative Chromatography:

Normal and reverse phase flash chromatography purifications have been performed on a CombiFlash Rf200 or Rf+ system. Alternatively, chromatography purifications on reverse phase have been performed on an Interchim Puriflash 4250 system or a Biotage system. Supercritical fluid chromatography (SFC) separations have been performed using a Waters preparative SFC-100-MS system with either a Waters 2998 photodiode array detector or a Waters MS single quadrupole detection using MeOH as modifier. Generally, the back pressure was 120 bar, the flow 100 g CO$_2$/min and the column temperature 40° C. Reverse phase HPLC purifications have been performed on a Waters HPLC preparative system with either a Waters 2998 photodiode array detector or a Waters MS single quadrupole detection.

Chiral Preparative Chromatography:
Method 1

| Instrument | Sepiatec SFC100 System |
|---|---|
| Back pressure: | 120 bar |
| Column | Chiralpak AD-H, 5 μm, 250 × 30 mm |
| Column temperature | 40° C. |
| Mobile Phase | CO$_2$/MeOH (80:20) |
| Flow rate | 80 ml/min |
| UV detection | 254 nm (DAD detector) |

Method 2

| Instrument | MG II preparative SFC |
|---|---|
| Back pressure: | 120 bar |
| Column | ChiralCel OJ, 5 μm, 250 × 30 mm |
| Column temperature | 38° C. |
| Mobile Phase | CO$_2$/EtOH (85:15) |
| Flow rate | 60 ml/min |
| UV detection | 220 nm (DAD detector) |

Solid Phase Extraction (SPE) Cartridges:

For acid removal: PL-HCO3 MP SPE cartridges were purchased from Agilent Stratosphere—Ref: PL-HCO$_3$ MP-resin, 1.8 mmol/g, 100 A, 150-300 μm, 500 mg, 6 ml.

For Catch and Release: SCX cartridges were purchased from Agilent—Ref.: HF Mega DE-SCX, 2 g, 12 ml.

Synthesis of Intermediates

Intermediate 1a 3-(2,4-Dioxotetrahydropyrimidin-1(2H)-yl)-4-methoxybenzoic acid

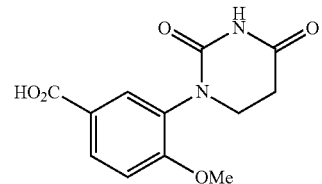 [SMILES: COc1ccc(C(=O)O)cc1N1CCC(=O)NC1=O]

Step 1:
3-((2-carboxyethyl)amino)-4-methoxybenzoic acid

3-Amino-4-methoxybenzoic acid (5.0 g, 29.3 mmol) was suspended in acrylic acid (8.05 ml, 117 mmol). The resulting beige suspension was stirred to 100° C. After 10 min, the stirring stopped and the RM was left at 100° C. for 3 h. The crude RM was directly used in the next step without further workup and further purification.

LC-MS (method A): Rt=0.56 min, [M+H]$^+$=240.2.

Step 2: 3-(2,4-dioxotetrahydropyrimidin-1 (2H)-yl)-4-methoxybenzoic acid

To the crude RM 3-((2-carboxyethyl)amino)-4-methoxybenzoic acid (7.01 g, 29.3 mmol) was added AcOH (33 ml). The suspension was heated to 100° C. and stirred for 10 min. Then, urea (11.00 g, 183 mmol) was added and the resulting mixture was stirred at 120° C. overnight. The resulting brown solution was then quenched into a cold solution of water (150 ml) and concentrated HCl (10 ml). After stirring, the resulting beige suspension was stored overnight in the fridge at 5° C., and then filtered. The filter cake was washed with water and dried to afford a brown solid. The brown solid was digested with 0.05M aq. HCl and filtered. The filter cake was washed with TBME (3×25 ml) and dried at 40° C. under reduced pressure to afford 6.29 g of the title compound as a beige solid.

LC-MS (method A): Rt=0.48 min, [M+H]$^+$=265.2.

Intermediate 1b

Pentafluorophenyl 3-(2,4-dioxotetrahydropyrimidin-1(2H)-yl)-4-methoxybenzoate

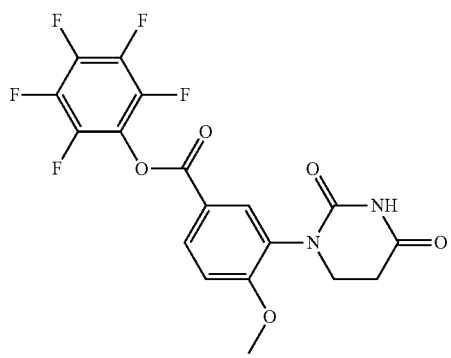 [SMILES: COc1ccc(C(=O)Oc2c(F)c(F)c(F)c(F)c2F)cc1N1CCC(=O)NC1=O]

To a 250 ml round bottom flask were added (3-(2,4)-dioxotetrahydropyrimidin-1(2H)-yl)-4-methoxybenzoic acid (intermediate 1a) (28 g, 106 mmol), pentafluorophenyl 2,2,2-trifluoroacetate (36 g, 127 mmol) and DMF (50 ml). Then, DIPEA (76 ml, 424 mmol) was added at 0° C. and the RM was stirred at RT for 2 h, then diluted with water (300 ml). The mixture was extracted with EtOAc (2×250 ml), the combined organic layers were washed with brine (2×10 ml), dried over Na$_2$SO$_4$, filtered and concentrated. Purification of the crude mixture by chromatography on silica gel eluting with 10-30% EtOAc in petroleum ether afforded 40 g of the title compound as a white solid.

LC-MS (method E): Rt=1.51 min, [M+H]$^+$=432.

Intermediate 1c 3-(2,4-Dioxotetrahydropyrimidin-1(2H)-yl)-4-ethoxybenzoic acid

3-Amino-4-ethoxybenzoic acid (2.7 g, 14.90 mmol) was suspended in acrylic acid (4.09 ml, 59.6 mmol) and the RM was stirred at 110° C. for 1 h. Urea (5.37 g, 89 mmol) and AcOH (18 ml) were added and the RM was stirred at 130° C. for 2 h. The RM was quenched with water, acidified with an aq. concentrated solution of HCl (37%) and extracted with EtOAc. The organic phases were combined and evaporated. Water was added, the mixture was filtered and the solids were washed with water and EtOAc yielding the title compound as a solid (1.1 g).

Method A: Rt=0.56 min; [M+H]$^+$=279.1.

Intermediate 2

4-Chloro-6-iodo-7-(phenylsulfonyl)-7H-pyrrolo[2,3-d]pyrimidine

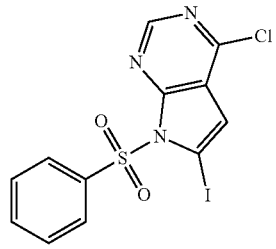 [SMILES: O=S(=O)(c1ccccc1)n1c(I)cc2c(Cl)ncnc21]

Step 1:4-chloro-7-(phenylsulfonyl)-7H-pyrrolo[2,3-d]pyrimidine

In a flame-dried flask placed under argon, sodium hydride 60% in mineral oil (1.563 g, 39.1 mmol) was added to DMF (60 ml) and the resulting mixture was cooled to 0° C. A solution of 6-chloro-7-deazapurine (4 g, 26.0 mmol) in DMF (20 ml) was slowly added over 10 min. The reaction was stirred for 10 min until hydrogen generation ceased. Then, benzenesulfonyl chloride (3.36 ml, 26.0 mmol) was added, and the reaction was stirred for 1 h at RT. Then, water was added and the resulting precipitate was filtered and dried under reduced pressure to afford 7.418 g of the title compound as a light grey solid.

LC-MS (Method C): Rt=1.01 min, [M+H]$^+$=294.1/296.0.

Step 2: 4-chloro-6-iodo-7-(phenylsulfonyl)-7H-pyrrolo[2,3-d]pyrimidine

To a stirred solution of 4-chloro-7-(phenylsulfonyl)-7H-pyrrolo[2,3-d]pyrimidine in dry THF (80 ml) under argon atmosphere, at −78° C., was added lithium diisopropylamide mono-THF 1.5 M in CHX (5.22 ml, 7.83 mmol) over 15 min. After 1 h, a solution of iodine (1.987 g, 7.83 mmol) in THF (20 ml) was added dropwise over 15 min. The resulting solution was stirred for 3 h. Then, water (2 ml) was then added and the mixture was allowed to warm to RT. The mixture was diluted with DCM, the orange organic layer was washed with brine (2×), dried over Na$_2$SO$_4$ and evaporated to dryness. The resulting orange-brown solid was triturated with ACN to afford 1.513 g of the title compound as beige solid.

LC-MS (Method C): Rt=1.12 min, [M+H]$^+$=419.9/421.9.

Intermediate 3a

4-(4-Chloro-7H-pyrrolo[2,3-d]pyrimidin-6-yl)benzaldehyde

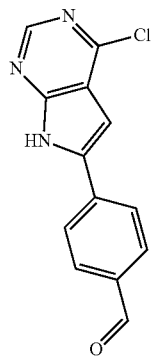 [SMILES: O=Cc1ccc(-c2cc3c(Cl)ncnc3[nH]2)cc1]

Step 1: (4-(4-chloro-7H-pyrrolo[2,3-d]pyrimidin-6-yl)phenyl)methanol

To a brown suspension of ethyl 4-(4-chloro-7H-pyrrolo[2,3-d]pyrimidin-6-yl)benzoate (which may be prepared according to the procedure described in published U.S. Pat. No. 6,140,332, column 45, example 30) (10.2 g, 33.8 mmol) in 100 ml THF under argon was slowly added a solution of lithium aluminum hydride 1M in THF (50.7 ml, 50.7 mmol) at 0-5° C. The RM was diluted with THF (5 ml) during the addition. After the addition, the RM was stirred at 0° C. for 10 min and was allowed to warm to RT. After 3 h stirring at RT, the RM was quenched at 0° C. with water (50 ml) and 15% aq. NaOH (50 ml) (exothermic, with gas evolution). The RM was filtered through Hyflo® (filter material), washed with THF (250 ml), and the filtrate was concentrated under reduced pressure to afford 9.32 g of the title compound.

LC-MS (Method A): Rt=0.78 min, [M+H]$^+$=260.1/262.1.

Step 2: 4-(4-chloro-7H-pyrrolo[2,3-d]pyrimidin-6-yl)benzaldehyde

A black suspension of (4-(4-chloro-7H-pyrrolo[2,3-d]pyrimidin-6-yl)phenyl)methanol (step 1) (9.32 g, 32.7 mmol) and manganese dioxide (28.4 g, 327 mmol) in THF (250 ml) was stirred at RT overnight. An additional batch of manganese dioxide (8.52 g, 98 mmol) was added to the RM and it was stirred at RT for another night. The RM was filtered through Hyflo® (filter material) and washed with THF (400 ml). The resulting filtrate was concentrated, diluted with THF, filtered through Hyflo® again and concentrated under reduced pressure to afford 5.68 g of the title compound.

LC-MS (Method A): Rt=0.88 min, [M+H]$^+$=258.1/260.1.

Intermediate 3b

4-(4-Chloro-7-(phenylsulfonyl)-7H-pyrrolo[2,3-d]pyrimidin-6-yl)benzaldehyde

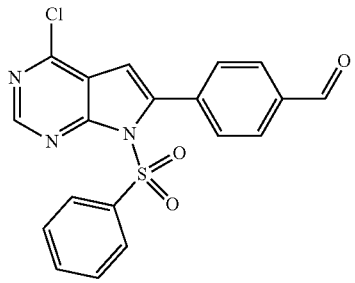 [SMILES: O=Cc1ccc(-c2cc3c(Cl)ncnc3n2S(=O)(=O)c2ccccc2)cc1]

To a 2 l flask, purged and maintained under inert atmosphere was added 4-chloro-6-iodo-7-(phenylsulfonyl)-7H-pyrrolo[2,3-d]pyrimidine (intermediate 2) (54 g, 129 mmol) and 4-formylphenylboronic acid (19 g, 129 mmol), Na$_2$CO$_3$ (40 g, 370 mmol) and PdCl$_2$(dppf) (9 g, 12.9 mmol). ACN (1200 ml) and water (300 ml) were added and the RM was stirred at 100° C. for 16 h under N$_2$. The RM was filtered and concentrated under vacuum. The crude mixture was purified by chromatography on silica gel eluting with 3-9% MeOH in DCM yielding 39 g of 4-(4-chloro-7-(phenylsulfonyl)-7H-pyrrolo[2,3-d]pyrimidin-6-yl)benzaldehyde as a yellow solid.

LC-MS (method I): Rt=1.99 min, [M+H]$^+$=398.

Intermediate 4

Tert-butyl 4-(2-oxoethoxy)piperidine-1-carboxylate

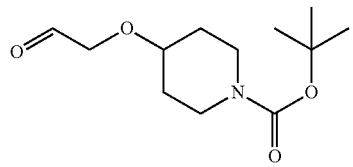 [SMILES: CC(C)(C)OC(=O)N1CCC(OCC=O)CC1]

Step 1: tert-butyl 4-(allyloxy)piperidine-1-carboxylate

Sodium hydride 60% in mineral oil (964 mg, 24.10 mmol) was added portionwise to a solution of 1-Boc-4-hydroxypiperidine (1000 mg, 4.82 mmol) in anhydrous THF (45 ml) under argon at RT. The stirring was continued for 30 min. Then allyl bromide (0.500 ml, 5.78 mmol) was dropped into the mixture and the RM was stirred at RT for 40 h. The RM was then quenched with water. The mixture was extracted with EtOAc, dried over Na$_2$SO$_4$, filtered and concentrated to afford the crude compound. Purification by flash chromatography on silica gel eluting with 0-20% EtOAc in CHX afforded 1130 mg of the title compound as a colorless liquid.

LC-MS (method A): Rt=1.13 min, [M-tBu+H]$^+$=186.1.

Step 2: tert-butyl 4-(2-oxoethoxy)piperidine-1-carboxylate

A solution of tert-butyl 4-(allyloxy)piperidine-1-carboxylate (1120 mg, 4.64 mmol) in anhydrous DCM (40 ml) was cooled to −78° C. in a two necked flask. Ozone was bubbled in RM for 70 min. Then the RM was allowed to warm up to RT and PPh₃ polymer bound (5 g, 16.00 mmol) was added to destroy ozonides. The RM was stirred at RT for 30 min. It was then filtered over Hyflo® and washed with DCM. The filtrate was evaporated to dryness affording 1147 mg of the title compound as colorless oil.

$^1$H NMR (400 MHz, DMSO-d6) δ 9.58 (s, 1H), 4.21 (s, 2H), 3.70-3.40 (m, 10H), 3.01 (s, 6H), 1.87-1.66 (m, 6H), 1.38 (dd, J=2.6, 1.2 Hz, 34H).

Intermediate 5

Tert-butyl 4-(4-(4-chloro-7H-pyrrolo[2,3-d]pyrimidin-6-yl)benzyl)piperazine-1-carboxylate

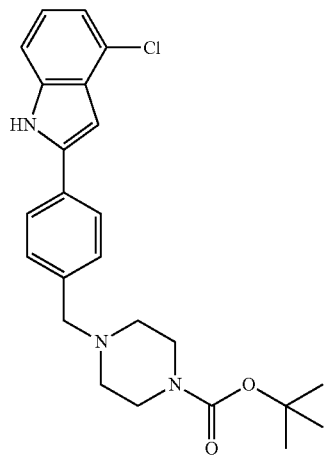 [SMILES: CC(C)(C)OC(=O)N1CCN(Cc2ccc(-c3cc4c(Cl)cccc4[nH]3)cc2)CC1]

A mixture of 4-chloro-6-iodo-7H-pyrrolo[2,3-d]pyrimidine (3.60 g, 12.88 mmol), Cs₂CO₃ (10.5 g, 32.2 mmol) and 4-(4-t-Boc-piperazinomethyl)phenylboronic acid (4.95 g, 15.46 mmol) in dioxane/water 1:1 (100 ml) was degassed with argon. Then PdCl₂(dppf)-CH₂Cl₂ adduct (1.052 g, 1.288 mmol) was added and the RM was stirred at 100° C. for 4 h. The RM was cooled to RT and then partitioned between EtOAc and water. Layers were separated, and the precipitate contained in the organic layer was filtered to afford 2.18 g of the title compound as a brown powder. The resulting filtrate was washed with brine, dried over MgSO₄ and concentrated to afford 4.65 g of the crude product. The crude product was triturated in ACN/Et₂O, filtered and dried under reduced pressure to afford 1.938 g more of the title compound as beige solid.

LC-MS (Method A): Rt=0.81 min, [M+H]⁺=428.2/430.2.

Intermediate 6

(trans-rac)-Tert-butyl 3-hydroxy-4-isobutylpyrrolidine-1-carboxylate

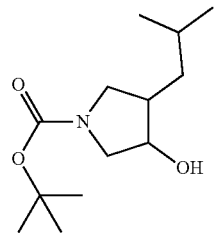 [SMILES: CC(C)CC1CN(C(=O)OC(C)(C)C)CC1O]

To a solution of tert-butyl 6-oxa-3-azabicyclo[3,1,0] hexane-3-carboxylate (10 g, 52.9 mmol) and copper(I) bromide-dimethyl sulfide complex (1.5 g, 7.30 mmol) in THF (200 ml) was added dropwise isobutylmagnesium chloride 2M in THF (100 ml, 200 mmol) at −30° C. under argon. The resulting dark solution was stirred below −15° C. for 1 h. Then the RM was quenched with 10% aq. NH₄Cl and became blue. EtOAc was added and the mixture was stirred at RT for 30 min. Then the layers were separated and the aq. layer was extracted with EtOAc (3×). The combined organic layers were washed with brine, dried over MgSO₄, filtered and concentrated under reduced pressure. Purification of the crude product by flash chromatography on silica gel eluting with 0-20% EtOAc in petroleum ether afforded 11.82 g of the title compound as a pale yellow oil.

$^1$H NMR (400 MHz, Chloroform-d) δ 3.96 (q, J=5.2 Hz, 1H), 3.59 (dd, J=11.2, 6.3 Hz, 2H), 3.19 (dd, J=11.5, 4.6 Hz, 1H), 3.00 (dd, J=10.9, 6.0 Hz, 1H), 2.07 (dp, J=12.3, 5.8 Hz, 1H), 1.91 (s, 1H), 1.60 (dt, J=13.2, 6.6 Hz, 1H), 1.43 (d, J=12.6 Hz, 13H), 1.31 (ddd, J=13.5, 8.3, 5.3 Hz, 1H), 1.13 (ddd, J=13.7, 9.4, 5.9 Hz, 1H), 0.90 (dd, J=8.8, 6.6 Hz, 6H).

Intermediate 7

(3R,4S)—N-(5-Fluoro-2-methyl-3-(4,4,5,5-tetramethyl-1,3,2-dioxaborolan-2-yl)phenyl)-3-hydroxy-4-isobutylpyrrolidine-1-carboxamide

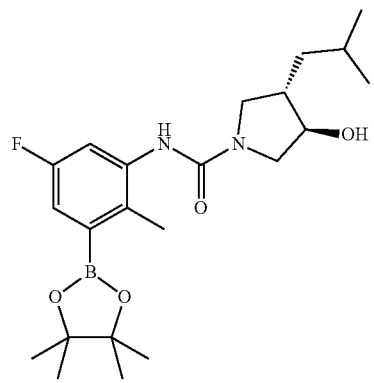 [SMILES: Cc1c(NC(=O)N2C[C@H](CC(C)C)[C@@H](O)C2)cc(F)cc1B1OC(C)(C)C(C)(C)O1]

Step 1: (trans-rac)-benzyl 3-hydroxy-4-isobutylpyrrolidine-1-carboxylate

To a suspension of benzyl 6-oxa-3-azabicyclo[3.1.0] hexane-3-carboxylate (8.9 g, 40.6 mmol) and copper(I)

bromide-dimethyl sulfide complex (0.835 g, 4.06 mmol) in THF (200 ml) under N$_2$ was added dropwise isobutylmagnesium chloride 2M in THF (79 ml, 158 mmol) over 20 min, the temperature remaining below −15° C. The resulting dark solution was stirred below −15° C. for 1 h. The RM was quenched with 10% aq. NH$_4$Cl (exothermic), and became blue. EtOAc and water were added and the mixture was stirred at RT for 30 min. Layers were separated and the aq. layer was extracted with EtOAc (2×). Combined organic layers were washed with water (2×) and with brine (1×), dried over Na$_2$SO$_4$, filtered and concentrated under reduced pressure to afford 10.62 g of the crude product. Purification of the crude product by flash chromatography on silica gel eluting with 0-50% EtOAc in hexane afforded 5.67 g of a material. Purification of the material by flash chromatography on silica gel eluting with 0-30% MeOH (+10% NH$_4$OH) in DCM afforded 3.911 g of the title compound.

LC-MS (Method A): Rt=1.05 min, [M+H]$^+$=278.4.

Step 2: (3S,4R)-benzyl 3-hydroxy-4-isobutylpyrrolidine-1-carboxylate and (3R,4S)-benzyl 3-hydroxy-4-isobutylpyrrolidine-1-carboxylate Chiral separation of (trans-rac)-benzyl 3-hydroxy-4-isobutylpyrrolidine-1-carboxylate using SFC (preparative method 1) afforded the individual enantiomers as colorless oils; 1$^{st}$ eluting peak (peak 1) gave 1.64 g (3S,4R)-benzyl 3-hydroxy-4-isobutylpyrrolidine-1-carboxylate and the 2$^{nd}$ eluting peak (peak 2) yielded 1.65 g of (3R,4S)-benzyl 3-hydroxy-4-isobutylpyrrolidine-1-carboxylate:

(3S,4R)-benzyl 3-hydroxy-4-isobutylpyrrolidine-1-carboxylate:
SFC (method M): Rt=2.51 min.
LC-MS (Method A): Rt=1.06 min, [M+H]$^+$=278.2.
(3R,4S)-benzyl 3-hydroxy-4-isobutylpyrrolidine-1-carboxylate:
SFC (method M): Rt=3.75 min.
LC-MS (Method A): Rt=1.06 min, [M+H]$^+$=278.2.

Step 3: (3R,4S)-4-isobutylpyrrolidin-3-ol

A solution of (3R,4S)-benzyl 3-hydroxy-4-isobutylpyrrolidine-1-carboxylate, the 2$^{nd}$ eluting peak of step 2, (1.65 g, 5.95 mmol) in MeOH (20 ml) was treated with 10% palladium on carbon (0.4 g, 3.76 mmol) and the RM was placed under 0.1 bar of hydrogen at 25-30° C. After 2 h, the RM was filtered through Hyflo® (filter material) and washed with MeOH. The filtrate was concentrated and dried under vacuum to afford a yellow oil. The oil was dissolved in DCM, and 4M HCl in dioxane (2.231 ml, 8.92 mmol) was added to form the hydrochloride salt. Then, Et$_2$O was added, the precipitate formed was filtered and dried under reduced pressure to afford 840 mg of the title compound as an HCl salt.

$^1$H NMR (600 MHz, DMSO-d$_6$) δ ppm 0.88 (dd, J=16.69, 6.60 Hz, 6H) 1.13 (ddd, J=13.66, 8.99, 6.33 Hz, 1H) 1.25 (ddd, J=13.75, 7.70, 6.42 Hz, 1H) 1.54-1.63 (m, 1H) 2.06-2.13 (m, 1H) 2.81 (dq, J=11.14, 5.70 Hz, 1H) 2.86-2.97 (m, 1H) 3.19-3.27 (m, 1H) 3.30-3.35 (m, 1H) 3.97 (q, J=3.85 Hz, 1H) 5.46 (brs, 1H) 9.12-9.58 (m, 2H).

Step 4: (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide To a solution of 5-fluoro-2-methyl-3-(4,4,5,5-tetramethyl-1,3,2-dioxaborolan-2-yl)aniline (commercially available, or could be prepared according to the procedure of published patent application WO2013/008095, page 37, intermediate 5) (1 g, 3.98 mmol) and DIPEA (2.78 ml, 15.93 mmol) in DCM (25 ml) was slowly added phosgene 20% in toluene (2.51 ml, 4.78 mmol) below 0° C. The resulting solution was stirred at 0° C. for 30 min, then added into a stirring solution of (3R,4S)-4-isobutylpyrrolidin-3-ol (step 3) (0.787 g, 4.38 mmol) in DCM (25 ml) at 0° C. The resulting mixture was stirred at 0° C. for 45 min. Then, the RM was concentrated, diluted with EtOAc/MeOH (9:1), washed with water (3×) and with brine (1×). The organic layer was then dried with MgSO$_4$ and concentrated to give 1.86 g of the crude product. Purification of the crude product by flash chromatography on silica gel eluting with 0-100% EtOAc (+5% EtOH) in hexane afforded 1.455 g of the title compound.

LC-MS (Method A): Rt=1.18 min, [M+H]$^+$=421.4.

Intermediate 8

(3S,4R)—N-(5-Fluoro-2-methyl-3-(4,4,5,5-tetramethyl-1,3,2-dioxaborolan-2-yl)phenyl)-3-hydroxy-4-isobutylpyrrolidine-1-carboxamide

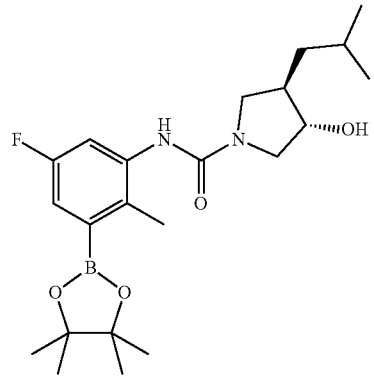 [SMILES: Cc1c(NC(=O)N2C[C@@H](CC(C)C)[C@H](O)C2)cc(F)cc1B1OC(C)(C)C(C)(C)O1]

Step 1 and 2: See Intermediate 7

Step 3: (3S,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide To a solution of 5-fluoro-2-methyl-3-(4,4,5,5-tetramethyl-1,3,2-dioxaborolan-2-yl)aniline (commercially available, or could be prepared according to the procedure of published patent application WO2013/008095, page 37, intermediate 5) (950 mg, 3.78 mmol) and DIPEA (2.64 ml, 15.13 mmol) in DCM (25 ml) was slowly added phosgene 20% in toluene (2.389 ml, 4.54 mmol) below 0° C. The resulting solution was stirred at 0° C. for 15 min, then added into a stirring solution of (3S,4R)-4-isobutylpyrrolidin-3-ol (748 mg, 4.16 mmol) in DCM (25 ml) at 0° C. The resulting mixture was stirred at 0° C. for 30 min. Then the RM was concentrated, diluted with EtOAc/MeOH (9:1), washed with water (3×) and with brine (1×). The organic layerwas then dried with MgSO$_4$ and concentrated to give 1.764 g of crude product. Purification of the crude product by flash chromatography on silica gel eluting with 0-100% EtOAc (+5% EtOH) in hexane afforded 1.38 g of the title compound as a white foam.

LC-MS (Method A): Rt=1.18 min, [M+H]$^+$=421.4.

Intermediate 9

(cis-rac)-N-(5-Fluoro-2-methyl-3-(4,4,5,5-tetramethyl-1,3,2-dioxaborolan-2-yl)phenyl)-3-hydroxy-4-isobutylpyrrolidine-1-carboxamide

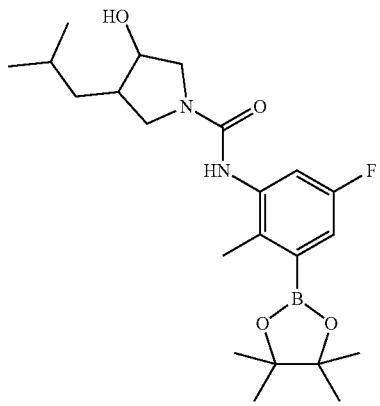 [SMILES: Cc1c(NC(=O)N2CC(O)C(CC(C)C)C2)cc(F)cc1B1OC(C)(C)C(C)(C)O1]

Step 1: cis-rac-tert-butyl 3-isobutyl-4-((4-nitrobenzoyl)oxy)pyrrolidine-1-carboxylate To a solution of (trans-rac)-tert-butyl 3-hydroxy-4-isobutylpyrrolidine-1-carboxylate (intermediate 6) (11.82 g, 43.2 mmol), 4-nitrobenzoic acid (11 g, 65.2 mmol) and PPh$_3$ (18 g, 65.2 mmol) at 0° C. in THF (250 ml) was added dropwise DIAD (13 ml, 65.5 mmol) over 1 h under argon. The resulting orange solution was allowed to slowly warm to RT for 3 additional hours. The RM was quenched with water, and THF was partially evaporated. EtOAc was added and the mixture was extracted with EtOAc (3×). The combined organic layers were washed with 0.2M HCl and brine, dried over MgSO$_4$, filtered and evaporated under reduced pressure. Purification of the crude product by flash chromatography on silica gel eluting with 0-15% EtOAc in CHX afforded 16.43 g of the title compound as a pale yellow foam.

LC-MS (Method A): Rt=1.41 min, [M-tBu+H]$^+$=337.2.

Step 2: (cis-rac)-tert-butyl 3-hydroxy-4-isobutylpyrrolidine-1-carboxylate

To a solution of (cis-rac)-tert-butyl 3-isobutyl-4-((4-nitrobenzoyl)oxy)pyrrolidine-1-carboxylate (step 1) (16.43 g, 41.9 mmol) in MeOH/H$_2$O 3:1 (160 ml) was added NaOH (3.35 g, 84 mmol). The RM was stirred at RT for 1.5 h. Then, the RM was adjusted to pH 6 using 1M aq. HCl. MeOH was partially evaporated, then EtOAc was added and the mixture was stirred at RT for 30 min. The mixture was extracted with EtOAc (3×), dried over MgSO$_4$, filtered and concentrated under reduced pressure. The resulting white residue was triturated in DCM and filtered. Purification of the resulting yellow filtrate by flash chromatography on silica gel eluting from 0-35% EtOAc in CHX afforded a material, that was then triturated in DCM and filtered. The resulting filtrate was concentrated to give 10.602 g of the title compound as yellow oil.

$^1$H NMR (400 MHz, Chloroform-d) δ 4.26-4.15 (m, 1H), 3.53 (t, J=9.1 Hz, 1H), 3.44 (d, J=1.7 Hz, 2H), 3.03 (t, J=10.7 Hz, 1H), 2.86-2.21 (m, 1H), 2.13 (dqd, J=11.4, 7.9, 3.8 Hz, 1H), 1.59 (dp, J=13.3, 6.7 Hz, 1H), 1.43 (d, J=13.2 Hz, 24H), 0.91 (d, J=6.6 Hz, 7H).

Step 3: (cis-rac)-4-isobutylpyrrolidin-3-ol

A solution of (cis-rac)-tert-butyl 3-hydroxy-4-isobutylpyrrolidine-1-carboxylate (step 2) (1.040 g, 4.06 mmol) and HCl 4M in dioxane (10 ml) was stirred at RT overnight. The RM was concentrated, then co-evaporated with DCM and dried under reduced pressure to afford 770 mg of the title compound as an HCl salt, as an off-white solid.

$^1$H NMR (400 MHz, DMSO-d6) δ 9.27 (s, 2H), 5.46-5.17 (m, 1H), 4.25-3.97 (m, 1H), 3.26-3.11 (m, 3H), 3.04 (d, J=12.1 Hz, 1H), 2.72 (t, J=11.3 Hz, 1H), 2.05 (dt, J=7.3, 3.8 Hz, 1H), 1.55 (dq, J=13.2, 6.6 Hz, 1H), 1.38 (dt, J=13.9, 7.1 Hz, 1H), 1.18 (dt, J=13.9, 7.2 Hz, 1H), 0.86 (d, J=6.3 Hz, 6H).

Step 4: (cis-rac)-N-(5-fluoro-2-methyl-3-(4,4,5,5-tetramethyl-1,3,2-dioxaborolan-2-yl)phenyl)-3-hydroxy-4-isobutylpyrrolidine-1-carboxamide Phosgene 15% in toluene (1.3 ml, 1.821 mmol) was dropped into a solution of 5-fluoro-2-methyl-3-(4,4,5,5-tetramethyl-1,3,2-dioxaborolan-2-yl)aniline (CAS 1227210-37-8) (commercially available, or could be prepared according to the procedure of published patent application WO2013/008095, page 37, intermediate 5) (438 mg, 1.708 mmol) and DIPEA (0.5 ml, 2.86 mmol) in dry DCM (10 ml) at 0° C. The RM was stirred at 0° C. for 30 min. Then a solution of (cis-rac)-4-isobutylpyrrolidin-3-ol (step 3) (323 mg, 1.705 mmol) and DIPEA (0.5 ml, 2.86 mmol) in dry DCM (1 ml) was added dropwise at 0° C. The resulting pale orange solution was stirred at 0° C. for 2 h. The mixture was partitioned between DCM and sat. aq. NaHCO$_3$ solution. The organic layer was washed with sat. aq. NH$_4$Cl and with brine, dried over Na$_2$SO$_4$ and evaporated. Purification of the crude compound by flash chromatography on silica gel eluting with 0-15% MeOH in DCM afforded 793 mg of the title compound.

LC-MS (Method A): Rt=1.22 min, [M+H]$^+$=421.4.

91

Intermediate 10

(cis-rac)-N-(5-Fluoro-3-(6-(4-formylphenyl)-7H-pyrrolo[2,3-d]pyrimidin-4-yl)-2-methylphenyl)-3-hydroxy-4-isobutylpyrrolidine-1-carboxamide

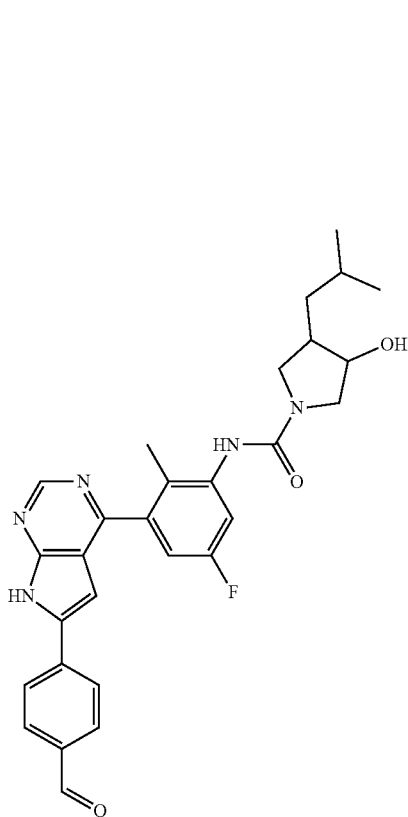 [SMILES: Cc1c(NC(=O)N2CC(O)C(CC(C)C)C2)cc(F)cc1-c1ncnc2[nH]c(-c3ccc(C=O)cc3)cc12]

A mixture of 4-(4-chloro-7H-pyrrolo[2,3-d]pyrimidin-6-yl)benzaldehyde (intermediate 3a) (375 mg, 1.323 mmol), K₂CO₃ (402 mg, 2.88 mmol) and (cis-rac)-N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 9) (701 mg, 1.151 mmol) in dioxane/water 1:1 (10 ml) was degassed with argon. Then, PdCl₂(dppf)-CH₂Cl₂ adduct (94 mg, 0.115 mmol) was added and the RM was stirred at 100° C. for 1 h. The RM was partitioned between EtOAc and water. The organic layer was washed with brine, dried over MgSO₄ and concentrated under reduced pressure. The crude product was diluted in MeOH/diisopropyl ether, cooled at 4° C., and the suspension was filtered to afford 190 mg of the title compound as a yellow solid. Purification of the filtrate by flash chromatography on silica gel eluting with 0-12.5% MeOH in DCM afforded an additional amount (311 mg) of the title compound.

LC-MS (Method A): Rt=0.98 min, [M+H]⁺=516.3.

92

Intermediate 11

(3R,4S)—N-(5-Fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide

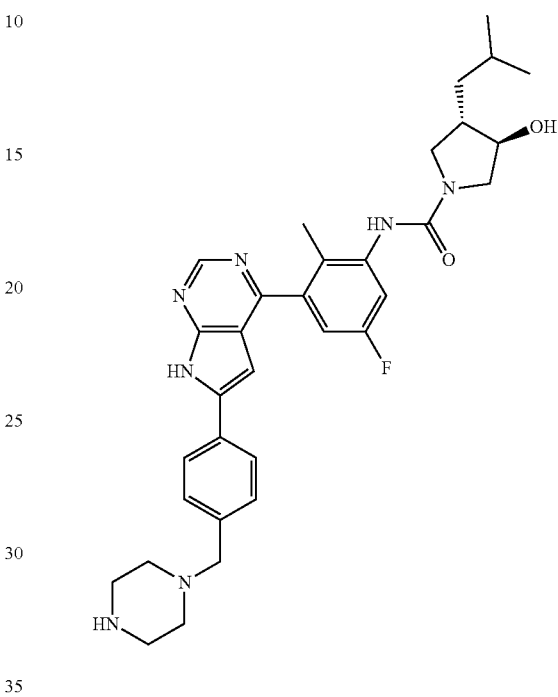

Step 1: tert-butyl 4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)piperazine-1-carboxylate A mixture of tert-butyl 4-(4-(4-chloro-7H-pyrrolo[2,3-d]pyrimidin-6-yl)benzyl)piperazine-1-carboxylate (intermediate 5) (500 mg, 1.110 mmol), K₂CO₃ (384 mg, 2.78 mmol) and (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 7) (500 mg, 1.13 mmol) in dioxane/water 1:1 (10 ml) was degassed with argon. PdCl₂(dppf).CH₂Cl₂ adduct (91 mg, 0.111 mmol) was then added and the RM was stirred at 100° C. for 2 h. The RM was cooled down to RT and then partitioned between EtOAc and water. Layers were separated. The organic layer was washed with brine, dried over MgSO₄ and concentrated under reduced pressure. Purification of the crude product by flash chromatography on silica gel eluting with 0-40% DCM/MeOH/NH₃ (80:20:1) in DCM afforded 514 mg of the title compound as an orange solid.

LC-MS (Method A): Rt=0.88 min, [M+H]⁺=686.5.

Step 2: (3R,4S)—N-(5-fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide A brownish solution of tert-butyl 4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)

piperazine-1-carboxylate (step1) (507 mg, 0.724 mmol) and HCl 4M in dioxane (2 ml, 8.00 mmol) in MeOH (2 ml) was stirred at RT for 2 h. The RM was concentrated and dried under reduced pressure to afford 509 mg of the title compound as an HCl salt.

LC-MS (Method A): Rt=0.71 min, [M+H]⁺=586.5.

Intermediate 12

(3R,4S)—N-(5-Fluoro-2-methyl-3-(6-(4-(piperidin-4-yloxy)phenyl)-7H-pyrrolo[2,3-d]pyrimidin-4-yl)phenyl)-3-hydroxy-4-isobutylpyrrolidine-1-carboxamide

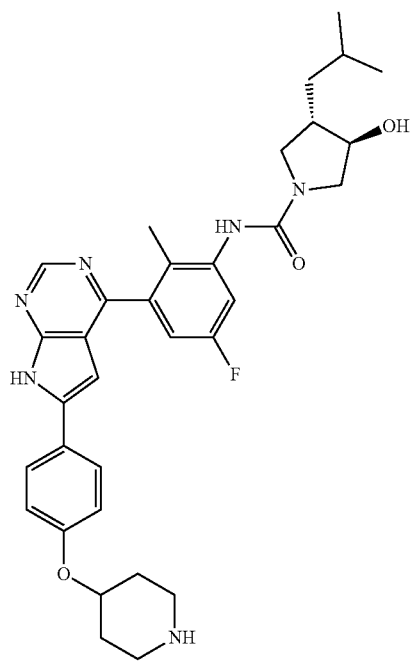 [SMILES: Cc1c(NC(=O)N2C[C@H](CC(C)C)[C@@H](O)C2)cc(F)cc1-c1ncnc2[nH]c(-c3ccc(OC4CCNCC4)cc3)cc12]

Step 1: tert-butyl 4-(4-(4,4,5,5-tetramethyl-1,3,2-dioxaborolan-2-yl)phenoxy)piperidine-1-carboxylate To a solution of 4-hydroxyphenylboronic acid pinacol ester (1.030 g, 4.68 mmol), 1-Boc-4-hydroxypiperidine (1.057 g, 5.15 mmol) and PPh₃ (1.35 g, 5.15 mmol) at 0° C. in THF (20 ml) was added dropwise DIAD (1 ml, 5.14 mmol) under argon. The resulting solution was stirred at RT for 3 days. The RM was partitioned between EtOAc and a sat. aq. NaHCO₃ solution. The organic layer was separated, washed with brine, dried over MgSO₄ and concentrated under reduced pressure. Purification of the crude product by flash chromatography on silica gel eluting with 0-20% EtOAc in CHX afforded 1.249 g of the title compound.

LC-MS (Method A): Rt=1.48 min, [M+H]⁺=404.2.

Step 2: tert-butyl 4-(4-(4-chloro-7H-pyrrolo[2,3-d]pyrimidin-6-yl)phenoxy)piperidine-1-carboxylate A mixture of 4-chloro-6-iodo-7H-pyrrolo[2,3-d]pyrimidine (Synnovator, Inc., CAS[876343-10-1]) (855 mg, 3.06 mmol), Cs₂CO₃ (2492 mg, 7.65 mmol) and tert-butyl 4-(4-(4,4,5,5-tetramethyl-1,3,2-dioxaborolan-2-yl)phenoxy)piperidine-1-carboxylate (step 1) (1234 mg, 3.06 mmol) in dioxane/water 1:1 (30 ml) was degassed with argon. PdCl₂(dppf)-CH₂Cl₂ adduct (250 mg, 0.306 mmol) was added and the RM was stirred at 100° C. for 3 h. The RM was cooled to RT and then partitioned between EtOAc and sat. aq. NaHCO₃. Layers were separated, then the organic layer was washed with brine, dried over MgSO₄ and concentrated under reduced pressure. Purification of the crude product by flash chromatography on silica gel eluting with 0-100% EtOAc in CHX afforded a brown residue. The residue was then triturated with MeOH, the resulting suspension was filtered, washed with Et₂O and dried under reduced pressure to afford 1.039 g of the title compound as a beige powder.

LC-MS (Method A): Rt=1.24 min, [M+H]⁺=429.3/431.2.

Step 3: tert-butyl 4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidine-1-carboxylate A mixture of tert-butyl 4-(4-(4-chloro-7H-pyrrolo[2,3-d]pyrimidin-6-yl)phenoxy)piperidine-1-carboxylate (step 2) (295 mg, 0.420 mmol), K₂CO₃ (145 mg, 1.049 mmol) and (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 7) (200 mg, 0.476 mmol) in dioxane/water 1:1 (4 ml) was degassed with argon. PdCl₂(dppf)-CH₂Cl₂ adduct (34 mg, 0.042 mmol) was added and the RM was stirred at 100° C. for 1 h. The RM was cooled down to RT and then partitioned between EtOAc and water. Layers were separated, then the organic layer was washed with brine, dried over MgSO₄ and concentrated under reduced pressure. Purification of the crude product by flash chromatography on silica gel eluting with 0-38% MeOH in DCM afforded 303 mg of the title compound.

LC-MS (Method A): Rt=1.22 min, [M+H]⁺=687.3.

Step 4: (3R,4S)—N-(5-fluoro-2-methyl-3-(6-(4-(piperidin-4-yloxy)phenyl)-7H-pyrrolo[2,3-d]pyrimidin-4-yl)phenyl)-3-hydroxy-4-isobutylpyrrolidine-1-carboxamide A brownish solution of tert-butyl 4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidine-1-carboxylate (step 3) (303 mg, 0.393 mmol) and HCl 4M in dioxane (2 ml, 8.00 mmol) in MeOH (2 ml) was stirred at RT for 1 h. Then, the RM was concentrated under reduced pressure. Purification of the crude product by reverse phase flash chromatography on a Redisep® C18 column eluting with 2-100% ACN in (water+0.1% TFA) afforded 317 mg of the title compound as an orange powder as a TFA salt.

LC-MS (Method A): Rt=0.76 min, [M+H]⁺=587.3.

Intermediate 13

Tert-butyl 9-(4-(4-chloro-7-(phenylsulfonyl)-7H-pyrrolo[2,3-d]pyrimidin-6-yl)phenethyl)-3,9-diaz-aspiro[5.5]undecane-3-carboxylate

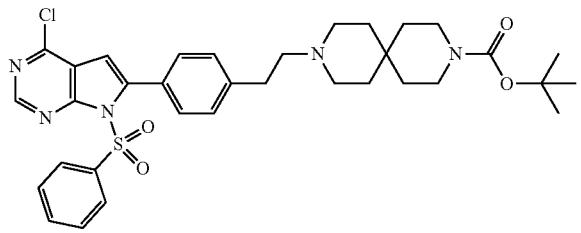 [SMILES: CC(C)(C)OC(=O)N1CCC2(CCN(CCc3ccc(-c4cc5c(Cl)ncnc5n4S(=O)(=O)c4ccccc4)cc3)CC2)CC1]

Step 1: 2-(4-(4,4,5,5-tetramethyl-1,3,2-dioxaborolan-2-yl)phenyl)ethan-1-ol

A mixture of 2-(4-bromophenyl)ethan-1-ol (CAS 4654-39-1) (60 g, 300 mmol), BISPIN (84 g, 330 mmol), KOAc (90 g, 900 mmol) and $PdCl_2(dppf)$ (6.6 g, 9 mmol) in dioxane (600 ml) was stirred under $N_2$ at 85° C. for 16 h. Then, the RM was cooled down to RT and filtered. The resulting solution was concentrated under reduced pressure. Purification of the crude residue by chromatography on silica gel eluting with 0-30% EtOAc in petroleum ether afforded 100 g of the title compound as a colorless oil.

LC-MS (Method I): Rt=1.87 min, $[M+NH_4]^+$=266.

Step 2: 4-(4,4,5,5-tetramethyl-1,3,2-dioxaborolan-2-yl)phenethyl methanesulfonate A mixture of 2-(4-(4,4,5,5-tetramethyl-1,3,2-dioxaborolan-2-yl)phenyl)ethan-1-ol (step 1) (100 g, 300 mmol) and TEA (240 g, 2400 mmol) in DCM (1300 ml) was stirred at 0° C. for 20 min. Then, MsCl (136 g, 1200 mmol) in DCM (200 ml) was dropwise added. After the addition, the RM was stirred at RT for 16 h. Then, the mixture was washed with water (3×300 ml), dried over $Na_2SO_4$ and concentrated under reduced pressure. Purification of the crude residue by chromatography on silica gel eluting with 0-50% EtOAc in DCM afforded 87 g of the title compound as a colorless oil.

LC-MS (Method H): Rt=1.92 min, $[M+H]^+$=327.

Step 3: tert-butyl 9-(4-(4,4,5,5-tetramethyl-1,3,2-dioxaborolan-2-yl)phenethyl)-3,9-diazaspiro[5.5]undecane-3-carboxylate A mixture of tert-butyl 3,9-diazaspiro[5.5]undecane-3-carboxylate (CAS 173405-78-2) (34 g, 133 mmol), 4-(4,4,5,5-tetramethyl-1,3,2-dioxaborolan-2-yl)phenethyl methanesulfonate (step 2) (86 g, 172 mmol), $K_2CO_3$ (47 g, 345 mmol) and KI (2.3 g, 13.8 mmol) in ACN (1000 ml) was stirred at 60° C. for 16 h. The RM was then filtered, and the solution was concentrated under reduced pressure. Purification of the crude residue by chromatography on silica gel eluting with 0-10% MeOH in DCM afforded 49 g of the title compound as a white solid.

LC-MS (method F): Rt=1.47 min, $[M+H]^+$=485.

Step 4: tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate A mixture of tert-butyl 9-(4-(4,4,5,5-tetramethyl-1,3,2-dioxaborolan-2-yl)phenethyl)-3,9-diazaspiro[5.5]undecane-3-carboxylate (step 3) (38 g, 79 mmol), intermediate 2 (37 g, 88 mmol), $K_2CO_3$ (22 g, 160 mmol) and $PdCl_2(dppf)$ (5.8 g, 8 mmol) in 5:1 dioxane/water (480 ml) was stirred under $N_2$ at 80° C. for 16 h. The RM was then poured into EtOAc (1500 ml), the organic layer was washed with water (100 ml), dried over $Na_2SO_4$, filtered and concentrated under reduced pressure. Purification of the crude residue by chromatography on silica gel eluting with 0-10% MeOH in DCM afforded 34 g of the title compound as a yellow solid.

LC-MS (method F): Rt=1.99 min, $[M+H]^+$=650.

Intermediate 14

1-(2-Methoxy-5-(3,9-diazaspiro[5.5]undecane-3-carbonyl)phenyl)dihydropyrimidine-2,4(1H,3H)-dione

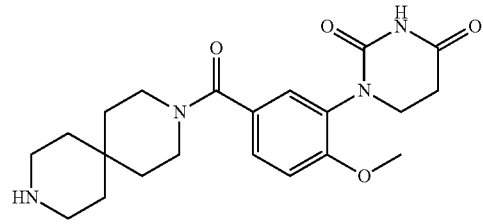 [SMILES: COc1ccc(C(=O)N2CCC3(CCNCC3)CC2)cc1N1CCC(=O)NC1=O]

Step 1: tert-butyl 9-(3-(2,4-dioxotetrahydropyrimidin-1 (2H)-yl)-4-methoxybenzoyl)-3,9-diazaspiro[5.5]undecane-3-carboxylate At RT, to a stirred solution of 3,9-diaza-spiro[5.5]undecane-3-carboxylic acid tert-butyl ester (432 mg, 1.698 mmol) and NMM (0.392 ml, 3.57 mmol) under argon in DMF (4 ml) was added intermediate 1a (471 mg, 1.783 mmol), followed by HATU (743 mg, 1.953 mmol). The clear RM was stirred at RT for 2.5 h and then quenched with sat. aq. $NaHCO_3$, and diluted with EtOAc. Layers were separated and the aq. layer was extracted with EtOAc (1×). Combined organic layers were washed with brine/water 1:1 (2×) and brine (1×), dried over $MgSO_4$, filtered and concentrated under reduced pressure to give 900 mg of the title compound.

LC-MS (Method A): Rt=0.91 min, $[M+H]^+$=501.4.

Step 2: 1-(2-methoxy-5-(3,9-diazaspiro[5.5]undecane-3-carbonyl)phenyl)dihydropyrimidine-2,4(1H,3H)-dione A solution of tert-butyl 9-(3-(2,4-dioxotetrahydropyrimidin-1(2H)-yl)-4-methoxybenzoyl)-3,9-diazaspiro[5.5]undecane-3-carboxylate (step 1) (100 mg, 0.200 mmol) and HCl 4M in dioxane (1 ml, 4 mmol) was stirred in MeOH (1 ml) at RT for 1.5 h. The RM was concentrated and dried under reduced pressure to afford 99 mg of the title compound as a hydrochloride salt.

LC-MS (Method D): Rt=0.76 min; $[M+H]^+$=401.4.

Intermediate 15

Tert-butyl 4-((4-(4-chloro-7H-pyrrolo[2,3-d]pyrimidin-6-yl)benzyl)oxy)piperidine-1-carboxylate

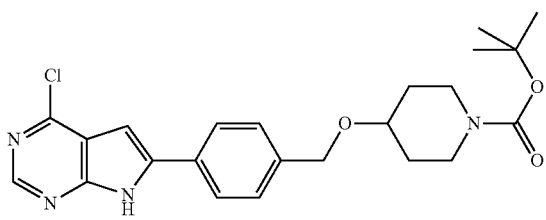 [SMILES: CC(C)(C)OC(=O)N1CCC(OCc2ccc(-c3cc4c(Cl)ncnc4[nH]3)cc2)CC1]

To an orange suspension of 4-chloro-6-iodo-7H-pyrrolo[2,3-d]pyrimidine (848 mg, 3.03 mmol) and (4-(((1-(tert-butoxycarbonyl)piperidin-4-yl)oxy)methyl)phenyl)boronic acid (1.068 g, 3.19 mmol) in 1-propanol (20 ml) under argon was added PdCl$_2$(PPh$_3$)$_2$ (106 mg, 0.152 mmol), followed by Na$_2$CO$_3$ 2M in water (3.03 ml, 6.07 mmol). The RM was stirred at 100° C. overnight. Then it was diluted with EtOAc, washed with water and brine. The organic layer was dried over MgSO$_4$, filtered and concentrated under reduced pressure. Purification of the crude product by flash chromatography on silica gel eluting with 0-100% EtOAc in CHX afforded 844 mg of the title compound.

LC-MS (Method A): Rt=1.29 min, [M+H]$^+$=443.3

Intermediate 16

Tert-butyl 4-(2-(4-((4-(4-chloro-7H-pyrrolo[2,3-d]pyrimidin-6-yl)benzyl)oxy)piperidin-1-yl)ethyl)piperidine-1-carboxylate

Step 1: 4-chloro-6-(4-((piperidin-4-yloxy)methyl)phenyl)-7H-pyrrolo[2,3-d]pyrimidine A yellow solution of tert-butyl 4-((4-(4-chloro-7H-pyrrolo[2,3-d]pyrimidin-6-yl)benzyl)oxy)piperidine-1-carboxylate (intermediate 15) (515 mg, 1.163 mmol) and TFA (2.69 ml, 34.9 mmol) in DCM (3 ml) was stirred at RT for 2 h under argon. The solution was then concentrated and then dried under reduced pressure to afford 664 mg of the title compound as a TFA salt.

LC-MS (Method A): Rt=0.66 min; [M+H]$^+$=343.2/345.2.

Step 2: tert-butyl 4-(2-(4-((4-(4-chloro-7H-pyrrolo[2,3-d]pyrimidin-6-yl)benzyl)oxy)piperidin-1-yl)ethyl)piperidine-1-carboxylate To a brown solution of 4-chloro-6-(4-((piperidin-4-yloxy)methyl)phenyl)-7H-pyrrolo[2,3-d]pyrimidine (step 1) (664 mg, 1.163 mmol), tert-butyl 4-(2-oxoethyl)piperidine-1-carboxylate (291 mg, 1.279 mmol) and TEA (0.486 ml, 3.49 mmol) in MeOH (4 ml) was added ZnCl$_2$ 0.5M in THF (2.56 ml, 1.279 mmol). The RM was stirred at RT for 3 h, then NaBH$_3$CN (80 mg, 1.279 mmol) was added and the RM was stirred at RT overnight under argon. The solution was diluted with DCM and washed with water and brine. The organic layer was dried over MgSO$_4$, filtered, concentrated and dried under reduced pressure to afford 730 mg of the title compound.

LC-MS (Method A): Rt=0.95 min, [M+H]$^+$=554.4/556.3.

Intermediate 17

2-(4-(4-Chloro-7H-pyrrolo[2,3-d]pyrimidin-6-yl)phenyl)ethanol

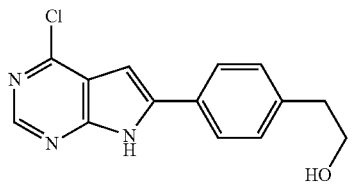

A yellow milky mixture of 4-chloro-6-iodo-7H-pyrrolo[2,3-d]pyrimidine (1.2 g, 4.29 mmol), 4-(2-hydroxyethyl)phenylboronic acid (750 mg, 4.29 mmol), Na$_2$CO$_3$ 2M in water (4.72 ml, 9.45 mmol) and PdCl$_2$(PPh$_3$)$_2$ (154 mg, 0.215 mmol) in 1-propanol (36 ml) was flushed with N$_2$ at RT and then stirred in a preheated oil bath at 105° C. After stirring at 105° C. overnight, the brown mixture was concentrated until dryness and dried under HV pump to yield a dark solid. Purification of the crude by flash chromatography on silica gel eluting with 40-100% EtOAc in CHX afforded 762 mg of the title compound as a yellow solid.

LC-MS (Method A): Rt=0.82 min, [M+H]$^+$=274.0.

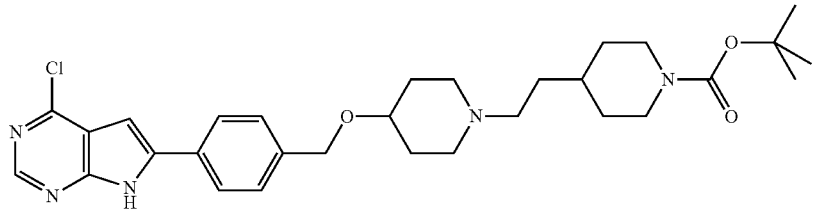 [SMILES: CC(C)(C)OC(=O)N1CCC(CCN2CCC(OCc3ccc(-c4cc5c(Cl)ncnc5[nH]4)cc3)CC2)CC1]

Intermediate 18

Tert-butyl 4-(piperidin-4-yloxy)piperidine-1-carboxylate

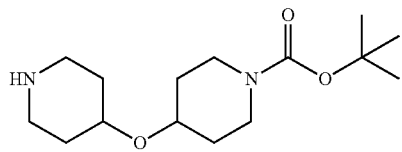 [SMILES: CC(C)(C)OC(=O)N1CCC(OC2CCNCC2)CC1]

Step 1: tert-butyl 4-(pyridin-4-yloxy)piperidine-1-carboxylate

In a 500 ml round bottom flask were mixed pyridin-4-ol (5 g, 52.6 mmol), dry THF (200 ml), tert-butyl 4-hydroxypiperidine-1-carboxylate (13.3 g, 65.8 mmol) and PPh$_3$ (18 g, 68.4 mmol). Then DEAD (12 g, 68.4 mmol) was added dropwise at RT. The RM was stirred at RT for 3 h, then the RM was concentrated. Purification by chromatography on silica gel eluting with 3% MeOH in DCM afforded 10 g of the title compound as a white solid.

LC-MS (method H): Rt=1.35 min, [M+H]$^+$=279.3.

Step 2: tert-butyl 4-(piperidin-4-yloxy)piperidine-1-carboxylate

In a 500 ml round bottom flask, purged and maintained under inert atmosphere were mixed tert-butyl 4-(pyridin-4-yloxy)piperidine-1-carboxylate (2 g, 7.2 mmol), EtOH (100 ml), AcOH (5 ml) and palladium on carbon (0.4 g). The RM was stirred at 80° C. for 16 h under H$_2$ atmosphere (4 MPa). The mixture was filtered through Hyflo®, and the filtrate was concentrated under reduced pressure. Purification of the crude mixture by chromatography on silica gel eluting with 10% MeOH in DCM afforded 0.5 g of the title compound as a colorless oil.

LC-MS (method H): Rt=1.32 min, [M+H]$^+$=285.3.

Synthesis of Final Compounds

Compound 1

(3S,4R)—N-(3-(6-(4-((9-(3-(2,4-Dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

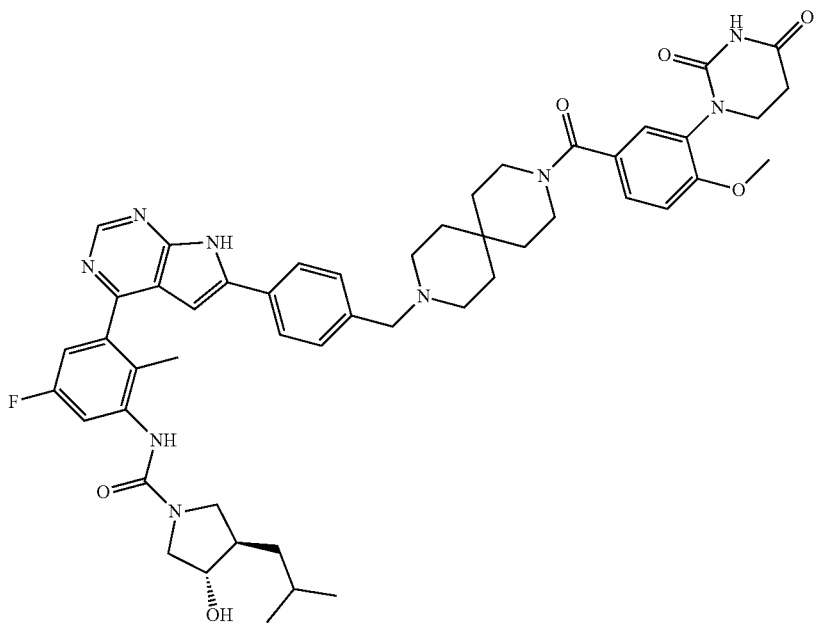 [SMILES: COc1ccc(C(=O)N2CCC3(CCN(Cc4ccc(-c5cc6c(-c7cc(F)cc(NC(=O)N8C[C@@H](CC(C)C)[C@H](O)C8)c7C)ncnc6[nH]5)cc4)CC3)CC2)cc1N1CCC(=O)NC1=O]

Step 1: (3S,4R)—N-(5-fluoro-3-(6-(4-formylphenyl)-7-(phenylsulfonyl)-7H-pyrrolo[2,3-c]pyrimidin-4-yl)-2-methylphenyl)-3-hydroxy-4-isobutylpyrrolidine-1-carboxamide To a 100 ml round bottom flask was added 4-(4-chloro-7-(phenylsulfonyl)-7H-pyrrolo[2,3-d]pyrimidin-6-yl)benzaldehyde (410 mg, 1.03 mmol) (intermediate 3b), (3S,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (420 mg, 1.0 mmol) (intermediate 8), PdCl$_2$(dppf) (110 mg, 0.15 mmol), Na$_2$CO$_3$ (280 mg, 2.64 mmol), ACN (16 ml) and H$_2$O (4 ml). The mixture was degassed, purged with N$_2$ (2×) and stirred at 100° C. for 1.5 h. The RM was concentrated under vacuum and cold water (30 ml) was added. The mixture was extracted with EtOAc (3×50 ml) and the combined organic layers were evaporated to yield 800 mg of the title compound.
LC-MS (Method J): Rt=1.74 min, [M+H]$^+$=656.

Step 2: tert-butyl 9-(4-(4-(5-fluoro-3-((3S,4R)-3-hydroxy-4-isobutylpyrrolidine-1-carboxamido)-2-methylphenyl)-7-(phenylsulfonyl)-7H-pyrrolo[2,3-d]pyrimidin-6-yl)benzyl)-3,9-diazaspiro[5.5]undecane-3-carboxylate To a round bottom flask (100 ml) was added (3S,4R)—N-(5-fluoro-3-(6-(4-formylphenyl)-7-(phenylsulfonyl)-7H-pyrrolo[2,3-d]pyrimidin-4-yl)-2-methylphenyl)-3-hydroxy-4-isobutylpyrrolidine-1-carboxamide (720 mg, 0.9 mmol) (step 1), tert-butyl 3,9-diazaspiro[5.5]undecane-3-carboxylate (360 mg, 1.41 mmol and MeOH (32 ml). TEA (53 mg, 0.52 mmol) and ZnCl$_2$ 1 M in THF (1.0 ml, 1.0 mmol) were added to the mixture. The mixture was stirred at 30° C. for 1.5 h, then NaBH$_3$CN (160 mg, 2.57 mmol) was added to the mixture at 5° C. The mixture was stirred at 30° C. for 1 h. The RM was evaporated and cold water (50 ml) was added. The mixture was extracted with EtOAc (3×50 ml) and the combined organic layers were evaporated to afford 1.2 g of the title compound.
LC-MS (method K): Rt=2.67 min, [M+H]$^+$=895.

Step 3: tert-butyl 9-(4-(4-(5-fluoro-3-((3S,4R)-3-hydroxy-4-isobutylpyrrolidine-1-carboxamido)-2-methylphenyl)-7H-pyrrolo[2,3-c]pyrimidin-6-yl)benzyl)-3,9-diazaspiro[5.5]undecane-3-carboxylate In a round bottom flask (50 ml) containing a solution of tert-butyl 9-(4-(4-(5-fluoro-3-((3S,4R)-3-hydroxy-4-isobutylpyrrolidine-1-carboxamido)-2-methylphenyl)-7-(phenylsulfonyl)-7H-pyrrolo[2,3-d]pyrimidin-6-yl)benzyl)-3,9-diazaspiro[5.5]undecane-3-carboxylate (610 mg, 0.45 mmol) (step 2) in DMSO (6 ml) was added NaOH (140 mg, 3.5 mmol) in H$_2$O (1.2 ml) at 0° C. The mixture was stirred at 0° C. for 3 h. To the mixture was added a mixture of ice and cold water (40 ml), the precipitated solid was collected and purified by chromatography on silica gel eluting with 0-18% MeOH in DCM yielding 230 mg of the title compound as a yellow solid.
LC-MS (method E): Rt=2.44 min, [M+H]$^+$=754.

Step 4: (3S,4R)—N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-3-hydroxy-4-isobutylpyrrolidine-1-carboxamide To a round bottom flask (100 ml) containing a solution of tert-butyl 9-(4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)benzyl)-3,9-diazaspiro[5.5]undecane-3-carboxylate (230 mg, 0.305 mmol) in DCM (1.8 ml) and EtOH (5.0 ml) was added a solution of HCl 4M in dioxane (2.0 ml, 8.0 mmol) dropwise at 5° C. The mixture was stirred at 30° C. for 4 h. An additional amount of HCl 4M in dioxane (2.0 ml, 8.0 mmol) was added dropwise and the RM was further stirred for 40 min. The RM was evaporated to afford the crude. The crude was triturated with petroleum ether/TBME 1:1 (3×30 ml), TBME (30 ml) and DCM/TBME 2:1 (30 ml), the solid was dried in vacuum to yield 172 mg of the title compound as a tan solid as a hydrochloride salt.
LC-MS (Method F): Rt=1.05 min, [M+H]$^+$=654.

Step 5: (3S,4R)—N-(3-(6-(4-((9-(3-(2,4-dioxotetrahydropyrimidin-1 (2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide In a 50 ml round bottom flask containing a solution of (3S,4R)—N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-3-hydroxy-4-isobutylpyrrolidine-1-carboxamide (172 mg, 0.237 mmol) (step 4) and 3-(2,4-dioxotetrahydropyrimidin-1 (2H)-yl)-4-methoxybenzoic acid (63 mg, 0.237 mmol) (intermediate 1a) in DMF (2.5 ml) was added DIPEA (183 mg, 1.42 mmol) at 5° C. Then HATU (90 mg, 0.237 mmol) was added at 5° C., and the mixture was stirred at 5° C. for 1 h. The RM was filtered and purified by preparative HPLC (XBridge C18, 21.2×250 mm, 10 μm) eluting with 0.01 M NH$_4$HCO$_3$ buffer in water/ACN yielding 63 mg of the title compound as a white solid.
LC-MS (Method E): Rt=1.85 min, [M/2+H]$^+$=450.7.

$^1$H NMR (500 MHz, DMSO-d6) δ 12.70 (s, 1H), 10.33 (s, 1H), 8.82 (s, 1H), 7.92 (d, J=8.2 Hz, 2H), 7.68 (s, 1H), 7.49 (dd, J=10.8, 2.7 Hz, 1H), 7.40-7.34 (m, 3H), 7.32 (d, J=2.1 Hz, 1H), 7.14 (d, J=8.7 Hz, 1H), 7.05 (dd, J=8.9, 2.8 Hz, 1H), 6.75 (s, 1H), 5.12 (s, 1H), 3.90-3.86 (m, 1H), 3.84 (s, 3H), 3.65 (dd, J=16.3, 9.2 Hz, 2H), 3.59 (t, J=6.6 Hz, 2H), 3.53-3.35 (m, 4H), 3.49 (s, 2H), 3.19 (dd, J=10.1, 4.7 Hz, 1H), 3.11-3.05 (m, 1H), 2.68 (t, J=6.3 Hz, 2H), 2.38-2.32 (m, 4H), 2.09 (s, 3H), 2.06-2.00 (m, 1H), 1.66-1.58 (m, 1H), 1.52-1.47 (m, 4H), 1.45-1.38 (m, 4H), 1.38-1.29 (m, 1H), 1.16-1.09 (m, 1H), 0.90 (dd, J=10.8, 6.6 Hz, 6H).

Compound 2

(3R,4S)—N-(3-(6-(4-((4-(2-((1-(3-(2,4-Dioxotetra-hydropyrimidin-1 (2H)-yl)-4-methoxybenzoyl)piperidin-4-yl)oxy)ethyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

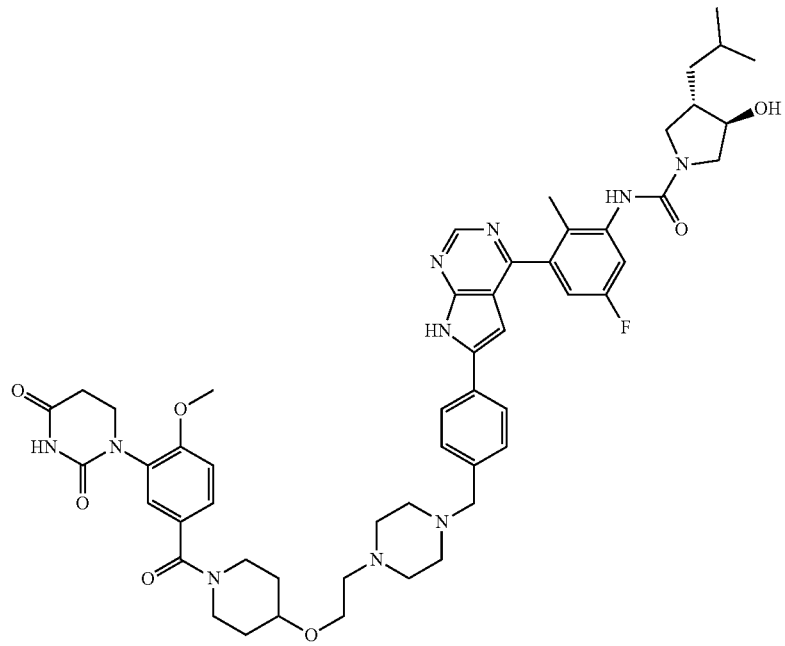 [SMILES: COc1ccc(C(=O)N2CCC(OCCN3CCN(Cc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

Step 1: 2-((1-(tert-butoxycarbonyl)piperidin-4-yl)oxy)-1-hydroxyethanesulfonic acid A solution of tert-butyl 4-(2-oxoethoxy)piperidine-1-carboxylate (intermediate 4) (1.0 g, 3.70 mmol) in EtOH (6 ml) was purged with argon. Then a solution of sodium metabisulfite (500 mg, 2.63 mmol) in water (1 ml) was added and the RM was stirred at 80° C. for 1 h. The heterogeneous mixture was then cooled down to RT. After stirring at RT for 2 days, the suspension was filtered, washed with EtOH and dried under reduced pressure to afford 833 mg of the title compound as a white solid.

$^1$H NMR (400 MHz, DMSO-d6) δ 5.32 (d, J=5.7 Hz, 1H), 3.96 (t, J=7.2 Hz, 1H), 3.80 (d, J=10.3 Hz, 1H), 3.61 (d, J=13.4 Hz, 2H), 3.46 (s, 1H), 3.35 (s, 2H), 2.99 (s, 2H), 1.73 (s, 2H), 1.39 (s, 9H), 1.30 (q, J=9.1, 5.9 Hz, 2H).

Step 2: tert-butyl 4-(2-(4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)piperazin-1-yl)ethoxy)piperidine-1-carboxylate To a solution of (3R,4S)—N-(5-fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide (intermediate 11) (200 mg, 0.321 mmol) in MeOH (3 ml) was added NaOAc (67 mg, 0.973 mmol) and the resulting orange solution was stirred at RT for 5 min. Then 2-((1-(tert-butoxycarbonyl)piperidin-4-yl)oxy)-1-hydroxyethanesulfonic acid (step 1) (130 mg, 0.380 mmol) and 2-picoline borane complex (21 mg, 0.167 mmol) were added and the RM was stirred at RT for 3 days, then concentrated under reduced pressure. Purification of the crude product by reverse phase flash chromatography on a Redisep® C18 column eluting with 5-100% ACN in (water+0.1% TFA) afforded 364 mg of the title compound as a TFA salt.

LC-MS (Method A): Rt=0.94 min, [M+H]$^+$=813.6.

Step 3: (3R,4S)—N-(5-fluoro-2-methyl-3-(6-(4-((4-(2-(piperidin-4-yloxy)ethyl)piperazin-1-yl)methyl)phenyl)-7H-pyrrolo[2,3-d]pyrimidin-4-yl)phenyl)-3-hydroxy-4-isobutylpyrrolidine-1-carboxamide A solution of tert-butyl 4-(2-(4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)piperazin-1-yl)ethoxy)piperidine-1-carboxylate (step 2) (364 mg, 0.224 mmol) and HCl 4M in dioxane (2 ml, 8.00 mmol) in MeOH (2 ml) was stirred at RT for 2 h. Then, the RM was concentrated under reduced pressure. Purification of the crude product by reverse phase flash chromatography on a Redisep® C18 column eluting from 2-100% ACN in (water+0.1% TFA) afforded 155 mg of the title compound as a TFA salt.

LC-MS (Method A): Rt=0.70 min, [M+H]$^+$=713.6.

Step 4: (3R,4S)—N-(3-(6-(4-((4-(2-((1-(3-(2,4-di-oxotetrahydropyrimidin-1(2H)-yl)-4-methoxyben-zoyl)piperidin-4-yl)oxy)ethyl)piperazin-1-yl)methyl) phenyl)-7H-pyrrolo[2,3-d]pyrimidin-4-yl)-5-fluoro-2-methylphenyl)-3-hydroxy-4-isobutylpyrrolidine-1-carboxamide To a solution of 3-(2,4-dioxotetrahydropyrimidin-1(2H)-yl)-4-methoxybenzoic acid (41 mg, 0.155 mmol) (intermediate 1a) in DMF (1 ml) at RT was added NMM (0.050 ml, 0.455 mmol), followed by HATU (59 mg, 0.155 mmol). After 30 min stirring at RT, a solution of (3R,4S)—N-(5-fluoro-2-methyl-3-(6-(4-((4-(2-(piperidin-4-yloxy)ethyl) piperazin-1-yl)methyl)phenyl)-7H-pyrrolo[2,3-d]pyrimidin-4-yl)phenyl)-3-hydroxy-4-isobutylpyrrolidine-1-carboxamide (step 3) (155 mg, 0.143 mmol) and NMM (0.050 ml, 0.455 mmol) in DMF (0.5 ml) was dropped into the mixture and the yellow RM was stirred at RT overnight. Then the RM was concentrated under reduced pressure. Purification of the crude product by reverse phase flash chromatography (Interchim) on a Redisep® C18 column eluting with 2-100% ACN in (water+0.1% NH$_4$HCO$_3$) afforded 114 mg of a material. Purification of the material by SFC (column: Princeton 4-EP, 60 A, 250×30 mm, 5 uM) eluting with 40-60% CO$_2$ in MeOH afforded 80 mg of the title compound as a solid.

LC-MS (Method B): Rt=3.52 min, [M+H]$^+$=959.7.

$^1$H NMR (400 MHz, DMSO-d6) δ ppm 12.72 (brs, 1H), 10.32 (s, 1H), 8.83 (s, 1H) 7.92 (brd, J=7.92 Hz, 2H), 7.67 (s, 1H), 7.50 (brd, J=10.71 Hz, 1H), 7.30-7.40 (m, 4H), 7.14 (brd, J=8.51 Hz, 1H), 7.06 (br d, J=8.80 Hz, 1H), 6.76 (s, 1H), 5.11 (br d, J=4.11 Hz, 1H), 3.81-3.89 (m, 4H), 3.42-3.77 (m, 11H), 3.19-3.25 (m, 2H), 3.05-3.16 (m, 2H), 2.67 (brt, J=5.94 Hz, 2H), 2.52-2.55 (m, 1H), 2.23-2.48 (m, 9H), 2.01-2.12 (m, 4H), 1.81 (brs, 2H), 1.62 (m, 1H), 1.30-1.48 (m, 3H), 1.07-1.17 (m, 1H), 0.90 (br t, J=7.48 Hz, 6H).

Compound 3

(3R,4S)—N-(3-(6-(4-((1-(2-(1-(3-(2,4-Dioxotetrahy-dropyrimidin-1(2H)-yl)-4-methoxybenzoyl)piperi-din-4-yl)ethyl)piperidin-4-yl)oxy)phenyl)-7H-pyr-rolo[2,3-d]pyrimidin-4-yl)-5-fluoro-2-methylphenyl)-3-hydroxy-4-isobutylpyrrolidine-1-carboxamide

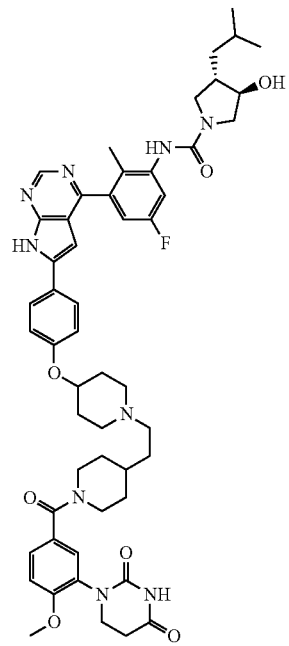 [SMILES: COc1ccc(C(=O)N2CCC(CCN3CCC(Oc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

Step 1: tert-butyl 4-(2-(4-(4-(4-(5-fluoro-3-((3R, 4S)-3-hydroxy-4-isobutylpyrrolidine-1-carbox-amido)-2-methylphenyl)-7H-pyrrolo[2,3-d]pyrimi-din-6-yl)phenoxy)piperidin-1-yl)ethyl)piperidine-1-carboxylate To a stirred solution of (3R,4S)—N-(5-fluoro-2-methyl-3-(6-(4-(piperidin-4-yloxy)phenyl)-7H-pyrrolo[2,3-d]py-rimidin-4-yl)phenyl)-3-hydroxy-4-isobutylpyrrolidine-1-carboxamide (intermediate 12) (200 mg, 0.248 mmol), TEA (0.100 ml, 0.717 mmol) and N-boc-4-piperidineacetalde-hyde (68 mg, 0.299 mmol) in MeOH (2 ml) at RT was added ZnCl$_2$ 0.5M in THF (0.600 ml, 0.300 mmol) and the RM was stirred at RT for 6 h under argon. Then, NaBH$_3$CN (18 mg, 0.286 mmol) was added. The RM was stirred at RT overnight and then concentrated under reduced pressure to afford 198 mg of the title compound.

LC-MS (Method A): Rt=0.96 min, [M+H]$^+$=798.6.

Step 2: (3R,4S)—N-(5-fluoro-2-methyl-3-(6-(4-((1-(2-(piperidin-4-yl)ethyl)piperidin-4-yl)oxy)phenyl)-7H-pyrrolo[2,3-d]pyrimidin-4-yl)phenyl)-3-hy-droxy-4-isobutylpyrrolidine-1-carboxamide A solution of tert-butyl 4-(2-(4-(4-(4-(5-fluoro-3-((3R, 4S)-3-hydroxy-4-isobutylpyrrolidine-1-carboxamido)-2-methylphenyl)-7H-pyrrolo[2,3-d]pyrimidin-6-yl)phenoxy) piperidin-1-yl)ethyl)piperidine-1-carboxylate (step 1) (198 mg, 0.248 mmol) and HCl 4M in dioxane (1.5 ml, 6.00 mmol) in MeOH (1.5 ml) was stirred at RT for 3 h. Then the RM was concentrated under reduced pressure. Purification of the crude product by reverse phase flash chromatography on a Redisep® C18 column eluting with 2-100% ACN in (water+0.1% TFA) afforded 235 mg of the title compound as a yellow solid, as a TFA salt.

LC-MS (Method A): Rt=0.70 min, [M+H]$^+$=698.6.

Step 3: (3R,4S)—N-(3-(6-(4-((1-(2-(1-(3-(2,4-dioxotetrahydropyrimidin-1(2H)-yl)-4-methoxybenzoyl)piperidin-4-yl)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide To a stirred solution of 3-(2,4-dioxotetrahydropyrimidin-1 (2H)-yl)-4-methoxybenzoic acid (intermediate 1a) (76 mg, 0.289 mmol) in DMF (1 ml) was added NMM (0.050 ml, 0.455 mmol) followed by HATU (110 mg, 0.289 mmol). The resulting RM was stirred at RT for 30 min. Then a solution of (3R,4S)—N-(5-fluoro-2-methyl-3-(6-(4-((1-(2-(piperidin-4-yl)ethyl)piperidin-4-yl)oxy)phenyl)-7H-pyrrolo[2,3-d]pyrimidin-4-yl)phenyl)-3-hydroxy-4-isobutylpyrrolidine-1-carboxamide (step 2) (235 mg, 0.241 mmol) and NMM (0.050 ml, 0.455 mmol) in DMF (0.5 ml) was dropped into the mixture and the yellow RM was stirred at RT for 3 h Purification of the crude product by reverse phase flash chromatography on a Redisep® C18 column eluting from 2-100% ACN in (water+0.1% NH$_4$HCO$_3$) afforded 125 mg of the title compound.

LC-MS (Method B): Rt=3.77 min, [M/2+H]$^+$=473.2.

$^1$H NMR (400 MHz, DMSO-d6) δ ppm 12.62 (brs, 1H), 10.33 (brs, 1H), 8.80 (brs, 1H), 7.78-8.00 (m, 2H), 7.59-7.74 (m, 1H), 7.44-7.54 (m, 1H), 7.25-7.41 (m, 2H), 6.94-7.20 (m, 4H), 6.65 (br s, 1H), 4.98-5.28 (m, 1H), 4.38-4.53 (m, 1H), 3.77-3.92 (m, 4H), 3.56-3.71 (m, 4H), 3.08-3.20 (m, 2H), 2.61-2.90 (m, 6H), 1.84-2.36 (m, 12H), 1.35-1.70 (m, 8H), 1.01-1.28 (m, 4H) 0.79-0.98 (m, 6H).

Compound 4

(cis-rac)-N-(3-(6-(4-(((1-(2-(1-(3-(2,4-Dioxotetrahydropyrimidin-1 (2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide Step 1

(cis-rac)-tert-butyl 4-((4-(4-(5-fluoro-3-(3-hydroxy-4-isobutylpyrrolidine-1-carboxamido)-2-methylphenyl)-7H-pyrrolo[2,3-d]pyrimidin-6-yl)benzyl)oxy) piperidine-1-carboxylate To a mixture of tert-butyl 4-((4-(4-chloro-7H-pyrrolo[2,3-d]pyrimidin-6-yl)benzyl)oxy)piperidine-1-carboxylate (intermediate 15) (150 mg, 0.339 mmol), (cis-rac)-N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 9) (157 mg, 0.373 mmol) and Na$_2$CO$_3$ 2M in water (0.339 ml, 0.677 mmol) in 1-propanol (20 ml) was added PdCl$_2$(PPh$_3$)$_2$ (11.88 mg, 0.017 mmol). The resulting RM was irradiated at 140° C. for 15 min in microwave. It was then concentrated under reduced pressure. Purification of the crude product by flash chromatography on silica gel eluting with 0-100% EtOAc in CHX afforded 94 mg of the title compound.

LC-MS (Method A): Rt=1.25 min, [M+H]$^+$=701.5.

Step 2: (cis-rac)-N-(5-fluoro-2-methyl-3-(6-(4-((piperidin-4-yloxy)methyl)phenyl)-7H-pyrrolo[2,3-d]pyrimidin-4-yl)phenyl)-3-hydroxy-4-isobutylpyrrolidine-1-carboxamide A yellow solution of (cis-rac)-tert-butyl 4-((4-(4-(5-fluoro-3-hydroxy-4-isobutylpyrrolidine-1-carboxamido)-2-methylphenyl)-7H-pyrrolo[2,3-d]pyrimidin-6-yl)benzyl)oxy)piperidine-1-carboxylate (step 1) (94 mg, 0.134 mmol) and TFA (0.310 ml, 4.02 mmol) in DCM (3 ml) was stirred at RT for 1 h under argon. Then it was concentrated under reduced pressure to afford 143 mg of the title compound as a TFA salt.

LC-MS (Method A): Rt=0.78 min, [M+H]$^+$=601.6.

Step 3

(cis-rac)-tert-butyl 4-(2-(4-((4-(4-(5-fluoro-3-hydroxy-4-isobutylpyrrolidine-1-carboxamido)-2-methylphenyl)-7H-pyrrolo[2,3-d]pyrimidin-6-yl)benzyl)oxy)piperidin-1-yl)ethyl)piperidine-1-carboxylate To a brown solution of (cis-rac)-N-(5-fluoro-2-methyl-3-(6-(4-((piperidin-4-yloxy)methyl)phenyl)-7H-pyrrolo[2,3-

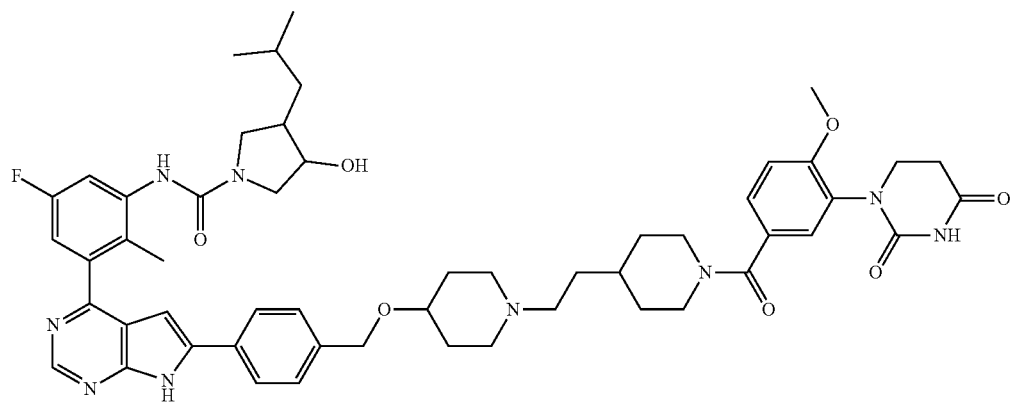 [SMILES: COc1ccc(C(=O)N2CCC(CCN3CCC(OCc4ccc(-c5cc6c(-c7cc(F)cc(NC(=O)N8CC(O)C(CC(C)C)C8)c7C)ncnc6[nH]5)cc4)CC3)CC2)cc1N1CCC(=O)NC1=O]

d]pyrimidin-4-yl)phenyl)-3-hydroxy-4-isobutylpyrrolidine-1-carboxamide (step 2) (143 mg, 0.173 mmol), tert-butyl 4-(2-oxoethyl)piperidine-1-carboxylate (43.1 mg, 0.190 mmol) and TEA (0.072 ml, 0.518 mmol) in MeOH (4 ml) was added ZnCl$_2$ 0.5M in THF (0.380 ml, 0.190 mmol). The resulting RM was stirred at RT for 3 h. Then NaBH$_3$CN (11.93 mg, 0.190 mmol) was added and the RM was stirred at RT overnight under argon. The resulting solution was diluted with DCM, washed with water and brine. The organic layer was dried over MgSO$_4$, filtered and concentrated under reduced pressure. Purification of the crude compound by flash chromatography on silica gel eluting with 0-20% MeOH in DCM afforded 83 mg of the title compound.

LC-MS (Method A): Rt=0.99 min, [M+H]$^+$=812.8.

Step 4: (cis-rac)-N-(5-fluoro-2-methyl-3-(6-(4-(((1-(2-(piperidin-4-yl)ethyl)piperidin-4-yl)oxy)methyl)phenyl)-7H-pyrrolo[2,3-d]pyrimidin-4-yl)phenyl)-3-hydroxy-4-isobutylpyrrolidine-1-carboxamide A yellow solution of (cis-rac)-tert-butyl 4-(2-(4-((4-(4-(5-fluoro-3-hydroxy-4-isobutylpyrrolidine-1-carboxamido)-2-methylphenyl)-7H-pyrrolo[2,3-d]pyrimidin-6-yl)benzyl)oxy)piperidin-1-yl)ethyl)piperidine-1-carboxylate (step 3) (83 mg, 0.102 mmol) and TFA (0.236 ml, 3.07 mmol) in DCM (3 ml) was stirred at RT for 1 h under argon. Then it was concentrated under reduced pressure to afford 142 mg of the title compound as a TFA salt.

LC-MS (Method A): Rt=0.71 min, [M+H]$^+$=712.4.

Step 5: (cis-rac)-N-(3-(6-(4-(((1-(2-(1-(3-(2,4-dioxo-tetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide To a brown solution of (cis-rac)-N-(5-fluoro-2-methyl-3-(6-(4-(((1-(2-(piperidin-4-yl)ethyl)piperidin-4-yl)oxy) methyl)phenyl)-7H-pyrrolo[2,3-d]pyrimidin-4-yl)phenyl)-3-hydroxy-4-isobutylpyrrolidine-1-carboxamide (step 4) (142 mg, 0.103 mmol), 3-(2,4-dioxotetrahydropyrimidin-1(2H)-yl)-4-methoxybenzoic acid (intermediate 1a) (29.9 mg, 0.113 mmol) and HBTU (46.8 mg, 0.123 mmol) in DMF (3 ml) was added DIPEA (0.108 ml, 0.616 mmol). The resulting RM was stirred at RT for 2 h under argon. It was then poured into water. The resulting white suspension was filtered, washed with water and dried under reduced pressure to afford 100 mg of a crude material. Purification of the material by reverse phase HPLC (column: XBridge C18, 250×50 mm, 5 um; flow: 100 ml/min) eluting from 38-58% ACN in (water+0.1% NH$_4$OH) afforded 28.5 mg of the title compound.

LC-MS (Method B): Rt=3.85 min, [M+H]$^+$=959.5.

$^1$H NMR (400 MHz, DMSO-d6) δ ppm 12.77 (brs, 1H), 10.35 (s, 1H), 8.85 (s, 1H), 7.96 (brd, J=7.80 Hz, 2H), 7.66 (s, 1H), 7.51 (m, 1H), 7.43 (brd, J=7.90 Hz, 2H), 7.37 (brd, J=8.40 Hz, 1H), 7.33 (s, 1H), 7.16 (d, J=8.31 Hz, 1H), 7.07 (brd, J=8.60 Hz, 1H), 6.80 (s, 1H), 4.84-4.99 (m, 1H), 4.55 (s, 2H), 4.07-4.16 (m, 1H), 3.85 (s, 3H), 3.61 (m, 3H), 3.43-3.52 (m, 3 H), 3.05-3.14 (m, 1H), 2.55-2.92 (m, 6H), 2.21-2.40 (m, 3H), 2.13-2.21 (m, 1H), 2.11 (s, 3H), 2.03 (brt, J=9.11 Hz, 2H), 1.88 (m, 2H), 1.04-1.75 (m, 13H), 0.92 (brd, J=6.48 Hz, 6H).

Compound 5 trans-rac-N-(3-(6-(4-((9-(3-(2,4-Dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

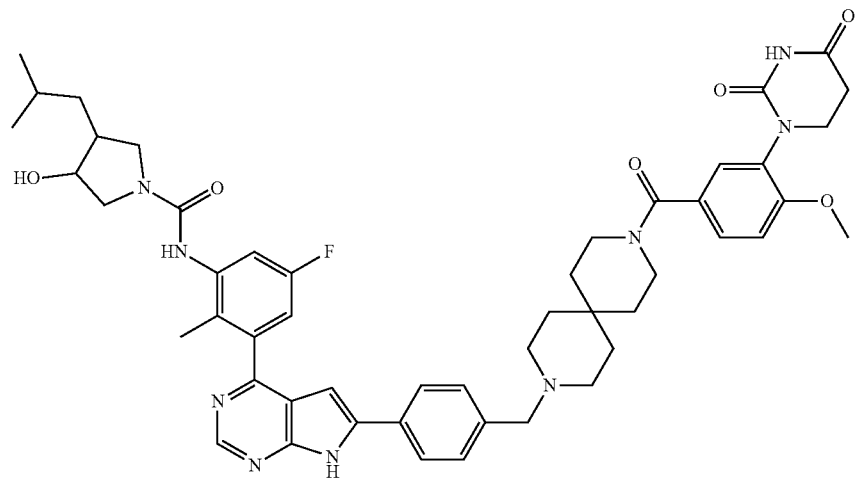 [SMILES: COc1ccc(C(=O)N2CCC3(CCN(Cc4ccc(-c5cc6c(-c7cc(F)cc(NC(=O)N8CC(O)C(CC(C)C)C8)c7C)ncnc6[nH]5)cc4)CC3)CC2)cc1N1CCC(=O)NC1=O]

Step 1: trans-rac-benzyl 3-hydroxy-4-isobutylpyrrolidine-1-carboxylate

In a 3l round-bottom flask, benzyl 6-oxa-3-azabicyclo[3.1.0]hexane-3-carboxylate (CAS 31865-25-5) (43.5 g, 148.1 mmol) and cuprous bromide dimethylsulfane complex (14 g, 68.4 mmol) were suspended in THF (1000 ml). The solution was cooled to −30° C. under $N_2$, then isobutylmagnesium bromide 2M in THF (913 ml, 1820 mmol) was added dropwise over 90 min. After the addition, the reaction was allowed to slowly warm to −15° C. over 45 min and the mixture was stirred at −15° C. for 2 h. Then, the reaction was quenched by HCl 2M (1000 ml) at 0° C., and the mixture was stirred at RT for 30 min. Then the layers are separated, the aq. layer was extracted with EtOAc (3×200 ml), dried over $Na_2SO_4$, filtered and concentrated. Purification of the crude mixture by chromatography on silica gel eluting with 0-20% EtOAc in petroleum ether afforded 108 g of the title compound as a yellow oil.

LC-MS (method F): Rt=1.51 min, $[M+H]^+$=278.

Step 2: trans-rac-4-isobutylpyrrolidin-3-ol

In a 250 ml round bottom flask, a mixture of trans-rac-benzyl 3-hydroxy-4-isobutylpyrrolidine-1-carboxylate (step 1) (1 g, 3.6 mmol) and 10% palladium on carbon (100 mg) in MeOH (40 ml) was stirred under $H_2$ at RT for 16 h. The mixture was filtered and the filtrate was concentrated to afford 510 mg of the title compound as a yellow oil.

LC-MS (method E): Rt=1.05 min, $[M+H]^+$=144.

Step 3: trans-rac-N-(5-fluoro-2-methyl-3-(4,4,5,5-tetramethyl-1,3,2-dioxaborolan-2-yl)phenyl)-3-hydroxy-4-isobutylpyrrolidine-1-carboxamide A mixture of 5-fluoro-2-methyl-3-(4,4,5,5-tetramethyl-1,3,2-dioxaborolan-2-yl)aniline (commercially available, or could be prepared according to published patent application WO 2013/008095, page 37, intermediate 5) (853 mg, 3.4 mmol) and DIPEA (2.2 g, 17 mmol) in THF (40 ml) was stirred at 0° C. for 15 min. Then, triphosgene (480 mg, 1.63 mmol) was added, and the mixture was stirred at 0° C. for 2 h. Then, trans-rac-4-isobutylpyrrolidin-3-ol (step 2) (486 mg, 3.4 mmol) was added. After the addition, the mixture was stirred at RT for 16 h. To the resulting mixture was added MeOH (10 ml). After concentration, purification of the crude mixture by chromatography on silica gel eluting with 0-5% MeOH in DCM afforded 1.0 g of the title compound.

LC-MS (method J): Rt=1.46 min, $[M+H]^+$=421.

Step 4: trans-rac-N-(5-fluoro-3-(6-(4-formylphenyl)-7-(phenylsulfonyl)-7H-pyrrolo[2,3-d]pyrimidin-4-yl)-2-methylphenyl)-3-hydroxy-4-isobutylpyrrolidine-1-carboxamide In a 50 ml round bottom flask, trans-rac-N-(5-fluoro-2-methyl-3-(4,4,5,5-tetramethyl-1,3,2-dioxaborolan-2-yl)phenyl)-3-hydroxy-4-isobutylpyrrolidine-1-carboxamide (step 3) (420 mg, 1 mmol), 4-(4-chloro-7-(phenylsulfonyl)-7H-pyrrolo[2,3-d]pyrimidin-6-yl)benzaldehyde (410 mg, 1.05 mmol) (intermediate 3b), $Na_2OO_3$ (280 mg, 2.6 mmol) and $PdCl_2(dppf)$ (110 mg, 0.15 mmol) were suspended in AON (12 ml) and water (3 ml). The mixture was stirred under $N_2$ at 100° C. for 16 h, then concentrated under reduced pressure. Purification of the crude mixture by reverse phase flash chromatography on a Agela C18 column eluting with 5-90% AON in water (10 mM $NH_4HCO_3$) afforded 400 mg of the title compound.

LC-MS (Method E): Rt=2.07 min, $[M+H]^+$=656.

Step 5: trans-rac-tert-butyl 9-(4-(4-(5-fluoro-3-(3-hydroxy-4-isobutylpyrrolidine-1-carboxamido)-2-methylphenyl)-7-(phenylsulfonyl)-7H-pyrrolo[2,3-d]pyrimidin-6-yl)benzyl)-3,9-diazaspiro[5.5]undecane-3-carboxylate In a 50 ml flask, trans-rac-N-(5-fluoro-3-(6-(4-formylphenyl)-7-(phenylsulfonyl)-7H-pyrrolo[2,3-d]pyrimidin-4-yl)-2-methylphenyl)-3-hydroxy-4-isobutylpyrrolidine-1-carboxamide (400 mg, 0.61 mmol), tert-butyl 3,9-diazaspiro[5.5]undecane-3-carboxylate (CAS 173405-78-2) (186 mg, 0.73 mmol) and $K_2CO_3$ (166 mg, 1.2 mmol) were suspended in DMSO (3 ml). After stirring at RT for 15 min, a solution of $ZnCl_2$ 1M in THF (0.78 ml, 0.78 mmol) was added and the mixture was stirred at RT for 3 h. Then, $NaBH_3CN$ (300 mg, 5 mmol) and MeOH (3 ml) were added and the mixture was stirred at RT for 16 h, then filtered. Purification of the filtrate by reverse phase flash chromatography on a Agela C18 column eluting with 5-80% ACN in water (10 mM $NH_4HCO_3$) afforded 200 mg of the title compound.

LC-MS (method F): Rt=1.61 min, $[M+H]^+$=894

Step 6: trans-rac-tert-butyl 9-(4-(4-(5-fluoro-3-(3-hydroxy-4-isobutylpyrrolidine-1-carboxamido)-2-methylphenyl)-7H-pyrrolo[2,3-cl]pyrimidin-6-yl)benzyl)-3,9-diazaspiro[5.5]undecane-3-carboxylate In a 25 ml round bottom flask, tert-butyl trans-rac-9-(4-(4-(5-fluoro-3-(3-hydroxy-4-isobutylpyrrolidine-1-carboxamido)-2-methylphenyl)-7-(phenylsulfonyl)-7H-pyrrolo[2,3-d]pyrimidin-6-yl)benzyl)-3,9-diazaspiro[5.5]undecane-3-carboxylate (step 5) (200 mg, 0.22 mmol) was suspended in DMSO (3 ml) and water (1 ml). The mixture was stirred at RT for 15 min, then the mixture was cooled to 0° C. A solution of NaOH (35 mg, 0.88 mmol) in water (1 ml) was added and the mixture was stirred at 0° C. for 30 min. The mixture was warmed to RT and stirred at RT for 16 h. Purification of the crude mixture by reverse phase flash chromatography on a Agela C18 column eluting with 5-90% ACN in water (10 mM $NH_4HCO_3$) afforded 100 mg of the title compound as a yellow solid.

LC-MS (method F): Rt=1.48 min, $[M+H]^+$=754

Step 7: trans-rac-N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-3-hydroxy-4-isobutylpyrrolidine-1-carboxamide In a 50 ml round bottom flask, trans-rac-tert-butyl 9-(4-(4-(5-fluoro-3-(-3-hydroxy-4-isobutylpyrrolidine-1-carboxamido)-2-methylphenyl)-7H-pyrrolo[2,3-d]pyrimidin-6-yl)benzyl)-3,9-diazaspiro[5.5]undecane-3-carboxylate (110 mg, 0.15 mmol) was suspended in DCM (5 ml). A solution of HCl 4M in dioxane (4 ml, 16 mmol) was added and the RM was stirred at RT for 3 h. The resulting mixture was concentrated and dried to afford 120 mg of the title compound as a grey solid hydrochloride salt.

LC-MS (Method E): Rt=1.74 min, [M+H]⁺=654

Step 8: trans-rac-N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide In a 25 ml round bottom flask, trans-rac-N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-3-hydroxy- 2H), 2.36 (s, 4H), 2.15-2.00 (m, 4H), 1.67-1.60 (m, 1H), 1.50-1.34 (m, 10H), 1.16-1.07 (m, 1H), 0.91 (d, J=6.6 Hz, 3H), 0.89 (d, J=6.6 Hz, 3H).

Compound 6

(3R,4S)—N-(3-(6-(4-((9-(3-(2,4-Dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

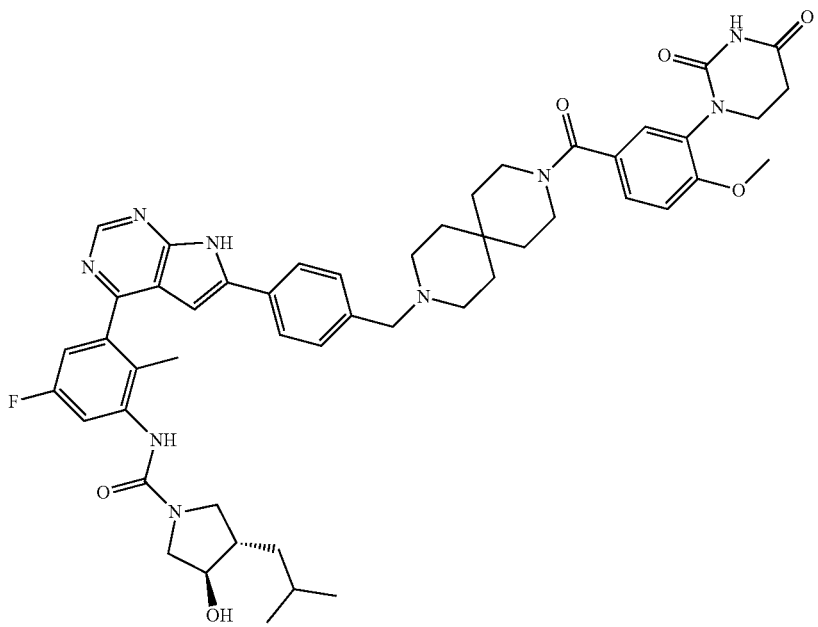 [SMILES: COc1ccc(C(=O)N2CCC3(CCN(Cc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

4-isobutylpyrrolidine-1-carboxamide (120 mg, 0.146 mmol), 3-(2,4-dioxotetrahydropyrimidin-1(2H)-yl)-4-methoxybenzoic acid (intermediate 1a) (47 mg, 0.18 mmol) and DIPEA (78 mg, 0.6 mmol) were suspended in DMF (3 ml). Then, HATU (68 mg, 0.18 mmol) was added and the mixture was stirred at RT for 16 h. Purification of the RM by reverse phase HPLC on a XBridge C18 column (21.2×250 mm, 10 μm) eluting with ACN and water (containing 0.01 M NH₄HCO₃ buffer) afforded 65 mg of the title compound as a white solid.

LC-MS (method E): Rt=1.73 min, [M/2+H]⁺=450.7.

¹H NMR (500 MHz, DMSO-d6) δ 12.73 (s, 1H), 10.34 (s, 1H), 8.83 (s, 1H), 7.92 (d, J=8.2 Hz, 2H), 7.68 (s, 1H), 7.49 (dd, J=10.8, 2.7 Hz, 1H), 7.37 (td, J=11.0, 4.9 Hz, 3H), 7.32 (d, J=2.1 Hz, 1H), 7.15 (d, J=8.7 Hz, 1H), 7.06 (dd, J=8.8, 2.8 Hz, 1H), 6.76 (d, J=2.8 Hz, 1H), 5.12 (d, J=4.5 Hz, 1H), 3.88-3.84 (m, 4H), 3.68-3.64 (m, 2H), 3.60-3.30 (m, 7H), 3.20-3.17 (m, 1H), 3.09-3.06 (m, 1H), 2.67 (t, J=6.4 Hz,

Step 1: (3R,4S)—N-(5-fluoro-3-(6-(4-formylphenyl)-7-(phenylsulfonyl)-7H-pyrrolo[2,3-d]pyrimidin-4-yl)-2-methylphenyl)-3-hydroxy-4-isobutylpyrrolidine-1-carboxamide To a 50 ml round bottom flask purged with N₂ and maintained under inert atmosphere were added (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 7) (420 mg, 1 mmol), 4-(4-chloro-7-(phenylsulfonyl)-7H-pyrrolo[2,3-d]pyrimidin-6-yl)benzaldehyde (intermediate 3b) (410 mg, 1.05 mmol), Na₂CO₃ (280 mg, 2.6 mmol) and PdCl₂(dppf) (110 mg, 0.15 mmol). Then, ACN (12 ml) and water (3 ml) were added and the RM was stirred at 100° C. for 2 h under N₂. Purification of the crude mixture by chromatography on silica gel eluting with 3-6% MeOH in DCM afforded 500 mg of the title compound as a yellow solid.

LC-MS (method E): Rt=1.99 min, [M+H]⁺=656;

Step 2: tert-butyl 9-(4-(4-(5-fluoro-3-((3R,4S)-3-hydroxy-4-isobutylpyrrolidine-1-carboxamido)-2-methylphenyl)-7-(phenylsulfonyl)-7H-pyrrolo[2,3-d]pyrimidin-6-yl)benzyl)-3,9-diazaspiro[5.5]undecane-3-carboxylate To a 50 ml round bottom flask were added (3R,4S)—N-(5-fluoro-3-(6-(4-formylphenyl)-7-(phenylsulfonyl)-7H-pyrrolo[2,3-d]pyrimidin-4-yl)-2-methylphenyl)-3-hydroxy-4-isobutylpyrrolidine-1-carboxamide (500 mg, 0.76 mmol), tert-butyl 3,9-diazaspiro[5.5]undecane-3-carboxylate (CAS 173405-78-2], 1 ClickChemistry, Inc.) (234 mg, 0.92 mmol), K₂CO₃ (207 mg, 1.5 mmol) and DMSO (3 ml). The RM was stirred at RT for 15 min, before the addition of ZnCl₂ 1M in THF (0.99 ml, 0.99 mmol). Then, the RM was stirred at RT for 3 h, and a solution of NaBH₃CN (378 mg, 6.0 mmol) in MeOH (3 ml) was added. After the addition, the RM was stirred at RT for 16 h, then filtered. Purification of the filtrate by reverse phase flash chromatography on a Agela C18 column eluting with ACN water (0.01 M NH₄HCO₃ buffer) gradient afforded 400 mg of the title compound as a yellow solid.

LC-MS (method F): Rt=1.50 min, [M+H]⁺=894.

Step 3: tert-butyl 9-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)-3,9-diazaspiro[5.5]undecane-3-carboxylate To a 50 ml round bottom flask were added tert-butyl 9-(4-(4-(5-fluoro-3-((3R,4S)-3-hydroxy-4-isobutylpyrrolidine-1-carboxamido)-2-methylphenyl)-7-(phenylsulfonyl)-7H-pyrrolo[2,3-d]pyrimidin-6-yl)benzyl)-3,9-diazaspiro[5.5]undecane-3-carboxylate (400 mg, 0.45 mmol) (step 2) and DMSO (2 ml). Then, a solution of NaOH (72 mg, 1.79 mmol) in water (1 ml) was added, and the RM was stirred at RT for 3 h. The RM was then poured into water (10 ml), extracted with EtOAc (4×10 ml). The combined organic layers were then dried to obtain the crude mixture. Purification of the crude mixture by chromatography on silica gel eluting with 3-6% MeOH in DCM afforded 160 mg of the title compound as a yellow solid.

LC-MS (method F): Rt=1.34 min, [M+H]⁺=754

Step 4: (3R,4S)—N-(3-(6-(4-((3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide To a 50 ml round bottom flask were added tert-butyl 9-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)-3,9-diazaspiro[5.5]undecane-3-carboxylate (160 mg, 0.21 mmol) and DCM (6 ml). The RM was stirred at RT, and a solution of HCl 4M in dioxane (5 ml, 20 mmol) was added. The RM was stirred at RT for 2 h, then concentrated to afford 92 mg of the title compound as a hydrochloride salt, as a yellow solid.

LC-MS (method F): Rt=1.02 min, [M+H]⁺=654.

Step 5: (3R,4S)—N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide To a 50 ml round bottom flask were added (3R,4S)—N-(3-(6-(4-((3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide (92 mg, 0.14 mmol), 3-(2,4-dioxotetrahydropyrimidin-1(2H)-yl)-4-methoxybenzoic acid (intermediate 1a) (45 mg, 0.17 mmol), DIPEA (91 mg, 0.71 mmol) and DMF (3 ml). Then, HATU (65 mg, 0.17 mmol) was added at RT, and the RM was stirred at RT for 16 h. Purification of the RM by reverse phase HPLC on a XBridge C18 column (21.2×250 mm, 10 μm) eluting with a ACN/water (containing 0.01 M NH₄HCO₃ buffer) gradient afforded 40 mg of the title compound as a white solid.

LC-MS (method F): Rt=1.19 min, [M+H]⁺=900.

¹H NMR (500 MHz, DMSO-d6) δ 12.69 (s, 1H), 10.33 (s, 1H), 8.80 (s, 1H), 7.92 (d, J=8.2 Hz, 2H), 7.67 (s, 1H), 7.49 (dd, J=10.7, 2.6 Hz, 1H), 7.37-7.35 (m, 3H), 7.31 (d, J=2.1 Hz, 1H), 7.14 (d, J=8.7 Hz, 1H), 7.05 (dd, J=8.9, 2.8 Hz, 1H), 6.73 (s, 1H), 5.12 (s, 1H), 3.89-3.84 (m, 4H), 3.71-3.41 (m, 9H), 3.20-3.17 (m, 1H), 3.09-3.06 (m, 1H), 2.67 (t, J=6.0 Hz, 2H), 2.36 (s, 4H), 2.09-2.04 (m, 4H), 1.65-1.60 (m, 1H), 1.50-1.32 (m, 10H), 1.16-1.08 (m, 1H), 0.91 (d, J=6.6 Hz, 3H), 0.89 (d, J=6.6 Hz, 3H).

Compound 7

(3R,4R)—N-(3-(6-(4-(2-(9-(3-(2,4-Dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide

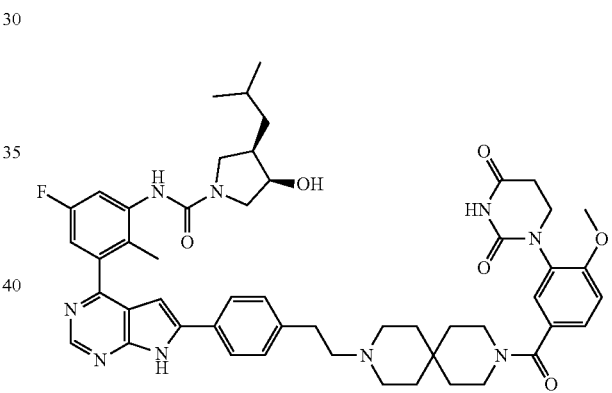

Step 1: (3S,4S)-tert-butyl 3-isobutyl-4-((4-nitrobenzoyl)oxy)pyrrolidine-1-carboxylate and (3R,4R)-tert-butyl 3-isobutyl-4-((4-nitrobenzoyl)oxy)pyrrolidine-1-carboxylate To a solution of (trans-rac)-tert-butyl 3-hydroxy-4-isobutylpyrrolidine-1-carboxylate (intermediate 6) (9.65 g, 39.7 mmol), 4-nitrobenzoic acid (11 g, 65.2 mmol) and PPh₃ (18 g, 65.2 mmol) in THF (250 ml) at RT was added dropwise DIAD (13 ml, 65.5 mmol) over 30 min under N₂. The resulting yellow solution was allowed to slowly warm to RT for 3 additional hours. The RM was quenched with water, and THF was partially evaporated. EtOAc was added and layers were separated. The aq. layer was extracted with EtOAc (3×), the combined organic layers were washed with 0.2M HCl and brine, dried over Na₂SO₄, filtered and concentrated under reduced pressure to afford 50.2 g of the crude product. Purification of % of the crude product by flash chromatography on silica gel eluting with 0-40% EtOAc in hexane afforded 4.28 g of product 1. Purification of % left of the crude product by flash chromatography on silica gel eluting with 0-13% EtOAc in hexane afforded 3.98 g of product 2 and 6.57 g of product 3. Purification of product 2 by flash chromatography on silica gel eluting with 0-25% EtOAc in hexane afforded 2.56 g of product 4. Purification of product 3 by flash chromatography on silica gel eluting with 0-15% EtOAc in hexane afforded 5.97 g of product 5. Combined products 1, 4 and 5 afforded 12.44 g of the racemate.

Chiral separation of the racemate using SFC (preparative method 2) afforded the individual enantiomers. After separation, each single enantiomer was analysed by chiral HPLC (method L) to confirm the chiral purity.

(3S,4S)-tert-butyl 3-isobutyl-4-((4-nitrobenzoyl)oxy)pyrrolidine-1-carboxylate: 6.01 g 1$^{st}$ eluting peak (peak1)

HPLC Rt (Method L)=5.99 min.

$^1$H NMR (600 MHz, DMSO-d$_6$) δ ppm 0.79-0.92 (m, 6H) 1.29-1.35 (m, 1H) 1.40 (d, J=19.44 Hz, 10H) 1.46-1.60 (m, 1H) 2.52-2.59 (m, 1H) 3.04-3.16 (m, 1H) 3.42-3.51 (m, 1H) 3.58-3.70 (m, 2H) 5.47 (t, J=3.85 Hz, 1H) 8.22 (dd, J=8.80, 3.30 Hz, 2H) 8.31-8.42 (m, 2H)

(3R,4R)-tert-butyl 3-isobutyl-4-((4-nitrobenzoyl)oxy)pyrrolidine-1-carboxylate: 6.09 g 2$^{nd}$ eluting peak (peak2)

HPLC Rt (Method L)=9.06 min.

$^1$H NMR (600 MHz, DMSO-d$_6$) δ ppm 0.79-0.95 (m, 6H) 1.28-1.36 (m, 1H) 1.40 (d, J=19.44 Hz, 10H) 1.48-1.57 (m, 1H) 2.52-2.59 (m, 1H) 3.06-3.15 (m, 1H) 3.44-3.49 (m, 1H) 3.60-3.70 (m, 2H) 5.47 (t, J=3.94 Hz, 1H) 8.22 (dd, J=8.80, 3.30 Hz, 2H) 8.30-8.46 (m, 2H)

Step 2: (3S,4S)-tert-butyl 3-hydroxy-4-isobutylpyrrolidine-1-carboxylate and (3R,4R)-tert-butyl 3-hydroxy-4-isobutylpyrrolidine-1-carboxylate To a solution of (3S,4S)-tert-butyl 3-isobutyl-4-((4-nitrobenzoyl)oxy)pyrrolidine-1-carboxylate (first eluting peak of step 1) (5.8 g, 14.78 mmol) in MeOH (20 ml) was added NaOH (14.78 ml, 29.6 mmol). The RM was stirred at RT for 30 min and then poured into a mixture of EtOAc and water. Layers were separated, the organic layer was washed with water (2×) and brine (1×), dried over Na$_2$SO$_4$, filtered and concentrated under reduced pressure to afford 3.331 g of the title compound (3S,4S)-tert-butyl 3-hydroxy-4-isobutylpyrrolidine-1-carboxylate.

$^1$H NMR (600 MHz, DMSO-d$_6$) δ ppm 0.83-0.91 (m, 6H) 1.17-1.23 (m, 1H) 1.39 (m, 10H) 1.49-1.58 (m, 1H) 2.00-2.11 (m, 1H) 2.79-2.92 (m, 1H) 3.19-3.24 (m, 1H) 3.26-3.32 (m, 1H) 3.33 (m, J=5.00 Hz, 1H) 3.98-4.02 (m, 1H) 4.81 (brs, 1H).

To a solution of (3R,4R)-tert-butyl 3-isobutyl-4-((4-nitrobenzoyl)oxy)pyrrolidine-1-carboxylate (second eluting peak of step 1) (5.8 g, 14.78 mmol), MeOH (20 ml) was added NaOH (14.78 ml, 29.6 mmol). The RM was stirred at RT for 1 h, then poured into a mixture of EtOAc and water. Layers were separated, the organic layer was washed with water (2×), 10% aq. citric acid (1×), brine (1×), dried over Na$_2$SO$_4$, filtered and concentrated under reduced pressure to afford 2.995 g of the title compound (3R,4R)-tert-butyl 3-hydroxy-4-isobutylpyrrolidine-1-carboxylate.

$^1$H NMR (600 MHz, DMSO-d$_6$) δ ppm 0.85-0.90 (m, 6H) 1.18-1.23 (m, 1H) 1.39 (m, 10H) 1.49-1.57 (m, 1H) 2.00-2.10 (m, 1H) 2.81-2.91 (m, 1H) 3.19-3.24 (m, 1H) 3.25-3.31 (m, 1H) 3.31-3.34 (m, 1H) 4.01 (m, 1H) 4.81 (t, J=3.30 Hz, 1H).

Step 3: (3R,4R)-4-isobutylpyrrolidin-3-ol

To a solution of (3R,4R)-tert-butyl 3-hydroxy-4-isobutylpyrrolidine-1-carboxylate (2.99 g, 12.29 mmol) in DCM (7 ml) was added HCl 4M in dioxane (20 ml, 80 mmol). The resulting solution was stirred at RT for 1 h. Then the RM was concentrated to an orange slurry, then diluted with Et$_2$O, stirred and cooled for 15 min. The precipitate formed was filtered, washed with Et$_2$O and dried under reduced pressure to afford 1.909 g of the title compound the title compound as an HCl salt as white crystals.

$^1$H NMR (600 MHz, DMSO-d$_6$) δ ppm 0.88 (dd, J=6.60, 2.57 Hz, 6H) 1.14-1.28 (m, 1H) 1.34-1.45 (m, 1H) 1.51-1.66 (m, 1H) 2.07 (dqd, J=11.55, 7.61, 7.61, 7.61, 3.76 Hz, 1H) 2.74 (t, J=11.37 Hz, 1H) 3.06 (d, J=12.10 Hz, 1H) 3.16-3.28 (m, 2H) 4.16 (q, J=3.48 Hz, 1H) 5.35 (d, J=3.85 Hz, 1H) 9.33 (brs, 2H).

Step 4: (3R,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide To a stirred solution of 5-fluoro-2-methyl-3-(4,4,5,5-tetramethyl-1,3,2-dioxaborolan-2-yl)aniline (used as a commercial, or prepared according to the procedure of published patent application WO2013/008095, page 37, intermediate 5) (1.2 g, 4.78 mmol) and DIPEA (3.34 ml, 19.12 mmol) in DCM (25 ml) under argon was slowly added phosgene 20% in toluene (3.02 ml, 5.73 mmol) below 0° C. The resulting solution was stirred at 0° C. for 10 min, then dropped into a stirring solution of (3R,4R)-4-isobutylpyrrolidin-3-ol (step 3) (0.945 g, 5.26 mmol) in DCM (25 ml) at 0° C. The resulting mixture was stirred at 0° C. for 1 h. The RM was concentrated, then poured into EtOAc/MeOH (9:1), washed with water (3×) and with brine (1×). The organic layers were then dried over MgSO$_4$ and concentrated under reduced pressure to afford 2.1 g of the crude product. Purification of the crude product by flash chromatography on silica gel eluting with 0-100% EtOAC (+5% EtOH) in hexane afforded 1.46 g of the title as a white foam.

LC-MS (Method A): Rt=1.21 min, [M+H]$^+$=421.4.

Step 5: (3R,4R)—N-(5-fluoro-3-(6-(4-(2-hydroxyethyl)phenyl)-7H-pyrrolo[2,3-d]pyrimidin-4-yl)-2-methylphenyl)-3-hydroxy-4-isobutylpyrrolidine-1-carboxamide To a mixture of 2-(4-(4-chloro-7H-pyrrolo[2,3-d]pyrimidin-6-yl)phenyl)ethanol (intermediate 17) (200 mg, 0.731 mmol), (3R,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (step 4) (307 mg, 0.731 mmol), and K$_2$CO$_3$ (252 mg, 1.827 mmol) in water (3 ml) was added PdCl$_2$(dppf) (53.5 mg, 0.073 mmol), followed by dioxane (3 ml). The resulting RM was stirred at 100° C. for 30 min and cooled down to RT. Purification by flash chromatography on silica gel eluting with 0-20% MeOH in DCM afforded 294 mg of the title compound.

LC-MS (Method A): Rt=0.90 min, [M+H]$^+$=532.2.

Step 6: 4-(4-(5-fluoro-3-((3R,4R)-3-hydroxy-4-isobutylpyrrolidine-1-carboxamido)-2-methylphenyl)-7H-pyrrolo[2,3-d]pyrimidin-6-yl)phenethyl methanesulfonate To a mixture of (3R,4R)—N-(5-fluoro-3-(6-(4-(2-hydroxyethyl)phenyl)-7H-pyrrolo[2,3-d]pyrimidin-4-yl)-2-methylphenyl)-3-hydroxy-4-isobutylpyrrolidine-1-carboxamide (step 5) (294 mg, 0.553 mmol) and TEA (0.385 ml, 2.77 mmol) in THF (3 ml) cooled at 0° C. was added Ms$_2$O (193 mg, 1.106 mmol). The RM was stirred at 0° C. for 30 min, then the solution was quenched at 0° C. with water. Layers were separated, then the aq. layer was extracted with DCM (2×). Combined organic layers were dried over MgSO$_4$, filtered and evaporated at RT to afford 343 mg of the title compound as a yellow solid.

LC-MS (Method A): Rt=0.97 min, [M+H]$^+$=610.3.

Step 7: tert-butyl 9-(4-(4-(5-fluoro-3-((3R,4R)-3-hydroxy-4-isobutylpyrrolidine-1-carboxamido)-2-methylphenyl)-7H-pyrrolo[2,3-d]pyrimidin-6-yl) phenethyl)-3,9-diazaspiro[5.5]undecane-3-carboxylate To a solution of 4-(4-(5-fluoro-3-((3R,4R)-3-hydroxy-4-isobutylpyrrolidine-1-carboxamido)-2-methylphenyl)-7H-pyrrolo[2,3-d]pyrimidin-6-yl)phenethyl methanesulfonate (step 6) (150 mg, 0.246 mmol), tert-butyl 3,9-diazaspiro [5.5]undecane-3-carboxylate (188 mg, 0.738 mmol) and K$_2$CO$_3$ (204 mg, 1.476 mmol) in DMF (1.5 ml) at RT was added ACN (6 ml). The resulting RM was stirred at 60° C. overnight, and then cooled down to RT. The yellow suspension was filtered, and then the filtrate was diluted with DCM/MeOH and filtered through a silica pad. The filtrate was concentrated under reduced pressure to afford 257 mg of the title compound.

LC-MS (Method A): Rt=0.98 min, [M+H]$^+$=768.5.

Step 8: (3R,4R)—N-(3-(6-(4-(2-(3,9-diazaspiro[5.5] undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide An orange solution of tert-butyl 9-(4-(4-(5-fluoro-3-((3R, 4R)-3-hydroxy-4-isobutylpyrrolidine-1-carboxamido)-2-methylphenyl)-7H-pyrrolo[2,3-d]pyrimidin-6-yl)phenethyl)-3,9-diazaspiro[5.5]undecane-3-carboxylate (step 7) (189 mg, 0.246 mmol) and TFA (0.569 ml, 7.38 mmol) in DCM (5 ml) was stirred at RT for 2 h and then concentrated under reduced pressure. Purification of the crude product by reverse phase flash chromatography on a Redisep® C18 column eluting with 10-100% ACN in (water+0.1% TFA) afforded 87.3 mg of the title compound as a TFA salt.

LC-MS (Method A): Rt=0.68 min, [M+H]$^+$=668.5.

Step 9: (3R,4R)—N-(3-(6-(4-(2-(9-(3-(2,4-dioxotetrahydropyrimidin-1 (2H)-yl)-4-methoxybenzoyl)-3, 9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide To a mixture of (3R,4R)—N-(3-(6-(4-(2-(3,9-diazaspiro [5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide (step 8) (87.3 mg, 0.086 mmol) and intermediate 1a (25.1 mg, 0.095 mmol) in DMF (3 ml) were added DIPEA (0.091 ml, 0.519 mmol) and HBTU (49.2 mg, 0.130 mmol). The resulting RM was stirred at RT for 2 h under argon, then poured into water and the resulting precipitate was filtered and dried under reduced pressure to give the crude product. Purification of the crude product by reverse phase flash chromatography on a Redisep® C18 column eluting with 10-100% ACN in (water+0.1% TFA) afforded the title compound as a TFA salt. The title compound as a TFA salt was then dissolved in MeOH, filtered on a SCX column and released from the SCX column with ammonia 7N in MeOH. The filtrate was then concentrated under reduced pressure to afford 47.3 mg of the title compound.

LC-MS (Method B): Rt=3.68 min, [M+H]$^+$=914.8.

$^1$H NMR (400 MHz, DMSO-d6) δ ppm 12.69 (s, 1H), 10.33 (s, 1H), 8.82 (s, 1H), 7.88 (brd, J=7.92 Hz, 2H), 7.63 (s, 1H), 7.49 (dd, J=10.78, 2.57 Hz, 1H), 7.37 (dd, J=8.51, 1.91 Hz, 1H), 7.27-7.34 (m, 3H), 7.15 (d, J=8.66 Hz, 1H), 7.05 (dd, J=8.80, 2.64 Hz, 1H), 6.74 (s, 1H), 4.88 (brd, J=3.37 Hz, 1H), 4.06-4.15 (m, 1H), 3.84 (s, 3H), 3.35-3.65 (m, 9H), 3.08 (brt, J=8.88 Hz, 1H), 2.71-2.82 (m, 2H), 2.68 (m, 2H), 2.52-2.61 (m, 2H), 2.34-2.47 (m, 4H), 2.12-2.21 (m, 1H), 2.09 (s, 3H), 1.56-1.63 (m, 1H), 1.34-1.56 (m, 9H), 1.21-1.30 (m, 1H), 0.90 (d, J=6.02 Hz, 6H).

Compound 8

(3R,4S)—N-(3-(6-(4-((4-((1-(3-(2,4-Dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

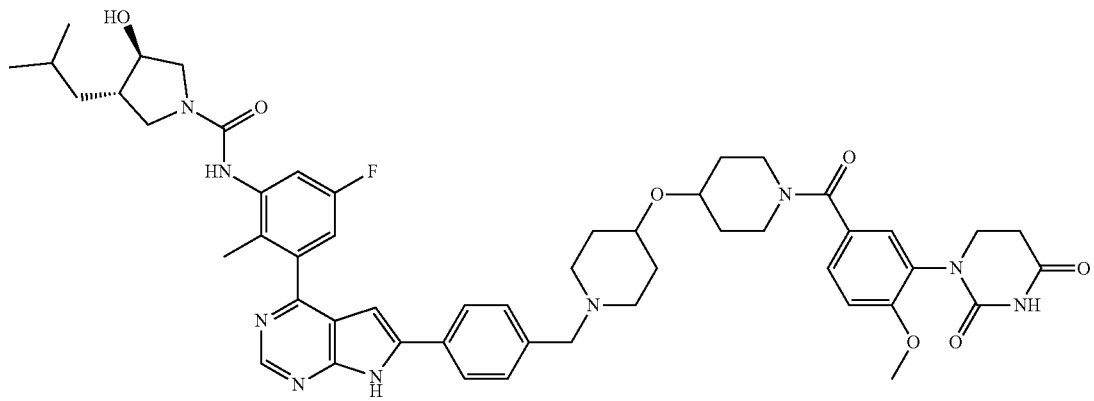 [SMILES: COc1ccc(C(=O)N2CCC(OC3CCN(Cc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

The title compound has been prepared by analogous methods to compound 6 using compound 6, step 1 and intermediates 18 and 1b.

LC-MS (method I): Rt=1.72 min, [M+H]⁺=930.

Compound 9

(cis-rac)-N-(3-(6-(4-((4-((1-(3-(2,4-Dioxotetrahydro-pyrimidin-1 (2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

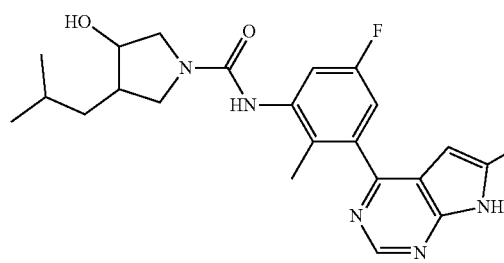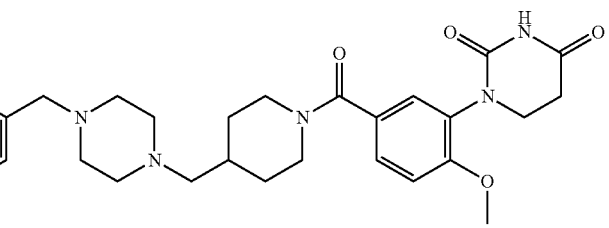

Step 1

(cis-rac)-tert-butyl 4-(4-(4-(5-fluoro-3-(3-hydroxy-4-isobutylpyrrolidine-1-carboxamido)-2-methylphenyl)-7H-pyrrolo[2,3-d]pyrimidin-6-yl)benzyl)piperazine-1-carboxylate To a mixture of 1-Boc-piperazine (77 mg, 0.413 mmol) (CAS 57260-71-6), TEA (0.100 ml, 0.717 mmol) and (cis-rac)-N-(5-fluoro-3-(6-(4-formylphenyl)-7H-pyrrolo[2,3-d]pyrimidin-4-yl)-2-methylphenyl)-3-hydroxy-4-isobutylpyrrolidine-1-carboxamide (214 mg, 0.345 mmol) (intermediate 10) in MeOH (3 ml) at RT was added ZnCl₂ 0.7M in THF (0.500 ml, 0.350 mmol). The resulting cloudy greenish solution was stirred at RT overnight, then NaBH₃CN (22 mg, 0.350 mmol) was added and the RM was further stirred at RT for 5 h. Then, the RM was concentrated under reduced pressure. Purification of the crude product by reverse phase flash chromatography on a Redisep® C18 column eluting with 2-100% ACN in (water+0.1% TFA) afforded 99 mg of the title compound as a TFA salt.

LC-MS (Method A): Rt=0.91 min, [M+H]⁺=686.5

Step 2: (cis-rac)-N-(5-fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide A solution of (cis-rac) tert-butyl 4-(4-(4-(5-fluoro-3-hydroxy-4-isobutylpyrrolidine-1-carboxamido)-2-methylphenyl)-7H-pyrrolo[2,3-d]pyrimidin-6-yl)benzyl)piperazine-1-carboxylate (step 1) (99 mg, 0.072 mmol) and HCl 4M in dioxane (0.5 ml, 2.00 mmol) in MeOH (2 ml) was stirred at RT for 3 h. Then the RM was concentrated under reduced pressure. Purification of the crude product by reverse phase flash chromatography on a Redisep® C18 column eluting with 2-100% ACN in (water+0.1% TFA) afforded 61.5 mg of the title compound as a TFA salt.

LC-MS (Method A): Rt=0.73 min, [M+H]⁺=586.6.

Step 3

(cis-rac)-tert-butyl 4-((4-(4-(4-(5-fluoro-3-(3-hydroxy-4-isobutylpyrrolidine-1-carboxamido)-2-methylphenyl)-7H-pyrrolo[2,3-d]pyrimidin-6-yl)benzyl)piperazin-1-yl)methyl)piperidine-1-carboxylate To a mixture of (cis-rac)-N-(5-fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide (step 2) (59 mg, 0.069 mmol), TEA (0.050 ml, 0.359 mmol) and 1-Boc-piperidine-carboxaldehyde (17 mg, 0.080 mmol) in MeOH (1 ml) at RT was added ZnCl₂ 0.7M in THF (0.120 ml, 0.084 mmol). The RM was stirred at RT for 6 h under argon. Then, NaBH₃CN (6 mg, 0.095 mmol) was added and the RM was stirred at RT overnight. The RM was concentrated under reduced pressure to afford 53.9 mg of the title compound.

LC-MS (Method A): Rt=0.92 min, [M+H]⁺=783.7.

Step 4: (cis-rac)-N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-3-hydroxy-4-isobutylpyrrolidine-1-carboxamide A yellow solution of (cis-rac)-tert-butyl 4-((4-(4-(4-(5-fluoro-3-hydroxy-4-isobutylpyrrolidine-1-carboxamido)-2-methylphenyl)-7H-pyrrolo[2,3-d]pyrimidin-6-yl)benzyl)piperazin-1-yl)methyl)piperidine-1-carboxylate (step 3) (0.069 mmol) and HCl 4M in dioxane (0.5 ml, 2.00 mmol) in MeOH (1 ml) was stirred at RT for 2 h. The RM was concentrated under reduced pressure to afford the title compound as a HCl salt.

LC-MS (Method A): Rt=0.66 min, [M+H]+=683.7.

Step 5: (cis-rac)-N-(3-(6-(4-((4-((1-(3-(2,4-dioxotetrahydropyrimidin-1 (2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide To a solution of intermediate 1a (27 mg, 0.104 mmol) in DMF (0.5 ml) was added NMM (0.025 ml, 0.227 mmol), followed by HATU (39 mg, 0.104 mmol). The RM was stirred at RT for 30 min. Then a solution of (cis-rac)-N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-3-hydroxy-4-isobutylpyrrolidine-1-carboxamide (step 4) (52 mg, 0.069 mmol) and NMM (0.025 ml, 0.227 mmol) in DMF (0.5 ml) was dropped into the RM and the resulting yellow mixture was stirred at RT for 2 days.

Purification of the crude product by reverse phase flash chromatography on a Redisep® C18 column eluting with 2-100% ACN in (water+0.1% NH₄HCO₃) afforded 38 mg of the title compound as a white powder.

LC-MS (Method B): Rt=3.68 min, [M/2+H]⁺=465.4.

¹H NMR (400 MHz, DMSO-d6) δ ppm 12.72 (s, 1H); 10.32 (s, 1H), 8.83 (s, 1H), 7.92 (d, J=7.95 Hz, 2H), 7.64 (s, 1H), 7.46-7.52 (m, 1H), 7.28-7.41 (m, 4H), 7.14 (d, J=8.44 Hz, 1H), 7.05 (dd, J=8.93, 2.32 Hz, 1H), 6.76 (s, 1H), 4.95-4.85 (m, 1H), 4.15-4.05 (m, 1H), 3.84 (s, 3H), 3.65-3.55 (m, 3H), 3.38-3.54 (m, 4H) 3.15-3.05 (m, 1H), 2.70-2.60 (m, 2H), 2.35-2.48 (m, 12H), 2.20-2.11 (m, 3H), 2.06-2.11 (m, 3H), 1.64-1.81 (m, 2H), 1.56-1.63 (m, 1H), 1.48-1.40 (m, 1H), 1.22-1.30 (m, 1H), 1.00-1.15 (m, 3H), 0.95-0.85 (m, 6H)

Compound 10

(3S,4R)—N-(3-(6-(4-((4-((1-(3-(2,4-Dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

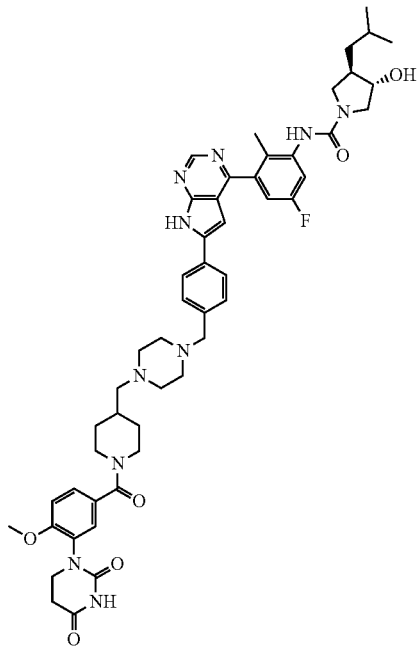 [SMILES: COc1ccc(C(=O)N2CCC(CN3CCN(Cc4ccc(-c5cc6c(-c7cc(F)cc(NC(=O)N8C[C@@H](CC(C)C)[C@H](O)C8)c7C)ncnc6[nH]5)cc4)CC3)CC2)cc1N1CCC(=O)NC1=O]

Step 1: tert-butyl 4-(4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)benzyl)piperazine-1-carboxylate To a mixture of tert-butyl 4-(4-(4-chloro-7H-pyrrolo[2,3-d]pyrimidin-6-yl)benzyl)piperazine-1-carboxylate (intermediate 5) (500 mg, 1.110 mmol), K₂CO₃ (384 mg, 2.78 mmol) and (3S,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 8) (500 mg, 1.13 mmol) in dioxane/water 1:1 (10 ml) degassed with argon was added PdCl₂(dppf)-DCM adduct (91 mg, 0.111 mmol). The RM was stirred at 100° C. for 2 h, then cooled down to RT and partitioned between EtOAc and water. Both layers were separated, the organic layer was washed with brine, dried over MgSO₄ and concentrated under reduced pressure. Purification of the crude product by flash chromatography on silica gel eluting with 0-17% MeOH in DCM afforded 692 mg of the title compound as a brown residue.

LC-MS (Method A): Rt=0.86 min, [M+H]⁺=686.5.

Step 2: (3S,4R)—N-(5-fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide A brownish solution of tert-butyl 4-(4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)benzyl)piperazine-1-carboxylate (step 1) (692 mg, 0.807 mmol) and HCl 4M in dioxane (2 ml, 8.00 mmol) in MeOH (2 ml) was stirred at RT for 2 h, then the RM was concentrated under reduced pressure. Purification of the crude product by reverse phase flash chromatography on a Redisep® C18 column eluting from 2-100% ACN in (water+0.1% TFA) afforded 570 mg of the title compound as a TFA salt.

LC-MS (Method A): Rt=0.72 min, [M+H]⁺=586.5.

Step 3: tert-butyl 4-((4-(4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)benzyl)piperazin-1-yl)methyl)piperidine-1-carboxylate To a solution of (3S,4R)—N-(5-fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide (step 2) (188 mg, 0.269 mmol), TEA (0.100 ml, 0.717 mmol) and 1-Boc-piperidine-carboxaldehyde (60 mg, 0.281 mmol) in MeOH (2 ml) at RT was added ZnCl₂ 0.5M in THF (0.550 ml, 0.275 mmol), and the RM was stirred at RT under argon for 3 days. Then, NaBH₃CN (16 mg, 0.255 mmol) was added. The RM was stirred at RT overnight and concentrated under reduced pressure. Purification of the crude product by reverse phase flash chromatography on a Redisep® C18 column eluting from 2-100% ACN in (water+0.1% TFA) afforded 223 mg of the title compound as a TFA salt.

LC-MS (Method A): Rt=0.90 min, [M+H]⁺=783.5.

Step 4: (3S,4R)—N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-3-hydroxy-4-isobutylpyrrolidine-1-carboxamide A yellow solution of tert-butyl 4-((4-(4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)benzyl)piperazin-1-yl)methyl)piperidine-1-carboxylate (step 3) (0.246 mmol) and HCl 4M in dioxane (1.5 ml, 6.00 mmol) in MeOH (2 ml) was stirred at RT for 2 h. The RM was concentrated under reduced pressure to afford 100 mg of the title compound as an HCl salt.

LC-MS (Method A): Rt=0.63 min, [M+H]⁺=683.6.

Step 5: (3S,4R)—N-(3-(6-(4-((4-((1-(3-(2,4-dioxotetrahydropyrimidin-1 (2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide To a solution of 3-(2,4-dioxotetrahydropyrimidin-1(2H)-yl)-4-methoxybenzoic (intermediate 1a) (40 mg, 0.151 mmol) in DMF (1 ml) was added NMM (0.050 ml, 0.455 mmol) followed by HATU (59 mg, 0.155 mmol). The resulting RM was stirred at RT for 30 min, then a solution of (3S,4R)—N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-3-hydroxy-4-isobutylpyrrolidine-1-carboxamide (step 4) (100 mg, 0.131 mmol) and NMM (0.050 ml, 0.455 mmol) in DMF (0.5 ml) was dropped into the mixture and the yellow RM was stirred at RT for 2 h, then concentrated under reduced pressure. Purification of the crude product by reverse phase flash chromatography on a Redisep® C18 column eluting from 2-100% ACN in (water+0.1% NH₄HCO₃) afforded, after ACN evaporation, a yellow suspension that was then filtered and dried under reduced pressure yielding 70 mg of the title compound as a solid.

LC-MS (Method B): Rt=3.55 min, [M/2+H]⁺=465.6.

¹H NMR (400 MHz, DMSO-d6) δ 13.95 (s, 1H), 10.32 (s, 1H), 9.12 (s, 1H), 8.20 (d, J=7.8 Hz, 2H), 7.95-7.78 (m, 2H), 7.66 (d, J=10.8 Hz, 1H), 7.55 (s, 1H), 7.38-7.31 (m, 2H), 7.25-7.12 (m, 3H), 3.95-3.65 (m, 10H), 3.58-2.89 (m, 13H), 2.67 (m, 2H), 2.18-2.01 (m, 6H), 1.99-1.82 (m, 2H), 1.60 (m, 1H), 1.40-1.27 (m, 1H,) 1.26-1.11 (m, 6H), 0.88 (m, 6H).

Compound 11

(3R,4S)—N-(3-(6-(4-((1-((1-(3-(2,4-Dioxotetrahydropyrimidin-1 (2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide concentrated. Purification of the residue by flash chromatography on silica gel eluting with 20% EtOAc in petroleum ether afforded 3 g of the title compound as a white solid.

LC-MS (method J): Rt=1.73 min, [M+NH₄]⁺=404.

Step 2: tert-butyl 4-(4-(4-chloro-7-(phenylsulfonyl)-7H-pyrrolo[2,3-d]pyrimidin-6-yl)phenoxy)piperidine-1-carboxylate In a 100 ml round bottom flask, purged and maintained under inert atmosphere were added 4-chloro-6-iodo-7-(phenylsulfonyl)-7H-pyrrolo[2,3-d]pyrimidine (intermediate 2) (400 mg, 0.954 mmol), tert-butyl 4-(4-(4,4,5,5-tetramethyl-1,3,2-dioxaborolan-2-yl)phenoxy)piperidine-1-carboxylate (CAS 889865-34-3) (385 mg, 0.954 mmol), K₂CO₃ (289 mg, 2.1 mmol) and PdCl₂(PPh₃)₂ (70 mg, 0.0954 mmol). Then, ACN (12 ml) and H₂O (3 ml) were added and the mixture was stirred at 100° C. for 2 h. The mixture was filtered and the filtrate was concentrated. The residue was extracted with EtOAc (30 ml), the organic layer was washed with water and brine, dried over Na₂SO₄ and concentrated under reduced pressure to afford 542 mg of the title compound.

LC-MS (method I): Rt=2.28 min, [M+H]⁺=570.

Step 3: tert-butyl 4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidine-1-carboxylate In a 100 ml round bottom flask purged and maintained under inert atmosphere were added tert-butyl 4-(4-(4-chloro-7-(phenylsulfonyl)-7H-pyrrolo[2,3-d]pyrimidin-6-

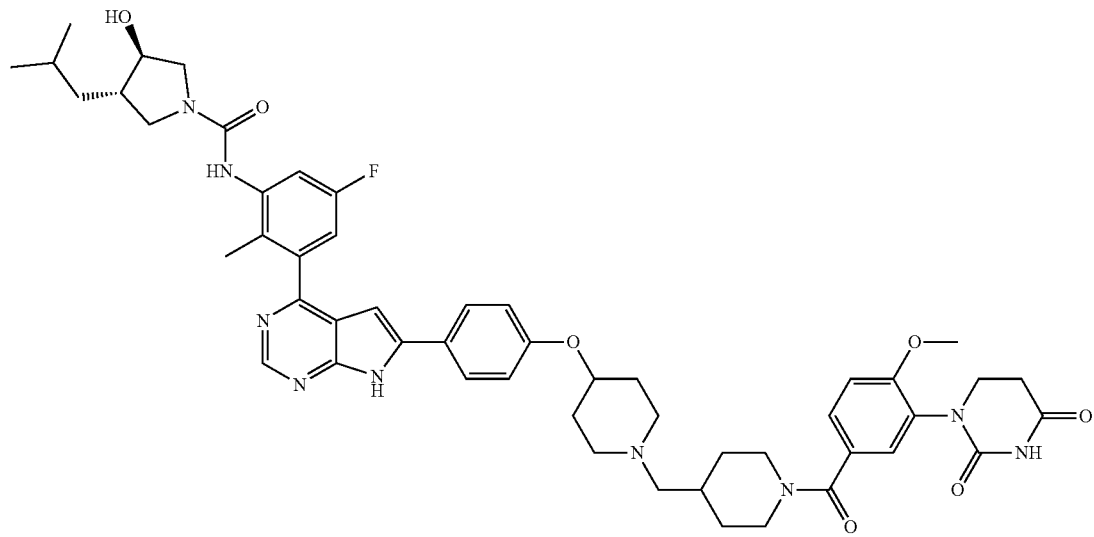 [SMILES: COc1ccc(C(=O)N2CCC(CN3CCC(Oc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

Step 1: tert-butyl 4-(4-(4,4,5,5-tetramethyl-1,3,2-dioxaborolan-2-yl)phenoxy)piperidine-1-carboxylate In a 500 ml round bottom flask, a mixture of tert-butyl 4-hydroxypiperidine-1-carboxylate (5 g, 24.88 mmol) (CAS 109384-19-2), 4-(4,4,5,5-tetramethyl-1,3,2-dioxaborolan-2-yl)phenol (CAS 269409-70-3) (6 g, 27.36 mmol) and PPh₃ (9.78 g, 37.31 mmol) in dry THF (200 ml) was stirred at 0° C. for 5 min. Then, DIAD (10 g, 49.75 mmol) was added dropwise at 0° C. and stirred for 3 h. The RM was then yl)phenoxy)piperidine-1-carboxylate (542 mg, 0.954 mmol), (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (400 mg, 0.954 mmol), K₂CO₃ (289 mg, 2.1 mmol) and PdCl₂(PPh₃)₂ (70 mg, 0.0954 mmol). Then, ACN (12 ml) and H₂O (3 ml) were added, and the mixture was stirred at 100° C. for 16 h. The mixture was filtered and the filtrate was concentrated. The residue was extracted with EtOAc (3×300 ml) and washed with water, brine, dried over Na₂SO₄ and concentrated under reduced pressure. Purification of the residue by chromatography on silica gel eluting with 10% MeOH in EtOAc afforded 300 mg of the title compound.

LC-MS (method I): Rt=2.02 min, [M+H]$^+$=687.

Step 4: (3R,4S)—N-(5-fluoro-2-methyl-3-(6-(4-(piperidin-4-yloxy)phenyl)-7H-pyrrolo[2,3-d]pyrimidin-4-yl)phenyl)-3-hydroxy-4-isobutylpyrrolidine-1-carboxamide To a 100 ml round bottom flask were added tert-butyl 4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidine-1-carboxylate (300 mg, 0.437 mmol) and DCM (10 ml). A solution of HCl 4M in dioxane (1 ml, 1 mmol) was added at 0° C. and the mixture was stirred at 0° C. for 1 h. The solvent was removed and the residue was dried under vacuum to afford 300 mg of the title compound as a white solid as an HCl salt.

LC-MS (method J): Rt=1.3 min; MS m/z [M+H]$^+$ 587.

Step 5: tert-butyl 4-formylpiperidine-1-carboxylate

To a mixture of oxalyl chloride (5.86 g, 46.51 mmol) in dry DCM (40 ml) was added a mixture of DMSO (7.25 g, 93.02 mmol) in dry DCM (20 ml) at −78° C. After stirring at −78° C. for 30 min, a mixture of N-Boc-4-piperidinemethanol (CAS 123855-51-6) (4 g, 18.6 mmol) in dry DCM (40 ml) was added, and the mixture was stirred at −78° C. for 30 min. Then, TEA (18.77 g, 186.05 mmol) was added at −78° C. and the RM was allowed to warm to RT over 30 min. Then, the RM was extracted with DCM (2×100 ml), the combined organic layers were washed with brine (100 ml), dried over Na$_2$SO$_4$, filtered and concentrated under reduced pressure. Purification of the crude product by chromatography on silica gel eluting with 25% EtOAc in petroleum ether afforded 3.04 g of the title compound.

LC-MS (method J): Rt=1.21 min, [M+tBu+H]$^+$=158.

Step 6: tert-butyl 4-((4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidin-1-yl)methyl)piperidine-1-carboxylate In a 100 ml of round bottom flask, a solution of (3R,4S)—N-(5-fluoro-2-methyl-3-(6-(4-(piperidin-4-yloxy)phenyl)-7H-pyrrolo[2,3-d]pyrimidin-4-yl)phenyl)-3-hydroxy-4-isobutylpyrrolidine-1-carboxamide hydrochloride (280 mg, 0.449 mmol) in DMF (4 ml) and TEA (49 mg, 0.493 mmol) was added. After stirring at RT for 10 min, tert-butyl 4-formylpiperidine-1-carboxylate (CAS 137076-22-3) (287 mg, 1.34 mmol) and a solution of ZnCl$_2$ 1M in THF (0.67 ml, 0.67 mmol) were added. The mixture was stirred at RT for 2 h, then NaBH$_3$CN (170 mg, 2.68 mmol) was added and the mixture was stirred overnight at RT. The RM was filtered and the solid was washed with DMF (1 ml). Purification of the filtrate by reverse phase flash chromatography (Biotage) on a Agela C18 column eluting with 0-60% ACN in water (10 mM NH$_4$HCO$_3$ buffer) afforded 210 mg of the title compound as a solid.

LC-MS (method G): Rt=1.39 min, [M+H]$^+$=784.

Step 7: (3R,4S)—N-(5-fluoro-2-methyl-3-(6-(4-((1-(piperidin-4-ylmethyl)piperidin-4-yl)oxy)phenyl)-7H-pyrrolo[2,3-d]pyrimidin-4-yl)phenyl)-3-hydroxy-4-isobutylpyrrolidine-1-carboxamide hydrochloride To a 100 ml round bottom flask were added tert-butyl 4-((4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidin-1-yl)methyl)piperidine-1-carboxylate (137 mg, 0.175 mmol)) and DCM (10 ml). A solution of HCl 4M in dioxane (1 ml, 4 mmol) was added and the mixture was stirred at RT for 1 h. The mixture was concentrated under reduced pressure to afford 100 mg of the title compound as a yellow solid as an HCl salt.

LC-MS (method I): Rt=1.67 min, [M+H]$^+$=684.

Step 8: (3R,4S)—N-(3-(6-(4-(1-((1-(3-(2,4-dioxotetrahydropyrimidin-1 (2H)-yl)-4-methoxybenzoyl)piperidin-4-yl)methyl)piperidin-4-yloxy)phenyl)-7H-pyrrolo[2,3-d]pyrimidin-4-yl)-5-fluoro-2-methylphenyl)-3-hydroxy-4-isobutylpyrrolidine-1-carboxamide In 100 ml round bottom flask were added (3R,4S)—N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide hydrochloride (100 mg, 0.137 mmol), TEA (0.54 ml, 0.27 mmol) and DMF (5 ml). Then, intermediate 1b (60 mg, 0.27 mmol) was added at 0° C. and the mixture was stirred at RT for 1 h. Purification of the mixture by reverse phase HPLC on a XBridge C18 column (21.2×250 mm, 10 μm) eluting with a gradient of ACN and water (0.01 M NH$_4$HCO$_3$ buffer) afforded 27 mg of the title compound as a white solid.

LC-MS (method I): Rt=1.75 min, [M+H]$^+$=931.

$^1$H NMR (500 MHz, DMSO-d6) δ 12.63 (m, 1H), 10.34 (s, 1H), 8.8 (s, 1H), 7.89 (d, J=8.0 Hz, 2H), 7.67 (s, 1H), 7.49 (dd, J$_1$=3.0 Hz, J$_2$=8.0 Hz, 1H), 7.37-7.31 (m, 2H), 7.16 (d, J=9.0 Hz, 1H), 7.06-7.02 (m, 3H), 6.65 (s, 1H), 5.13 (m, 1H), 4.46 (m, 2H), 3.88-3.84 (m, 4H), 3.67-3.58 (m, 5H), 3.2 (m, 1H), 3.07 (m, 2H), 2.69 (m, 5H), 2.17 (m, 4H), 2.08 (m, 4H), 1.94 (m, 2H), 1.79-1.59 (m, 6H), 1.35 (m, 1H), 1.15-1.05 (m, 3H), 0.9 (m, 6H).

Compound 12

(3R,4S)—N-(3-(6-(4-((4-((1-(3-(2,4-Dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

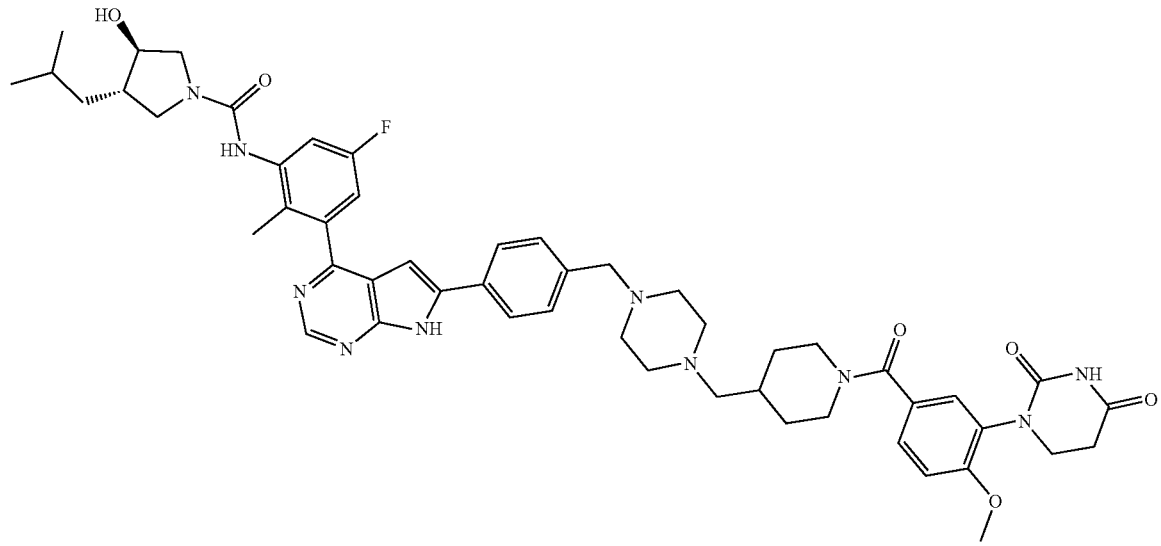 [SMILES: COc1ccc(C(=O)N2CCC(CN3CCN(Cc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

Step 1: tert-butyl 4-((4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)piperazin-1-yl)methyl)piperidine-1-carboxylate To a solution of (3R,4S)—N-(5-fluoro-2-methyl-3-(6-(4-(piperazin-1-ylmethyl)phenyl)-7H-pyrrolo[2,3-d]pyrimidin-4-yl)phenyl)-3-hydroxy-4-isobutylpyrrolidine-1-carboxamide (intermediate 11) (128 mg, 0.195 mmol), TEA (0.100 ml, 0.717 mmol) and 1-Boc-piperidine-carboxaldehyde (50 mg, 0.234 mmol) in MeOH (2 ml) at RT was added $ZnCl_2$ 0.7M in THF (0.300 ml, 0.210 mmol) and the resulting RM was stirred at RT under argon for 7 h. Then, $NaBH_3CN$ (14 mg, 0.223 mmol) was added and the RM was stirred at RT for 4 days, and concentrated under reduced pressure to afford 153 mg of the title compound.
LC-MS (Method A): Rt=0.91 min, [M+H]$^+$=783.7.

Step 2: (3R,4S)—N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-3-hydroxy-4-isobutylpyrrolidine-1-carboxamide A yellow solution of tert-butyl 4-((4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)piperazin-1-yl)methyl)piperidine-1-carboxylate (step 1) (0.195 mmol) and HCl 4M in dioxane (1 ml, 4.00 mmol) in MeOH (2 ml) was stirred at RT for 2 h, then the RM was concentrated under reduced pressure. Purification of the crude product by reverse phase flash chromatography on a Redisep® C18 column eluting with 2-100% ACN in (water+0.1% TFA) afforded 160 mg of the title compound as a TFA salt.
LC-MS (Method A): Rt=0.65 min, [M+H]$^+$=683.7.

Step 3: (3R,4S)—N-(3-(6-(4-((4-((1-(3-(2,4-dioxotetrahydropyrimidin-1 (2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide To a solution of 3-(2,4-dioxotetrahydropyrimidin-1 (2H)-yl)-4-methoxybenzoic acid (intermediate 1a) (46 mg, 0.174 mmol) in DMF (1 ml) was added NMM (0.050 ml, 0.455 mmol) followed by HATU (67 mg, 0.176 mmol). The resulting RM was stirred at RT for 30 min, then a solution of (3R,4S)—N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-3-hydroxy-4-isobutylpyrrolidine-1-carboxamide (step 2) (160 mg, 0.158 mmol) and NMM (0.050 ml, 0.455 mmol) in DMF (0.5 ml) was dropped into the mixture and the yellow RM was stirred at RT for 3 h before concentration under reduced pressure. Purification of the crude product by reverse phase flash chromatography on a Redisep® C18 column eluting with 2-100% ACN in (water+0.1% $NH_4HCO_3$) afforded 127 mg of the title compound as a white powder.
LC-MS (Method B): Rt=3.63 min, [M/2+H]$^+$=465.5.
$^1$H NMR (400 MHz, DMSO-d6) δ 12.72 (s, 1H), 10.32 (s, 1H), 8.83 (s, 1H), 7.92 (d, J=7.8 Hz, 2H), 7.67 (s, 1H), 7.49 (dd, J=10.8, 2.7 Hz, 1H), 7.45-7.27 (m, 4H), 7.14 (d, J=8.5 Hz, 1H), 7.05 (dd, J=9.1, 2.7 Hz, 1H), 6.76 (s, 1H), 5.12 (d, J=4.6 Hz, 1H), 4.35 (s, 1H), 3.85 (s, 4H), 3.62 (dt, J=26.9, 7.8 Hz, 5H), 3.48 (s, 2H), 3.19 (dt, J=8.6, 4.7 Hz, 1H), 3.14-3.04 (m, 1H), 2.73-2.60 (m, 2H), 2.37 (s, 7H), 2.09 (d, J=11.7 Hz, 7H), 1.85-1.53 (m, 4H), 1.35 (dt, J=13.9, 6.7 Hz, 1H), 1.21-0.96 (m, 3H), 0.89 (t, J=7.6 Hz, 6H).

Compound 13

(3R,4S)—N-(3-(6-(4-(2-(4-((1-(3-(2,4-Dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide

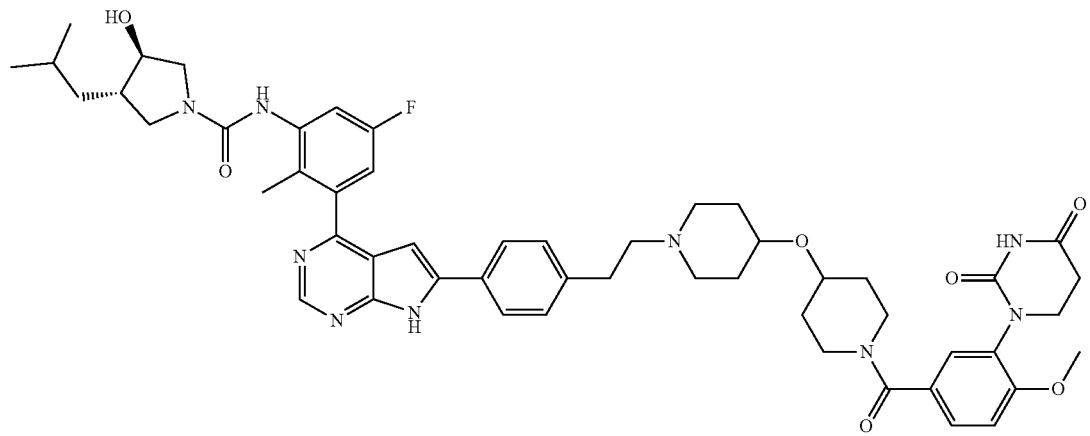 [SMILES: COc1ccc(C(=O)N2CCC(OC3CCN(CCc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

Step 1: tert-butyl 4-((1-(4-(4,4,5,5-tetramethyl-1,3,2-dioxaborolan-2-yl)phenethyl)piperidin-4-yl)oxy)piperidine-1-carboxylate To a 100 ml round bottom flask was added 4-(4,4,5,5-tetramethyl-1,3,2-dioxaborolan-2-yl)phenethyl methanesulfonate (1 g, 3.0 mmol), tert-butyl 4-(piperidin-4-yloxy)piperidine-1-carboxylate (intermediate 18) (1.7 g, 6.0 mmol), K$_2$CO$_3$ (828 mg, 6.0 mmol), KI (50 mg, 0.3 mmol) and ACN (20 ml). The RM was stirred at 50° C. for 16 h before it was filtered. The filter cake was washed with DCM (2×30 ml), and combined with the filtrate and concentrated. The crude mixture was purified by chromatography on silica gel eluting with 0-10% MeOH in DCM yielding 1.3 g of the title compound as a white solid.

LC-MS (method I): Rt=2.54 min, [M+H]$^+$=515.

Step 2: tert-butyl 4-((1-(4-(4-chloro-7-(phenylsulfonyl)-7H-pyrrolo[2,3-d]pyrimidin-6-yl)phenethyl)piperidin-4-yl)oxy)piperidine-1-carboxylate To a 100 ml round bottom flask, purged and maintained under inert atmosphere were added 4-chloro-6-iodo-7-(phenylsulfonyl)-7H-pyrrolo[2,3-d]pyrimidine (intermediate 2) (163 mg, 0.39 mmol), tert-butyl 4-((1-(4-(4,4,5,5-tetramethyl-1,3,2-dioxaborolan-2-yl)phenethyl)piperidin-4-yl)oxy)piperidine-1-carboxylate (step 1) (200 mg, 0.39 mmol), Na$_2$CO$_3$ (83 mg, 0.78 mmol) and PdCl$_2$(dppf)-CH$_2$Cl$_2$ (43 mg, 0.06 mmol). Then, ACN (8 ml) and water (2 ml) were added and the RM was stirred at 100° C. for 16 h under N$_2$. The RM was diluted with water (10 ml) and extracted with DCM (4×20 ml). The combined organic layers were dried over Na$_2$SO$_4$ and concentrated under reduced pressure. The crude mixture was purified by chromatography on silica gel eluting with 0-8% MeOH in DCM yielding 130 mg of the title compound tert-butyl 4-((1-(4-(4-chloro-7-(phenylsulfonyl)-7H-pyrrolo[2,3-d]pyrimidin-6-yl)phenethyl)piperidin-4-yl)oxy)piperidine-1-carboxylate (P1) as a yellow solid and 50 mg of tert-butyl 4-((1-(4-(4-chloro-7H-pyrrolo[2,3-d]pyrimidin-6-yl)phenethyl)piperidin-4-yl)oxy)piperidine-1-carboxylate as a yellow solid (P2). P1: LC-MS (method I): Rt=2.42 min, [M+H]$^+$=680.

P2: LC-MS (method I): Rt=2.16 min, [M+H]$^+$=540.

Step 3: tert-butyl 4-((1-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenethyl)piperidin-4-yl)oxy)piperidine-1-carboxylate To a 100 ml round bottom flask, purged and maintained under inert atmosphere was added P1 of step 2 (130 mg, 0.19 mmol), P2 of step 2 (50 mg, 0.09 mmol), intermediate 7 (114 mg, 0.28 mmol), Na$_2$CO$_3$ (74 mg, 0.7 mmol) and PdCl$_2$(dppf)-CH$_2$Cl$_2$ (30 mg, 0.04 mmol). ACN (8 ml) and water (2 ml) were added and the RM was stirred at 100° C. for 16 h under N$_2$. The RM was diluted with water (10 ml) and extracted with DCM (4×20 ml). The combined organic layers were dried over Na$_2$SO$_4$, concentrated under reduced pressure. The crude mixture was purified by chromatography on silica gel eluting with 0-10% MeOH in DCM yielding 85 mg of the title compound as a dark yellow solid.

LC-MS (method I): Rt=2.03 min, [M+H]$^+$=798.

Step 4: (3R,4S)—N-(5-fluoro-2-methyl-3-(6-(4-(2-(4-(piperidin-4-yloxy)piperidin-1-yl)ethyl)phenyl)-7H-pyrrolo[2,3-d]pyrimidin-4-yl)phenyl)-3-hydroxy-4-isobutylpyrrolidine-1-carboxamide To a 50 ml round bottom flask was added tert-butyl 4-((1-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenethyl)piperidin-4-yl)oxy)piperidine-1-carboxylate (step 3) (85 mg, 0.1 mmol) and DCM (3 ml) and the RM was stirred at RT. A solution of HCl 4M in dioxane (3 ml, 12 mmol) was slowly added. After addition, the RM was stirred at RT for 1 h, then concentrated under reduced pressure to afford 120 mg of the title compound as a yellow solid as an HCl salt.

LC-MS (method F): Rt=1.40 min, [M+H]$^+$=698.

Step 5: (3R,4S)—N-(3-(6-(4-(2-(4-((1-(3-(2,4-di-oxotetrahydropyrimidin-1(2H)-yl)-4-methoxyben-zoyl)piperidin-4-yl)oxy)piperidin-1-yl)ethyl)phe-nyl)-7H-pyrrolo[2,3-c]pyrimidin-4-yl)-5-fluoro-2-methylphenyl)-3-hydroxy-4-isobutylpyrrolidine-1-carboxamide To a 25 ml round bottom flask was added (3R,4S)—N-(5-fluoro-2-methyl-3-(6-(4-(2-(4-(piperidin-4-yloxy)piperi-din-1-yl)ethyl)phenyl)-7H-pyrrolo[2,3-d]pyrimidin-4-yl)phenyl)-3-hydroxy-4-isobutylpyrrolidine-1-carboxamide (step 4) (120 mg, 0.1 mmol), pentafluorophenyl 3-(2, 4-di-oxotetrahydropyrimidin-1(2H)-yl)-4-methoxybenzoate (43 mg, 0.1 mmol) (intermediate 1b), DIPEA (64 mg, 0.5 mmol) and DMF (2 ml). The RM was stirred at RT for 2 h. The RM was purified by preparative HPLC (XBridge C18, 21.2×250 mm, 10 μm) eluting with 0.01 M NH$_4$HCO$_3$ buffer in water/ACN yielding 40 mg of the title compound as a white solid.

LC-MS (method I): Rt=1.71 min, [M+H]$^+$=944.

$^1$H NMR (500 MHz, DMSO-d6) δ 8.82 (s, 1H), 7.87 (d, J=8.1 Hz, 2H), 7.67 (s, 1H), 7.49 (dd, J=10.7, 2.7 Hz, 1H), 7.38 (dd, J=8.4, 2.1 Hz, 1H), 7.35-7.30 (m, 3H), 7.15 (d, J=8.6 Hz, 1H), 7.06 (dd, J=8.9, 2.7 Hz, 1H), 6.74 (s, 1H), 5.12 (s, 1H), 3.95-3.79 (m, 5H), 3.72-3.55 (m, 6H), 3.43 (s, 1H), 3.27-3.13 (m, 4H), 3.11-3.04 (m, 1H), 2.83-2.71 (m, 4H), 2.68 (t, J=6.6 Hz, 2H), 2.20-1.95 (m, 6H), 1.87-1.75 (m, 4H), 1.66-1.58 (m, 1H), 1.45-1.31 (m, 5H), 1.17-1.08 (m, 1H), 0.91-0.88 (m, 6H).

Compound 14

(3R,4S)—N-(3-(6-(4-((1-((1-(3-(2,4-Dioxotetrahy-dropyrimidin-1 (2H)-yl)-4-methoxybenzoyl)piperi-din-4-yl)methyl)piperidin-4-yl)methoxy)phenyl)-7H-pyrrolo[2,3-d]pyrimidin-4-yl)-5-fluoro-2-methylphenyl)-3-hydroxy-4-isobutylpyrrolidine-1-carboxamide

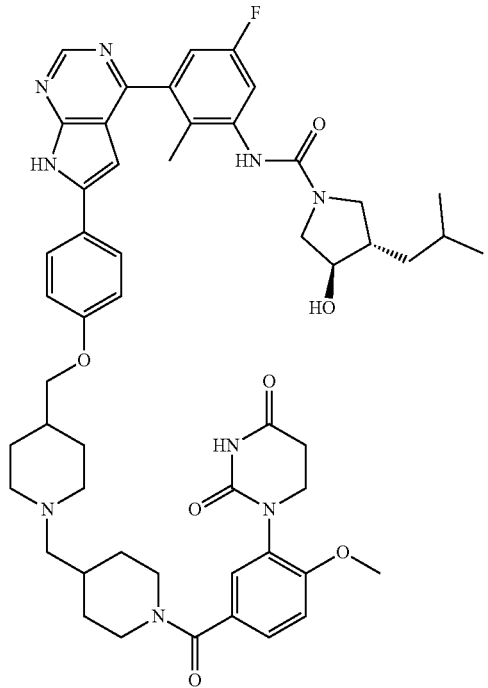 [SMILES: COc1ccc(C(=O)N2CCC(CN3CCC(COc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

Step 1: tert-butyl 4-((4-(4,4,5,5-tetramethyl-1,3,2-dioxaborolan-2-yl)phenoxy)methyl)piperidine-1-carboxylate To a solution of 4-hydroxyphenylboronic acid pinacol ester (4.5 g, 20.44 mmol), tert-butyl 4-(hydroxymethyl)piperidine-1-carboxylate (4 g, 18.58 mmol) and PPh$_3$ (7.3 g, 27.9 mmol) at 0° C. in THF (70 ml) was added dropwise DIAD (5.4 ml, 27.8 mmol) under argon. The resulting solution was stirred at RT for 3 days. Then it was partitioned between EtOAc and sat. NaHCO$_3$. Layers were separated, the organic layer was washed with brine, dried over MgSO$_4$ and concentrated under reduced pressure. Purification of the crude product by flash chromatography on silica gel eluting from 0-15% EtOAc in CHX afforded 1.636 g of the title compound.

LC-MS (Method A): Rt=1.51 min, [M+H]$^+$=418.2.

Step 2: 4-((4-(4,4,5,5-tetramethyl-1,3,2-dioxaboro-lan-2-yl)phenoxy)methyl)piperidine A solution of tert-butyl 4-((4-(4,4,5,5-tetramethyl-1,3,2-dioxaborolan-2-yl)phenoxy)methyl)piperidine-1-carboxy-late (step 1) (1.626 g, 3.70 mmol) and HCl 4M in dioxane (10 ml, 40.00 mmol) in DCM/MeOH 1:1 (10 ml) was stirred at RT for 5 h, then concentrated under reduced pressure to afford 1.347 g of the title compound as an HCl salt, as a white solid.

LC-MS (Method A): Rt=0.83 min, [M+H]$^+$=318.1.

Step 3: tert-butyl 4-((4-((4-(4,4,5,5-tetramethyl-1,3,2-dioxaborolan-2-yl)phenoxy)methyl)piperidin-1-yl)methyl)piperidine-1-carboxylate To a solution of 4-((4-(4,4,5,5-tetramethyl-1,3,2-dioxaborolan-2-yl)phenoxy)methyl)piperidine (step 2) (348 mg, 0.886 mmol), TEA (0.300 ml, 2.152 mmol) and 1-Boc-piperidine-4-carboxaldehyde (200 mg, 0.919 mmol) in MeOH (8 ml) at RT was added ZnCl$_2$ 0.5M in THF (2 ml, 1.000 mmol), and the RM was stirred at RT under argon for 1 h. Then NaBH$_3$CN (60 mg, 0.955 mmol) was added. The RM was stirred at RT for 1.5 h and concentrated under reduced pressure. Purification of the crude product by flash chromatography on silica gel eluting from 0-15% DCM/MeOH/NH$_3$ (95:4:1) in DCM afforded 372 mg of the title compound as a colorless residue.

LC-MS (Method A): Rt=1.05 min, [M+H]$^+$=515.3.

Step 4: tert-butyl 4-((4-((4-(4-chloro-7H-pyrrolo[2,3-d]pyrimidin-6-yl)phenoxy)methyl)piperidin-1-yl)methyl)piperidine-1-carboxylate To a mixture of 4-chloro-6-iodo-7H-pyrrolo[2,3-d]py-rimidine (177 mg, 0.633 mmol), Cs$_2$CO$_3$ (516 mg, 1.583 mmol) and tert-butyl 4-((4-((4-(4,4,5,5-tetramethyl-1,3,2-dioxaborolan-2-yl)phenoxy)methyl)piperidin-1-yl)methyl)piperidine-1-carboxylate (step 3) (362 mg, 0.633 mmol) in dioxane/water 1:1 (6 ml) degassed with argon was added PdCl$_2$(dppf)-CH$_2$Cl$_2$ (51 mg, 0.062 mmol). The resulting RM was stirred at 100° C. for 5 h, then cooled down to RT and partitioned between EtOAc and water. Both layers were separated. Then the organic layer was washed with brine, dried over MgSO$_4$ and concentrated under reduced pressure. Purification of the crude product by flash chromatography on silica gel eluting with 0-60% DCM/MeOH/NH$_3$ (95:4:1) in DCM afforded 268 mg of the title compound as a beige solid.

LC-MS (Method A): Rt=0.93 min, [M+H]$^+$=540.3/542.2.

Step 5: tert-butyl 4-((4-((4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)methyl)piperidin-1-yl)methyl)piperidine-1-carboxylate To a mixture of tert-butyl 4-((4-((4-(4-chloro-7H-pyrrolo[2,3-d]pyrimidin-6-yl)phenoxy)methyl)piperidin-1-yl)methyl)piperidine-1-carboxylate (step 4) (134 mg, 0.223 mmol), K₂CO₃ (77 mg, 0.558 mmol) and (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 7) (113 mg, 0.268 mmol) in dioxane/water 1:1 (3 ml) degassed with argon was added PdCl₂(dppf)-CH₂Cl₂ adduct (18 mg, 0.022 mmol) and the resulting RM was stirred at 100° C. for 2 h. Then, the RM was cooled down to RT, filtered over Hyflo® (filter material), and the resulting filtrate was concentrated under reduced pressure. Purification of the crude product by reverse phase flash chromatography on a Redisep® C18 column eluting from 2-100% ACN in (water+0.1% TFA) afforded 201 mg of the title compound as a TFA salt, as a yellow solid.

LC-MS (Method A): Rt=0.96 min, [M+H]⁺=798.5.

Step 6: (3R,4S)—N-(5-fluoro-2-methyl-3-(6-(4-((1-(piperidin-4-ylmethyl)piperidin-4-yl)methoxy)phenyl)-7H-pyrrolo[2,3-d]pyrimidin-4-yl)phenyl)-3-hydroxy-4-isobutylpyrrolidine-1-carboxamide A solution of tert-butyl 4-((4-((4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)methyl)piperidin-1-yl)methyl)piperidine-1-carboxylate (step 5) (201 mg, 0.198 mmol) and HCl 4M in dioxane (1 ml, 8.00 mmol) in MeOH (1 ml) was stirred at RT for 2 h, then concentrated under reduced pressure. Purification of the crude product by reverse phase flash chromatography on a Redisep® C18 column eluting from 2-100% ACN in (water+0.1% TFA) afforded 133 mg of the title compound as a TFA salt, as a yellow powder.

LC-MS (Method A): Rt=0.70 min, [M+H]⁺=698.7.

Step 7: (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)methoxy)phenyl)-7H-pyrrolo[2,3-d]pyrimidin-4-yl)-5-fluoro-2-methylphenyl)-3-hydroxy-4-isobutylpyrrolidine-1-carboxamide To a solution of 3-(2,4-dioxotetrahydropyrimidin-1(2H)-yl)-4-methoxybenzoic acid (intermediate 1a) (43 mg, 0.163 mmol) in DMF (1 ml) was added NMM (0.050 ml, 0.455 mmol), followed by HATU (62 mg, 0.163 mmol). The resulting RM was stirred at RT for 30 min, then a solution of (3R,4S)—N-(5-fluoro-2-methyl-3-(6-(4-((1-(piperidin-4-ylmethyl)piperidin-4-yl)methoxy)phenyl)-7H-pyrrolo[2,3-d]pyrimidin-4-yl)phenyl)-3-hydroxy-4-isobutylpyrrolidine-1-carboxamide (step 6) (133 mg, 0.136 mmol) and NMM (0.050 ml, 0.455 mmol) in DMF (0.5 ml) was dropped into the mixture and the yellow RM was stirred at RT for 1.5 h, then concentrated under reduced pressure. Purification of the crude product by reverse phase flash chromatography on a Redisep® C18 column eluting from 2-100% ACN in (water+0.1% NH₄HCO₃) afforded 97 mg of a material. The material was diluted in MeOH/DCM 4:1 (1 ml). The formed precipitate was filtered and dried under reduced pressure to afford 75 mg of the title compound as a white solid.

LC-MS (Method B): Rt=3.82 min; [M+H]⁺=944.7.

¹H NMR (400 MHz, DMSO-d6) δ 12.60 (s, 1H), 10.31 (s, 1H), 8.77 (s, 1H), 7.86 (d, J=8.8 Hz, 2H), 7.73 (s, 1H), 7.43 (dd, J=10.7, 2.8 Hz, 1H), 7.35 (dd, J=8.5, 2.2 Hz, 1H), 7.29 (d, J=2.1 Hz, 1H), 7.14 (d, J=8.6 Hz, 1H), 7.07-6.94 (m, 3H), 6.63 (s, 1H), 5.23 (m, 1H), 3.84 (m, 6H), 3.24-2.79 (m, 13H), 2.75-2.60 (m, 4H), 2.22-1.54 (m, 12H), 1.50-0.94 (m, 6H), 0.88 (m, 6H).

Compound 15

(3R,4S)—N-(3-(6-(4-(2-(9-(3-(2,4-Dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide

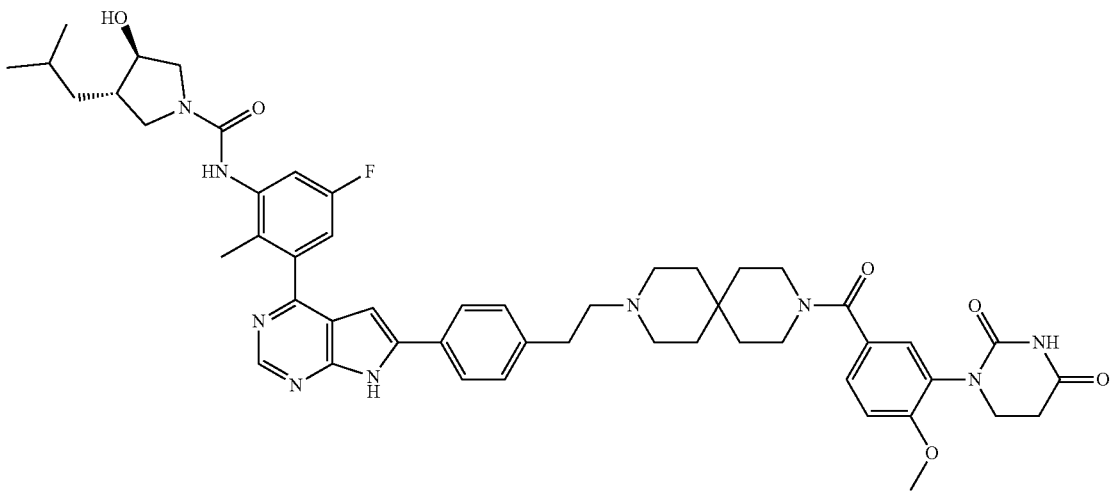 [SMILES: COc1ccc(C(=O)N2CCC3(CCN(CCc4ccc(-c5cc6c(-c7cc(F)cc(NC(=O)N8C[C@H](CC(C)C)[C@@H](O)C8)c7C)ncnc6[nH]5)cc4)CC3)CC2)cc1N1CCC(=O)NC1=O]

Step 1: tert-butyl 9-(4-(4-(5-fluoro-3-((3R,4S)-3-hydroxy-4-isobutylpyrrolidine-1-carboxamido)-2-methylphenyl)-7-(phenylsulfonyl)-7H-pyrrolo[2,3-d]pyrimidin-6-yl)phenethyl)-3,9-diazaspiro[5.5]undecane-3-carboxylate To a 50 ml round bottom flask were added (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 7) (168 mg, 0.40 mmol), tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate (intermediate 13) (250 mg, 0.38 mmol), $Na_2CO_3$ (101 mg, 0.95 mmol) and $PdCl_2$(dppf) (41 mg, 0.06 mmol). Then, ACN (8 ml) and water (2 ml) were added and the RM was stirred at 100° C. for 2 h under $N_2$. The RM was concentrated under reduced pressure. Purification of the crude residue by chromatography on silica gel eluting with 6% MeOH in DCM afforded 250 mg of the title compound as a yellow solid.

LC-MS (method F): Rt=1.51 min, $[M+H]^+$=908.

Step 2: tert-butyl 9-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenethyl)-3,9-diazaspiro[5.5]undecane-3-carboxylate To a 25 ml round bottom flask were added tert-butyl 9-(4-(4-(5-fluoro-3-((3R,4S)-3-hydroxy-4-isobutylpyrrolidine-1-carboxamido)-2-methylphenyl)-7-(phenylsulfonyl)-7H-pyrrolo[2,3-d]pyrimidin-6-yl)phenethyl)-3,9-diazaspiro[5.5]undecane-3-carboxylate (250 mg, 0.27 mmol), DMSO (2 ml) and water (1 ml). The RM was stirred at 0° C. for 15 min, then a solution of NaOH (86 mg, 2.16 mmol) in water (2 ml) was added. The RM was allowed to warm to RT, then stirred at RT for 16 h. After dilution with water (20 ml), it was extracted with EtOAc (3×20 ml). The combined organic layers were dried over $Na_2SO_4$, filtered and concentrated. Purification of the crude residue by chromatography on silica gel eluting with MeOH in DCM afforded 130 mg of the title compound as a yellow solid.

LC-MS (method F): Rt=1.35 min, $[M+H]^+$=768.

Step 3: (3R,4S)—N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide To a 50 ml flask were added tert-butyl 9-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenethyl)-3,9-diazaspiro[5.5]undecane-3-carboxylate (130 mg, 0.17 mmol) and DCM (10 ml) and then the RM was cooled to 0° C. A solution of HCl 4M in dioxane (2 ml, 8 mmol) was slowly added, then the RM was allowed to warm to RT, stirred at RT for 3 h and concentrated to afford 130 mg of the title compound as a grey solid as an HCl salt.

LC-MS (method F): Rt=1.06 min, $[M+H]^+$=668.

Step 4: (3R,4S)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide To a 25 ml flask were added (3R,4S)—N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide hydrochloride (120 mg, 0.17 mmol), intermediate 1a (50 mg, 0.19 mmol), DIPEA (88 mg, 0.68 mmol) and DMF (3 ml). Then, HATU (76 mg, 0.20 mmol) was added and the RM was stirred at RT for 16 h. Purification of the crude mixture by reverse phase HPLC on a XBridge C18 column (21.2×250 mm, 10 μm) eluting with ACN in water (0.01 M $NH_4HCO_3$ buffer) afforded 72 mg of the title compound as a white solid.

LC-MS (method J): Rt=1.41 min, $[M/2+H]^+$=457.6.

$^1$H NMR (400 MHz, DMSO-$d_6$) δ 0.90 (dd, J=8.44, 6.68 Hz, 6H) 1.08-1.16 (m, 1H) 1.31-1.36 (m, 1H) 1.37-1.45 (m, 4H) 1.49 (br s, 4H) 1.62 (dt, J=13.86, 6.71 Hz, 1H) 2.01-2.07 (m, 1H) 2.09 (s, 3H) 2.41 (br s, 4H) 2.55 (br s, 2H) 2.66-2.70 (m, 2H) 2.72-2.79 (m, 2H) 3.08 (br dd, J=9.39, 6.46 Hz, 1H) 3.19 (br dd, J=10.34, 4.92 Hz, 1H) 3.35-3.6 (m, 4H) 3.59 (brt, J=6.68 Hz, 2H) 3.62-3.69 (m, 2H) 3.84 (s, 3H) 3.85-3.92 (m, 1H) 5.11 (d, J=4.55 Hz, 1H) 6.74 (s, 1H) 7.05 (dd, J=8.88, 2.57 Hz, 1H) 7.15 (d, J=8.66 Hz, 1H) 7.28-7.33 (m, 3H) 7.37 (dd, J=8.51, 1.91 Hz, 1H) 7.49 (dd, J=10.71, 2.64 Hz, 1H) 7.66 (s, 1H) 7.87 (d, J=8.22 Hz, 2H) 8.82 (s, 1H) 10.32 (s, 1H) 12.69 (s, 1H).

Compound 16

(3R,4S)—N-(3-(6-(4-(2-(9-(3-(2,4-dioxotetrahydro-pyrimidin-1(2H)-yl)-4-ethoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide

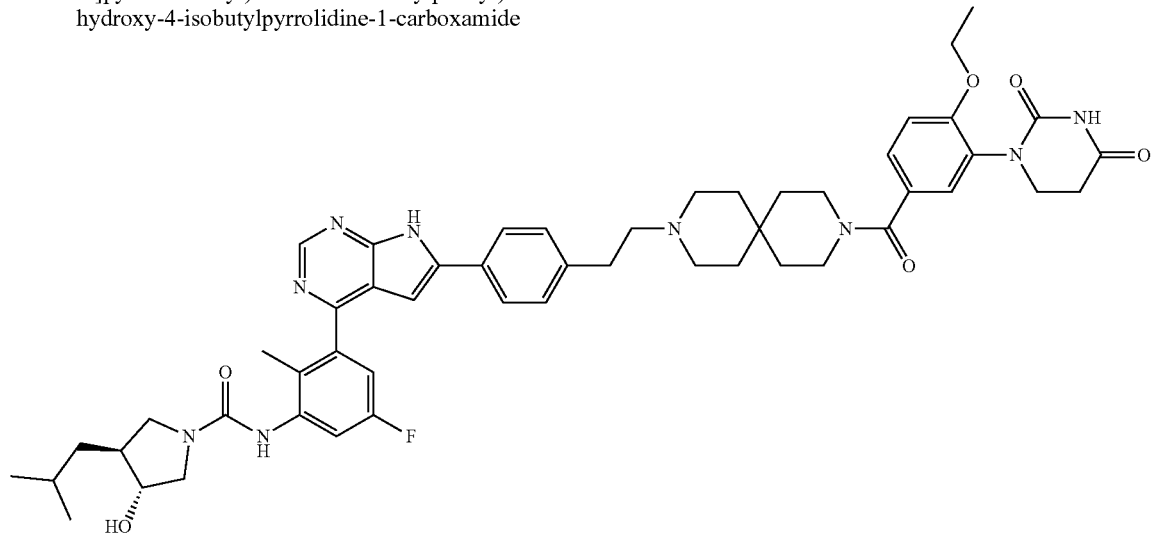

This compound has been prepared by analogous methods to previously described analogs. The coupling of (3R,4S)—N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide (compound 15, step 3) and intermediate 1c under standard amide formation conditions yielded the title compound as a yellow solid.

LC-MS (method K): Rt=2.03 min, [M+H]$^+$=928.

Compound 17

(3R,4S)—N-(3-(6-(4-(2-(9-(3-(2,4-dioxotetrahydro-pyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide

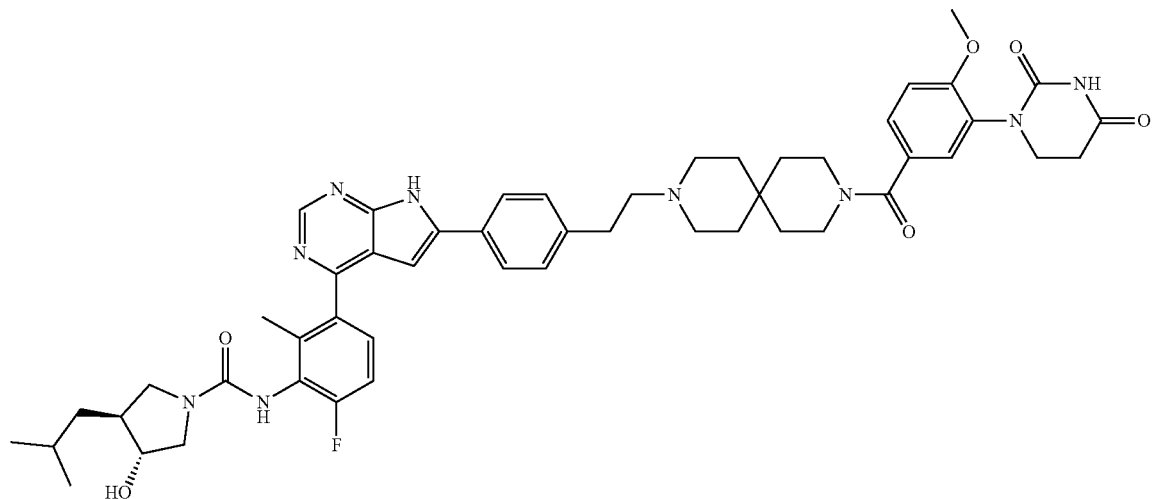 [SMILES: COc1ccc(C(=O)N2CCC3(CCN(CCc4ccc(-c5cc6c(-c7ccc(F)c(NC(=O)N8C[C@H](CC(C)C)[C@@H](O)C8)c7C)ncnc6[nH]5)cc4)CC3)CC2)cc1N1CCC(=O)NC1=O]

The compound has been prepared by analogous methods to previously described analogs. Coupling of (3R,4S)—N-(3-(6-(4-(2-(3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide with intermediate 1b yielded the title compound as a white solid.
LC-MS (method K): Rt=1.93 min, [M+H]$^+$=915.2.
Compound 18

(cis-rac)-N-(3-(6-(4-(2-(9-(3-(2,4-dioxotetrahydro-pyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide

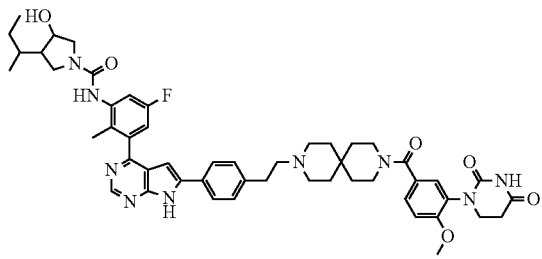 [SMILES: CCC(C)C1CN(C(=O)Nc2cc(F)cc(-c3ncnc4[nH]c(-c5ccc(CCN6CCC7(CC6)CCN(C(=O)c6ccc(OC)c(N8CCC(=O)NC8=O)c6)CC7)cc5)cc34)c2C)CC1O]

Step 1: tert-butyl 9-(4-(4-(5-fluoro-3-((cis-rac)-3-hydroxy-4-isobutylpyrrolidine-1-carboxamido)-2-methylphenyl)-7-(phenylsulfonyl)-7H-pyrrolo[2,3-d]pyrimidin-6-yl)phenethyl)-3,9-diazaspiro[5.5]undecane-3-carboxylate To a 50 ml round bottom flask purged and maintained under inert atmosphere were added tert-butyl-9-(4-(4-chloro-7-(phenylsulfonyl)-7H-pyrrolo[2,3-d]pyrimidin-6-yl)phenethyl)-3,9-diazaspiro[5.5]undecane-3-carboxylate (intermediate 13) (200 mg, 0.31 mmol), (cis-rac)-N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 9) (155 mg, 0.37 mmol), Na$_2$CO$_3$ (85 mg, 0.8 mmol) and PdCl$_2$(dppf) (34 mg, 0.05 mmol). ACN (12 ml) and water (3 ml) were added, the RM was stirred at 100° C. for 2 h, then concentrated under reduced pressure. Purification of the crude mixture by chromatography on silica gel eluting with 3-6% MeOH in DCM afforded 380 mg of the title compound as a yellow solid.
LC-MS (method F): Rt=1.54 min, [M+H]$^+$=909.

Step 2: tert-butyl 9-(4-(4-(5-fluoro-3-((cis-rac)-3-hydroxy-4-isobutylpyrrolidine-1-carboxamido)-2-methylphenyl)-7H-pyrrolo[2,3-d]pyrimidin-6-yl)phenethyl)-3,9-diazaspiro[5.5]undecane-3-carboxylate To a 50 ml round bottom flask were added tert-butyl 9-(4-(4-(5-fluoro-3-((cis-rac)-3-hydroxy-4-isobutylpyrrolidine-1-carboxamido)-2-methylphenyl)-7-(phenylsulfonyl)-7H-pyrrolo[2,3-d]pyrimidin-6-yl)phenethyl)-3,9-diazaspiro[5.5]undecane-3-carboxylate (380 mg, 0.31 mmol) and DMSO (2 ml). A solution of NaOH (50 mg, 1.24 mmol) in water (1 ml) was added slowly at RT, the RM was stirred at RT for 16 h. The RM was poured into water (10 ml) and extracted with EtOAc (4×10 ml). The combined organic layers were then dried to afford the crude mixture. Purification of the crude mixture by chromatography on silica gel eluting with 3-6% MeOH in DCM afforded 130 mg of the title compound as a yellow solid.
LC-MS (method F): Rt=1.37 min, [M+H]$^+$=769.

Step 3: (cis-rac)-N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide To a 50 ml round bottom flask were added tert-butyl 9-(4-(4-(5-fluoro-3-((cis-rac)-3-hydroxy-4-isobutylpyrrolidine-1-carboxamido)-2-methylphenyl)-7H-pyrrolo[2,3-d]pyrimidin-6-yl)phenethyl)-3,9-diazaspiro[5.5]undecane-3-carboxylate (100 mg, 0.13 mmol) (step 2) and DCM (6 ml). The RM was stirred at RT and a solution of HCl 4M in dioxane (3.5 ml, 14 mmol) was added. After the addition, the mixture was stirred at RT for 3 h. The RM was concentrated to afford 120 mg of the title compound as a yellow solid as an HCl salt.
LC-MS (method F): Rt=1.09 min, [M+H]$^+$=668.

Step 4: (cis-rac)-N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide To a 50 ml round bottom flask was added (cis-rac)-N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide hydrochloride (120 mg, 0.17 mmol) (step 3), 3-(2,4-dioxotetrahydropyrimidin-1(2H)-yl)-4-methoxybenzoic acid (intermediate 1a) (53 mg, 0.20 mmol), DIPEA (110 mg, 0.85 mmol) and DMF (3 ml). The RM was stirred at RT before HATU (76 mg, 0.20 mmol) was added and stirred for further 2 h at RT. Purification of the RM by reverse phase HPLC eluting with a ACN/water (containing 0.01 M NH$_4$HCO$_3$ buffer) gradient, afforded 70 mg of the title compound as a white solid.
LC-MS (method E): Rt=1.75 min, [M+H]$^+$=914.

$^1$H NMR (500 MHz, DMSO) δ 12.71 (s, 1H), 10.35 (s, 1H), 8.82 (s, 1H), 7.88 (d, J=8.2 Hz, 2H), 7.65 (s, 1H), 7.49 (dd, J=10.9, 2.7 Hz, 1H), 7.38 (dd, J=8.4, 2.1 Hz, 1H), 7.33-7.31 (m, 3H), 7.16 (d, J=8.6 Hz, 1H), 7.06 (dd, J=8.8, 2.7 Hz, 1H), 6.75 (s, 1H), 4.91 (s, 1H), 4.11 (s, 1H), 3.85 (s, 3H) 3.68-3.40 (m, 9H), 3.08 (s, 1H), 2.76 (t, J=6.4 Hz, 2H), 2.66 (m, 2H), 2.54 (m, 2H) 2.42-2.37 (m, 4H), 2.17 (s, 1H), 2.10 (s, 3H), 1.64-1.56 (m, 1H), 1.49-1.42 (m, 9H), 1.29-1.25 (m, 1H), 0.92-0.90 (m, 6H).

Compound 19

(3S,4R)—N-(3-(6-(4-(2-(9-(3-(2,4-dioxotetrahydro-pyrimidin-1(2H)-yl)-4-methoxybenzoyl)-3,9-diaz-aspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide

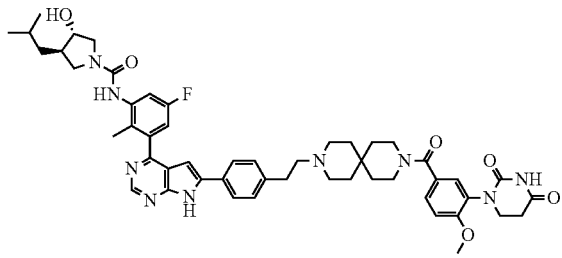 [SMILES: COc1ccc(C(=O)N2CCC3(CCN(CCc4ccc(-c5cc6c(-c7cc(F)cc(NC(=O)N8C[C@@H](CC(C)C)[C@H](O)C8)c7C)ncnc6[nH]5)cc4)CC3)CC2)cc1N1CCC(=O)NC1=O]

Step 1: tert-butyl 9-(4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)phenethyl)-3,9-diazaspiro[5.5]undecane-3-carboxylate To a 50 ml round bottom flask purged and maintained under inert atmosphere were added (3S,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 8) (154 mg, 0.37 mmol), tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate (intermediate 13) (250 mg, 0.38 mmol), Na$_2$CO$_3$ (101 mg, 0.95 mmol) and PdCl$_2$(dppf) (41 mg, 0.06 mmol). ACN (8 ml) and water (2 ml) were added and the RM was stirred at 100° C. for 2 h under N$_2$, then concentrated under reduced pressure. Purification of the crude mixture by chromatography on silica gel eluting with 3-6% MeOH in DCM afforded 200 mg of the title compound as a yellow solid.

LC-MS (method F): Rt=1.34 min, [M+H]$^+$=768.

Step 2: (3S,4R)—N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide To a 50 ml round bottom flask were added tert-butyl 9-(4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)phenethyl)-3,9-diazaspiro[5.5]undecane-3-carboxylate (120 mg, 0.16 mmol) and DCM (6 ml). The RM was stirred at RT, then a solution of HCl 4M in dioxane (4 ml, 16 mmol) was added. After the addition, the RM was stirred at RT for 3 h and concentrated to afford 115 mg of the title compound as a yellow solid as an HCl salt.

LC-MS (method F): Rt=1.08 min, [M+H]$^+$=668.

Step 3: (3S,4R)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide To a 50 ml flask were added (3S,4R)—N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide (step 2) (106 mg, 0.16 mmol), 3-(2,4-dioxotetrahydropyrimidin-1(2H)-yl)-4-methoxybenzoic acid (intermediate 1a) (50 mg, 0.19 mmol), DIPEA (103 mg, 0.8 mmol) and DMF (3 ml). HATU (72 mg, 0.19 mmol) was added at RT and the RM was stirred at RT for 16 h. Purification of the RM by reverse phase HPLC on a XBridge C18 column eluting with a ACN/water (containing 0.01 M NH$_4$HCO$_3$ buffer) gradient afforded 41 mg of the title compound as a white solid.

LC-MS (method F): Rt=1.20 min, [M+H]$^+$=914.

$^1$H NMR (500 MHz, DMSO-d6) δ 12.67 (s, 1H), 10.34 (s, 1H), 8.79 (s, 1H), 7.87 (d, J=8.2 Hz, 2H), 7.66 (s, 1H), 7.48 (dd, J=10.7, 2.6 Hz, 1H), 7.38-7.29 (m, 4H), 7.15 (d, J=8.6 Hz, 1H), 7.05 (dd, J=8.8, 2.8 Hz, 1H), 6.71 (s, 1H), 5.13 (s, 1H), 3.87-3.84 (m, 4H), 3.73-3.38 (m, 8H), 3.20-3.17 (m, 1H), 3.09-3.06 (m, 1H), 2.80-2.72 (m, 2H), 2.68 (t, J=6.5 Hz, 2H), 2.41-2.36 (m, 6H), 2.09-2.04 (m, 4H), 1.66-1.58 (m, 1H), 1.56-1.27 (m, 9H), 1.16-1.10 (m, 1H), 0.91 (d, J=6.6 Hz, 3H), 0.89 (d, J=6.6 Hz, 3H).

Compound 20

(3R,4S)—N-(3-(6-(4-((1-(2-((1-(3-(2,4-Dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide

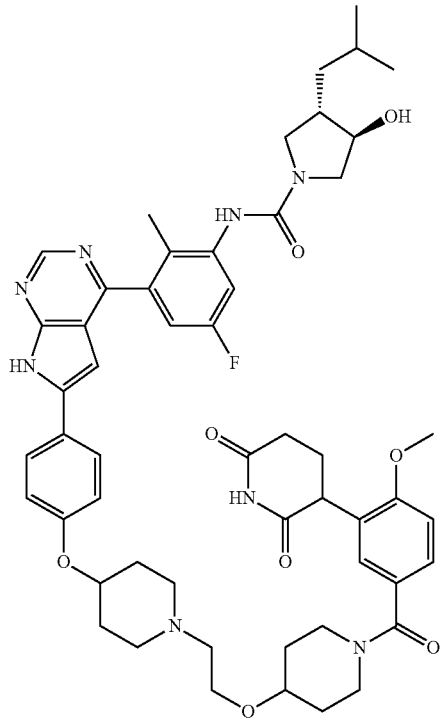 [SMILES: COc1ccc(C(=O)N2CCC(OCCN3CCC(Oc4ccc(-c5cc6c(-c7cc(F)cc(NC(=O)N8C[C@H](CC(C)C)[C@@H](O)C8)c7C)ncnc6[nH]5)cc4)CC3)CC2)cc1C1CCC(=O)NC1=O]

Step 1

2-((1-(tert-butoxycarbonyl)piperidin-4-yl)oxy)-1-hydroxyethanesulfonic acid

A solution of tert-butyl 4-(2-oxoethoxy)piperidine-1-carboxylate (intermediate 4) (1000 mg, 3.70 mmol) in EtOH (6 ml) was purged with argon, then a solution of sodium metabisulfite (500 mg, 2.63 mmol) in water (1 ml) was added and the RM was then stirred at 80° C. for 1 h. The heterogeneous RM was cooled to RT, stirred for 2 days and then filtered. The solid cake was washed with EtOH and dried under reduced pressure to afford 833 mg of the title compound as a white solid.

¹H NMR (400 MHz, DMSO-d6) δ 5.32 (d, J=5.7 Hz, 1H), 3.96 (t, J=7.2 Hz, 1H), 3.80 (d, J=10.3 Hz, 1H), 3.61 (d, J=13.4 Hz, 2H), 3.46 (s, 1H), 3.35 (s, 2H), 2.99 (s, 2H), 1.73 (s, 2H), 1.39 (s, 9H), 1.30 (q, J=9.1, 5.9 Hz, 2H).

Step 2 tert-butyl 4-(2-(4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidin-1-yl)ethoxy)piperidine-1-carboxylate (3R,4S)—N-(5-fluoro-2-methyl-3-(6-(4-(piperidin-4-yloxy)phenyl)-7H-pyrrolo[2,3-d]pyrimidin-4-yl)phenyl)-3-hydroxy-4-isobutylpyrrolidine-1-carboxamide (intermediate 12) (130 mg, 0.161 mmol) was dissolved in MeOH (1.5 ml) at RT. Then, NaOAc (33 mg, 0.402 mmol) was added and the orange solution was stirred at RT for 5 min. Then, 2-((1-(tert-butoxycarbonyl)piperidin-4-yl)oxy)-1-hydroxyethanesulfonic acid (90 mg, 0.277 mmol) and 2-picoline borane complex (CAS 3999-38-0) (8 mg, 0.064 mmol) were added and the RM was stirred overnight at RT. Then, an additional batch of 2-((1-(tert-butoxycarbonyl)piperidin-4-yl)oxy)-1-hydroxyethanesulfonic acid (15 mg, 0.046 mmol) and 2-picoline borane complex (4 mg, 0.032 mmol) were added and the RM was stirred for 2 days, then concentrated to dryness. Purification of the crude product by reverse phase flash chromatography on a Redisep® C18 column eluting with 2-90% ACN in water+0.1% TFA afforded 128 mg of the title compound.

LC-MS (Method A): Rt=0.96 min, [M+H]⁺=814.7

Step 3: (3R,4S)—N-(5-fluoro-2-methyl-3-(6-(4-((1-(2-(piperidin-4-yloxy)ethyl)piperidin-4-yl)oxy)phenyl)-7H-pyrrolo[2,3-d]pyrimidin-4-yl)phenyl)-3-hydroxy-4-isobutylpyrrolidine-1-carboxamide A solution of tert-butyl 4-(2-(4-(4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)phenoxy)piperidin-1-yl)ethoxy)piperidine-1-carboxylate (step 2) (128 mg, 0.127 mmol) and HCl 4M in dioxane (1 ml, 4.00 mmol) in MeOH (1.5 ml) was stirred for 1 h at RT, then the RM was concentrated to dryness. Purification of the crude product by reverse phase flash chromatography on a Redisep® C18 column eluting with 2-100% ACN in water+0.1% TFA afforded 94 mg of the title compound as a yellow powder as a TFA salt.

LC-MS (Method A): Rt=0.64 min, [M+H]⁺=714.5

Step 4: (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide 3-(2,4-dioxotetrahydropyrimidin-1 (2H)-yl)-4-methoxybenzoic acid (intermediate 1a) (31 mg, 0.117 mmol) was dissolved in DMF (1 ml). Then NMM (0.050 ml, 0.455 mmol) was added followed by HATU (45 mg, 0.118 mmol). After 30 min, a solution of (3R,4S)—N-(5-fluoro-2-methyl-3-(6-(4-((1-(2-(piperidin-4-yloxy)ethyl)piperidin-4-yl)oxy)phenyl)-7H-pyrrolo[2,3-d]pyrimidin-4-yl)phenyl)-3-hydroxy-4-isobutylpyrrolidine-1-carboxamide (94 mg, 0.098 mmol) (step 3) and NMM (0.050 ml, 0.455 mmol) in DMF (0.5 ml) was dropped into the mixture and the yellow RM was stirred at RT for 3 h. Purification of the crude product by reverse phase flash chromatography on a Redisep® C18 column eluting with 2-100% ACN in water+0.1% NH₄HCO₃ afforded 43 mg of the title compound.

LC-MS (Method B): Rt=3.69 min, [M+H]⁺=960.5

¹H NMR (400 MHz, DMSO-d6) δ 12.62 (s, 1H), 10.32 (s, 1H), 8.80 (s, 1H), 7.88 (d, J=8.4 Hz, 2H), 7.67 (s, 1H), 7.48 (dd, J=10.8, 2.8 Hz, 1H), 7.44-7.29 (m, 2H), 7.15 (d, J=8.5 Hz, 1H), 7.04 (m, 2.9 Hz, 3H), 6.65 (s, 1H), 5.12 (d, J=4.6 Hz, 1H), 4.45 (s, 1H), 3.85 (m, 4H), 3.74-3.44 (m, 7H), 3.27-3.01 (m, 4H), 2.83-2.61 (m, 4H), 2.50 (m, 2H), 2.32 (m, 4H), 2.08 (m, 4H), 1.93 (m, 2H), 1.83 (m, 2H), 1.62 (m, 3H), 1.55-1.29 (m, 3H), 1.13 (m, 1H), 0.89 (m, 6H).

Compound 21

(3S,4R)—N-(3-(6-(4-(((1-(2-(1-(3-(2,4-Dioxotetrahydropyrimidin-1 (2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide

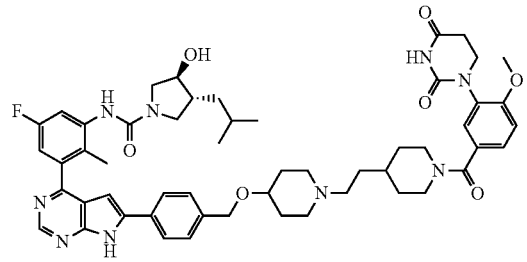 [SMILES: COc1ccc(C(=O)N2CCC(CCN3CCC(OCc4ccc(-c5cc6c(-c7cc(F)cc(NC(=O)N8C[C@@H](CC(C)C)[C@H](O)C8)c7C)ncnc6[nH]5)cc4)CC3)CC2)cc1N1CCC(=O)NC1=O]

Step 1: tert-butyl 4-(2-(4-((4-(4-(5-fluoro-3-((3S, 4R)-3-hydroxy-4-isobutylpyrrolidine-1-carboxamido)-2-methylphenyl)-7H-pyrrolo[2,3-d]pyrimidin-6-yl)benzyl)oxy)piperidin-1-yl)ethyl)piperidine-1-carboxylate To a mixture of tert-butyl 4-(2-(4-((4-(4-chloro-7H-pyrrolo[2,3-d]pyrimidin-6-yl)benzyl)oxy)piperidin-1-yl)ethyl)piperidine-1-carboxylate (intermediate 16) (130 mg, 0.195 mmol), (3S,4R)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 8) (90 mg, 0.214 mmol), and Na₂CO₃ 2M in water (0.195 ml, 0.389 mmol) in 1-propanol (15 ml) was added PdCl₂(PPh₃)₂ (6.83 mg, 9.74 μmol). The resulting RM was irradiated at 140° C.

for 15 min in microwave. Then it was concentrated under reduced pressure. Purification of the crude product by flash chromatography on silica gel eluting with 0-16% MeOH in DCM afforded 25 mg of the title compound.

LC-MS (Method A): Rt=0.96 min, [M+H]⁺=812.7.

Step 2: (3S,4R)—N-(5-fluoro-2-methyl-3-(6-(4-(((1-(2-(piperidin-4-yl)ethyl)piperidin-4-yl)oxy)methyl)phenyl)-7H-pyrrolo[2,3-d]pyrimidin-4-yl)phenyl)-3-hydroxy-4-isobutylpyrrolidine-1-carboxamide A green solution of tert-butyl 4-(2-(4-(((4-(4-(5-fluoro-3-((3S,4R)-3-hydroxy-4-isobutylpyrrolidine-1-carboxamido)-2-methylphenyl)-7H-pyrrolo[2,3-d]pyrimidin-6-yl)benzyl)oxy)piperidin-1-yl)ethyl)piperidine-1-carboxylate (step 1) (25 mg, 0.031 mmol) and TFA (0.071 ml, 0.924 mmol) in DCM (3 ml) was stirred at RT for 24 h. Then the solution was concentrated and dried under pressure to afford 47 mg of the title compound as a TFA salt.

LC-MS (Method A): Rt=0.70 min; [M+H]⁺=712.5.

Step 3: (3S,4R)—N-(3-(6-(4-(((1-(2-(1-(3-(2,4-dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide To a mixture of (3S,4R)—N-(5-fluoro-2-methyl-3-(6-(4-(((1-(2-(piperidin-4-yl)ethyl)piperidin-4-yl)oxy)methyl)phenyl)-7H-pyrrolo[2,3-d]pyrimidin-4-yl)phenyl)-3-hydroxy-4-isobutylpyrrolidine-1-carboxamide (step 2) (28.9 mg, 0.031 mmol) and 3-(2,4-dioxotetrahydropyrimidin-1(2H)-yl)-4-methoxybenzoic acid (intermediate 1a) (8.94 mg, 0.034 mmol) in DMF (3 ml) was added DIPEA (0.032 ml, 0.184 mmol) followed by HBTU (17.49 mg, 0.046 mmol). The resulting RM was stirred at RT for 2 h, then poured into H₂O and filtered. The resulting filtrate was filtered a second time. Combined solids were dissolved in MeOH and concentrated under reduced pressure. The resulting crude product was adsorbed on Isolute® (sorbent material) and purified by reverse phase flash chromatography on a Redisep® C18 column eluting with 10-100% ACN in (water+0.1% TFA) to afford 7.5 mg of the title compound as a TFA salt.

LC-MS (Method B): Rt=3.82 min, [M/2+H]⁺=480.1

¹H NMR (400 MHz, DMSO-d6) δ 12.83 (s, 1H), 10.35 (s, 1H), 9.05 (s, 1H), 8.87 (s, 1H), 7.99 (d, J=8.1 Hz, 2H), 7.72 (s, 1H), 7.63-7.28 (m, 5H), 7.13 (dd, J=33.8, 7.4 Hz, 2H), 4.59 (d, J=9.7 Hz, 2H), 3.98-3.78 (m, 5H), 3.75-3.54 (m, 6H), 3.14 (d, J=33.2 Hz, 9H), 2.77-2.64 (m, 3H), 2.40-2.17 (m, 3H), 2.09 (d, J=16.7 Hz, 5H), 1.86 (s, 1H), 1.63 (d, J=6.6 Hz, 7H), 1.37 (s, 1H), 1.15 (d, J=8.7 Hz, 3H), 1.00-0.83 (m, 6H).

Compound 22

(3R,4S)—N-(3-(6-(4-(((1-(2-(1-(3-(2,4-Dioxotetrahydropyrimidin-1 (2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide

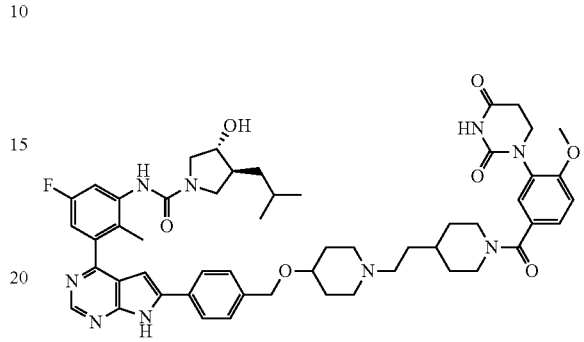

Step 1: tert-butyl 4-(2-(4-(((4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)oxy)piperidin-1-yl)ethyl)piperidine-1-carboxylate To a mixture of tert-butyl 4-(2-(4-(((4-(4-chloro-7H-pyrrolo[2,3-d]pyrimidin-6-yl)benzyl)oxy)piperidin-1-yl)ethyl)piperidine-1-carboxylate (intermediate 16) (358 mg, 0.646 mmol), (3R,4S)—N-(5-fluoro-2-methyl-3-(4,4,5,5-tetramethyl-1,3,2-dioxaborolan-2-yl)phenyl)-3-hydroxy-4-isobutylpyrrolidine-1-carboxamide (intermediate 7) (272 mg, 0.646 mmol), and K₂CO₃ (223 mg, 1.615 mmol) in water (10 ml) was added PdCl₂(dppf) (47.3 mg, 0.065 mmol), followed by dioxane (10 ml). The resulting RM was then stirred at 100° C. for 1 h, and then diluted with EtOAc and water. Both layers were separated, then the aq. layer was extracted with EtOAc (3×). Combined organic layers were washed with brine, dried over MgSO₄, filtered and concentrated under reduced pressure. Purification of the crude product by flash chromatography on silica gel eluting with 0-20% MeOH in DCM afforded 300 mg of the title compound.

LC-MS (Method A): Rt=0.95 min, [M+H]⁺=812.6.

Step 2: (3R,4S)—N-(5-fluoro-2-methyl-3-(6-(4-(((1-(2-(piperidin-4-yl)ethyl)piperidin-4-yl)oxy)methyl)phenyl)-7H-pyrrolo[2,3-d]pyrimidin-4-yl)phenyl)-3-hydroxy-4-isobutylpyrrolidine-1-carboxamide A green solution of tert-butyl 4-(2-(4-(((4-(4-(5-fluoro-3-((3R,4S)-3-hydroxy-4-isobutylpyrrolidine-1-carboxamido)-2-methylphenyl)-7H-pyrrolo[2,3-d]pyrimidin-6-yl)benzyl)oxy)piperidin-1-yl)ethyl)piperidine-1-carboxylate (step 1) (300 mg, 0.314 mmol) and TFA (0.726 ml, 9.42 mmol) in DCM (3 ml) was stirred at RT for 2 h, then the RM was concentrated under reduced pressure to afford 300 mg of the title compound as a TFA salt.

LC-MS (Method A): Rt=0.68 min, [M+H]⁺=712.6.

Step 3: (3R,4S)—N-(3-(6-(4-(((1-(2-(1-(3-(2,4-di-oxotetrahydropyrimidin-1(2H)-yl)-4-methoxyben-zoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide To a mixture of (3R,4S)—N-(5-fluoro-2-methyl-3-(6-(4-(((1-(2-(piperidin-4-yl)ethyl)piperidin-4-yl)oxy)methyl)phenyl)-7H-pyrrolo[2,3-d]pyrimidin-4-yl)phenyl)-3-hydroxy-4-isobutylpyrrolidine-1-carboxamide (step 2) (295 mg, 0.314 mmol) and 3-(2,4-dioxotetrahydropyrimidin-1(2H)-yl)-4-methoxybenzoic acid (intermediate 1a) (91 mg, 0.345 mmol) in DMF (3 ml) were added DIPEA (0.329 ml, 1.883 mmol) and HBTU (179 mg, 0.471 mmol). The RM was stirred at RT under argon for 2 h, then poured into water and DCM. Both layers were separated, then the organic layer, containing some sticky solid, was diluted with MeOH to dissolve the solid. The resulting clear organic layer was then concentrated under reduced pressure and absorbed on Isolute® (sorbent material). Purification of the crude product by reverse phase flash chromatography on a Redisep® C18 column eluting with 10-100% ACN in (water+0.1% TFA) afforded the title compound as a TFA salt. The title compound as a TFA salt was then dissolved in MeOH, filtered on a SCX column and released from the SCX column with ammonia 7N in MeOH. The filtrate was concentrated under reduced pressure to afford 142 mg of the title compound as a solid.

LC-MS (Method B): Rt=3.88 min, [M+H]$^+$=959.

$^1$H NMR (400 MHz, DMSO-d6) δ 12.75 (s, 1H), 10.33 (s, 1H), 8.84 (s, 1H), 7.95 (d, J=8.2 Hz, 2H), 7.67 (s, 1H), 7.49 (dd, J=10.8, 2.6 Hz, 1H), 7.41 (d, J=8.1 Hz, 2H), 7.35 (dd, J=8.5, 1.9 Hz, 1H), 7.31 (d, J=1.9 Hz, 1H), 7.15 (d, J=8.6 Hz, 1H), 7.06 (dd, J=8.8, 2.6 Hz, 1H), 6.82-6.75 (m, 1H), 5.12 (d, J=4.4 Hz, 1H), 4.53 (s, 2H), 4.47-4.20 (m, 1H), 3.92-3.85 (m, 1H), 3.84 (s, 3H), 3.71-3.61 (m, 2H), 3.59 (t, J=6.6 Hz, 2H), 3.45-3.34 (m, 1H), 3.24-3.14 (m, 1H), 3.14-3.03 (m, 1H), 2.91-2.52 (m, 6H), 2.32-2.20 (m, 2H), 2.09 (s, 3H), 2.06-1.94 (m, 3H), 1.93-1.82 (m, 2H), 1.80-1.21 (m, 10H), 1.18-1.02 (m, 3H), 0.94-0.84 (m, 6H).

Compound 23

(cis-rac)-N-(3-(6-(4-((9-(3-(2,4-Dioxotetrahydropy-rimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide

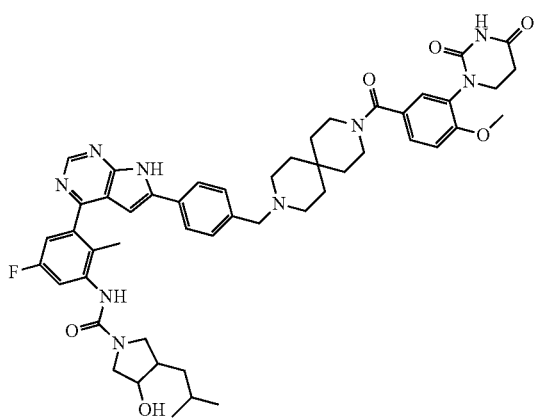 [SMILES: COc1ccc(C(=O)N2CCC3(CCN(Cc4ccc(-c5cc6c(-c7cc(F)cc(NC(=O)N8CC(O)C(CC(C)C)C8)c7C)ncnc6[nH]5)cc4)CC3)CC2)cc1N1CCC(=O)NC1=O]

Step 1: tert-butyl 9-(3-(2,4-dioxotetrahydropyrimi-din-1 (2H)-yl)-4-methoxybenzoyl)-3,9-diazaspiro[5.5]undecane-3-carboxylate To a stirred solution of 3,9-diaza-spiro[5.5]undecane-3-carboxylic acid tert-butyl ester (432 mg, 1.698 mmol) and NMM (0.392 ml, 3.57 mmol) at RT under argon in DMF (4 ml) was added 3-(2,4-dioxotetrahydropyrimidin-1(2H)-yl)-4-methoxybenzoic acid (intermediate 1a) (471 mg, 1.783 mmol), followed by HATU (743 mg, 1.953 mmol). The clear RM was stirred at RT for 2.5 h, and then quenched with sat. aq. NaHCO$_3$, and diluted with EtOAc. Both layers were separated and the aq. layer was extracted with EtOAc (1×). Combined organic layers were washed with brine/water 1:1 (2×) and brine (1×), dried over MgSO$_4$, filtered and evaporated to afford 900 mg of the title compound.

LC-MS (Method A): Rt=0.91 min, [M+H]+=501.4.

Step 2: 1-(2-methoxy-5-(3,9-diazaspiro[5.5]unde-cane-3-carbonyl)phenyl)dihydropyrimidine-2,4(1H,3H)-dione A solution of tert-butyl 9-(3-(2,4-dioxotetrahydropyrimi-din-1(2H)-yl)-4-methoxybenzoyl)-3,9-diazaspiro[5.5]unde-cane-3-carboxylate (step 1) (100 mg, 0.200 mmol) and HCl 4M in dioxane (1 ml, 4 mmol) was stirred in MeOH (1 ml) at RT for 1.5 h. The RM was concentrated and dried under reduced pressure to afford 99 mg of the title compound as an HCl salt.

LC-MS (Method D): Rt=0.76 min; [M+H]+=401.4.

Step 3: (cis-rac)-N-(3-(6-(4-((9-(3-(2,4-dioxotetra-hydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide To a stirred mixture of (cis-rac)-N-(5-fluoro-3-(6-(4-formylphenyl)-7H-pyrrolo[2,3-d]pyrimidin-4-yl)-2-methylphenyl)-3-hydroxy-4-isobutylpyrrolidine-1-carboxamide (intermediate 10) (100 mg, 0.193 mmol), TEA (0.100 ml, 0.717 mmol) and 1-(2-methoxy-5-(3,9-diazaspiro[5.5]unde-cane-3-carbonyl)phenyl)dihydropyrimidine-2,4(1H,3H)-di-one (step 2) (96 mg, 0.193 mmol) at RT in MeOH (2 ml) was added ZnCl$_2$ 0.5M in THF (0.450 ml, 0.225 mmol) and the RM was stirred at RT overnight. Then, NaBH$_3$CN (15 mg, 0.239 mmol) was added and RM was stirred at RT for 3 days. It was then concentrated under reduced pressure. Purification of the crude product by reverse phase flash chromatography on a Redisep® C18 column eluting with 2-100% ACN in (water+0.1% TFA) afforded a solution that was filtered over a PL-HCO$_3$ MP SPE cartridge and lyophilised to give 210 mg of a material. Purification of the material by SFC (column: Princeton PPU, 250×30 mm, 100 A, 5 um) eluting with 30-50% CO$_2$ in MeOH afforded 130 mg of the title compound as a white powder.

LC-MS (Method B): Rt=3.61 min, [M+H]$^+$=900.7.

$^1$H NMR (400 MHz, DMSO-d6) δ 12.78 (s, 1H), 10.31 (s, 1H), 8.84 (s, 1H), 8.02 (d, J=33.4 Hz, 2H), 7.64 (s, 1H), 7.60-7.41 (m, 3H), 7.35 (d, J=8.5 Hz, 1H), 7.30 (s, 1H), 7.14 (d, J=8.5 Hz, 1H), 7.09-6.99 (m, 1H), 6.85 (s, 1H), 4.88 (s, 1H), 4.09 (m, 1H), 3.83 (s, 3H), 3.57 (m, 3H), 3.52-3.37 (m, 7H), 3.06 (m, 1H), 2.66-2.61 (m, 6H), 2.14 (m, 1H), 2.08 (s, 3H), 1.68-1.18 (m, 12H), 0.89 (m, 6H).

Assay Description

Compounds of the invention were tested in the following cellular assays. The data obtained is shown in Table 1. The terms in Table 1 are defined as follows: $DC_{50}$ refers to the concentration at which 50% maximal degradation was observed; deg Amax is the extent of degradation and the value refers to the % protein remaining at the concentration at which maximum degradation is seen; Prol $GI_{50}$ refers to the proliferation data and defines the concentration at which 50% growth inhibition was observed compared to the vehicle treated control at the end of the incubation time. TMD8 cells are BTK dependent and OCI-LY3 cells are BTK independent.

BTK-GFP and IKZF3-GFP Protein Abundance Flow Cytometry Assay in HEK293A Cells:

Degradation of BTK or IKZF3 was measured in HEK293A cells (Invitrogen R70507) expressing either BTK-GFP and RFP or IKZF3-GFP and RFP from a stably integrated bicistronic BTK-GFP-iresRFP or IKZF3-GFP-iresRFP construct, respectively. Reduction of the GFP signal measured by flow cytometry served as readout for BTK or IKZF3 degradation after degrader treatment.

j) Cloning of the pLenti6-BTK-GFP-Ires-RFP and IKZF3-GFP-Ires-RFP sensor vectors The bicistronic BTK-GFP-iresRFP construct is based on a pLenti6-DEST vector backbone where GFP was introduced into the unique Xho1 site downstream of the destination cassette (DEST) and RFP was cloned behind an internal ribosomal entry site (Ires).

In detail, the sensor construct was engineered by replacing NanoLuciferase (NLuc) by GFP and FireFly luciferase (FF) by RFP from pLenti6-DEST-NLuc-Ires-FF.

The pLenti6-DEST-NLuc-Ires-FF sensor construct was cloned by replacing eGFP from pLenti6-DEST-Ires-eGFP with a synthesized stuffer element (encoding Ires-FF with FF flanked by two Nhe1 restriction sites) using blunt end cloning replacing Ires-eGFP between the two Pmll. To enable C-terminal tagging with NanoLuciferase (NLuc), NLuc was amplified from pNL1.1 (Promega #N1001) using linker primers with Xho1 sites for ligating into linearized pLenti6-DEST-Ires-FF using Xho1 digest resulting in the construct pLenti6-DEST-NLuc-Ires-FF.

The pLenti6-DEST-NLuc-Ires-FF served as base vector for cloning pLenti6-DEST-GFP-Ires-RFP using Gibson assembly to replace FF with RFP and NLuc with GFP. In a first round FF was replaced by RFP by amplifying RFP from a template using the following Gibson assembly linker primers (Gibson-Nhe1 RFPfw, CGATGAATTCGC-CACCgctagcATGGTGAGCAAGGGCGAGGAGC (SEQ ID NO: 1); Gibson-Nhe1 RFP-Stoprev, CTCAT-TACTAACCGGctagcTTACTTGTACAGCTCGTCCATGC (SEQ ID NO: 2)) to clone into pLenti6-DEST-NLuc-Ires-FF digested with Nhe1 and gel-purified to remove the FF fragment. The resulting pLenti6-DEST-NLuc-Ires-RFP vector served as the template to replace NLuc with GFP by amplifying GFP from a template using following Gibson assembly linker primers (Gibson-Xho1 GFPfw, CCAGCACAGTGGCGGCCGCTCGAGcATGGT-GAGCAAGGGCGAGGAGCTGTTCACC (SEQ ID NO: 3); Gibson-Xho1 GFP-Stoprev, CCGCGGGCCCTCTA-GACTCGAGTTACTTGTACAGCTCGTC-CATGCCGAGAGT (SEQ ID NO: 4)) to clone into pLenti6-DEST-NLuc-Ires-RFP digested with Xho1 and gel-purified to remove the NLuc fragment. All Gibson assembly reactions were performed with Gibson assembly Master Mix (New England Biolabs NEB E2611L) according to manufacturer's manual, resulting in the destination vector pLenti6-DEST-GFP-Ires-RFP to allow Gateway cloning.

To enable gateway cloning and C-terminal GFP tagging of BTK, the BTK open reading frame (ORF) was first shuttled from a pcDNA-DEST40-BTK vector (Invitrogen library ID INV_20090504v1) into pDONR221 (Invitrogen 12536-017) vector using a gateway BP reaction according to the manufacturer's manual (Invitrogen 11789-013) resulting in the novel construct pENTR221-BTK. For C-terminal tagging the STOP codon was mutated to a leucine performing a mutagenesis reaction with the following primers (pENTR221-BTK Quikchange STOP-Leu fw, gtcatggat-gaagaatccTTGaacccagctttcttgtac; pENTR221-BTK Quikchange STOP-Leu REVC, gtacaagaaagctgggtt-CAAggattcttcatccatgac) using the QuikChange Lightning mutagenesis kit (Agilent Technologies #210518) according to the manufacturer's manual, resulting in pENTR221-BTK (STOP-Leu).

To get the final pLenti6-BTK-GFP-Ires-RFP sensor construct, a Gateway LR reaction was performed between pLenti6-DEST-GFP-Ires-RFP and pENTR221-BTK (STOP-Leu) using the LR Clonase kit (Invitrogen 11791-019) according to the manufacturer's manual. All vectors described have been sequenced for verification.

By analogy the bicistronic pLenti6-IKZF3-GFP-iresRFP was engineered by gateway cloning of IKZF3 from a pENTR221-IKZF3(STOP-Leu) construct into the previously described pLenti6-DEST-GFP-Ires-RFP vector using the LR Clonase kit (Invitrogen 11791-019) according to the manufacturer's manual. All vectors described have been sequenced for verification.

To enable gateway cloning and C-terminal GFP tagging of IKZF3 the STOP codon was mutated to a leucine from pENTR221-IKZF3 (Invitrogen #INVE089_A8) performing a mutagenesis reaction with following primers (pENTR221-IKZF3 Quikchange STOP-Leu fw, AGAGCCCTGCT-GAAGttgaaccCAGCTTTcttgtac (SEQ ID NO: 5); pENTR221-IKZF3 Quikchange STOP-Leu REVC, gta-caagAAAGCTGggttcaaCTTCAGCAGGGCTCT (SEQ ID NO: 6)) using the QuikChange Lightning mutagenesis kit (Agilent Technologies #210518) according to the manufacturer's manual, resulting in pENTR221-IKZF3 (STOP-Leu).

ii) Engineering of Stably Expressing 293A BTK-GFP-Ires-RFP and IKZF3-GFP-Ires-RFP Sensor Cells 293A BTK-GFP-Ires-RFP and IKZF3-GFP-Ires-RFP sensor cells were generated by lentiviral vector transduction using the pLenti6-BTK-GFP-Ires-RFP or pLenti6-IKZF3-GFP-Ires-RFP sensor construct described before. Lentiviral particles were produced in HEK293FT cells (Invitrogen R70007) by co-transfection of 500 ng pLenti6-BTK-GFP-Ires-RFP or pLenti6-IKZF3-GFP-Ires-RFP, 500 ng delta8.71 and 200 ng pVSVG diluted in 100 µl OptiMEM serum free medium (Invitrogen #11058-021) that was mixed after 5 min preincubation with 3 µl of Lipofectamine2000 (Invitrogen #11668-019) in 97 µl OptiMEM serum free medium. The mix was incubated for another 20 min at RT and then added on 1 ml of a freshly prepared suspension of HEK293FT cells in a well of a 6-well plate (concentration $1.2 \times 10^6$ cells/ml). 1 day after transfection, the medium was replaced with 1.5 ml of complete growth medium (DMEM high Glucose+10% FCS+1% L-Glutamine+1% NEAA+1% NaPyr.). 48 h post transfection supernatant containing viral transducing particles was collected and frozen at −80° C.

Two days before transduction with viral particles $1 \times 10^5$ HEK293A cells (Invitrogen R70507) were seeded in 2 ml growth medium in a well of a 6-well plate. Infection was performed with 90 µl of collected supernatant containing viral transducing particles in 1 ml medium including 8 μg/ml polybrene. 24 h post infection, stably transfected cells were selected with blasticidin at a concentration of 8 μg/ml.

iii) Quantitative BTK-GFP and IKZF3-GFP Abundance Measurements

Stable HEK293A-BTK-GFP-iresRFP cells were maintained in complete growth medium (DMEM high Glucose+ 10% FCS+1% L-Glutamine+1% NEAA+1% NaPyr.) with passaging performed twice per week. On Day 0, HEK293A-BTK-GFP-iresRFP or HEK293A-IKZF3-GFP-iresRFP and HEK293A-iresRFP cells were seeded at 10,000 cells/well in a 96-well microtiter plate in 260 μl complete medium. On Day 1, cells were treated in duplicate with 10-point 1:3 dilution series of compound using the HP D300 Digital Dispenser (Tecan). DMSO concentrations were normalized across the plate to 0.1%. On Day 2, after 24 h of incubation at 37° C., treatment media was discarded, cells rinsed with 100 ul/well PBS and then detached using 40 ul trypsin/well for 5 min. Trypsin was neutralized with 100 ul/well PBS+ 20% FCS). Flow cytometry was performed on the samples using the BD FACS CANTO II (Becton Dickinson). Cell identification was then performed using forward (FSC) vs. side scatter (SSC) plots. Single cell discrimination is performed using SSC-Width (SSC-W) vs. SSC-Height (SSC-H) plots. Median GFP values for 5,000 single cells are used to determine BTK levels. Median GFP values from HEK293A-iresRFP are used as a background signal and thus defining 0% BTK signal. Median GFP values from DMSO treated HEK293A-BTK-GFP-iresRFP or HEK293A-IKZF3-GFP-iresRFP are used to define 100% BTK signal for subsequent $DC_{50}$ curves (concentration at 50% BTK degradation). GFP and RFP are read in the channels called FITC and PE, respectively.

Concentration response curves plotting relative reduction of the GFP signal (measured by flow cytometry) versus 10 compound concentrations (starting concentration 10 μM, 3 fold dilution steps) of the compounds allowed generation of $DC_{50}$ values.

For the IKZF3 abundance assay, the literature molecules pomalidomide and lenalidomide were tested as positive control compounds. Data is shown in Table 2, in which, $DC_{50}$ refers to the concentration at which 50% maximal degradation was observed; deg Amax is the extent of degradation and the value refers to the % protein remaining at the concentration at which maximum degradation is seen.

BTK(C481S)-GFP Protein Abundance Flow Cytometry Assay in TMD8 Cells:

Degradation of BTK(C481S) was measured in TMD8 cells expressing BTK(C481S)-GFP and mCherry from a stably integrated second generation bicistronic BTK (C481S)-GFP-CHYSEL-mCherry construct. Reduction of the GFP signal measured by flow cytometry served as readout for BTK(C481S) degradation after degrader treatment.

Cloning of the pLenti6-BTK(C481S)-GFP-CHYSEL-mCherry Sensor Vectors

The BTK(C481S) protein abundance sensor is based on a second generation bicistronic construct, where the 2 reading frames BTK(C481S) and mCherry control are separated by a cis-acting hydrolase element (see: Lo et al., 2015 Cell Reports 13, 2634), replacing the Ires from the first generation vector described before.

The bicistronic BTK(C481S)-GFP-CHYSEL-mCherry construct is based on a pLenti6-DEST vector backbone where a GFP-CHYSEL-mCherry cassette was synthesized and inserted downstream of the DEST cassette by Gibson assembly resulting in the new gateway compatible vector pLenti6-DEST-GFP-CHYSEL-mCherry to allow Gateway cloning with pENTR221-BTK(C481 S)(STOP-Leu) to obtain the final sensor construct pLenti6-BTK(C481 S)-GFP-CHYSEL-mCherry. The pENTR221-BTK(C481S)(STOP-Leu) was generated by mutating wild-type BTK to BTK(C481S) with a mutagenesis reaction on pENTR221-BTK (STOP-Leu) with the following primers (BTK C481S Quikchange fw, gagtacatggccaatggctCcctcctgaactacctgagg (SEQ ID NO: 7); BTK C481S Quikchange REVC, cctcaggtagttcaggaggGagccattggccatgtactc (SEQ ID NO: 8)) using the QuikChange Lightning mutagenesis kit (Agilent Technologies #210518) performed according to the manufacturer's manual, resulting in pENTR221-BTK(C481 S)(STOP-Leu).

Sequence of the synthesized construct (Xho1 sites are shown in bold, mCherry-ORF is shown in small letters):

(SEQ ID NO: 9)
```
GATATCCAGCACAGTGGCGGCCGCTCGAGcATGGTGAGCAAGGGCGAGG

AGCTGTTCACCGGGGTGGTGCCCATCCTGGTCGAGCTGGACGGCGACGT

AAACGGCCACAAGTTCAGCGTGTCCGGCGAGGGCGAGGGCGATGCCACC

TACGGCAAGCTGACCCTGAAGTTCATCTGCACCACCGGCAAGCTGCCCG

TGCCCTGGCCCACCCTCGTGACCACCCTGACCTACGGCGTGCAGTGCTT

CAGCCGCTACCCCGACCACATGAAGCAGCACGACTTCTTCAAGTCCGCC

ATGCCCGAAGGCTACGTCCAGGAGCGCACCATCTTCTTCAAGGACGACG

GCAACTACAAGACCCGCGCCGAGGTGAAGTTCGAGGGCGACACCCTGGT

GAACCGCATCGAGCTGAAGGGCATCGACTTCAAGGAGGACGGCAACATC

CTGGGGCACAAGCTGGAGTACAACTACAACAGCCACAACGTCTATATCA

TGGCCGACAAGCAGAAGAACGGCATCAAGGTGAACTTCAAGATCCGCCA

CAACATCGAGGACGGCAGCGTGCAGCTCGCCGACCACTACCAGCAGAAC

ACCCCCATCGGCGACGGCCCCGTGCTGCTGCCCGACAACCACTACCTGA

GCACCCAGTCCGCCCTGAGCAAAGACCCCAACGAGAAGCGCGATCACAT

GGTCCTGCTGGAGTTCGTGACCGCCGCCGGGATCACTCTCGGCATGGAC

GAGCTGTACAAGGGAAGCGGAGCGACGAATTTTAGTCTACTGAAACAAG

CGGGAGACGTGGAGGAAAACCCTGGACCTatggtgagcaagggcgagga ggataacatggccatcatcaaggagttcatgcgcttcaaggtgcacatg gagggctccgtgaacggccacgagttcgagatcgagggcgagggcgagg gccgcccctacgagggcacccagaccgccaagctgaaggtgaccaaggg tggcccctgcccttcgcctgggacatcctgtcccctcagttcatgtac ggctccaaggcctacgtgaagcacccgccgacatccccgactacttga agctgtccttccccgagggcttcaagtgggagcgcgtgatgaacttcga ggacggcggcgtggtgaccgtgacccaggactcctccctgcaggacggc gagttcatctacaaggtgaagctgcgcggcaccaacttcccctccgacg gccccgtaatgcagaagaagaccatgggctgggaggcctcctccgagcg gatgtacccgaggacggcgccctgaagggcgagatcaagcagaggctg aagctgaaggacggcggccactacgacgctgaggtcaagaccacctaca aggccaagaagcccgtgcagctgcccggcgcctacaacgtcaacatcaa gttggacatcacctcccacaacgaggactacaccatcgtggaacagtac
```

-continued gaacgcgccgagggccgccactccaccggcggcatggacgagctgtaca agtagCTCGAGTCTAGAGGGCCCGCGGTTAAC Engineering of Stably Expressing TMD8 BTK(C481S)-GFP-CHYSEL-mCherry Sensor Cells TMD8 BTK(C481S)-GFP-CHYSEL-mCherry sensor cells were generated by lentiviral vector transduction using the pLenti6-BTK(C481S)-GFP-CHYSEL-mCherry sensor construct described before. Lentiviral particles were produced in HEK293FT cells (Invitrogen R70007) by co-transfection of 500 ng pLenti6-BTK-GFP-Ires-RFP or pLenti6-IKZF3-GFP-Ires-RFP, 500 ng delta8.71 and 200 ng pVSVG diluted in 100 μl OptiMEM serum free medium (Invitrogen #11058-021) that was mixed after 5 min preincubation with 3 μl of Lipofectamine2000 (Invitrogen #11668-019) in 97 μl OptiMEM serum free medium. The mix was incubated for another 20 min at RT and then added to 1 ml of a freshly prepared suspension of HEK293FT cells in a well of a 6-well plate (concentration $1.2 \times 10^6$ cells/ml). 1 day after transfection, the medium was replaced with 1.5 ml of complete growth medium (DMEM high Glucose+10% FCS+1% L-Glutamine+1% NEAA+1% NaPyr.). 48 h post transfection supernatant containing viral transducing particles was collected and frozen at −80° C.

Two days before transduction with viral particles $1 \times 10^5$ HEK293A cells (Invitrogen R70507) were seeded in 2 ml growth medium in a well of a 6-well plate. Infection was performed with 90 μl of collected supernatant containing viral transducing particles in 1 ml medium including 8 μg/ml polybrene. 24 h post infection, stably transfected cells were selected with blasticidin at a concentration of 8 μg/ml.

Cell Viability Assay in DLBCL (Diffuse Large B-Cell Lymphoma) Cells:

The effect of the BTK compounds on cell proliferation was measured by a Resazurin (Sigma, #R7017) based cell viability assay. TMD8 (BTK compound sensitive) and OCI-LY3 (BTK compound insensitive) cells were incubated for 72 h at 37° C. and 5% $CO_2$ with the corresponding compound. Resazurin is a non-toxic, cell-permeable substrate that is virtually non-fluorescent. Upon entering living cells, Resazurin (Sigma, #R7017) is reduced to highly fluorescent Resorufin. The metabolic activity was assessed by measuring the fluorescence signal (ex. 530 nm; em. 600 nm).

TMD8 and OCI-Ly3 cells were seeded at day 0 in triplicates at a cell density of $1 \times 10^4$ cells per 150 μl/well in a 96-well plate (Costar #3904). Additional plates were prepared, in order to assess the basal metabolic activity of both cell lines at the beginning of the experiment. For these reference plates, Resazurin (Sigma, #R7017) was added to a final concentration of 13 μg/ml 3 h post seeding and was incubated for 2 h at 37° C. and 5% $CO_2$. Following incubation, the fluorescent signal intensity of the 96-well plates was measured on a Mithras LB940 multimode plate reader at 530/600 nm (Berthold Technologies, Germany).

In parallel, 3 h post-seeding, test-plates were treated with compound at various concentrations, or with vehicle (DMSO) alone for 3 days. The compound addition to the plates was performed by using a HP D300 digital dispenser (TECAN, Switzerland). The compounds were tested in triplicate, 8-point serial dilution (1:4), with a start concentration of 10 μM for OCI-LY3 and 1 μM for the TMD8 cells, respectively. To assess the relative proliferation of the cells, Resazurin was added to each well directly to the medium to a final concentration of 13 μg/ml. The plates were incubated for 2 h at 37° C. and 5% $CO_2$ to result in a 72 h endpoint. Following incubation, the fluorescent signal intensity of the 96-well plates were measured on a Mithras LB940 multimode plate reader at 530/600 nm (Berthold Technologies, Germany). The formation of Resorufin dye directly correlates with the number of metabolically active cells. For each triplicate treatment the mean and standard deviation were calculated and analyzed via curve fitting software to determine the respective compound concentration resulting in 50% growth inhibition ($GI_{50}$) values. For each compound $GI_{50}$ values were typically determined from at least 2 entirely independent experiments.

OCI-LY3 cells were acquired through a license agreement with University Health Network, Toronto, Canada. Cells are cultivated in RPMI1640 media (Gibco, #61870-010, lot. 1894759), supplemented with 10% FCS (HyClone, GE #SH30066.03, lot AB217603), 2 mM L-Glutamine (BioConcept, #5-10K50-H, lot. LA03467P), 1 mM Sodium Pyruvate (BioConcept, #5-60F00-H, lot. LB10510P), 10 mM HEPES (Gibco, #15630-056, lot. 1854074), 1% Pen/Strep (BioConcept, #4-01F00-H, lot. LB04235P).

TMD8 cells were acquired through a license agreement with Tokyo Medical and Dental University, Japan. Cells are cultivated in MEM Alpha (BioConcept, #1-23F01-I, lot. LB04262P) supplemented with 10% FCS (HyClone, GE #SH30066.03, lot AB217603), 2 mM L-Glutamine (BioConcept, #5-10K50-H, lot. LA03467P), 1% Pen/Strep (BioConcept, #4-01F00-H, lot. LB04235P).

TABLE 1

| Compound No. | BTK DC50 [uM] | BTK deg Amax % | BTK (C481S) DC50 [uM] | BTK (C481S) Amax % | TMD8 Prol $GI_{50}$ [uM] | OCI-LY3 Prol $GI_{50}$ [uM] | IKZF3 DC50 [uM] | IKZF3 deg Amax % |
|---|---|---|---|---|---|---|---|---|
| 1 | 0.1640 | 15 | 0.0410 | 3.6 | 0.01404 | 7.120 | >1.1 | 102.7 |
| 2 | 0.0014 | 2 | 0.0004 | 2.0 | 0.00031 | 7.730 | >3.3 | 101.8 |
| 3 | 0.0008 | 3 | n.d. | n.d. | 0.00019 | 4.478 | n.d. | n.d. |
| 4 | 0.0015 | 1.9 | n.d. | n.d. | 0.00034 | 8.223 | n.d. | n.d. |
| 5 | 0.0049 | 4 | 0.0013 | 2.0 | 0.00073 | 7.460 | >3.3 | 103.7 |
| 6 | 0.0034 | 6.2 | 0.0007 | 2.1 | 0.00045 | 9.920 | >3.3 | 93.5 |
| 7 | 0.0015 | 3.7 | n.d. | n.d. | 0.00028 | >10 | n.d. | n.d. |
| 8 | 0.0010 | 4.5 | 0.0004 | 2.7 | 0.00040 | >10 | >1 | 107.4 |
| 9 | 0.0017 | 6.3 | n.d. | n.d. | 0.00075 | 7.150 | n.d. | n.d. |
| 10 | 0.0155 | 7.4 | n.d. | n.d. | 0.00231 | 4.075 | >0.370 | 99.3 |
| 11 | 0.0006 | 2.3 | 0.0002 | 2.2 | 0.00018 | 3.510 | >10 | 96.7 |
| 12 | 0.0007 | 4.3 | 0.0003 | 3.0 | 0.00030 | >10 | >1.1 | 104.0 |
| 13 | 0.0005 | 2.9 | 0.0002 | 1.1 | 0.00024 | 9.220 | >3.3 | 99.7 |
| 14 | 0.0007 | 3.4 | n.d. | n.d. | 0.00024 | 3.816 | n.d. | n.d. |
| 15 | 0.0018 | 4 | 0.0009 | 3.0 | 0.00022 | 7.250 | >5.5 | 100.2 |
| 16 | 0.0047 | 19 | n.d. | n.d. | 0.00026 | 5.223 | n.d. | n.d. |

TABLE 1-continued

| Compound No. | BTK DC50 [uM] | BTK deg Amax % | BTK (C481S) DC50 [uM] | BTK (C481S) Amax % | TMD8 Prol $GI_{50}$ [uM] | OCI-LY3 Prol $GI_{50}$ [uM] | IKZF3 DC50 [uM] | IKZF3 deg Amax % |
|---|---|---|---|---|---|---|---|---|
| 17 | 0.0055 | 4 | n.d. | n.d. | 0.00049 | >10 | n.d. | n.d. |
| 18 | 0.0029 | 4.3 | 0.0008 | 2.5 | 0.00050 | >10 | >3.3 | 98.0 |
| 19 | 0.0855 | 13 | 0.0160 | 2.9 | 0.00487 | >10 | >1.1 | 102.4 |
| 20 | 0.0011 | 2.4 | n.d. | n.d. | 0.00029 | 3.700 | n.d. | n.d. |
| 21 | 0.0156 | 4 | n.d. | n.d. | 0.00117 | 3.600 | n.d. | n.d. |
| 22 | 0.0014 | 1.4 | 0.0004 | 2.1 | 0.00023 | 6.677 | >1.1 | 100.2 |
| 23 | 0.0061 | 3.3 | n.d. | n.d. | 0.00236 | >10 | n.d. | n.d. | n.d. = not determined

TABLE 2

| Compound name | IKZF3 DC50 [uM] | IKZF deg Amax % |
|---|---|---|
| Lenalidomide | 0.069 | 16.8 |
| Pomalidomide | 0.039 | 13.2 |

The invention claimed is:

1. A compound of formula (I),

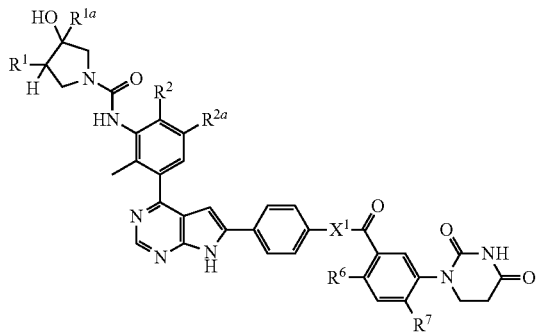

(I)

wherein:
$R^1$ is isobutyl;
$R^{1a}$ is H;
$R^2$ is H or F;
$R^{2a}$ is H or F;
$R^6$ is H or F;
$R^7$ is selected from H, F, Cl, —$CH_3$, —$OCH_3$, and —$OCH_2CH_3$;
$X^1$ is a group of formula (A or B):

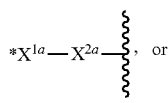

(A)

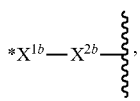

(B)

wherein,
$X^{1a}$ is selected from *—$(CH_2)_{1-3}$—, and *—$CH_2C(CH_3)_2$—, wherein the * indicates the point of attachment of the $X^{1a}$ group to the phenyl ring in formula (I);
*$X^{1b}$ is selected from *—O—, *—$OCH_2$—, and *—$CH_2O$— wherein the * indicates the point of attachment of the $X^{1b}$ group to the phenyl ring in formula (I);
$X^{2a}$ is selected from formula (C), (D), (E), (F), and (G):

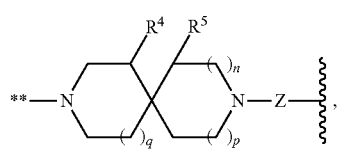

(C)

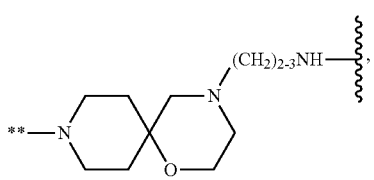

(D)

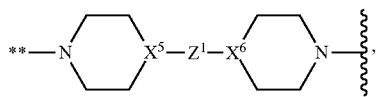

(E)

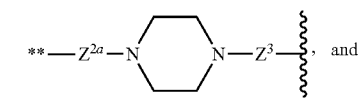

(F)

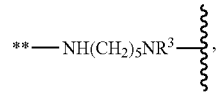

(G)

wherein ** indicates the point of attachment to $X^{1a}$;
$X^{2b}$ is selected from formula (E1) and (F1):

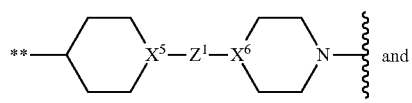

(E1)

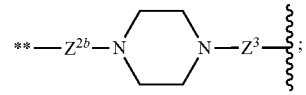

(F1)

wherein ** indicates the point of attachment to $X^{1b}$;
$X^5$ is CH or N;
$X^6$ is CH or N;
$R^3$ is H or —$CH_3$;
$R^4$ is H or —$CH_2OH$;
$R^5$ is H or —$CH_2OH$;
Z is absent or *—$(CH_2)_{2-3}NH$—, wherein * indicates the point of attachment of Z to the N atom in formula (C);
$Z^1$ is selected from *—O—, *—C(O)—, *—$(CH_2)_{1-3}$—, *—$(CH_2)_2O$—, and *—$CH_2CH(CH_2OH)$ O—, wherein * indicates the point of attachment of $Z^1$ to $X^5$ in formula (E) and formula (E1);
$Z^{2a}$ is absent or —$NH(CH_2)_4$—**;
$Z^{2b}$ is —$(CH_2)_{3-4}NH(CH_2)_2$—**;
$Z^3$ is absent or —$(CH_2)_4NH$—, wherein $Z^{2a}$ and $Z^3$ are not both at the same time absent; and wherein  in each of $Z^{2a}$, $Z^{2b}$ and $Z^3$ indicates the point of attachment to the respective N atoms in formulae (F) and (F1);
q is 0 or 1; and
n and p are independently 0 or 1; and
wherein (i) when $Z^1$ in formula (E) or formula (E1) is *—O—, then $X^5$ and $X^6$ are not N, and (ii) when $Z^1$ in formula (E) or formula (E1) is **—$(CH_2)_2O$—, and *—$CH_2CH(CH_2OH)$ O—, then $X^6$ is not N;
or a pharmaceutically acceptable salt thereof.

2. A compound, or a pharmaceutically acceptable salt thereof, according to claim 1, wherein $R^6$ is H.

3. A compound, or a pharmaceutically acceptable salt thereof, according to claim 1, wherein $R^7$ is —$OCH_3$.

4. A compound, or a pharmaceutically acceptable salt thereof, according to claim 1, wherein $X^1$ is a group of formula (A):

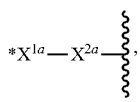
(A)

and $X^{2a}$ is selected from formula (C) and (E):

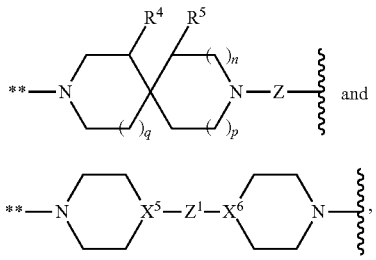
(C)
(E)

wherein ** indicates the point of attachment to $X^{1a}$.

5. A compound, or a pharmaceutically acceptable salt thereof, according to claim 1, wherein $X^1$ is a group of formula (A):

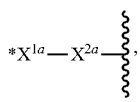
(A)

and $X^{2b}$ is formula (E1):

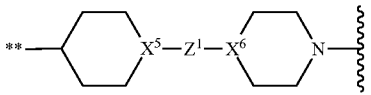
(E1)

wherein ** indicates the point of attachment to $X^{1b}$.

6. A compound, or a pharmaceutically acceptable salt thereof, according to claim 1, wherein, $X^1$ is selected from:

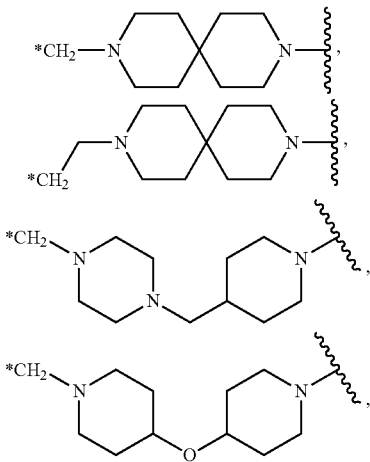

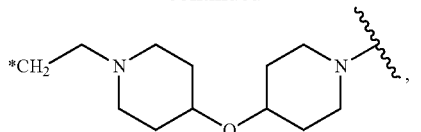
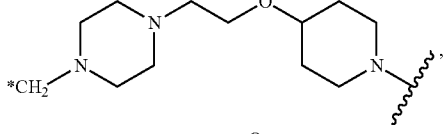
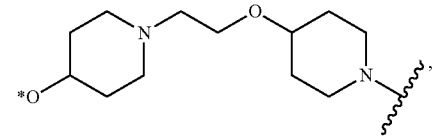
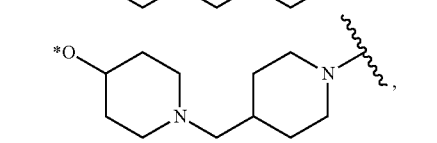
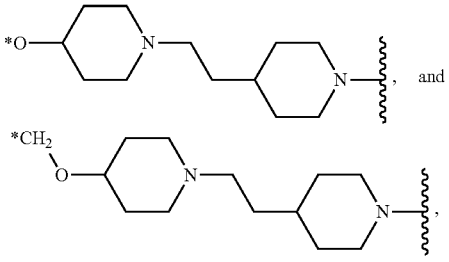

wherein * indicates the atom which is attached to the phenyl ring in Formula (I) or (Ia).

7. A compound according to claim 1 which is:
(3S,4R)—N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-((4-(2-((1-(3-(2,4-dioxotetrahydropyrimidin-1(2H)-yl)-4-methoxybenzoyl)piperidin-4-yl)oxy)ethyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide,
(3R,4S)—N-(3-(6-(4-(((1-(2-(1-(3-(2,4-dioxotetrahydropyrimidin-1 (2H)-yl)-4-methoxybenzoyl)piperidin-4-yl)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide,
(cis-rac)-N-(3-(6-(4-(((1-(2-(1-(3-(2,4-dioxotetrahydropyrimidin-1 (2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide,
trans-rac-N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((9-(3-(2,4-dioxotetrahydropyrimidin-1 (2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4R)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (cis-rac-N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3S,4R)—N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(4-((1-(3-(2,4-dioxotetrahydropyrimidin-1 (2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-((1-(3-(2,4-dioxotetrahydropyrimidin-1(2H)-yl)-4-methoxybenzoyl)piperidin-4-yl)methyl)piperidin-4-yl)methoxy)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1 (2H)-yl)-4-ethoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-6-fluoro-2-methylphenyl)-3-hydroxy-4-isobutylpyrrolidine-1-carboxamide, (cis-rac)-N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3S,4R)—N-(3-(6-(4-(2-(9-(3-(2,4-dioxotetrahydropyrimidin-1 (2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-3-hydroxy-4-isobutylpyrrolidine-1-carboxamide, (3S,4R)—N-(3-(6-(4-(((1-(2-(1-(3-(2,4-dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide, (3R,4S)—N-(3-(6-(4-(((1-(2-(1-(3-(2,4-dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-3-hydroxy-4-isobutylpyrrolidine-1-carboxamide, or (cis-rac)-N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-3-hydroxy-4-isobutylpyrrolidine-1-carboxamide or a pharmaceutically acceptable salt thereof.

8. A pharmaceutical composition comprising a compound according to claim 1 or a pharmaceutically acceptable salt thereof and one or more pharmaceutically acceptable carriers.

9. A combination comprising a compound according to claim 1 or a pharmaceutically acceptable salt thereof and one or more therapeutically active agents.

10. A method of treating a disease mediated by BTK comprising administering to a patient in need thereof a therapeutically acceptable amount of the compound according to claim 1, or a pharmaceutically acceptable salt thereof.

11. A method of treating cancer comprising administering to a patient in need thereof a therapeutically acceptable amount of the compound according to claim 1, or a pharmaceutically acceptable salt thereof.

12. A method according to claim 11, wherein the cancer is selected from chronic lymphocytic leukemia (CLL), mantle cell lymphoma (MCL), small lymphocytic lymphoma (SLL), Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia, Hodgkin lymphoma, non-Hodgkin lymphoma, post-transplant lymphoproliferative disorder, hairy cell leukemia, Histiocytic and dendritic neoplasms.

13. A method of treating an autoimmune disorder, inflammatory disorder, allergic disease, anaphylaxis, allergic asthma and airway diseases comprising administering to a patient in need thereof a therapeutically acceptable amount of the compound according to claim 1, or a pharmaceutically acceptable salt thereof.

* * * * *

SEQUENCE LISTING

```
<160> NUMBER OF SEQ ID NOS: 11

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgatgaattc gccaccgcta gcatggtgag caagggcgag gagc              44

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcattacta accggctagc ttacttgtac agctcgtcca tgc               43

<210> SEQ ID NO 3
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccagcacagt ggcggccgct cgagcatggt gagcaagggc gaggagctgt tcacc   55

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 4
ccgcgggccc tctagactcg agttacttgt acagctcgtc catgccgaga gt         52

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agagccctgc tgaagttgaa cccagctttc ttgtac                           36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtacaagaaa gctgggttca acttcagcag ggctct                           36

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagtacatgg ccaatggctc cctcctgaac tacctgagg                        39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctcaggtag ttcaggaggg agccattggc catgtactc                        39

<210> SEQ ID NO 9
<211> LENGTH: 1551
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gatatccagc acagtggcgg ccgctcgagc atggtgagca agggcgagga gctgttcacc    60
ggggtggtgc ccatcctggt cgagctggac ggcgacgtaa acggccacaa gttcagcgtg   120
tccggcgagg gcgagggcga tgccacctac ggcaagctga ccctgaagtt catctgcacc   180
accggcaagc tgcccgtgcc ctggcccacc ctcgtgacca ccctgaccta cggcgtgcag   240
tgcttcagcc gctaccccga ccacatgaag cagcacgact tcttcaagtc cgccatgccc   300
gaaggctacg tccaggagcg caccatcttc ttcaaggacg acggcaacta caagacccgc   360

```
gccgaggtga agttcgaggg cgacaccctg gtgaaccgca tcgagctgaa gggcatcgac      420
ttcaaggagg acggcaacat cctggggcac aagctggagt acaactacaa cagccacaac      480
gtctatatca tggccgacaa gcagaagaac ggcatcaagg tgaacttcaa gatccgccac      540
aacatcgagg acggcagcgt gcagctcgcc gaccactacc agcagaacac ccccatcggc      600
gacggccccg tgctgctgcc cgacaaccac tacctgagca cccagtccgc cctgagcaaa      660
gaccccaacg agaagcgcga tcacatggtc ctgctggagt tcgtgaccgc cgccgggatc      720
actctcggca tggacgagct gtacaaggga gcggagcga cgaattttag tctactgaaa       780
caagcgggag acgtggagga aaaccctgga cctatggtga gcaagggcga ggaggataac      840
atggccatca tcaaggagtt catgcgcttc aaggtgcaca tggagggctc cgtgaacggc      900
cacgagttcg agatcgaggg cgagggcgag ggccgcccct acgagggcac ccagaccgcc      960
aagctgaagg tgaccaaggg tggcccccctg cccttcgcct gggacatcct gtcccctcag    1020
ttcatgtacg gctccaaggc ctacgtgaag caccccgccg acatcccccga ctacttgaag    1080 ctgtccttcc ccgagggctt caagtgggag cgcgtgatga acttcgagga cggcggcgtg    1140
gtgaccgtga cccaggactc ctccctgcag gacggcgagt tcatctacaa ggtgaagctg    1200
cgcggcacca acttcccctc cgacggcccc gtaatgcaga gaagaccat gggctgggag      1260 gcctcctccg agcggatgta ccccgaggac ggcgccctga agggcgagat caagcagagg    1320
ctgaagctga aggacggcgg ccactacgac gctgaggtca agaccaccta caaggccaag    1380
aagcccgtgc agctgcccgg cgcctacaac gtcaacatca gttggacat cacctcccac     1440 aacgaggact acaccatcgt ggaacagtac gaacgcgccg agggccgcca ctccaccggc    1500
ggcatggacg agctgtacaa gtagctcgag tctagagggc ccgcggttaa c              1551

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcatggatg aagaatcctt gaacccagct ttcttgtac                              39

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtacaagaaa gctgggttca aggattcttc atccatgac                              39
```